US006974864B2

(12) United States Patent
Maertens et al.

(10) Patent No.: US 6,974,864 B2
(45) Date of Patent: Dec. 13, 2005

(54) SEQUENCES OF HEPATITIS C VIRUS GENOTYPES AND THEIR USE AS PROPHYLACTIC, THERAPEUTIC AND DIAGNOSTIC AGENTS

(75) Inventors: Geert Maertens, Bruges (BE); Lieven Stuyver, Herzele (BE)

(73) Assignee: Innogenetics N.V., Ghent (BE)

( * ) Notice: Subject to any disclaimer, the term of this patent is extended or adjusted under 35 U.S.C. 154(b) by 280 days.

(21) Appl. No.: 09/851,138

(22) Filed: May 9, 2001

(65) Prior Publication Data

US 2002/0183508 A1 Dec. 5, 2002

Related U.S. Application Data

(62) Division of application No. 08/836,075, filed as application No. PCT/EP95/04155 on Oct. 23, 1995.

(30) Foreign Application Priority Data

Oct. 21, 1994 (EP) ............................................. 94870166
Jun. 28, 1995 (EP) ............................................. 95870076

(51) Int. Cl.⁷ ........................ C07H 21/00; C12N 15/51; C12N 15/36; C12N 7/00; C12N 5/00
(52) U.S. Cl. ..................... 536/23.1; 536/23.72; 514/44; 530/300; 530/324; 530/328; 530/327; 435/320.1; 435/325; 435/69.1; 424/228.1
(58) Field of Search ............................ 536/23.1, 23.72, 536/23.7; 514/44; 530/300, 324, 328, 327; 435/320.1, 325, 69.1; 424/228.1

(56) References Cited

U.S. PATENT DOCUMENTS

| 5,372,928 A | 12/1994 | Miyamura et al. |
| 5,514,539 A | 5/1996 | Bukh et al. |

FOREIGN PATENT DOCUMENTS

| EP | 0 388 232 | 9/1990 |
| EP | 419182 A1 | 3/1991 |
| EP | 0 532 167 | 3/1993 |
| EP | A-0 532 167 | 3/1993 |
| JP | 6-319563 | 11/1994 |
| WO | WO 92/19743 | 11/1992 |
| WO | 93-00365 | 1/1993 |
| WO | WO 93/06126 | 4/1993 |
| WO | WO 93/10239 | 5/1993 |
| WO | 94-25601 | 11/1994 |
| WO | WO 95/01442 | 1/1995 |
| WO | WO-A-95 01442 | 1/1995 |

OTHER PUBLICATIONS

Sequence search reports from PTO.*
Apichartpikyakul et al., Journal of Clinical Microbiology, Sep. 1994, pp 2276–2279, vol. 32, No. 9.
van Doorn et al, Journal of Hepatology 1994, vol. 21, pp 122–129.

van Doorn et al, Journal of General Virology, 1995, vol. 76, pp 1871–1876.
GenBank Accession No. L39317, Version L39317.1, printed Aug. 25, 2004.
Choo et al. PNAS 1991 88, 2451–2455.
Genbank Accession No. M62321. Hepatitis C virus . . . [gi:329873] Hepatitis C virus polyprotein precursor (HCV–1) mRNA, complete cds; VRL Aug. 2, 1993 Choo, Q.–L., Richman,K., Han,J.H., Berger,K., Lee,C., Dong,C., Gallegos,C., Coit,D., Medina–Selby,A., Barr,P.J., Weiner, A., Bradley,D.W., Kuo,G. and Houghton,M. :Genetic organization and diversity of the hepatitis C virus, Proc. Natl. Acad. Sci. U.S.A. 88 (6), 2451–2455 (1991).
Liu et al, 1992 Gene 114 (2) 245–250.
Stuyver et al, 1994 Journal of General Virology 74 (6) 1093–1102.
Stuyver et al, 1994 PNAS USA 91 (21) 10134–10138.
van Doorn et al, 1994 Journal of Hepatology 21 (1) 122–129.
Qu et al, 1994 Journal of General Virology 75 (5) 1063–1070.
Mori, S. et al, "A new type of hepatitis C in patients in Thailand", Biochem. Biophys. Res. Commun., vol. 183, No. 1, 1992, pp. 334–342.
Chan, S.W. et al, "Analysis of a new hepatitis C type and its phylogenetic relationsip to existing variants", J. Gen. Virol., vol. 73, 1992, pp. 1131–1141.
Chen et al, Virology 188, 102–113 (1992).

(Continued)

*Primary Examiner*—James Housel
*Assistant Examiner*—Bao Qun Li
(74) *Attorney, Agent, or Firm*—Nixon & Vanderhye P.C.

(57) ABSTRACT

The present invention relates to new genomic nucleotide sequences and amino acid sequences corresponding to the coding region of these genomes. The invention relates to new HCV types and subtypes sequences which are different from the known HCV types and subtypes. More particularly, the present invention relates to new HCV type 7 sequences, new HCV type 9 sequences, new HCV type 10 and new HCV type 11 sequences. Also, the present invention relates to new HCV type 1 sequences of subtypes 1d, 1e, 1f and 1g; new HCV type 2 sequences of subtypes 2e, 2f, 2g, 2h, 2I, 2k and 2l; new HCV type 3 sequences of subtype 3g, new HCV type 4 sequences of subtypes 4k, 4l and 4m; a process for preparing them, and their use for diagnosis, prophylaxis and therapy. More particularly, the present invention provides new type-specific sequences of the Core, the E1 and the NS5 regions of new HCV types 7, 9, 10 and 11, as well as of new variants (subtypes) of HCV types 1, 2, 3 and 4. These new HCV sequences are useful to diagnose the presence of HCV type 1, and/or type 2, and/or type 3, and/or type 4, and/or type 7, and/or 9, and/or type 10, and/or type 11 genotypes or serotypes in a biological sample. Moreover, the availability of these new type-specific sequences can increase the overall sensitivity of HCV detection and should also prove to be useful for prophylactic and therapeutic purposes.

7 Claims, 74 Drawing Sheets

OTHER PUBLICATIONS

George et al, "Macromolecular Sequencing and Synthesis, Selected Methods and Applications", pp. 127–149, 1988 Allan R. Liss, Inc.

Innis et al, "PCR Profocos. A Guide to Methods and Applications", 1990 Academic Press, 11$^3$–12.

Van Doorn et al, "Sequence analysis of hepatitis C virus genotypes 1 to 5", Embl/Genbank/DDBJ database entry HC3NL96 Accesion No. X78863 (1994).

Hotta et al, "Subtype analysis of hepatitis C virus in Indonesia", DDBJ database entry HPCN S5P5 Accesion No. D26387 (1994).

Kato, N. et al, "Molecular cloning of the human hepatitis C virus genome form Japanese patients with non–A non–B hepatitis", Proc. Natl. Acad. Sci. USA, vol. 87, 1990, pp. 9254–9528.

Kato et al, "Molecular Cloning of the Human Hepatitis C Virus Genome Form Japanese Patients with Non–A Non–B Hepatitis", Proc. Natl. Acad. Sci. USA, vol. 87, 1990, pp. 9254–9258, XP000168621.

Database Genban —Online! Accession No. X78863, May 20, 1994 Van Doorn et al: "Sequence Analysis of Hepatitis C Virus Genotypes 1 to 5", XP002017147 * abstract * and J. Gen. Virol., vol. 76, 1994, pp. 1871–1876.

Database Genban —Online! Accession No. D26387, Feb. 4, 1994 Hotta et al: Subtype Analysis of Hepatitis C Virus in Indonesia XP002017146 * abstract * and J. Clin. Microbiol., vol. 32, 1994, pp. 3049–3051.

Biochem. Biophys. Res. Commun., vol. 170, No. 3, 1990, pp. 1021–1025, XPOO2017145 N. Enomoto et al: "There are Two Major Types of Hepatitis C Virus in Japan".

Bukh, J. et al, "At least 12 genotypes of hepatitis C virus predicted by sequence analysis of the putative E1 gene of isolates collected worldwide", Proceedings of the National Academy of Sciences of USA, vol. 90, pp. 8234–8238 (1993).

Bukh, J. et al, "Sequence analysis of the core gene of the 14 hepatitis C virus genotypes", Proceedings of the National Academy of Sciences of USA, vol. 91, pp. 8239–8424; (1994).

Enomoto, N., et al "There are two major types of hepatitis C virus in Japan", Biochem. Biophys. Res. Commun., vol. 170, No. 3, 1990, pp. 1021–1025, XPOO2017145 (1990).

Driesel, G. et al, "Hepatitis C virus (HCV) genotype distribution in german isolates: studies on the sequence variabiity in the E2 and NS5 region", Archives of Virology, vol. 139, No. 3/04, pp. 379–388.

Tokita, H. et al, "Hepatitis C virus variants from vietnam are classifiable into the seventh, eighth and ninth major genenetic groups", Proceedings of the National Academy of Sciencies of USA, vol. 91, No. 23, pp. 11022–11026 (1994).

Stuyver et al, "Hepatisis C virus genotyping by means of 5'–UR/core line probe assays and molecular analysis of untypeable samples", Virus Research, vol. 30, No. 2–3, pp. 137–157 (1995).

Simmonds, P. et al, "Mapping of serotype–specific immunodominant epitopes in the NS4 region of hepatitis C virus", J. Clin. Micro., vol. 31, No. 6, 1993, pp. 1493–1503.

Stuyver, L. et al, "Analays of the putative E1 envelope and NS4a epitope regions of HCV type 3", Biochem. Biophys. Res. Commun., vol. 192, No. 2, 1993, pp. 635–641.

Chayama, K. et al, "Genotypic subtyping of hepatitis C virus", J. Gastroenterol. Hepatol., vol. 8, 1993, pp. 150–156.

Weiner et al, "Variable and hypervariable regions are found in the regions of HCV correspoinding to the flavivirus envelope and NS1 proteins", Virology, vol. 180, 1991, pp. 842–848.

Bukh et al, PNAS 89 4942–4946, Jun. 1992.

Wallace et al, "Methods in Enzymology", 152:432 (1987).

Cha, T.A. et al, "At least five related but distinct genotypes of hepatitis C virus exist", Proc. Natl. Acad. Sci. USA, vol. 89, 1992, pp. 7144–7148.

* cited by examiner

Fig.1A

```
SEQID
NO150
208     HCV-11a ATGAGCACGAATCCTAAACCTCAAAAAAAAAACAAACGTAACACCAACCG
209     HCV-J1b--------A----------------G-----C-------------------
210     HCG91c------------------------G-----C-------------------
1       BNL11d------:-----------------G-----C-------------------
5       BNL21d-----------------------G-----C-------------------
9       CAM10781e----------------------G-----C----A-A-----------
11      FR21f------------------------G-----C------C------------

211     HC-J62a--------A----------------G-----C----A-A-----------
212     HC-J82b--------A----------------G-----C----A-A-----A-----
213     S832c---------A----------------G-----C----A-A-----T-----
214     NE922d--------A----------------G-----C----A-A-----T-----
17      FR42f---------A----------------G-----CT---A-A-----T-----
13      BNL3  2e-------A----------------G-----C----A-A--T--------
21      BNL52h---------A----------------G-----C----A-A-----T-----

215     NZL13a--------ACT---------------G-----C----A-A-------T---
216     HCV-TR3b-------ACT---------------G-C---C----A-A-----ACT---
217     NE483c--------ACT---A-----C----G-----C----A-A-------T---
218     NE2743d-------ACT---A-----C----G-----C----A-A-------T---
219     NE1453e-------ACT---A-----C----G-----C----A-A-----GT---
220     NE1253f--------ATT--------------G-C--CC----A-A-----ACC---

221     Z44a----------------------G-----C-------------------
222     Z14b--------A----------------G-----C-------------------
223     GB3584c-----------------------G-----C-------------------
224     DK134d------------------------G-----C-------------------
225     GB8094e-----------------T-----G-----C-------------------
27      BNL74k------------------------G-----C-------------------

226     BE955a------------------------G-----C----A-A-----------

227     HK26a--------ACT---A-----C----G-----C----A-A-----------

228     FR17a--------ACT---A-----C----G-----C----A-A--T--T-----

43      VN48a--------ACT---A-----C----G-----C----A-A-------T---
45      VN138b-------ACT---------------G-----C------A-----------

47      VN129a--------ACT---A-----C----G-----C----A-A-----A-----

49      NE9810a-------ACT---------A----G-----C----A-A----------N
```

Fig.1B

```
SEQID
NO51100
208 HCV-11a TCGCCCACAGGACGTCAAGTTCCCGGGTGGCGGTCAGATCGTTGGTGGAG
209 HCV-J1bC--------------T-----------C--T------------------
210 HC-G91cC--------------T---------------C-----------C----
  1 BNL11dC-----T--K-GS--NNNNNNN-------------------------
  5 BNL21dC-----------------N----------T-----------------
  9 CAM10781eC-------------------------C--T--C-------------
 11 FR21fC-------------T--A-----------G--G---------G-------

211 HC-J62a---------A-----T-----T-----C-----C-----------C----
212 HC-J82bC-------------T---------------------------C----
213 S832cC--------------------------C--T--C-----------C----
214 NE922dC--------------------------C--T--C---------------
 17 FR42f-------------T-----------C-----C-----------C----
 13 BNL32eC--------------------------C-----C-----------C----
 21 BNL52hC--------------T-----------C--T--C-----------C----

215   NZL13a-----------------------------------A---------------
216   HCV-TR3b----------A----T-----------C-----A---------------
217   NE483c-----------------------------C----------------------
218   NE2743d--------------T-----------C-----C---------------
219   NE1453e------G--A-----T-----------C-----C---------------
220   NE1253fC--------------------------C--T--G---------------

221   Z44aC-----CAT------A---------------T--C-----------C----
222   Z14b------CAT---T--G--A---------C-----C-----------C----
223   GB3584cC-----CAT------T-----------C--T--C-----------C----
224   DK134dC------AT------T------------------C-----------C----
225   GB8094eC-----CAT------T--------------T--C-----------C----
 27   BNL74kC-----CAT------T---------------T--C-----------C----

226   BE955a------------------------------C--T--------------C----

227   HK26a-------AC-----------------------------------------C----

228   FR17a-----TAT------------------C-----C-----------------

43   VN48aC--------------------------------C---------------
 45   VN138b---------------------------------------------------

47   VN129a-------AT---T-------------C-----------------------

49   NE9810aC--G-----------T--------A--C-----------------------
```

Fig. 1C

```
SEQID
NO101150
208  HCV-11a TTTACTTGTTGCCGCGCAGGGGCCCTAGATTGGGTGTGCGCGCGACGAGA
209  HCV-J1b -----C-------------------C--G-----------------T--G
210   HC-G91c ------------------------C---G---------------------G
  1  BNL11d  -----C-------------------C--GNN---------------T--G
  5  BNL21d  -----C-------------------C--G--------------------C--G
  9  CAM1078 1e-C---G--C-A------------------------------AG--C-G
 11  FR21f   -------------------------C--G---------------------G

211   HC-J62a -A----------------------C--G-----------------A--G
212   HC-J82b --------C---------------C--G-----------------A--G
213   S832c   -A------C---------------G--------------------------G
214   NE922d  -A----------------------CC-G-----------------------G
 17   FR42f   ------------------------C--G--------------C-A--G
 13   BNL32e  -----------------------------C---------------------
 21   BNL52h  -A----------------------CC-G-----------------------G

215   NZL13a  -A---G------------------AC-------------------C-T
216   HCV-TR3b-A--TG--C-------T-------AC-------------AGTAC-T
217   NE483c  -A---G------------------CT-------------T--AC-T
218   NE2743d -C-----AC---------------A--------------AGTTC-T
219   NE1453e -A----------------------AC-------------A--TC-T
220   NE1253f -A---G-A----------------AC-------------AGT-C-T

221   Z44a    ------------------------C--G-----------------TC--
222   Z14b    --------C---------------CC-G-----------AG-TC-G
223   GB3584c -------------------------C--G-----------------T--G
224   DK134d  -----------------------------------------T--G
225   GB8094e -----------------------G---------------------TC-G
 27   BNL74k  ------------------------C--G-----------------TC-G

226   BE955a  ----------------------GA---------------TC-G
227   HK26a   ----------------------CC-G-----------------------

228   FR17a   -----------------------C-T-----------------------

43   VN48a   -C------C---------------GC-C-----------------------
 45   VN138b  -----------------------C-T-----------------------G

47   VN129a  -C--------A-------------AC-T-----------------------G

49   NE9810a -----G--C-A--A----------CCAG-----------T--AGT-C-C
```

Fig.1D

```
SEQID
NO151200
208HCV-11aAAGACTTCCGAGCGGTCGCAACCTCGAGGTAGACGTCAGCCTATCCCCAA
209HCV-J1b-----------------------T--A--G--A--A-----------
210HC-G91c-------------------------C--G--G-----------T-----
1BNL11d-----------------A---------T--C--G--A-------------
5BNL21d--------------------G-----T-AC--G--A--------T--T--
9CAM10781e--------G------------------T--G--G--C--A-----T-----
11FR21f-------------------------C--A--G--A---------------

211HC-J62a---------G---------C--G--A--T--A--G--C-----C-----T--
212HC-J82b---------T------A--C--G--G--T--AC----C-----C-----G--
213S832c--A---------A-----C--G--A--T--G--G--C-----C-----T--
214NE922d--A--------------C--G--A--T--G--G--C-----C--------
17FR42f--------T--A-----C--G--A--T--A--G--C-----C-----A--
13BNL32e--------T--A-----C--G--A--T--A--G--C-----C-----T--
21BNL52h--A---------A-----C--G--A--T--G--G--C-----C-----T--

215NZL13a--A-----T--A-----A--G-----C--AC----A-------------
216HCV-TR3b-------------------G-----CAAACAG-----C-T---------
217NE483c-----------------A--G-----C-CGC-G--G--------------
218NE2743d--A------------AG----C--CAACC-G--G---------------
219NE1453e--------A---------A-----C--C--AC-G--A--------T-----
220NE1253f--AT-------------------C--AC-G--G---------------

221Z44a--------G-----------------T--C--G-----A-----------
222Z14b--------G--------A--------T--C--G------------------
223GB3584c--------G-----------------T--G---------------------
224DK134d--------G-----------------T--G--G--C---------------
225GB8094e--------G-----------------T--G--G--C--A------------
27BNL74k---------G-----------------T--G-----C--A-----------

226BE955a--------G--A---------C--T--AC-G-----------T-----

227HK26a-------------A--C--G--CA----C--G--C--A-----A--A--

228FR17a-----C-----A------C--G---A----C--G--C-----C--A--A--

43VN48a--------T--A-----C--G--CA--------G--C--A--A--A-----
45VN138b--A-----T--A-----C--G--CA-G--------C--A-----A--G--

47VN129a--------G--A-----C--GG-CA-------G--C--A--A--A-----

49NE9810a------------------------CA----G--C--A--C-------G
```

Fig.1E

```
SEQID
NO201250
208HCV-11aGGCTCGTCGGCCCGAGGGCAGGACCTGGGCTCAGCCCGGGTACCCTTGGC
209HCV-J1b------C-----------T----------------------------
210HC-G91c---C--C--A--------A---T------G-------------------
1BNL11d------Y---Y----------T--------------------T-------
5BNL21d------C-A-T----T-----NN-------------A---C-T--C----
9CAM10781e--AG--C--A------------T
11FR21f------C--A------------T-------------T--------A----

211HC-J62a--A---G--CT--ACT----AAT------GAA-A--A--A-----C----
212HC-J82bA-A---G--CT--ACC----A-T------GAA----A--A--T-------
213S832cA-A---G--CA--ACT----A-T------GAAG---A--A----------
214NE922dA-A---G--C---ACT----A-T------GAA-A--A--A----------
17FR42fA-A---G--CG--ACT----A-T------GA-GT--A--A----------
13BNL32eA-A---GN-NG--ACT------T------GA-GT--A--A--T--C----
21BNL52hA-A---G--CT--ACT----AAT------GA-GT--A--A----------

215NZL13a---G------AG---A---C--T---------------------
216HCV-TR3b------CTC--G-------C--T-------------------
217NE483c---G-----TGG------AC--T--------G-------------
218NE2743d---A------AG-------C--T------------T--------
219NE1453e---A--C-C-AG--GA--AC--T--------G-----T--------C----
220NE1253f---A--C--AAG-------C--T-------C-----T------------

221Z44a---G--C-A---A---------AT-------G-----------------
222Z14b---G--C---T-----------T---------------------
223GB3584c---A-----AT-T-----A---T----------------------A----
224DK134d---G--C-AA-T------T---T------------T-----T-------
225GB8094e---G--C--AT----------AT-------G-----------T-------
27BNL74k---G-----AT-------A---T-------A-----A--A--T--A----

226BE955a---G--C-A----AC----C--T------G---A---------------

227HK26a---G--C-A----C--------CA---------------A---------

228FR17a--TA--C-A---GACA---C-T-G-----G---A-----C---------

43VN48aA-TG--C-AC-AAAC----C-T--------C--------------C----
45VN138b--TG----AC-AAAC----C-T----------A----------C----

47VN129a--TG--C-A-AA-C-A---C-A--------------T-------C----

49NE9810a---G--C--AA-----------T--------------------------
```

Fig.1F

```
SEQID
NO251300
208HCV-11aCCCTCTATGGCAATGAGGGCTGCGGGTGGGCGGGATGGCTCCTGTCTCCC
209HCV-J1b------------C-----TATG--------A---------------A---
210HC-G91c------------C--------T-----------------------C---
1BNL11d-----------------------------N----------------C---
5BNL21d---------------------A------------------------C---
11FR21f--------CT--C-------------A---------------------C--T

211HC-J62a----A--C--G--------ACT---C-----A---------------C---
212HC-J82b----G--C--A--C-----T----C--------T-----------C---
213S832c----G-----G---------CT---C-----A--G-----------C---
214NE922d----G--C--G---------CT---C-----A--G-----------C---
17FR42f----G--C--G--C------CT---C-----A--G-----------C---
13BNL32e----G-----G--C-----GCT---C-----A---------------C---
21BNL52h----G-----G--C------CTT--T-----A---------T----C--T

215NZL13a----------T--C----------------A--G-----------C--A
216HCV-TR3b-------C--G---A--------T----T---A---------T----C---
217NE483c-------C--T--------------------------------C---
218NE2743d-T--T-----------------T--------A---------T----C---
219NE1453e---------T--C-----------------A--G------T-------T
220NE1253f----------G------------T-----A--------------------

221Z44a---------------------------A--G--------------T
222Z14b----T--C---------------T--------A--G----------C---
223GB3584c-T--T--C--T--------T----------------------A--T
224DK134d----T--C----------------------------------A---
225GB8094e----T--C------------------T--------A--G----------C--T
27BNL74k-T--T--C--T--------T----------ANN------T----C---

226BE955a----T--C-C---------CT--------A--G-----G--C--C--T

227HK26a-T--T-----A--C--------T-------A--T----------C---

228FR17a----T--------C----------A-------------------C---

43VN48a-T--T-----A-----------T--T-----A--C-----------C---
45VN138b-T--T-----G--------T--T--C-----A--G----------C---

47VN129a----T-----G--C---------C------G------T----C---

49NE9810a----A-----G------------------A--G----------C--G
```

Fig.1G

```
SEQID
NO301350
208HCV-11aCGTGGCTCTCGGCCTAGCTGGGGCCCCACAGACCCCCGGCGTAGGTCGCG
209HCV-J1b-----------------T--------------------------------
210HC-G91c--C---------------T--------TT-T-----------G-----A--
1BNL11d--C-------
5BNL21d--C-------
11FR21f--C-----C--T---------------AT--------A-----A--A--

211HC-J62a--A--T--C--T--CTCT----------AT----------A------C--
212HC-J82b--C--G-----T----CT-----------C----------A---A--A--
213S832c--C--T-----C---TCA-----------C----------A--AA-----
214NE922d--A--G-----C--GTCA--------A--T----------AC-----A--
17FR42f--G---------C--CTCG--------A-AC----------AC-----A--
13BNL32e--A-------
21BNL52h--A-------

215NZL13a--C-----C--T--ATC---------A-AT----------G-----C--
216HCV-TR3b-----T-----C-----T---------A-AT-------------A--C--
217NE483c--C--T--------G-----------A-AT-----------A--A--C--
218NE2743d--C----------ATCT---------AT----------A-----T--
219NE1453e--C-----C--A--G--T----------AC------------A-----C--
220NE1253f--------C--C-----T---------A-AT-------------A--A--

221Z44a--C-----------ATCT--------A-AT--T--------G--A-----
222Z14b--C--T--CA----GTCT---------AT--T--------------C--
223GB3584c-----------A--GTCT--------A-AT--T---------A-----C--
224DK134d--------------GTCT--------G-AT--T---------G-----C--
225GB8094e--C--G--------GTCT--------T-AT--T---------G-----C--
27BNL74k--C--T----

226BE955a--A------------AT----------AT----------A-AA-----

227HK26a--C-----C-----ACAT----------AT------------C-A--C--

228FR17a--C--G-----T----AT----------AC-----------A-----C--

43VN48a--C---------C--A-AT--------A-AC-----------G-----C--
45VN138b-NC--------C----AT--------T-AT---------N-G-----C--

47VN129a----------C--GGA------N----AT----------N-G-----C--

49NE9810a--C-------
```

Fig.1H

```
SEQID
NO351400
208HCV-11aCAATTTGGGTAAGGTCATCGATACCCTTACGTGCGGCTTCGCCGACCTCA
209HCV-J1bT------------------------------A-------------------
210HC-G91c-----------------------------C-----T---------------
11FR21f-----------------------------A-----T----------T----

211HC-J62a---CG---------------------A-----------T----------
212HC-J82b--------C-GA--------------A--------T--T--T----------
213S832c---C-------------------------A--------T--T----------
214NE922d---C-----------------------------T-----T-----------
17FR42f---C-----------------------C-----T-----T-S---------
15BNL32e--------N-NT-----------

215NZL13a-----------A--------------A---------A---------
216HCV-TR3b---C--T-------------------A-----T--A-----------
217NE483c-----------------------------A-----G-------------
218NE2743d---CC-------A----------------A--------A--------T----
219NE1453e--------------------C--T--C--A-----G---------T----
220NE1253f---C----------------------C-----T--A--------T----

221Z44a----C--------------------G----------------------
222Z14bT---C-------A--------------G-----T----------------
223GB3584c---C----------------------A--C--------T----------
224DK134d---C----------------------A--T------------------
225GB8094e---CC---------------------A--A-------------------

226BE955aT-----------------------A--------A--------T----

227HK26aG-------------------------A-----T--G--------T----

228FR17a---C-----------------------A-N---NC-A----------

43VN48a---C--------A--------C--------T--------------------
45VN138b---CC----------------------T--N--S--------------

47VN129a---CC-----------------C-----C--T--------------------
```

Fig.1l

```
SEQID
NO401450
208HCV-11aTGGGGTACATACCGCTCGTCGGCGCCCCTCTTGGAGGCGCTGCCAGGGCC
209HCV-J1b---------T-----T----------C--A--G---------------
210HC-G91c---------C---------------T-----A--G---------A--T
11FR21f----------T-----------------C--A--G------T----AA--

211HC-J62a----------C--TG----A--------G--C--C----TC-----A--T
212HC-J82b----------C--TG----T--------GG----------TC-----A--T
213S832c-------------CG----T-----T--CG----C----T------A---
214NE922d----------C--TG-------------AG----T--T-TC-----A--T
17FR42f--------------TG---------------G-G--C----T------A---
15BNL32e----------N--CG-T----.------GG-G--C--G-TN---------

215NZL13a----------C---------------T---G-A-------TC--A--A---
216HCV-TR3b---------T------------------G-G--G----TC--A--A---
217NE483c----------T-----------------CG-G--G----T---A-------
218NE2743d---------T----------------T---G-A--G----TC--A--A--T
219NE1453e-------T--T---------------T--GG-A------TC--G------
220NE1253f----------T---------T--T----CG-A--G----TC--A------

221Z44a----A-----C---A----G--------CG-G--G----TC--------T
222Z14b----A-----T--------A---------G-G--T----TC--------
223GB3584c----A-----C--------A--------CG-G--T----TC--------
224DK134d----A-----C---G----A--------CG-G--T----TC-----A---
225GB8094e----A-----C-----T--A--------CG-G--T----TC-----A---

226BE955a-------T--C--------A----G---CA----G----TC--A-----T

227HK26a----------T--CG----G-----G---T-G--C----TC--GGCT--G

228FR17a----------C--TG--C-A--A-GG--G-----C----T---GGCT---

43VN48a-------T--C--TG----A-----T--GW-G-------TC--GGN----
45VN138b-A-A------T--

47VN129a---A------C--TG----T--------C----------T---GGC--AA
```

Fig.1J

```
SEQID
NO451500
208HCV-11aCTGGCGCATGGCGTCCGGGTTCTGGAAGACGGCGTGAACTATGCAACAGG
209HCV-J1b-----A-----T--------------G-----------------------
210HC-G91c-----A-----T--TA-A--C-----------------T--C--------
3BNL11d----------------------
7BNL21d----------------------
11FR21f---N-A-----T--------C----N--G--------TNNNNNNNNNNNNN

211HC-J62a--C-----------GA-A--C-----G-----G--T--T-T---------
212HC-J82b-----A--C--T--TA----C-----G-----GA-A--T--C--------
213S832c--C--C-----G--GA----------G-----GA-A--T--------G--
214NE922d--C-----------GA-A--------------GA-A--------------
15BNL32e--C---N-------G-----C-----G-----GA-A--T----N------
17FR42f--C-----------G-----C-----G-----GA-A--T----------
19BNL42g-----G--A--T-----------
23BNL52h-----GA-A-----C--------
25BNL62i-----GA-A--------------

215NZL13a--C-----------GA---CC--T--------GA-A--T-TC--------
216HCV-TR3b--C--T-----T--GA---CA--T-GG-----A-----------------
217NE483c--C-----------GA---C---T--G-----GA-T----TC--------
218NE2743d--C--A-----T--GA-A-CC--T--G-----AA-A--T-TC--------
219NE1453e--C--A--C--G--AA---C--C--G-----AA-A--T-T---------
220NE1253f--A--A-----T--GA---C---T--G-----AA-A----T---------

221Z44a---------------A---C-G----G-----GA-T--------------
222Z14b---------------A---CCG----G-----AA-T-----C--------
223GB3584c-----A--C--T--TA---C-G----G-----GA-C--T-----G-----
224DK134d---------------A--C-------G-----G--C--T-----------
225GB8094e-----A--C--T--TA---C-G---------GA-C-----C--------
29BNL74k-----GA-C--T-T---------
31BNL84k-----GA-C--T-----------
33BNL94k-----GA-T--T-----------
35BNL104k-----GA-C--T-----------
37BNL114k-----GA-T--T-----------
39BNL124l-----GA-C--T-----------

226BE955a--C--A--C--T--GA----C--T--G-----G--A--------------

227HK26a--C--A--------GA---CAA-C--G-----GA-C--T-----------

228FR17a--------------TA---CAA-C--G-----G--C--T--C--------

43VN48aT---------G---AN--NCA-C--G-----N--A--T--C------N

47VN129a----NA-----T---A---CCA-C--G-----GA-A--------------

51NE9810a------AA-T--T-TC--------
```

Fig.1K

```
SEQID
NO501550
208HCV-11aGAACCTTCCTGGTTGCTCTTTCTCTATCTTCCTTCTGGCCCTGCTCTCTT
209HCV-J1b---T--G--C----------------------CT-A--TT----G----
210HC-G91c------C--C-----------T---------T-G--C--T--T--A--C-
3BNL11d----T-G--C----------------------CT----TT----G--C-
7BNL21d---TT-G-------------------------CT-A--TT-T--G--C-
11FR21fN--------N-----------NN----------CT----NT-A-------

211HC-J62a----T-A--C---------C--T---------T-G------------G--C-
212HC-J82b---TT-A--C-----------T--------TT-G--T--T--T--G--A-
213S832c---TT-G--C---------------------T--CT-------CT-G----
214NE922d----T-G--C--------C--T---------T-AT----------A----
15BNL32e------C-------------C--T---------TNGT----T--T--G----
17FR42f----T-G--C--------C--T---------T-G-----T--CT-G----
19BNL42g---T--G---------------------T-GT----T--T--G----
23BNL52h---T--G--C--------C--T---------T-G------T----A--C-
25BNL62i------G-----------C--T---------T-A-----------T----

215NZL13a----T-G--C--------C--T--------------T--T---T------
216HCV-TR3b---T-------------C--T-----T-----C--C--T--CT----C-
217NE483c---TT-A-----------C--T---------T-G--T--T--CT----A-
218NE2743d---TT-A--C---------------------T-G--T--TT---------
219NE1453e--------C-----------T---------T-G--T--T-----G--A-
220NE1253f---TT-G--C--------C--T--------------T--T--CT----A-

221Z44a---T-----C-----------------------T----A--T--T--G-
222Z14b----------------------------T-----T--A--T-----G-
223GB3584c---T-----C----------------------T-CT----A--T--T--G-
224DK134d---T-----C----------------------CT----A--------G-
225GB8094e---T--C--C--------C--T----------CT----A--T-----G-
29BNL74k------C--C--------C--T----------CT----A--C-----G-
31BNL84k--------C-----------T----------CT----A--C-----G-
33BNL94k---T-----C--------C--T----------CT----A--T-----G-
35BNL104k---TA----C---------Y--T----------Y----A--T-----G-
37BNL114k---Y--C--C----------T----------CT----A--T-----G-
39BNL124l------C--C-----------------------A-C----A--T-----G-

226BE955a---TT-A--C--------------------TA----T--T--T-----G-

227HK26a---T--C--C---------------------T----A--A-----G-

228FR17a---T-------------C--T----------CT-A--A---T-A--G-

43VN48a---T-----C--NN-----N----------N--CT----A--T-----G-

47VN129a---T--------------------------WCT----A--T-----G-

51NE9810a---TT-A---------------------------TT--T----A-
```

Fig.1L

```
SEQID
NO551600
208HCV-11aGCTTGACTGTGCCCGCTTCGGCCTACCAAGTGCGCAACTCCACGGGGCTT
209HCV-J1b-T-----CA-C--A-----C--T---G-G---------GTGT-C---A-A
210HC-G91c--C----A--C--T---------GT-GG------------TT-----G-G
3BNL11d-------G--T--AA-KA-C--TC--G-G---------G-AT-C---G-G
7BNL21d-------G--T--AA--A-C--TC-TG-G---------G-AT-C---G-A
11FR21f--C-C--A--C---A-C--T-----TG-G----A--G-A-A--C-ATGGC

211HC-J62a--A-C--CACC--G-TC--C--TGC-G-----AAG---AT--GTACCGGC
212HC-J82b--G-C--A-----A-TG--T--AGTGG----CA-G---ATT-GTTCTAGC
213S832c--A-CT-------A-T---C---GTGG-G--CAAGG--A--GGC-ACTCC
214NE922d-TA-C--------G-TC--C-G--TG--G--CAAG---A---GCA-CTC-
15BNL32e-TG-C--C-----T-TC--T-N-GTTG-G--CAAA--TA---GTCA-GCC
17FR42f-TA-C--C-------TG--T---ATA--G--TAAG---AA--GCCACT-C
19BNL42g-TG-C--C-----T-TC--T---GTG--G--TAAG---A---GTACCA-G
23BNL52h-TC-C--------G--G--C--TGTG--G--CAAG---A---GCCACTC-
25BNL62i--A-C--C-----G-TC--T---GTG-----TGCG---CG--GT--TTC-

215NZL13a----A-T-CAT--A--AG-CAGTCTAG-GTG---G--TA-GT-T--C--C
216HCV-TR3b--------TGC-----G--T-G--TAG-GTACACG---A-GT-T--C--A
217NE483c-----GTCTGT--T--AG-A-GGCT-G-GTAC--G--TGTAT-C--C--C
218NE2743d-----GTCTGT--T---G-A-GGATTG--TAC--G--TGTGT-T--C--C
219NE1453e-----CT-TGC--T--AGTC-GG-TGG-G--T------G-AT-C--T--C
220NE1253f-----GT-TCC-----AG---GGCTAG-GTACA-G---A-GT-C--C--A

221Z44a--C-C-----T--A--G-----TG-G--CTAC--G--TG-TT----CA-C
222Z14b--C-----AACA--A--A--T---GTG--CTAC--G--TG-TT----CG-C
223GB3584c--C-------T---A-C------GT-A-CTAT-----TG--T----CA-C
224DK134d--C-------T---------------A-CTAT------AG-T----TG-C
225GB8094e--C-C-----T-----G----G-GTTA-CTAT-----TG-TT----CG--
29BNL74k--C-------C-----------AT-A-CTAT-----TGT-T----CA--
31BNL84k--C-------T-----------ATTA-CTAC------A--T----CA-C
33BNL94k--C-------C-----------ATTA-CTAC-A----A--T----CA-C
35BNL104k-TC-------C-----------ACTA-CTAT------GT-T----CA-C
37BNL114k--C-------C-----------AC-A-CTAC-----TGT-T----CA--
39BNL124l--C-------C--G--C-----TC-G--TTAT--G--TGT-T----CA--

226BE955a-TC-----C--T--G--C--T--AGTT-CCTAC--A--TG--T-T---A--

227HK26a--C-C--AAC---A--------TCTTACCTACG---------GT-----A

228FR17a--C-C---ACA--A--C--A--AATT-----CAAG---G--T-T---A-C

43VN48a--C-T--AACA--A--C--C--GGCG--TTATAC----AAGT-T--C--G

47VN129a--C-C--CAC---T--C--C--ACTAA-CTATGCT---AAGT-T-----G

51NE9810a-----CT-ACA---A-AG-C-GGCTGG-GTAC--T--TG--T-C--A--C
```

Fig.1M

```
SEQID
NO601650
208HCV-11aTACCACGTCACCAATGATTGCCCTAACTCGAGTATTGTGTACGAGGCGGC
209HCV-J1b-----T-----G--C--C---T-C-----A-----------T-----A--
210HC-G91c-----T---------------C--TG--TCCG-----------A---A
3BNL11d--T--T--------C--C--TT-C--------C--CA-C--T---AT--A
7BNL21d--T--TC---------C--TT-C--------C--CA-C--T---AT-AG
11FR21f-----T-----T-----C--TT-C---GGC--C--C--A--T-----AAA

211HC-J62a---ATG--G-----C--C---A-C--TGAT--C---ACC-GGC-ACTCCA
212HC-J82b---T---C---T---------T-A---AAC--C--CACC-GGC--CTCA-
213S832c---ATGCCG-----C------T-C-----T-----C--T-GGC--CTT-A
214NE922d---ATG--A--------C----AG---AGT--C--C--C-GGC--CTCAG
15BNL32e--TATG-CA-----C--C---T-C--AAC--C--C--A-GGC-ATT--N
17FR42f---ATG-CG--T-----C--TG-C--TGAC--C--C--C-GGC--CTCAG
19BNL42g---ATG-CA--------C--TT-C--AAC--C--CA-C-GGC-AAT-CA
23BNL52h--TATG--G-----------T-A--AGC--C-----C-GGC--CTTAA
25BNL62i---ATG--G-----------T-G--AGC--C--C--T-GGC--CTC-A

215NZL13a---GT-C-T-----C--C--TT-C--TAGC-----------T-----C-A
216HCV-TR3b--TGTGC-T-----C--C---T----TGG---C--------------C-A
217NE483c---ATAC---------C--TT-G---AGC--C--A-----T-----C-A
218NE2743d---GTGC-------C--C---T-----GGC-----C-----T-----CC-
219NE1453e---ATGC----------C---T-A---AGC--C--A--A--T------A
220NE1253f---ATAC-T-----C--C---T-----AGC--C--C-----T-----T-A

221Z44a--T---A--------------T--G--T--C-----A--C--T--A--T-A
222Z14b--T--T----------------------A-C--C--A---------A---A
223GB3584c--T---A-----------C-----G--------C--A---------A-C-A
224DK134d-----T--------C--------G--------C--A--C--T--AA-C-A
225GB8094e--T---A--------C--C-----G--TG----C--A---------A-C-A
29BNL74k---T-T----------------G--T--A--C--A-----T-----C-A
31BNL84k----------------C-----G--------C--A--T--T-----C-A
33BNL94k--T--TA-------C--C----G--T--A--C--A-----T-----C-A
35BNL104k-----T-----------C-----G--T--A--C--A-----T-----C-A
37BNL114k-----T-----------C-----G--T--A--C--A----TT-----C-A
39BNL124l-------------C--C-----G-----C--C--A-----T---T-C-A

226BE955a--T--T--T--------------A-----TTCC--A--C--T-----A-A

227HK26a-----TC----A-----------C-----C--C--C---CTG------A

228FR17a-----TC-T---------C---T-G---AAC--C--C--T-TT------A

43VN48a-----TC--------C--C-----C---AGC--C--C--T--T------A

47VN129a--T--TC-A--------C-----C--TAGC--C--------T------AA

51NE9810a---ATG--A--T--C--C---AG----GGT-----C-----T-----C-G
```

Fig.1N

```
SEQID
NO651700
208HCV-11aCGATGCCATCCTGCACACTCCGGGGTGCGTCCCTTGCGTTCGTGAGGGCA
209HCV-J1bG--CATG---A-------C--C---------G--C-----C--G---A-T-
210HC-G91cGA-CCTG---A----TCTG--C-----T--G--C-A---A--C-------
3BNL11d--G-ATG---A-----TAC--A--------G--C--------G----AT-
7BNL21dT-G-ATG---T-----G-C--A-----T--G--C--------G---AA--
11FR21fG--CAT------T-----G--T-----N--G--C---A-A--G--A----

211HC-J62aG-C---TG----C---GTC--C-----------G----AGAAA-T---G-
212HC-J82bT--C--AG-T--C--TCT---T--A--------A--T-AGAA---TAATG
213S832cA-GA--AG-G--T--T-----T--A-----------T-AG---ACC-C--
214NE922dG-----TG-T--T---GTC--C-----T--------T-AGGAGA------
15BNL32eG--C--GG-G--T--TGT---T--A--T-----C----AGAA-AGCTC-G
17FR42fG--C--GG-G--C--TGT---T--A--T-----C--T-AGA-GTCA--T-
19BNL42gG-GC--GG-G--T--TGT---T--A--T-----G--T-AGTTGC------
23BNL52hG-----TG-G--T---GTC--T--A--T--T--A--T-AGA-GC-CCAA-
25BNL62iG--G---G----T---GTC--T--A--T--T--C--T-AGT-GA---A--

215NZL13aT----T---T--------A--C--C--T--A-----T--C-AG--C----
216HCV-TR3bA----TG---T-----TTA--C--A-----G--C-----CACAACC----
217NE483c-C---T----T-----TTG--C--T-----A--C-----C-AAA-CAAT-
218NE2743dT--A-T----T-----TTG--A--T--T--G--C-------AATCA----
219NE1453eA----TG----------TG--T--T-----T--C-----G-AGA-C----
220NE1253fTA---T-----------TG--C--C--T--G--C---AC---C-----T-

221Z44a-C--CA------A---TTG-----------A--C--T--GATGACT--G-
222Z14bGC-CCA----A-----TTG--A-----T-----C--T--G--GAC--AG-
223GB3584cGC-CCA------A---CTC--A-----TT-A--C-----GA-G-TT--G-
224DK134dTT-CCA----T-A---CTC----A-----T--------GA-G--A--G-
225GB8094e-A--CA----T-A---CTC--A--------A--C--T--GAAGACC--G-
29BNL74k-C--CA----T-----CTC--A--T-----G--C-----GA-A-----G-
31BNL84k-C-CCA----T----CT---A--T-----G--C-----GA-AACT--G-
33BNL94k-C--CA----T----TCTC--A--T-----G--C-----GA-A-T---G-
35BNL104k-C--CA----T-AGCACT---A--T-----G--C-----GA-A-T---G-
37BNL114k-C--CA----T-----CT---A--A-----G--C-----GAAA-----A-
39BNL124l-C--CA----T-A---CTA--A-----T--A--C--T--GAAGACT--G-

226BE955aTA-CCTG-----A---G-A--T--T-----G-----T--CATGACA--T-

227HK26aT-C-ATG---T----TTTG--T--A---T-G-----T--GA-G-TC-ATG

228FR17aGACCATG--A-----TCT---A--T--T-----A--TA-CAAG-C---G-

43VN48aGACACTG--TT-----TTG--T-----T--A-----T--GAAGRT-RA--

47VN129aT-GCATG--------TCTC-----T--------C-----GAAGACC----

51NE9810aG---ATT-----C---TTA--T--C--T-----C-----A--CTCT----
```

Fig.10

```
SEQID
NO701750
208HCV-11aACGCCTCGAGGTGTTGGGTGGCGATGACCCCTACGGTGGCCACCAGGGAT
209HCV-J1b-TTT---CC-T--C-----A---C-C--T--C---C-C--GG-----A-C
210HC-G91c------------------CT-CC-T-GT--C--C--A---G--------
3BNL11d--CATCTCC-C--C---A-----C-C-----C---C-T--GGT--AAA-Y
7BNL21d--T-T--TC-T--C---A--C-RC-C-----C---C-T--GGT--AA--C
11FR21f-TAT---CC-T--C-----AC--C-C-----C---C-C--AG-GC--ATC

211HC-J62a-TA-A--TC----C---A-AC--G-CT-A--G-AT------GTGCA-C-G
212HC-J82bG-A---T-CAT--C---A-ACAAG-A--A--C-AC-----TGTG-AAC-C
213S832c---T---TC-A---------C--G-TG----C-ATC-C----TA--TC-A
214NE922d--ATA--CC-C------A-AC--G-TT-G--C-ATA-A--TGTG--CC-A
15BNL32eGTCGG-TCCAC------A-CC----CT-G--C-ACA-A---GTG--CA-A
17FR42f-TAGGA-CTTC------ACA---G-CT-G--C-AC-----TGTG--CCGA
19BNL42g-TAAG--CC----C---A-AC--G-C--T--C-AC-----TGTG-ACC-G
23BNL52h-TCAG--TC-C--C---A-AC-TG----A--C-AT------GTG--CC-A
25BNL62i--A----CC-C--C---A-AC--G-C-------ACA-C--TGTG--CC-A

215NZL13a-TA-A--T-C---C---ACCC-AG----A-----A-----AGT----T-C
216HCV-TR3b--CAA--ATCA--C---ACAA--G-CT-AA-G---------GTT---ACC
217NE483c--A--A---C----C---A-AC--G----T--G--A-----GGT---TC-C
218NE2743d--T-----CAA--C---A-TC--G--G-A--A--A-----GGTT-A-T-C
219NE1453e--A-A---GA---C---ACCC--GC---A--A--------AGT---AT-C
220NE1253f--CAG--A-----C---AC-C-AG-A--A--G--A-----TGT--AAC--

221Z44a--A-A---C-T--C---AC-C--G----G-----A-----TGT-GCAC-C
222Z14b-TA-T--TC-C--C------C-CT-------C--T------G-GCCCT--
223GB3584c-TCAG--AC-C--C--------CC-C--T--C--C-----GG-GCCTT-C
224DK134d--AAG--T-CA--C------T-TC-C-----C--C-----TG-GCAAC--
225GB8094e--CAG---C------------CC-C--T--C--A-----GT-GCCTT-C
29BNL74k-TCAG--AC-T--C-----A--CC-T--------C--C--AG-GCCAT-C
31BNL84k-TCAG--AC-T--C--------CC-T--T-----C--C--AG-GCCAT-C
33BNL94k-TCAG-----T--C--------CC-T--------CA-C--AG-GCCAT-C
35BNL104k--CAG--AC-C--C--------CC-T--------C--C--AG-GCCAT-C
37BNL114k-TCAT--AC-C--C--------CC-T--------C--C--AG-GCCAT-C
39BNL124l--A-T---C-C--C--------CT-A--A-----C------G-GCCATA

226BE955a-T-TGAGT--A--C-----CCAA--T--------AC--T-AG--CC-AGC

227HK26a-TCGG--C-CC------CAT--TG-------C--CC------TACCAA--

228FR17a-T-AG--AC-A------C-CC-TG-CT----C--CT-A---GT-CCCA-C

43VN48a-TCAA--CC----C------CA-GCCT----G--CC----AGTGCC-A-C

47VN129a--CTGA-C-A-------C--T--GCCT----G--AT----GGTGCA-A--

51NE9810a-TA-A--A--A--C---A-CC-TG---G----Y--C--C---GTG-A-TCG
```

Fig.1P

```
SEQID
NO751800
208HCV-11aGGCAAACTCCCCGCGACGCAGCTTCGACGTCACATCGATCTGCTTGTCGG
209HCV-J1bA---GCA-----A-C---ACAA-A-----C---G-----T----C--T--
210HC-G91cTCGCGCG------TC-GTG--G----G----GTG----CTC-A-------
3BNL11d-CT-GTG-----A-TR--GCAA-C---------G----CT-------T--
7BNL21d-CT--TG----TA-TG--GCAA-C-----C--TG----CT----G--T--
11FR21f-CG--CGCT---ATCGATG--G-G--G------G----C--C--C--G--

211HC-J62aCC-GGCGC--T-A--CA-GGCT-A--GACG-----T--CA--G----GAT
212HC-J82bC--GGTGCG-T-A-TCGTAGC--G---ACA---G----CA--A-C--AAT
213S832cCCTGGCGCT-T-A-T-A-GGC--G---GCA---------A-CA-C--GAT
214NE922dCCTGGTGCG-TTA-C-A-GGC--G--GACG--T--T---ACCA-CA-T-C
15BNL32eCCTGGTGCT-T-A-C-A-GGA--G--GGCA-G---T---GCCG-C--GAT
17FR42fCCTGGTGCT-T-A-T-GAGGT--G--GGC------T---ACCA-C--GAT
19BNL42gCC-GGCGC--T-A-T-G-GGCT-G--GACG-----T--CACCA-C--GAT
23BNL52hCCTGGCGCG-T-A-C-G-GGTT-G--GACG-----T--CACCA-C--T-C
25BNL62iCCTGGCGCG-TTA-C-A-GGC--G--GACA--T--T--CA-CA------C
215NZL13a-T-GG-GCAA-TA-TG-TTC-A-A--CA----TG-G--C--AT-A--A--
216HCV-TR3bCTTGGCG-GA--A-CG--TC-A-C---ACC--TG-G---A----G--A--
217NE483c-T-GGTGCGA--A-CG-ATC-A-C--CG-G---G-G--------G--G--
218NE2743d-CTGGCGCGA--A-TG-ATC-A-C--CA----TG-G--------G--G--
219NE1453e-CTGGTGCAA-GA--G-TTCCG-A--CG-A---G-G---T----A-----
220NE1253fCCTGGCGCAGT-A-CG-ATCAA-C--CA-G--TG-G---T--A-G--G--

221Z44aCCGGGCGCT--GCTTGA-TC-T-C--G--A--TG-G--CT-AA-G--A--
222Z14bCC---CGCA--GTTAGA-TCCA-G--CA-G--TG-A--C---A-G--G--
223GB3584cAT-GGCGCT--GCTTGAATCC--C--GA----TG-G------A-G--A--
224DK134dCTG--TGCT--GCTTGA-TCTT-GA--------G-G------A-G--G--
225GB8094e-T-GGTGCT--GCTCGA--CCT-G--G--C--TG-G--C---A-G--A--
29BNL74kAT-GGCGCG--ACTTGA-TCT--A--GA----TG-G--CT--A-G--G--
31BNL84kAT-GGCGCA--GCTTGA-TCT--G--GA----TG-G------A-G--G--
33BNL94kAT-GGCGCA--GCTTGA-TCCT-G--GA----TG-G------A-G--G--
35BNL104kAC-GCGGCG--GCTTGA-TCC--G--GA----TG-G------A-G--G--
37BNL114kAT-GGCGCG--ACTTGA-TCT--A--GA----TG-G---G--A-G--G--
39BNL1241CTTTCGGCT--ACTT-T-TCCG-A--G--G--TG-G------A-G--G--
226BE955aCT-GG-GCAGT-A--G-T-CT-----GA-AGC-G-T--CTAC--A-CG--

227HK26a-CTTCCACG-----A---GGAT-C--CA-G--TG-G-----T----CG--

228FR17aTCATC-G-G--AATCCACGG-T----C--A---G-A--C--C--C--T--

43VN48a-CGTCTACG--A-TC--CGG-T-C--CAAA--TG-G--CA-CA-G--G--

47VN129a-CGTCGG-GT--ATC-G-GGTG-C--CGAG---G-G--C--CT-G--G--

51NE9810aCC-TGCGC-G--A-CG-CTCT--C--CACG---G-G---A--A-G--G--
```

Fig.1Q

```
SEQID
NO801850
208HCV-11aGAGCGCCACCCTCTGTTCGGCCCTCTACGTGGGGGACCTATGCGGGTCTG
209HCV-J1b-GCG--TG-T--------C--TA-G-----T-----T--C-----A--C-
210HC-G91c-GC---TG-GT----------TA-G--T--A--------------C--CA
3BNL11d-G-NN----GT-------C--TA-G---------R-----T----------
7BNL21d--CA---G-GT-TC----C--TA-G---------------C-----A--C-
11FR21f-GCA---GTGT----C--A---A-G---A-T--------T--T---GGC-

211HC-J62a-TC------G-----C--C--T--T---------------C-----TGGG-
212HC-J82b-GCA--T--GGC---C------T-G--T-----A--TG-G------G-C-
213S832c-TCT--T--GG-------T-----T--T---------G-G--T--CG-GC
214NE922dATC---T--GT-T--C--T-----G---A-A--A-----G--T--CG-G-
15BNL32e-TC-----------C--T----G---------A--TG-G-----CG-A-
17FR42f-TC-----------C--T-----A---A-A--------------CG----
19BNL42g-GT---T--G--------T--A------A-C------G-G--T--CG-G-
23BNL52h-TCT--T---G----C--A--TT-G--T-----C---T-C-----CG-A-
25BNL62i-TC------GT----C--T---T-G--T-----

215NZL13aCGCG-----GA-G--C--T--G-----------T--TA-G--T---G---
216HCV-TR3bCGCACGACAA--G--------G--G-----C------GCT-T----G---
217NE483cT-CG--T--AT-G--------A--T-----C--T-----T------G-A-
218NE2743dAGCT--T--GT-G--C--C--G--G--T--T--C--TA-G--T--AG-C-
219NE1453eC--T-----T--G--C--C--G-----T--C--T-----T------G-C-
220NE1253fTGCA-----G--G-----A--A-----T--T--A--TT-G------G---

221Z44aCGCG-----TT-G-----T--------T--T---------C-----AGG--
222214bTGCG--T--TA-G-----C---T-----A-T--A--T--G--T--AGGC-
223GB3584cTGC---T--TGCG--C--C--T--T---A-C--A-----G-----TGGC-
224DK134dCG-------T-----C--C----------A-C--A---G-G--T---GG--
225GB8094eTGCT------G-G--C--C-----------C--C-----G-----TGGCT
29BNL74k-GC------TG-T-----A-----T---A-C-----TT-R--T--YGGCT
31BNL84k-GCT-----TG-T--C--A-----T---A-C-----TT-G--T--CGGCT
33BNL94k-GCG-----TG-------A-----T---A-C-----TT-G--T--CGG--
35BNL104kAGCT-----TG-T-----A-----T---A-C-----YT-G--T--CGGCT
37BNL114k-GCT-----TG-T-----A-----T---A-C-----T--G-----TGGCT
39BNL124lTGCA--T-----A-CG--T-----------T--A-----C------GG--
226BE955aAG-G--TG-------C--C--GT-A-----A--A---GCG--T---G-AC
227HK26aCGC---AGTGG-T--C--AT----G---A-C--------G--T--C---C

228FR17a-GCA--GG-AT-T---------A-G---A-C--A-----C--T--TAGCA

43VN48aCGCT---G-GT-------A--TA-G--T----------G------GGCC

47VN129aTGCT--TG-GT----C--T---A-G--------C---T-------TGGGC

51NE9810aRGCG--------A--C--A--T--------A--A-----T--T--AG-GC
```

Fig.1R

```
SEQID
NO851900
208HCV-11aTCTTTCTTGTCGGCCAACTGTTCACCTTCTCTCCCAGGCGCCACTGGACG
209HCV-J1b-T-----C---TC---G--------------A--TC-C--GT-TGA----
210HC-G91c----C-----T-----GA-C-------------------A---T------
3BNL11d----C--C-CT-----G--A--------T--A---C-CATG---CAT--A
7BNL21d----C-----------G--A--------T--A---C-CTTGT--CAT--A
11FR21f----C--C--T--G---T----------A-GT--C----G--T------

211HC-J62a-GA-G----CA-C---GA------TTG----G--ACA--A-------TTT
212HC-J82b-GA-GA--C-ATCG--GGCT----TGG-A--A--ACAA------AACTTC
213S832c-GA-G--G-C--CT--GG-CG--GT-G-G--G--ACAA-A---TAC-TTT
214NE922d-GA-GT-G-CTTCT---G-C----T-A----G---CA--AT--TAA-TTT
15BNL32e-GA-GA-A-CT-CA--GGCT----T-G-GG-A--G-A------T-ACTTC
17FR42f-GA-GA-A-CA-CG---G-TGC-GT-G----A--GCAATA---TACTTTT
19BNL42g-GA-GA-A-CT-CT--GG-TG---TTG----G--GCAA-AT---AACTTT
23BNL52h-GA-GT-G---TCT---T-T----TGA----C--TCA--A----ATCTTC

215NZL13a-------C--G--A---GCC-----G---AGA--TC-A-----TCAA---
216HCV-TR3b-G--------G--A---GC----------AGA--TC-C------AC---C
217NE483c-T--C--C--A--A---GCA-----A---AGA---C-A------CA---A
218NE2743d----CT-G--G--A--GGCT---------AGA--TC-T-AG---AAC---
219NE1453e----C-----G--G--GGCC--T--A---AGG--TC-T--T--TAC---T
220NE1253f-T--C-----G------GC------T---AGAG-TC---AA--T-AT--C
221Z44aC---C--GA-G--G--GA--A----T--TCGG--GC-T----------C
222Z14b----C--A--G-----G------GA----CGA--GC-C--G--------C
223GB3584c-A---T-G--T--T--GA-----T-T---CAG--GC-------------T
224DK134d-G--CT-G-----T--------------CAA--TC-C-----------C
225GB8094e-A--CT-G--A-------A-----------CAA--GC-A-----------
29BNL74k-G--C--A-----T--GA-----T-T---CGA--A-------------T
31BNL84k-G--CT-G--T--T--GA----TT-T---CGA--AC-A----------T
33BNL94kCG--CT-G--T--T--GA-----T-T---CGA--AC------------C
35BNL104k-G--CT-G--T--T--GA-----T-T--YCAG--TC-------------T
37BNL114k-G--C--G--T--T--GA-----T-T---CGA--AC-------------T
39BNL1241C---C--A--G--G--GA----------CAG--GC-T----------T

226BE955a-A--CT-G--A------A---------ATAGG--TC-C-AG---GCT---

227HK26a-----T-G-CG--A-----A--------TCAG---C-C--T--T-----T

228FR17a-AA-CT-G--A--G--G--T--T--T---AGG--T-A-TA---TCA-GTT

43VN48a-T--C--C--T--A--G--C-----GC--AGG--TC--ATG--TCA-GTT

47VN129a------C--T--G--GT-------G---AGA------ATGT-TGA--TC

51NE9810a-A---------Y--G--GGG----T-A-GGAGA-ATC-C-AG--T-----T
```

Fig.1S

```
SEQID
NO901950
208HCV-11aACGCAAGGTTGCAATTGCTCTATCTATCCCGGCCATATAACGGGTCACCG
209HCV-J1bGTA----A-------------A---------------CG--T-A--------
210HC-G91c------AC------------C-----C--A------G-G--A-----T--
3BNL11d-----G-AG-----C-----A---
7BNL21d--A--G-AG-----C-----A---
11FR21fGT---G-AC--T-----T--C--T--CT-T-----C--------C-----

211HC-J62aGT-----AC------------C-----C--T--TACC--C--T--A-----
212HC-J82b--C----AG-----C--T--C-----C-AA--T--C--C--C--C--T--
213S832cGTC--G-AA------C--T--C--A--C--G----GC--T-----A-----
214NE922dGTC--G-AC-----C--T--C--A--C--A-----C--C--T--A--T--
15BNL32eGTC--G-AA-----------C--A--C--A-----C--T--A-----T--
17FR42fGTC--G-AA-----C-----C--A--C--A--------C--A--A--T--
19BNL42gT-C--G-A---------T--C---
23BNL52hGTC--G-A------C-----G--A

215NZL13aGTC--GACC--T--C-----GC-G--C--A------C-TT-A--A--T--
216HCV-TR3bGT---GACG-----C-----G--A--C--A------G-TT-A--A--T--
217NE483cGTT--GCA------C-----AC-G--C--A--T---G-TT-A-----T--
218NE2743dGT---GACC----------AC-G--C--T--T--C---T-A--A---A-
219NE1453eGTC--GACC-----C-----GT-G--C--A--------C--A--A--T--
220NE1253fGTC--GTTG----------AC-A--C--A--C--T--A--A--T-A

221Z44a-----G-AG--------T--C-----CA-T---------C--C--C---A-
222Z14b--C--G-A------C-----C---------T--T--CG-CT----C---A-
223GB3584c-----G-AC--------T--C-----CG-G--G--CG-T-----C---A-
224DK134d--C----AC--------T--C-----CA-A--A-----C--A--A---A-
225GB8094e--C--G-AC--T-----T--C-----CG-A--G-----T-----C--T--
29BNL74k--T----A---------T--C---
31BNL84kG-C--G-A---------T------
33BNL94k--C----A------C-----C---
35BNL104k--C--G-A---------T--C---
37BNL114k--C--G-AA--------T--C---
39BNL124lGTC----AC-----C--T--C---

226BE955aGT---GAAC-----C--T--C--T--CAGT------G-T--C--C-----

227HK26aGT-----AC-----C-----C------A-A----CG-C--C--C---A-

228FR17a--C--G-A---T--C--------NA-CN-T-----CG-C-----A---A-

43VN48aGTC--G-AG--T--C--T--C-----CA-A--G-----C--T--A-----

47VN129aG-C--G-AC-----C--T--C------G-A-----C--C--T--G-----

51NE9810aGTC--G-AC-----C--T--C---
```

Fig.1T

```
SEQID
NO951957
208HCV-11aCATGGCA
209HCV-J1b------T
210HC-G91cA-----T
11FR21fNNNNNNN

211HC-J62a------G
212HC-J82b-------
213S832c------T
214NE922dG-----G
15BNL32e------G
17FR42fA----NN

215NZL13aA-----T
216HCV-TR3bT-----G
217NE483cG-----T
218NE2743dG-----T
219NE1453e-------
220NE1253fT-----T

221Z44aG-----G
222Z14bG-----C
223GB3584cG------
224DK134dA-----T
225GB8094eG-----T

226BE955aG------

227HK26aG-----T

228FR17aG------

43VN48aA------

47VN129aG-----G
```

Fig.2A

```
SEQID
 NO150
229HCV11aMSTNPKPQKKNKRNTNRRPQDVKFPGGGQIVGGVYLLPRRGPRLGVRATR
230HCV-J1b--------R-T---------------------------------------
  2BNL11d--------R-T-------XXXXX-------------------X-------
  6BNL21d--------R-T-----------X-----------------------------
 10CAM10781e--------R-T-----------------------V-----------A-
 12FR21f--------R-T---------------------------------------

231HCJ62a--------R-T---------------------------------------
232HCJ82b--------R-T---------------------------------------
233CH6102c--------R-T---------------------------------------
234NE922d--------R-T---------------------------------------
 14BNL32e--------R-T---------------------------------------
 18FR42f--------R-T----------------------------------P-

235HCVTR3b---L----RQT----L----N-------------V-----------V-

236DK134d--------R-T--------M-------------------------------
237CAM6004e--------R-T--------M------------------------------
238GB8094e------L-R-T--------M------------------------------
 28BNL74k--------R-T--------M-------------------------------

239BE955a--------R-T----------------------------------M------

240HK26a---L----R-T--------T-------------------------------

42FR17a---L----R-T--------M-------------------------

44VN48a---L----R-T----I----------------------------
 46VN138b---L----R-T---------------------------------

48VN129a---L----R-T--------M---------------------------

50NE9810a---L----R-T-----X------------------V------Q-----V-
```

Fig.2B

```
SEQID
NO51100
229HCV11a  KTSERSQPRGRRQPIPKARRPEGRTWAQPGYPWPLYGNEGCGWAGWLLSP
230HCV-J1b ------------------------------------------M---------
2BNL11d    ----------------X-X---S------------------------X-----
6BNL21d    ---------D---------QSD-XX-----H----------------------
10CAM10781e ----------------E------
12FR21f    ----------------------S-----------A--------------

231HCJ62a  ----------------D--ST-KS-GK-----------L---------
232HCJ82b  ----------------D--ST-KS-GK----------------------
233CH6102c ----------------D--TT-KS-GR-----------L---------
234NE922d  ----------------D---T-KS-GK-----------L---------
14BNL32e   ----------------D-XAT--S-GR-----------L---------
18FR42f    ----------------D--AT-KS-GR-----------L---------

235HCVTR3b ---------KQ-HL-----SR---S--------------K---L-------

236DK134d  ------------------QL---S-------------------------
237CAM6004e ------------------T---S-------------------------
238GB8094e ------------------S---S-------------------------
28BNL74k   ------------------S---S------------------X-----

239BE955a  ------------------Q-T--S-G---------A---L---------

240HK26a   ------------------Q-Q--H-------------------------

42FR17a    --------------V-Q-T--S-G-----------------

44VN48a    --------------V-HQT----------------------
46VN138b   --------------V-HQT----------------------

48VN129a   --------A-------V-QNQ--------------------

50NE9810a  ---------S------R---T---S-----------------
```

Fig.2C

```
SEQID
NO101150
229HCV11aRGSRPSWGPTDPRRRSRNLGKVIDTLTCGFADLMGYIPLVGAPLGGAARA
230HCV-J1b--------------------------------------------------
2BNL11d-----N---
6BNL21d---------
12FR21f--------N-----------------------------------------S-T

231HC-J62a---------N---H----V--------------------V--------V---
232HC-J82b-----T-------H------R----I------------V----V--V---
233CH6102c-----------H-------------------------V----V--V---
234NE922d-----------H--------------------------V----V--V---
14BNL32e---------XX------X-V----V--X---
18FR42f---------N---H---------------X-------V----V--V---

235HCV-TR3b---------N--------F----------------------V--V---

241GB1164c-----------------V--V---
236DK134d---------N----------------------------V----V--V---
237CAM6004e-X--X----N---X-------------------------V--V---
238GB8094e---------N------------------------------V--V---
242G224f-----------------V--V---
243GB5494g-----------------V--V---
244GB4384h-----------------V--V---
28BNL74k---------N-------

239BE955a-----N---N----K----------------------G-I--V---
240HK26a-----H---N-------------------------V-------V-A-

42FR17a-----N---N----------------XXL--------VL-G----V-A-

44VN48a-----N---N---------------------------V----X--V-X-
46VN138bX----N---N---X-------------XX----IE--

48VN129a-----D-X-N---X--------------------E---V------V-AE

50NE9810a---------N-----
```

Fig.2D

```
SEQID
NO151200
229HCV11aLAHGVRVLEDGVNYATGNLPGCSFSIFLLALLSCLTVPASAYQVRNSTGL
230HCV-J1b--------------------------------I-----E---VS-I
 2BNL11d-------------------------XT-HE---AS-V
 6BNL21d--------------------F-------TT-HE---AS-V
12FR21f-X------XG--XXXXX--X---XX----X--------T---E-HST-DG

231HC-J62a-------------F--------------------I-T-V--AE-K-ISTG
232HC-J82b-----------I----------------------V---V--VE---ISSS
233CH6102c----------I--------------------S-----IS--V--VE-K-TSTS
234NE922d----------I-----------------------I---V-GL--K-TSSS
14BNL32e--X--------I--X------------X------V---V-XVE-K-TSQA
18FR42f-----------I----------------------I---V--I--K-NSHF
22BNL42g----------------------------V---V--V--K-TSTM
24BNL52h--I----------------------------V--K-TSHS
26BNL62i--I---------------------I---V--V--A-RS-S

235HCV-TR3b------A-G--------------------F----C---GLEYT-TS--

241GB1164c-E----AV---I-------------S----------T--VNY--AS-V
236DK134d------L-----------------------------NY---S-V
237CAM6004e-----AV---I-------------------------T--VNY--AS-I
238GB8094e------AV---I--------------------------GVNY--AS-V
242G224f------AV---I---------------------------VHYH-TS-I
243GB5494g------AV---I---------------------------QHY--IS-I
244GB4384h------AV---I------------V---R-------QHY--AS-I
30BNL74k--I-F----------------------------INY--VS-I
32BNL84k--I------------------------------INY--TS-I
34BNL94k--I------------------------------INYH-TS-I
245BNL94k--I------I---X-----X-----------TNY--VS-I
36BNL104k--I-----X-----------------------TNY--VS-I
38BNL114l--I--------------I-------------QHY--VS-I

239BE955a------------------------I-----------VPY--AS-I

240HK26a------AI---I--------------------T----LTYG--S--

42FR17a------AI----------------------T----I--K-AS-I

44VN48a-----XXI--X-----X---XX-X--X---------T----AHYT-KS--

48VN129a-X----AI---I--------------X-------T----LNYA-KS--

52NE9810a--I-F--------------F---LT-TAGLEY--AS--
```

Fig.2E

```
SEQID
NO201250
229HCV-11aYHVTNDCPNSSIVYEAADAILHTPGCVPCVREGNASRCWVAMTPTVATRD
230HCV-J1b-------S----------M-M-----------S-F------L---L-A-N
2BNL11d-------S----I--MDGM-M-Y---------D-HL---M-L---L-VKX
6BNL21d--L----S----I--MSGM---A----------N-S----MXL---L-VK-
12FR21f-------S-G------K-I------X---I----I-----PL---L-A-I

231HC-J62a-M-----T-D--TWQLQA-V--V------EKV--T----IPVS-N--VQQ
232HC-J82b-YA----S-N--TWQLT--V--L------ENDNGTLH--IQV--N--VKH
233CH6102c-M-----S-----WQLEG-V---------EQI--------PVS-N--I-Q
234NE922d-M-----Q-----WQLR--V--V------EEK--I----IPVS-NI-VSQ
14BNL32e-MA----S-N---WQLX--V--V------ENSSGRFH--IPIS-NI-VSK
18FR42f-MA----A-D---WQLR--V--V------E-S--RTF--T-VS-N--VSR
20BNL42g-MA----S-N--IWQMQG-V--V------ELQ--K----IPV--N--VNQ
24BNL52h-M-----S----WQLK--V--V------E-HQ-Q----IPV--N--VSQ
26BNL62i-M-----S----WQLEE-V--V------EWKD-T----IPV--NI-VSQ

235HCVTR3b-VL----S-G------E-V---L--------TT--Q-S--TTVST---V-T

241GB1164c--I------------DYH---L----L----V--Q------L-----APY
236DK134d--------------TDYH---L-----------K-T---SL-----AQH
237CAM6004e--I------A-----TENH---L--------T--Q------L-----SPY
238GB8094e--I------A-----TDNH---L--------KT--Q------L-----SPY
242G224f--L---------F--VHH---L--------T--Q------L---L-APY
243GB5494g---------------DHH-M-L--------T--T-----PL-----APY
244GB4384h---------------DHH-M-L--------T--V----IPL-----VPY
30BNL74k-Y--------------DHH---L-----------Q------L-----APY
32BNL84k---------------DHH---L--------T--Q------L-----APY
34BNL94k--I------------DHH---L--------V--Q-S----L---I-APY
245BNL94k---------------DHH--AL--------V--Q------L-----APY
36BNL104k-----------F--DHH---L--------K---H------L-----APY
38BNL114l--------------SDHH---L--------KT--T------L-----API
246GB7244x--I--------V---TDHH---L--------T--V----TPV-----AVS

239BE955a---------------DNL---A-------MT--V-----QI---LSAPS

240HK26a--L----------L--DAM---L---L----VDDR-T--H-V---L-IPN

42FR17a--L----S-N---F--ETM---L------IKA--E----LPVS--L-VPN

44VN48a--L-------------ETL---L-------KXX-Q-----QAS--L-VPN

46VN129a--L-------------NGM---L-------KT--LTK--LSAS--L-VQN

52NE9810a-M-----S-G------G-I---L--------S--T----IPVSX---VKS
```

Fig.2F

```
SEQID
NO251300
229HCV-11aGKLPATQLRRHIDLLVGSATLCSALYVGDLCGSVFLVGQLFTFSPRRHWT
230HCV-J1bSSI-T-TI---V-----A-A----M-------------S---------YE-
2BNL11dASV-TXAI---V-----XX-F---M--X---------A---------M-H-
6BNL21dANV-TAAI---V-----T-AFR--M---------------------LYH-
12FR21fANA-IDEV---V-----A-VF---M-I-----G----------TS-----

231HC-J62aPGALTQG--T---MV-M--------------G-M-AA-M-IV--QH--F
232HC-J82bRGALTRS--T-V-MI-MA--A--------V--A-MILS-A-MV--Q--NF
233CH6102cPGTLTKG--A-V-VI-M-----------V--ALMIAA-AVIA--Q--TF
234NE922dPGALTKG--T---TIIA---F------I-----A-M-AS-V-II--QH-KF
14BNL32ePGALTKG--AR--AV-M-------------V--A-MIAA-A-IVA-K--YF
18FR42fPGALTRG--A---TI-M----------I-----A-MIAA-VAVV--QY-TF
20BNL42gPGALTRG--T---TI-MV--------I--V--A-MIAA-VVIV--QH-NF
24BNL52hPGALTRG--T---TI-A---V--------F--A-M--S-F-MI--QH-IF
26BNL62iPGAXTKG--T---II-A---F-----

235HCVTR3bLGVTTASI-T-V-M---ARQ---------AF-A------A---R----T-

241GB1164cVGA-LES--S-V--M--A--V-----I-----G------M-S-Q------
236DK134dLNA-LES----V--M--G---------I--V--G----------Q------
237CAM6004eAGA-LEP----V--M--A--M-----I-----GL-----M---Q------
238GB8094eVGA-LEP----V--M--A--V----------GL-----M---Q------
242G224fLGA-LESM---V--M--T--------------GI--A--M---R--L---
243GB5494gVGA-LESM---V--M--A--V-----I-----G------M---R------
244GB4384hLGA-L-SV-Q-V--M--A--------I--H--G---A--MVS-Q------
30BNL74kIGA-LES--S-V--M--A--V-----I--X-XGL-----M-S-R------
32BNL84kIGA-LES--S-V--M--A--V-----I-----GL-----M-S-R------
34BNL94kIGA-LES--S-V--M--A--V-----I-----GA-----M-S-R------
245BNL94kTAA-LES--S-V--M--A--V-----I-X--GL-----M-SXQ------
36BNL104kIGA-LES--S-V-VM--A--V-----I-----GL-----M-S-R------
38BNL1141LSA-LMSV---V--M--A---S---------GA-----M---Q------
246GB7244xVDA-LESF---V--M--A-----V--------GA-----M---Q-----

239BE955aLGAVTAP---AV-Y-A-G-A---------A--AL------M--YR--Q-A-

240HK26aAST---GF---V---A-A-VV--S--I-------L--A------Q------

42FR17aSSV-IHGF---V-----A-AF---M-I------II--------R-KY-QV

44VN48aAST-V-GF-K-V-IM--A-AF---M-------GL--------LR--M-QV

48VN129aASVSIRGV-E-V-----A-AF---M-------GL---------R--MYEI

52NE9810aPCAATAS--T-V-MM-XA-------------AL--X--G-SWRH-Q---
```

Fig.2G

```
SEQID
NO301319
229HCV-11aTQGCNCSIYPGHITGHRMA
230HCV-J1bV-D--------VS-----
2BNL11d--E-----
6BNL21d--E-----
12FR21fV-D------S------XXX

231HC-J62aV-D--------T-------
232HC-J82b--E------Q---------
233CH6102cV-E--------------X
234NE922dV-D---------------
14BNL32eV-E---------------
18FR42fV-E--------------X
20BNL42gS-D-----
24BNL52hV-D-----

235HCVTR3bV-T---------VS-----

241GB1164c--D------A--V------
236DK134d--D------T---------
237CAM6004e--D------T---------
238GB8094e--D------A---------
242G224f--E----T----------
243GB5494g--D------D---------
244GB4384h--D------V---------
30BNL74k--D-----
32BNL84kA-D-----
34BNL94k--D-----
245BNL94k--D-----
36BNL104k--E-----
38BNL114lV-D-----
246GB7244x--D------T---------

239BE955aV-N------S--V------

240HK26aV-D------T--V------

42FR17a--D----XNX--V------

44VN48aV-E------T---------

48VN129aA-D------A---------

52NE9810aV-D-----
```

Fig.3A

SEQ ID NO. 1 (BNL1, 1d)
ATGAGCACGAATCCTAAACCTCAAAGAAAAACCAAACGTAACACCAACCGCCGCCCTCAKGGSGTN
NNNNNNCCGGGTGGCGGTCAGATCGTTGGTGGAGTTTACCTGTTGCCGCGCAGGGGCCCCAGGNNG
GGTGTGCGCGCGACTAGGAAGACTTCCGAGCGGTCACAACCTCGTGGCAGGCGACAGCCTATCCCC
AAGGCTCGYCGGYCCGAGGGCAGGTCCTGGGCTCAGCCCGGGTATCCTTGGCCCCTCTATGGCAAT
GAGGGCTGCGGGTGGGCGGGNTGGCTCCTGTCCCCCCGCGGCTCTCGGCCCAATTGGGGCCCC

SEQ ID NO. 3 (BNL1, 1d)
GACGGCGTGAACTATGCAACAGGGAACTTGCCCGGTTGCTCTTTCTCTATCTTCCTCTTGGCTTTG
CTGTCCTGCTTGACGGTTCCAACKACCGCTCACGAGGTGCGCAACGCATCCGGGGTGTATCATGTC
ACCAACGACTGTTCCAACTCGAGCATCATCTATGAGATGGACGGTATGATCATGCACTACCCAGGG
TGCGTGCCCTGCGTTCGGGAGGATAACCATCTCCGCTGCTGGATGGCGCTCACCCCCACGCTTGCG
GTCAAAAAYGCTAGTGTCCCCACTRCGGCAATCCGACGTCACGTCGACTTGCTTGTTGGGGGNNCC
ACGTTCTGTTCCGCTATGTACGTGGGRGACCTTTGCGGGTCTGTCTTCCTCGCTGGCCAGCTATTC
ACCTTTTCACCCCGCATGCACCATACAACGCAGGAGTGCAACTGCTCAATC

SEQ ID NO. 5 (BNL2, 1d)
ATGAGCACGAATCCTAAACCTCAAAGAAAAACCAAACGTAACACCAACCGCCGCCCACAGGACGTC
AAGNTCCCGGGTGGTGGTCAGATCGTTGGTGGAGTTTACCTGTTGCCGCGCAGGGGCCCCAGGTTG
GGTGTGCGCGCGACCAGGAAGACTTCCGAGCGGTCGCAGCCTCGTGACAGGCGACAGCCTATTCCT
AAGGCTCGCCAGTCCGATGGCAGNNCCTGGGCTCAGCCAGGGCATCCCTGGCCCCTCTATGGCAAT
GAGGGCTGCGGATGGGCGGGATGGCTCCTGTCCCCCGCGGCTCTCGGCCCAGTTGGGGCCCC

SEQ ID NO. 7 (BNL2, 1d)
GACGGCGTGAACTATGCAACAGGGAATTTGCCTGGTTGCTCTTTCTCTATCTTCCTCTTAGCTTTT
CTGTCCTGCTTGACGGTTCCAACTACCGCTCATGAGGTGCGCAACGCATCCGGGGTATATCATCTC
ACCAATGACTGTTCCAACTCGAGCATCATCTATGAGATGAGTGGTATGATCTTGCACGCCCAGGG
TGTGTGCCCTGCGTTCGGGAGAACAACTCTTCTCGTTGCTGGATGCCRCTCACCCCCACGCTTGCG
GTCAAAGACGCTAATGTCCCTACTGCGGCAATCCGACGCCATGTCGACTTGCTGGTTGGGACAGCC
GCGTTTCGTTCCGCTATGTACGTGGGGGACCTCTGCGGATCCGTCTTCCTTGTCGGCCAGCTATTC
ACCTTTTCACCCCGCTTGTACCATACAACACAGGAGTGCAACTGCTCAATC

SEQ ID NO. 9 (CAM1078, 1e)
ATGAGCACGAATCCTAAACCTCAAAGAAAAACCAAAAGAAACACCAACCGCCGCCCACAGGACGTC
AAGTTCCCGGGCGGTGGCCAGATCGTTGGTGGAGTCTACGTGCTACCGCGCAGGGGCCCTAGATTG
GGTGTGCGCGCAGCGCGGAAGACTTCGGAGCGGTCGCAACCTCGTGGGAGGCGCCAACCTATTCCC
AAGGAGCGCCGACCCGAGGGCAGGT

Fig. 3B

SEQ ID NO. 11 (FR2, 1f)
ATGAGCACGAATCCTAAACCTCAAAGAAAAACCAAACGCAACACCAACCGCCGCCCACAGGACGTT
AAATTCCCGGGTGGGGGGCAGATCGTGGGTGGAGTTTACTTGTTGCCGCGCAGGGGCCCCAGGTTG
GGTGTGCGCGCGACGAGGAAGACTTCCGAGCGGTCGCAACCTCGCGGAAGGC
GACAGCCTATCCCCAAGGCTCGCCGACCCGAGGGCAGGTCCTGGGCTCAGCCTGGGTACC
CATGGCCCCTCTATGCTAACGAGGGCTGCGGATGGGCGGGATGGCTCCTGTCCCCTCGCG
GCTCCCGTCCTAGCTGGGGCCCCAATGACCCCCGACGTAGATCACGCAATTTGGGTAAGG
TCATCGATACCCTAACGTGTGGCTTCGCCGATCTCATGGGGTACATTCCGCTCGTCGGCGC
CCCCCTAGGGGGCGCTTCCAGAACCCTGNCACATGGTGTCCGGGTCCTGGNAGGCGGCGTGATNNN
NNNNNNNNNNNAACCTTCCNGGTTGCTCTTTNNCTATCTTCCTCTTGGCNTTACTCTCTTGCCTCAC
AGTCCCCACCTCTGCCTATGAGGTGCACAGCACAACCGATGGCTACCATGTCACTAATGACTGTTC
CAACGGCAGCATCGTATATGAGGCAAAGGACATCATCCTTCACACGCCTGGGTGNGTGCCCTGCAT
ACGGGAAGGCAATATCTCCCGTTGCTGGGTACCGCTCACCCCCACGCTCGCAGCGCGGATCGCGAA
CGCTCCCATCGATGAGGTGCGGCGTCACGTCGACCTCCTCGTGGGGGCAGCCGTGTTCTGCTCAGC
CATGTACATTGGGGACCTTTGTGGGGGCGTCTTCCTCGTTGGGCAATTGTTCACCTTCACGTCCCG
GCGGCATTGGACGGTGCAGGACTGTAATTGTTCCATTTACTCTGGCCACATAACGGGCCACCGNNN
NNNN

SEQ ID NO. 13 (BNL3, 2e)
ATGAGCACAAATCCTAAACCTCAAAGAAAAACCAAAAGAAATACCAACCGCCGCCCACAGGACGTC
AAGTTCCCGGGCGGCGGCCAGATCGTTGGCGGAGTTTACTTGTTGCCGCGCAGGGGCCCCAGATTG
GGTGTGCGCGCGACGAGAGAAAGACTTCTGAACGGTCCCAGCCACGTGGAAGGCGCCAGCCCATCCCT
AAAGATCGNGNGNGCCACTGGCAGGTCCTGGGGACGTCCAGGATATCCCTGGCCCCTGTATGGGAAC
GAGGGGCTCGGCTGGGCAGGATGGCTCCTGTCCCCCGAGGCTCTC

SEQ ID NO. 15 (BNL3, 2e)
ACGTGCGGNTNTGCCGACCTCATGGGGTACATNCCCGTTGTCGGCGCCCCGGTGGGCGGGGTNGC
CAGGGCCCTCGCGNATGGCGTGCGGGTCCTGGAGGACGGGATAAATTATGNAACAGGGAACCTCCC
TGGTTGCTCCTTTTCTATCTTCTNGTTGGCTCTTCTGTCTTGTGTCACCGTGCCTGTCTCTGNCGT
TGAGGTCAAAAATACCAGTCAGGCCTATATGGCAACCAACGACTGCTCCAACAACAGCATCGTATG
GCAATTGGNGGACGCGGTGCTTCATGTTCCTGGATGTGTCCCCTGCGAGAATAGCTCCGGTCGGTT
CCACTGTTGGATCCCGATCTCGCCCAACATAGCCGTGAGCAAACCTGGTGCTCTCACCAAGGGACT
GCGGGCACGCATTGATGCCGTCGTGATGTCCGCCACCCTCTGCTCTGCCCTGTACGTGGGAGATGT
GTGCGGCGCAGTGATGATAGCTGCACAGGCTTTCATCGTGGCACCGAAGCGCCATTACTTCGTCCA
GGAATGCAATTGCTCCATATACCCAGGCCACATTACAGGTCATCGCATGGCG

SEQ ID NO. 17 (FR4, 2f)
ATGAGCACAAATCCTAAACCTCAAAGAAAAACTAAAAGAAACACTAACCGTCGCCCACAGGAC
GTTAAGTTCCCGGGCGGCGGCCAGATCGTTGGCGGAGTTTACTTGTTGCCGCGCAGGGGCCCCAG
GTTGGGTGTGCGCGCGCCAAGGAAGACTTCTGAACGGTCCCAGCCACGTGGAAGGCGCCAGCCC
ATCCCAAAAGATCGGCGCGCCACTGGCAAGTCCTGGGGACGTCCAGGATACCCTTGGCCCCTGT
ACGGGAACGAGGGCCTCGGCTGGGCAGGGTGGCTCCTGTCCCCCGGGGCTCTCGCCCCTCGTG
GGGCCCAAACGACCCCCGGCACAGGTCACGCAACTTGGGTAAGGTCATCGATACCCTCACGTG
TGGCTTTGSCGACCTCATGGGGTACATACCTGTCGTCGGCGCCCCTGTGGGCGGCGTTGCCAGA
GCCCTCGCGCATGGCGTGCGGGTCCTGGAGGACGGGATAAATTATGCAACAGGGAACTTGCCCGGT
TGCTCCTTTTCTATCTTCTTGCTGGCTCTCTTGTCTTGTATCACCGTGCCCGTGTCTGCCATACAG
GTTAAGAACAACAGCCACTTCTACATGGCGACTAATGACTGTGCCAATGACAGCATCGTCTGGCAG
CTCAGGCACGCGGTGCTCCATGTTCCTGGATGTGTCCCCTGTGAGAGGTCAGGTAATAGGACTTC
TGTTGGACAGCGGTCTCGCCCAACGTGGCTGTGAGCCGACCTGGTGCTCTCACTAGAGGTCTGCGG
GCTCACATTGATACCATCGTGATGTCCGCCACCCTCTGCTCTGCCCTATACATAGGGGACCTATGC
GGCGCTGTGATGATAGCAGCGCAAGTTGCCGTCGTCTCACCGCAATACCATACTTTTGTCCAGGAA
TGCAACTGCTCCATATACCCAGGCCATATCACAGGACATCGAATGGNN

Fig. 3C

SEQ ID NO. 19 (BNL4, 2g)
GACGGGTAAATTATGCAACAGGGAATCTGCCTGGTTGCTCTTTCTCTATCTTCTTGTTGGCTCTT
CTGTCTTGTGTCACCGTGCCTGTCTCTGCCGTGCAGGTTAAGAACACCAGTACCATGTACATGGCA
ACCAATGACTGTTCCAACAACAGCATCATCTGGCAAATGCAGGGCGCGGTGCTTCATGTTCCTGGA
TGTGTCCCGTGTGAGTTGCAGGGCAATAAGTCCCGGTGCTGGATACCGGTCACTCCCAACGTGGCT
GTGAACCAGCCCGGCGCCCTCACTAGGGGCTTGCGGACGCACATTGACACCATCGTGATGGTCGCT
ACGCTCTGTTCTGCACTCTACATCGGGGACGTGTGTGGCGCGGTGATGATAGCTGCTCAGGTTGTC
ATTGTCTCGCCGCAACATCACAACTTTTCCCAGGATTGCAATTGTTCCATC

SEQ ID NO. 21 (BNL5, 2h)
ATGAGCACAAAATCCTAAACCTCAAAGAAAAACCAAAAGAAACACTAACCGCCGCCCACAGGACGTT
AAGTTCCCGGGCGGTGGCCAGATCGTTGGCGGAGTATACTTGTTGCCGCGCAGGGGCCCCCGGTTG
GGTGTGCGCGCGACGAGGAAAACTTCCGAACGGTCCCAGCCACGTGGGAGGCGCCAGCCCATCCCT
AAAGATCGGCGCTCCACTGGCAAATCCTGGGGACGTCCAGGATACCCTTGGCCCCTGTATGGGAAC
GAGGGCCTTGGTTGGGCAGGATGGCTCTTGTCCCCTCGAGGCTCTC

SEQ ID NO. 23 (BNL5, 2h)
GACGGGATAAACTACGCAACAGGGAATCTGCCCGGTTGCTCCTTTTCTATCTTCTTGCTGGCCTTG
CTATCCTGTCTCACTGTGCCGGCGTCCGCTGTGCAGGTCAAGAACACCAGCCACTCTTATATGGTG
ACCAATGATTGCTCAAACAGCAGCATTGTCTGGCAGCTTAAGGATGCTGTGCTTCACGTCCCTGGA
TGTGTTCCATGTGAGAGGCACCAAAATCAGTCTCGCTGCTGGATACCTGTGACACCCAATGTGGCC
GTGAGCCAACCTGGCGCGCTCACCAGGGGTTTGCGGACGCACATTGACACCATCGTTGCGTCTGCT
ACCGTCTGCTCAGCTTTGTATGTGGGCGACTTCTGCGGCGCAGTGATGTTGGTCTCTCAATTTTTC
ATGATCTCCCCTCAGCACCACATCTTCGTCCAGGATTGCAACTGCTCGATA

SEQ ID NO. 25 (BNL6, 2i)
GACGGGATAAACTATGCAACAGGGAACCTGCCTGGTTGCTCCTTTTCTATCTTCTTACTGGCCCTG
CTTTCTTGCATCACCGTGCCGGTCTCTGCCGTGCAAGTTGCGAACCGCAGTGGTTCTTACATGGTG
ACCAATGATTGCTCGAACAGCAGCATCGTTTGGCAGCTCGAGGAGGCCGTCCTTCACGTCCCTGGA
TGTGTTCCCTGTGAGTGGAAGGACAACACCTCCCGCTGCTGGATACCGGTCACCCCTAACATCGCT
GTGAGCCAACCTGGCGCGCTTACCAAGGGCCTGCGGACACATATTGACATCATTGTCGCGTCCGCC
ACGTTCTGCTCTGCCTTGTATGTGGG

SEQ ID NO. 27 (BNL7, 4k)
ATGAGCACGAATCCTAAACCTCAAAGAAAAACCAAACGTAACACCAACCGCCGCCCCATGGACGTT
AAGTTCCCGGGTGGTGGCCAGATCGTTGGCGGAGTTTACTTGTTGCCGCGCAGGGGCCCCAGGTTG
GGTGTGCGCGCGACTCGGAAGACTTCGGAGCGGTCGCAACCTCGTGGGAGACGCCAACCTATCCCC
AAGGCGCGTCGATCCGAGGGAAGGTCCTGGGCACAGCCAGGATATCCATGGCCTCTTTACGGTAAT
GAGGGTTGCGGGTGGGCANNATGGCTCTTGTCCCCCCGCGGTTCTC

SEQ ID NO. 29 (BNL7, 4k)
GACGGGATCAATTTTGCAACAGGGAACCTCCCCGGTTGCTCCTTTTCTATCTTCCTCTTGGCACTC
CTCTCGTGCCTGACTGTCCCCGCTTCGGCCATCAACTATCGCAATGTCTCGGGCATTTACTATGTC
ACCAATGATTGCCCGAATTCAAGCATAGTGTATGAGGCCGACCATCACATCTTGCACCTCCCAGGT
TGCGTGCCCTGCGTGAGAGAGGGGAATCAGTCACGTTGCTGGGTAGCCCTTACCCCTACCGTCGCA
GCGCCATACATCGGCGCGCCACTTGAGTCTCTACGGAGTCATGTGGACTTGATGGTGGGGCCGCC
ACTGTTTGTTCAGCCCTTTACATCGGGGATTTRTGTGGYGGCTTGTTCCTAGTCGGTCAGATGTTC
TCTTTCCGACCAAGGCGCCACTGGACTACTCAAGATTGCAATTGTTCCATC

Fig. 3D

SEQ ID NO 31 (BNL8, 4k)
GACGGGATCAATTATGCAACAGGGAACCTTCCCGGTTGCTCTTTTTCTATCTTCCTCTTGGCACTC
CTCTCGTGCCTGACTGTTCCCGCTTCGGCCATTAACTACCGCAACACCTCGGGCATCTACCACGTC
ACCAATGACTGCCCGAACTCGAGCATAGTTTATGAGGCCGACCACCACATCTTGCACCTTCCAGGT
TGCGTGCCCTGCGTGAGAACTGGGAATCAGTCACGTTGCTGGGTGGCCCTTACTCCTACCGTCGCA
GCGCCATACATCGGCGCACCGCTTGAGTCTCTGCGGAGTCATGTGGATCTGATGGTGGGGCTGCC
ACTGTTTGCTCAGCCCTTTACATCGGGGATTTGTGTGGCGGCTTGTTCTTGGTTGGTCAGATGTTT
TCTTTCCGACCACGACGCCACTGGACTGCCCAGGATTGCAATTGTTCTATC

SEQ ID NO. 33 (BNL9, 4k)
GACGGGATTAATTATGCAACAGGGAATCTTCCCGGTTGCTCCTTTTCTATCTTCCTCTTGGCACTT
CTCTCGTGCCTGACTGTCCCCGCTTCGGCCATTAACTACCACAACACCTCGGGCATCTATCATATC
ACCAACGACTGCCCGAATTCAAGCATAGTGTATGAGGCCGACCATCACATCTTGCATCTCCCAGGT
TGCGTGCCCTGCGTGAGAGTGGGGAATCAGTCGAGTTGCTGGGTGGCCCTTACCCCTACCATCGCA
GCGCCATACATCGGCGCACCGCTTGAGTCCTTGCGGAGTCATGTGGATCTGATGGTGGGGCGGCC
ACTGTCTGTTCAGCCCTTTACATCGGGGATTTGTGTGGCGGTGCGTTCTTGGTTGGTCAGATGTTC
TCTTTCCGACCACGGCGCCACTGGACCACCCAAGATTGCAACTGCTCCATC

SEQ ID NO. 35 (BNL10, 4k)
GACGGGATCAATTATGCAACAGGGAATATTCCCGGTTGCTCYTTTTCTATCTTCCTTYTGGCACTT
CTCTCGTGTCTGACTGTCCCCGCTTCGGCCACTAACTATCGCAACGTCTCGGGCATCTACCATGTC
ACCAATGACTGCCCGAATTCAAGCATAGTGTATGAGGCCGACCATCACATCTTAGCACTTCCAGGT
TGCGTGCCCTGCGTGAGAGTGGGGAACCAGTCACGCTGCTGGGTGGCCCTTACCCCTACCGTCGCA
GCGCCATACACCGCGGCGCCGCTTGAGTCCCTGCGGAGTCATGTGGATCTGATGGTGGGAGCTGCC
ACTGTTGTTCAGCCCTTTACATCGGGGAYTTGTGTGGCGGCTTGTTCTTGGTTGGTCAGATGTTC
TCTTTYCAGCCTCGGCGCCACTGGACTACCCAGGATTGCAATTGTTCCATC

SEQ ID NO. 37 (BNL11, 4k)
GACGGGATTAATTATGCAACAGGGAAYCTCCCCGGTTGCTCTTTTTCTATCTTCCTCTTGGCACTT
CTCTCGTGCCTGACTGTCCCCGCTTCGGCCACCAACTACCGCAATGTCTCGGGCATTTACCATGTC
ACCAATGACTGCCCGAATTCAAGCATAGTGTTTGAGGCCGACCATCACATCTTGCACCTTCCAGGA
TGCGTGCCCTGCGTGAAAGAGGGAAATCATTCACGCTGCTGGGTGGCCCTTACCCCTACCGTCGCA
GCGCCATACATCGGCGCGCCACTTGAGTCTCTACGGAGTCATGTGGATGTGATGGTGGGGGCTGCC
ACTGTTTGTTCAGCCCTTTACATCGGGGATCTGTGCGGTGGCTTGTTCCTGGTTGGTCAGATGTTC
TCTTTCCGACCACGGCGCCACTGGACTACCCAGGAATGCAATTGTTCCATC

SEQ ID NO. 39 (BNL12, 41)
GACGGGATCAATTATGCAACAGGGAACCTCCCCGGTTGCTCTTTCTCTATCTTCATCCTGGCACTT
CTCTCGTGCCTGACTGTCCCGGCCTCGGCTCAGCATTATCGGAATGTCTCGGGCATTTACCACGTC
ACCAACGACTGCCCGAACTCCAGCATAGTGTATGAGTCCGACCATCACATCTTACACCTACCAGGG
TGTGTACCCTGTGTGAAGACTGGGAACACTTCGCGCTGCTGGGTGGCCTTAACACCTACCGTGGCC
GCGCCATACTTTCGGCTCCACTTATGTCCGTACGGCGGCATGTGGATCTGATGGTGGGTGCAGCT
ACCCTATCGTCTGCCCTCTACGTTGGAGACCTCTGCGGGGGTGCCTTCCTAGTGGGGCAGATGTTC
ACCTTCCAGCCGCGTCGCCACTGGACTGTCCAAGACTGCAACTGTTCCATC

SEQ ID NO. 45 (VN13, 7a)
ATGAGCACACTTCCTAAACCTCAAAGAAAAACCAAACGAAACACCAACCGTCGCCCACAGGACGTC
AAGTTCCCGGGTGGCGGTCAGATCGTTGGTGGAGTTTACTTGTTGCCGCGCAGGGGCCTCGTTTG
GGTGTGCGCGCGACGAGGAAAACTTCTGAACGGTCCCAGCCCAGGGGTAGACGCCAACCTATACCG
AAGGTGCGTCACCAAACGGGCCGTACCTGGGCTCAACCCGGGTACCCCTGGCCTCTTTATGGGAAT
GAGGGTTGTGGCTGGGCAGGGTGGCTCCTGTCCCCCNCGGCTCTCGCCCTAATTGGGGCCCTAAT
GACCCCCGGNGGAGGTCCCGCAACCTGGGTAAGGTCATCGATACCCTTACTTGNGGSTTCGCCGAC
CTCATAGAGTACATTCC

Fig.3E

SEQ ID NO. 43 (VN4, 7c)
ATGAGCACACTTCCAAAACCCCAAAGAAAAACCAAAAGAAACACCATCCGCCGCCCACA
GGACGTCAAGTTCCCGGGTGGCGGCCAGATCGTTGGTGGAGTCTACTTGCTGCCGCGCAG
GGGCCCGCGCTTGGGTGTGCGCGCGACGAGAAAGACTTCTGAACGGTCCCAGCCCAGAGG
TAGGCGCCAACCAATACCCAAAGTGCGCCACCAAACGGGCCGTACCTGGGCCCAGCCCGG
GTACCCCTGGCCTCTTTATGGAAATGAGGGCTGTGGTTGGGCAGGCTGGCTCCTGTCCCC
CCGCGGCTCTCGCCCAAATTGGGGCCCAAACGACCCCCGGCGGAGGTCCCGCAACTTGGG
TAAAGTCATCGACACCCTTACTTGCGGCTTCGCCGACCTCATGGGGTATATCCCTGTCGTAG
GCGCTCCGWTGGGAGGCGTCGCGGNGGCCTTGGCGCATGGGGTCANGGNCATCGAGGACGGNGTAA
ATTACGCAACAGNGAATCTTCCCGGNNGCTCTNTCTCTATCTTNCTCTTGGCACTTCTCTCGTGCC
TTACAACACCAGCCTCCGCGGCGCATTATACCAACAAGTCTGGCCTGTACCATCTCACCAACGACT
GCCCCAACAGCAGCATCGTTTATGAGGCGGAGACACTGATTTTGCACTTGCCTGGGTGTGTACCTT
GTGTGAAGRTGRACAATCAATCCCGTGCTGGGTGCAGGCCTCCCCGACCCTGGCAGTGCCGAACG
CGTCTACGCCAGTCACCGGGTTCCGCAAACATGTGGACATCATGGTGGGCGCTGCCGCGTTCTGTT
CAGCTATGTATGTGGGGACCTGTGCGGGGGCCTTTTCCTCGTTGGACAGCTCTTCACGCTCAGGC
CTCGGATGCATCAGGTTGTCCAGGAGTGTAACTGTTCCATCTACACAGGGCATATCACTGGACACC
GAATGGCA

SEQ ID NO. 47 (VN12, 7d)
ATGAGCACACTTCCAAAACCCCAAAGAAAAACCAAAAGAAACACAAACCGTCGCCCAATGGATGTC
AAGTTCCCGGGCGGCGGTCAGATCGTTGGTGGAGTCTACTTGTTACCGCGCAGGGGCCCACGTTTG
GGTGTGCGCGCGACGAGGAAGACTTCGGAACGGTCCCAGGCCTGGGTACCCCTGGCCCCTTTATGGGAAC
AAGGTGCGCCAGAACCAAGGCCGAACCTGGGCTCAGCCTGGGTACCCCTGGCCCCTTTATGGGAAC
GAGGGCTGCGGCTGGGCGGGGTGGCTCTTGTCCCCCCGTGGCTCTCGCCCGGACTGGGGNCCCAAT
GACCCCCGGNGGAGGTCCCGCAACCTGGGTAAGGTCATCG
ACACCCTCACTTGCGGCTTCGCCGACCTCATGGAGTACATCCCTGTCGTTGGCGCCCCCT
TGGAGGCGTTGCGGCGGAACTGGNACATGGTGTCAGGGCCATCGAGGACGGGATAAACTATGCAAC
AGGGAATCTTCCTGGTTGCTCTTTCTCTATCTTCCWCTTGGCACTTCTCTCGTGCCTCACCACGCC
TGCCTCCGCACTAAACTATGCTAACAAGTCTGGGCTGTATCATCTAACCAATGACTGCCCAATAG
CAGCATTGTGTATGAGGCGAATGGCATGATCCTGCATCTCCCGGGTTGCGTCCCCTGCGTGAAGAC
CGGCAACCTGACCAAGTGTTGGCTGTCGGCCTCCCCGACATTGGCGGTGCAGAATGCGTCGGTGTC
CATCAGGGGTGTCCGCGAGCACGTGGACCTCTTGGTGGGTGCTGCTGCGTTCTGCTCTGCCATGTA
CGTGGGCGACTTATGCGGTGGGCTCTTTCTCGTTGGGCAGTTGTTCACGTTCAGACCCAGGATGTA
TGAGATCGCCCAGGACTGCAACTGTTCCATCTATGCAGGCCACATCACTGGGCACCGGATGGCG

SEQ ID NO. 41 (FR1, 9a)
ATGAGCACACTTCCAAAACCCCAAAGAAAAACCAAAAGAAATACTAACCGTCGCCCTATGGAC
GTCAAGTTCCCGGGCGGCGGCCAGATCGTTGGTGGAGTTTACTTGTTGCCGCGCAGGGGC
CCTCGTTTGGGTGTGCGCGCGACGAGAAAGACCTCCGAACGGTCCCAGCCTAGAGGCAGG
CGCCAGCCCATACCAAAGGTACGCCAGCCGACAGGCCGTAGCTGGGGTCAACCCGGCTAC
CCTTGGCCCCTTTATGGCAACGAGGGCTGCGGATGGGCGGGATGGCTCCTGTCCCCCCGC
GGGTCTCGTCCTAATTGGGGCCCCAACGACCCCCGGCGAAGGTCCCGCAACTTGGGTAAG
GTCATCGATACCCTTACATNCGGNCTAGCCGACCTCATGGGGTACATCCCTGTCCTAGGAGG
GCCGCTTGGCGGCGTTGCGGCTGCCTGGCGCATGGCGTTAGGGCAATCGAGGACGGGGTCAATTA
CGCAACAGGGAATCTTCCTGGTTGCTCCTTTTCTATCTTCCTCTTAGCACTGTTATCGTGCCTCAC
TACACCAGCCTCAGCAATTCAAGTCAAGAACGCCTCTGGGATCTACCATCTTACCAATGACTGCTC
GAACAACAGCATCGTTTTTGAGGCGGAGACCATGATACTGCATCTTCCAGGTTGTGTCCCATGTAT
CAAGGCGGGGAATGAGTCACGATGTTGGCTCCCTGTCTCCCCCACCTTAGCCGTCCCCAACTCATC
AGTGCCAATCCACGGGTTTCGCCGACACGTAGACCTCCTCGTTGGGGCAGCGGCATTTTGTTCGGC
CATGTACATCGGAGACCTCTGTGGTAGCATAATCTTGGTAGGGCAGCTTTTTACTTTCAGGCCTAA
GTACCATCAGGTTACCCAGGATTGTAACTGCTCTATNAACNCTGGCCACGTCACGGGACACAGGAT
GGCA

Fig. 3F

SEQ ID NO. 49 (NE98, 10a)
ATGAGCACACTTCCTAAACCACAAAGAAAAACCAAAAGAAACACCAACC?CCGGCCACAGGACGTT
AAGTTCCCAGGCGGCGGTCAGATCGTTGGTGGAGTTTACGTGCTACCACGCAGGGGCCCCCAGTTG
GGTGTGCGTGCAGTGCGCAAGACTTCCGAGCGGTCGCAACCTCGCAGTAGGCGCCAACCCATCCCC
AGGGCGCGCCGAACCGAGGGCAGGTCCTGGGCTCAGCCCGGGTACCCTTGGCCCCTATATGGGAAT
GAGGGCTGCGGGTGGGCAGGGTGGCTCCTGTCCCCGCGCGGCTCTC

SEQ ID NO. 51 (NE98, 10a)
GACGGAATTAATTTCGCAACAGGGAATTTACCTGGTTGCTCTTTCTCTATCTTCCTTCTGGCTTTG
TTCTCATGCTTGCTTACACCCACAGCCGGGCTGGAGTACCGTAATGCCTCCGGACTCTACATGGTA
ACTAACGACTGCAGTAACGGTAGTATCGTGTATGAGGCCGGGGATATTATCCTCCACTTACCTGGC
TGTGTCCCTGCGTACGCTCTGGCAATACATCAAGATGCTGGATCCCTGTGAGCCCYACCGTCGCC
GTGAAGTCGCCCTGCGCCGCCACCGCCTCTCTCCGCACGCACGTGGATATGATGGTGGGRGCGGCC
ACCCTATGCTCAGCTCTCTACGTAGGAGACCTTTGTGGAGCGCTATTTCTTGTYGGGCAGGGGTTC
TCATGGAGACATCGCCAGCATTGGACTGTCCAGGACTGCAACTGTTCCATC

SEQ ID NO. 53 (BNL1,1d)
CTCGACAGTTACTGAGAATGACATCCGTGTCGAGGAATCAATATACCAATGTTGTGACTTGGCCCC
CGAGGCTCGCAAGGCCATAAAGTCGCTCACCGAGCGGCTGTACATCGGGGGCCCYCTAACCAATTC
AAAAGGACAGAACTGCGGCTACCGTCGGTGCCGCGCCAGCGGCGTGCTGACTACCAGCTGCGGCAA
CACCCTGACATGCTACTTGAAAGCCAGAGCGGCCTGTCGAGCTGCAAAGCTCCGGGACTGCACCAT
GCTCGTGTGCGGGGATGACCTTGTCGTTATCTGTGAGAGTGCGGGAGTCGAGGAAGACGCGGCGAA
CCTACGAGCT

SEQ ID NO. 55 (BNL2,1d)
CTCGACAGTTACTGAGAACGACATCCGTACCGAGGRATCAATCTATCAATGTTGTGACTTGGCCCC
YGAGGCCCGCAAGGCCATAAAGTCGCTCACCGAGCGGCTGTACGTCGGGGGCCCCCTAACCAATTC
AAAGGGGCAGAACTGCGGCTATCGTCGGTGTCGCGCTAGCGGCGTGCTGACCACCAGCTGCGGCAA
CACCCTCACATGCTACTTGAAAGCCAGGGCGGCCTGTCGAGCTGCAAAGCTCCAGGACTGCACGAT
GCTCGTGTCCGGAGACGACCTTGTCGTTATCTGTGAGAGCGCGGGAGTCGAGGAGGACGCGGCGAA
CCTACGAGTC

SEQ ID NO. 57 (FR17,1d)
CTCGACAGTTACTGAGAACGACATTCGTGTCGAGGAATCAATCTACCAGTGCTGTGACTTGGCCCC
CGAGGCCCGCAAGGCCATAAAGTCGCTCACCGAGCGGCTGTATATCGGGGGTCCCCTAACCAACTC
AAAAGGGCAGAACTGCGGCTACCGTCGGTGCCGCGCCAGCGGCGTGCTGACTACCAGCTGCGGTAA
TACCCTCACATGTTACTTGAAAGCCAGGGCGGCCTGTCGAGCTGCGAAGCTCCAGGACTGCACAAT
GCTCGTGTGCGGAGACGACCTTGTCGTTATCTGTGAGAGTGCRGGACTCGAGGAGGATGCGGCGAA
CCTACGAGTC

SEQ ID NO. 59 (CAM1078,1e)
CGTACAGCCTCCAGGACCCCCCCTCCCGGGAGAGCCATAGTGGTCTGCGGAACCGGTGAG
TACACCGGAATTGCCAGGACGACCGGGTCCTTTCTTGGATCAACCCGCTCAATGCCTGGA
GATTTGGGCGTGCCCCCGCAAGACTGCTAGCCGAGTAGTGTTGGGTCGCGAAAGGCCTTG
TGGTACTGCCTGATAGGGTGCTTGCGAGTGCCCCGGGAGGTCTCGTAGACCGTGCACCAT
GAGCACGAATCCTAAACCTCAAAGAAAAACCAAAAGAAACACCAACCGCCGCCCACAGGA
CGTCAAGTTCCCGGGCGGTGGCCAGATCGTTGGTGGAGTCTACGTGCTACCGCAGGGG
CCCTAGATTGGGTGTGCGCGCAGCGCGGAAGACTTCGGAGCGGTCGCAACCTCGTGGGAG
GCGCCAACCTATTCCCAAGGAGCGCCGACCCAGGGCAGGTCCTGGGCGCAGCCCGGGTA
CCCCTGGCCCCTCTATGGTAACGAGGGCTGCGGGTGGGCAGGTNGGCTCCTGTCCCCTCG
CGGCTCCCGTCCTAGTTGGGGTCCTACTGACCCCCGGCGTAGGTCACGCAATTTGGGTAA
GGTCATCGATACCCTCACGTGTTGNTTCGCCGACCTCATGGGGTACATACCG

Fig. 3G

SEQ ID NO. 61 (CAM1078,1e)

CTCAACGGTCACTGAAGCTGATATCCGAACAGAGGAGTCCATATACCAATGCTGTGACCTGCACCC
CGAAGCACGTGTAGCCATCAAGTCTTTGACTGAAAGGCTGTACGTCGGGGGGCCCTTGACCAATTC
AAAAGGGGAGAACTGCGGCTATCGCAGATGCCGTGCCAGCGGCGTCTTGACAACCAGCTGCGGCAA
CACCCTCACCTGCTATATCAAGGCCCTAGCAGCCTGTAGAGCTGCCAAGCTCCAGGACTGCACCAT
GCTCGTCTGTGGCGACGACCTGGTCGTGATCTGCGAGAGTGTAGGGACCCAGGAGGATGCGGCGAG
CCTGCGAGCC

SEQ ID NO. 63 (FR2, 1f)

NTCAACAGTCACTGAGAGTGATATCCGTACAGAGGAGTCCATCTACCAATGCTGTGATCTAGACCC
CGAGGCTCGCAAGGCCATAAGGTCCCTCACAGAGAGGCTTTATATCGGGGGTCCCCTGACAAACTC
AAAAGGGCAGAACTGCGGCTACCGCCGATGCCGTGCAAGCGGCGTCCTGACGACTAGCTGCGGCAA
CACCCTCACCTGTTACATAAAGGCCAGGGCAGCCTGTCGAGCTGCGAAGCTCCAGGATTGCTCAAT
GCTCGTCTGTGGCGACGACCTTGTCGTTATCTGCGAGATCGAGGGGNTCCANGAGGATCCGTCGAN
NNNNNNNNNN

SEQ ID NO. 65 (FR16,1g)

CGTAGACCGTGCACCATGAGCACGAATCCTAAACCTCAAAGAAAAACCAAACGTAACATC
AACCGCCGCCCACAGGACGTCAAGTTCCCGGGCGGTGGCCAGATCGTCGGTGGAGTTTAC
CTGTTGCCGCGCAGGGGCCCTAGATTGGGTGTGCGCGCGACTAGGAAGACTTCCGAGCGG
TCGCAACCTCGTGGGAGGCGACAGCCTATCCCCAAGGCTCGCCGATCCGAGGGCAGGTCC
TGGGCTCAGCCCGGGTACCCTTGGCCCCTCTATGGCAATGAGGGCATGGGTTGGGCAGGG
TGGCTCCTGTCCCCCCATGGCTCCCGGCCTAGTTGGGGCCCTTCAGACCCCCGGCGTAGG
TCGCGTAATTTGGGTAAGGTCATCGATACCCTCACATGCGGCTTCGCCGACCTCATGGGG
TACATTCCGCTCGTCGGCGCCCCCCTAGGGGCGTTGCCAGGGCCCTGGCGCAAGGCTTC
CGGGATCTACCACGTCACCAACGATTGTTCCAATGGGAGCATTGTGTATGAGGCGGAAGG
CATGATCATGCATCTCCCCGGGTGCGTGCCCTGCGTTCGGGAAGGTAATATCTCTCGTTG
CTGGGTACCGTTTTCCCCCACGCTCGCAGCCAGGAATGCTAGCGTCCCCACTCAGGCAAT
TCGGCGACACGTCGACTTGCTTGTTGGGGCGGCCACACTCTGTTCTGCTATGTATGTGGG
GGACCTCTGTGGGTCCGTCTTCCTCGTCGGCCAACTGTTCACCTTCACANCCCGCCAGNA
CTACACAGTGCAAGACTGCAATTGTTCCATCTACCCCGGCCATATAACGGG

SEQ ID NO. 67 (FR16,1g)

NNNNNNNGTCACTGAGAGTGATATCCGTGTCGAGGAATCAATTTACCAATGCTGTGACCTGGCCCC
CGAGGCTCGCGTAGCCATAAAGTCGCTCACTGAGCGGCTATATGTCGGGGGCCCTCTCACCAACTC
AAAAGGACAGAACTGCGGCTATCGCCGGTGCCGTGCGAGCGGTGTGCTGACTACTAGCTGCGGTAA
CACCCTCACATGCTACCTGAAAGCCGCCGCGGCCTGTCGAGCTGCAAAGCTCCGGGAATGCACAAT
GCTCGTGTGTGGCGACGACCTCGTCGTTATCTGTGAGAGTGCGGGGGTCCAGGAGGATGCTGCAAG
CCTNNNNNNN

SEQ ID NO. 69 (BNL3,2e)

CTCGACAGTCACAGAGAGAGATATAAGNACTGAGGAGTCCATATACCAGGCTTGTTCCTTACCCGA
GCAGGCCAGAACTGCCATACACTCATTGACTGAGAGACTCTACGTAGGAGGGCCCATGATGAACAG
CAAAGGGCAATCCTGCGGATACAGGCATTGCCGCGCCAGCGGAGTGCTCACCACCAGTATGGGGAA
TACCATCACGTGCTACATCAAGGCCCTAGCGGCTTGTAAAGCAGCAGGAATAGTGGCCCCCACCAT
GCTGGTGTGCGGCGATGACCTAGTTGTCATCTCAGAGAGTCAGGGAGTCGAGGAGGACGACCGGAA
CCTGANNNNN

Fig.3H

SEQ ID NO. 71 (FR4, 2f)

CTCAACCGTCACAGAGAGGGATATAAGAACTGAGGAGTCCATATACCTGGCCTGCTCCTTACCCGA
GCAGGCCCGGACTGCCATACATTCATTAACTGAGAGACTTTACGTGGGAGGGCCCATGATGAACAG
CAAAGGGCAGTCCTGCGGATACAGGCGTTGCCGCGCTAGCGGAGTGCTCACCACCAGTATGGGGAA
CACCATCACGTGTTATGTGAAAGCCCTCGCAGCTTGTAAAGCTGCGGGCATTGTTGCCCCCACGAT
GCTGGTGTGCGGCGATGACCTGGTTGTCATCTCAGAGAGTCAGGGGGCTGAGGAGGACGAGCGAAA
CCTGAGAGTC

SEQ ID NO. 73 (BNL5,2h)

CTCAACAGTCGCGGAGAGAGACATCAGGACCGAGGAGTCCATTTACCTTGCCTGCTCCTTACCCGA
GCAAGCCCGAACTGCCATACATTCATTGACTGAGAGACTTTACGTAGGAGGGCCCATGATGAACAG
CAAGGGACAGTCCTGCGGTTACAGACGTTGCCGCGCCAGCGGAGTGCTCACCACCAGCATGGGGAA
TACCATCACATGCTATGTGAAGGCATTAGCTGCCTGCAAAGCTGCAGGCATCGTTGCTCCCACGAT
GCTGGTTTGTGGCGACGATCTGGTCATCATCTCAGAGAGTCAGGGAACCGAGGAGGATGAGCGGAA
CCTGAGAGTC

SEQ ID NO. 75 (FR13,2k)

CGNACANCCTCCAGGCCCCCCCCTCCCGGGAGAGCCATAGTGGTCTGCGGAACCGGTGAG
TACACCGGAATTGCCGGGAAGACTGGGTCCTTTCTTGGATAAACCCACTCTATGCCCGGC
CATTTGGGCGTGCCCCCGCAAGACTGCTARCCGAGTAGCGTTGGGTTGCGAAAGGCCTTG
TGGTACTGCCTGATAGGGTGCTTGCGAGTGCCCCGGGAGGTCTCGTAGACCGTGCATCAT
GAGCACAAATCCTAAACCTCAAAGAAAAACCAAAAGAAACACTAACCGCCGCCCACAGGA
CGTTAAGTTCCCGGGCGGTGGCCAGATCGTTGGCGGAGTATACTTGTTGCCNTGCAGGGG
NCCCAGGTNGNGTNTATGCGCAACGANGAAGACTNCCGAACAGTCCCAGCCACGTGGGAG
GCGCCAGCCCATCCCGAAAGATCGGNGCACCACTGGCAAGTCCTGGGGACGTCCAGGATA
TCCCTGGCCCCTGTATGGGAACGAGGGCCTCGGGTGGGCAGGGTGGCTCCTGTCCCCCCG
GGGCTCCCGCCCGTCATGGGGCCCCACGGACCCCCGGCATAGGTCGCGCAACTTGGGTAA
GGTCATCGATACCCTCACGTNCGGCTTTNCCGACCTCATGGGGTACATTCCCGTCGTTGG
CGCCCCAGTAGGNGGCGTCGCCAGAGCTCTCGCGCATGGCGTGAGAGTCCTGGAGGACGG
GATAAACTATGAAACAGGGAACCTCCCCGGTTGCTCTTTCTCTATCTCCCTCCTTGCTCT
TCTGTCCTGAATTACCGNGCCAGTTTCTGCTGTGGAAATCAAAAACACCAGMAACACATA
CATGGTGACTAACGACTGTTCAAACAGYAGCATCACCTGGCAGCTTNNGNNCGCGGTGCT
TCACGTTCCTGGATGCGTCCCCTGTGAACGAGAGGGCAACAGTTCCCGGTGCTGGATTCC
AGTCACGCCCACGTAKNCGTGAGCCGACCTGGTGCCCTAACCGAGGGTTTGCGATCGCA
CATCGACACCATCGTAGCGTCCGCAACATTTTGTTCTGCCCTCTACATAGGGGATGTATG
TGGCGCGATAATGATAGCTGCCCAAGTGGTCATCGTCTCGCCGGAGCATCATCACTTTGT
CCAGGACTGTAACTGTTCCATCTACCCGGGCCACATAACGGGGCCTCGTATGTNG

SEQ ID NO. 77 (FR13,2k)

ATCCACAGTCACTGAAAGAGACATCAGAGTTGAAGAGTCCGTTTATCTGTCCTGTTCACTTCCCGA
GGAGGCCCGAGCTGCCATACACTCACTAACTGAGAGGCTGTACGTGGGAGGTCCCATGCAGAACAG
CAAGGGGCAATCCTGCGGATACAGGCGCTGCCGCGCCAGCGGGGTGCTCACCACTAGCATGGGGAA
TACTCTCACATGCTACTTGAAGGCCCAGGCGGCCTGCAGGGCCGCGGGCATTGTTGCACCCACAAT
GCTGGTGTGTGGCGACGACCTGGTCGTCATCTCAGAGAGTCAGGGGACTGAGAGGGACGAGAACAA
CCTGAGACCT

Fig. 3I

SEQ ID NO. 79 (FR18,2l)

```
CTCAACAGTCACGGAGAGGGACATCAGGAATGAGGAGTCCATATTCCTGGCCTGCTCGTTGCCCGA
GGAGGCCCGGACTGTCATACATTCGCTCACTGAGAGACTCTACATAGGCGGGCCGATGATGAACAG
CAAAGGCCAGTCCTGTGGATACAGGCGTTGTCGCGCCAGCGGGGTGTTCACCACTAGCATGGCAA
TACCATCACGTGCTATGTGAAAGCCATGGCAGCTTGCAGAGCTGCCGGGATTGACGCCCCCACAAT
GTTGGTATGTGGCGACGACCTGGTGGTCATCTCAGAGAGTCAGGGGACCGAGGAGGACGAGCGAAA
TCTGAGAGTC
```

SEQ ID NO. 81 (PAK64,3g)

```
CTCTTGACTCTACTGTCACTGAACAGGATATCAGGGTAGAAGAAGAAATATACCAATGTTGTGACC
TTGAGCCGGAGGCTAGACGGGCAATCAAATCGCTCACGGAACGGCTTTACGTTGGAGGTCCCATGT
TCAACAGCAAGGGGCTCAAATGCGGATATCGCCGTTGCCGTGCTAGCGGTGTATTGCCCACTAGCT
ACGGTAATACAATCACCTGCTACATCAAGGCCAGAGCGGCTGCTCGAGCTGCGGGCCTTCAAGACC
CATCATTCCTTGTCTGCGGAGATGATTTGGTGGTAGTGGCTGAGAGTTGCGKCGTTGATGAGGAGG
ATAGGGCAGC
```

SEQ ID NO. 83 (BNL8,4k)

```
CTCCACTGTAACCGAAAAGGACATCAGGCCCGAGGAAGAGGTCTATCAGTGTTGTGACCTGGAGCC
CGAAGCTCGCAAGGTTATTACCGCCCTCACAGAAAGACTCTACGTGGGCGGCCCCATGCACAACAG
CAAGGGAGACCTTTGTGGGTATCGGAGATGCCGCGCAAGCGGCGTCTACACGACCAGCTTCGGAAA
CACACTGACGTGCTACCTCAAAGCCTCAGCTGCTATTAGAGCGGCAGGGCTGAGAGACTGCACCAT
GCTGGTTTGCGGTGACGACTTGGTCGTCATCGCTGAGAGCGATGGCGTAGAGGAGGATAACCGAGC
CCTCCNAGCC
```

SEQ ID NO. 85 (BNL12,4l)

```
CTCCACGGTGACTGAAAAGGACATCAGGGTCGAGGAAGAGATCTATCAATGTTGTGACCTGGARCC
CGAAGCCCGCAAAGCAATATCCGCCCTCACAGAGAGCTCTACTTGGGCGGCCCCATGTATAACAG
CAAAGGGGAGCTCTGCGGGTATCGGAGGTGCCGCGCGAGCGGAGTGTACACCACAAGTTTCGGGAA
CACAGTGACCTGCTATCTTAAGGCCACCGCAGCTACCAGGGCTGCAGGCCTAAAAGACTGCACCAT
GCTGGTCTGCGGTGACGACTTGGTCGTCATCGCCGAGAGCGAGGGCGTAGAGGAGGATTCCCAACC
CCTCCGAGCC
```

SEQ ID NO. 87 (EGE1,4m)

```
CTCCACCGTAACCGAAAGGGACATCAGGGTCGAGGAGGAGGTCTATCAGTGTTGTGATCTGGAGCC
AGAGGCCCGCAAGGCAATATCCGCCCTCACGGAGAGACTCTATGTGGGCGGTCCCATGTTTAACAG
CAAGGGAGACCTATGTGGCTACCGCAGGTGCCGCGCAAGCGGCGTCTACACCACCAGCTTCGGAAA
CACACTGACCTGCTACCTCAAGGCCACGGCCGCTACCAGAGCGGCCGGCCTGAAGGATTGCACAAT
GCTGGTTTGCGGGGACGACCTGGTCGTCATCGCAGAGAGCGATGGCGTGGACGAGGACCGCCGAGC
CCTCCAAGCT
```

SEQ ID NO. 89 (VN13,7a)

```
CTCAACAGTCACAGAGCGCGATGTCCAGACGGAGCATGACATCTACCAGTGCTGTAAGTTGGAGCC
CGCAGCACGGACAGCCATCACATCGCTTACTGACCGATTGTACTNCGGTGGTCCCATGTNTAACTC
TAAAGGTCAGGCATGTGGATACCGTAGGTGCAGGGCCAGTGGCGTCTTGACCACCATCCTGGCCAA
TACTCTGACTTGCTACTTGAAAGCTCAGGCGGCATGCAGAGCTGCCGGGCTGAAGGACTTTGACAT
GTTGGTCTGCGGAGACGACCTTGTCGTTATTTCGGAGAGTTTGCGGGTCTCGGAGGACACTAGTGC
ACTGCGAGCT
```

Fig. 3J

SEQ ID NO. 91 (VN4,7c)

CTCGACAGTCACCGAGCGCGACATCCRCACCGAGCACGACATCTACCAATGCTGCCAACTTGACCC
GGTGGCACGCAAGGCTATTACATCTCTGACTGAGCGGCTGTACTGCGGWGGGCCCATGATGAACTC
CCGTGGTCAATCATGTGGATACCGTAGGTGCCGAGCCAGTGGCGTGCTCACCACGAGCTTGGGCAA
TACCCTAACATGCTATTTGAAAGCACAAGCAGCGTGTAGGGCAGCAAAGCTCAAAAACTATGACAT
GTTAGTCTGCGGAGACGATCTAGTCGTTATCGCGGAGAGTGGAGGAGTCTCTGAGGATGTTGACGC
CCTGCGAGCA

SEQ ID NO. 93 (VN12,7d)

CTCCTCCGTCACGGAGCGTGACATCCGCACTGAACACGACATCTATCAGTGCTGCCAATTAGATCC
GGTAGCACGGAAAGCCATTACATCTCTTACTGAGCGGCTGTACTGCGGCGGCCCCATGTACAACTC
TCGAGGTCAGTCATGTGGGTACCGCAGGTGCCGGGCTAGTGGTGTCTTCACCACAAGCTTGGGCAA
CACCATGACATGCTACCTGAAGGCTCAGGCGGCTTGTAGGGCAGCAAGCTCAAAAACTTTGACAT
GTTGGTCTGCGGAGACGACCTAGTCGTTATTGCTGAGAGCGGAGGAGTCCCTGAGGATGCCGGGGC
CCTGCGAGTC

SEQ ID NO. 95 (FR1,9a)

ATCCACAGTCACGGGGCGCGACATACGCACAGAACNAGACATTTACCTGTCCTGCCAGCTCGACCC
AGAGGCCCGGAAAGCCATAAAGTCTCTCACTGAGAGGCTCTATGTCGGGGGCCCTATGTACAACTC
AAAGGGCCAACTCTGTGGTCAACGCCGATGCCGAGCAAGCGGAGTACTCCCCACAAGCATGGGTAA
CACCATCACATGCTTCCTGAAGGCAACCGCCGCTTGCCGAGCAGCCGGCTTTACAGATTATGACAT
GTTGGTCTGCGGAGACGATTTGGTTGTCGTAACTGAGAGTGCTGGAGTCAACGAGGATATCGCTAA
CCTGCGAGCC

SEQ ID NO. 97 (NE98,10a)

CTCCACTGTCACTGAGCAGGACATCAGGGTAGAACTTTCCATCTTTCAGGCCTGTGACCTCAAGGA
CGAGGCTAGGAGGGTGATAACTTCACTCACGGAGCGGCTTTACTGTGGTGGTCCTATGTTCAACAG
CAAGGGACAACACTGCGGTTACCGCCGCTGCCGTGCTAGTGGGGTGCTACCCACCAGCTTCGGGAA
CACAATCACCTGTTACATCAAAGCAAAGGCAGCTACCAAAGCTGCCGGAATTAAAAATCCATCATT
CCTTGTCTGCGGAGATGACTTGGTCGTGATTGCTGAGAGTGCAGGGATCGATGAGGACAAGAGCGC
CTTGAGAGCT

SEQ ID NO. 99 (FR14,11a)

CTCTACCGTCACAGAGAGGGACATACGGACAGAAGAATCCATCTATCTGTCTTGTCAATTGCCTGA
AGAGGCCCGGAAAGCCATTAAATCGCTGACAGAGAGACTATACGTGGGCGGCCCGATGGAAAACAG
CAAGGGCCAGGCTTGCGGATATAGGCGTTGCCGCGCAAGCGGGGTATTCACCACAAGCTTGGGGAA
CACCATGACTTGTTACATCAAAGCTAAAGCGGCTTGTAAAGCCGCTGGCATTGTAGACCCGGTGAT
GCTCGTGTGCGGTGACGACCTAGTGGTCATCTCAGAAAGCAAGGGGGTGGAGGAGGACCAGCGGGA
CCTACGAGTC

SEQ ID NO. 101 (FR15,11a)

CTCCACTGTCACTGAGAGAGACATACGGACAGAGAGAATCCATCTAYYTGGCTTGTCAATTGCCCGA
AGAGGCCCGGAAGGCCATTAAATCACTGACAGAGCGCAAGCGGGGTATTCACCACAAGCTTGGGGAA
CAAAGGCCAGGCCTGCGGATATAGGCGTTGCCGCGCAAGCGGGGTATTCACCACAAGCTTGGGGAA
CACCATGACTTGTTACATCAAGGCCAARGCAGCTTGTAAAGCYGCTGGCATTGTTGACCCGGTGAT
GCTCGTGTGCGGCGACGACCTAGTGGTCATCTCAGAGAGCAAGGGGGTAGAGGAGGACCAGCGAGA
CCTAC

Fig. 3K

SEQ ID NO. 103 (FR19,11a)
CGTACAGCCTCCAGGACCCCCCCTCCCGGGAGAGCCATAGTGGTCTGCGGAACCGGTGAGTACACC
GGAATTGCCGGGAAGACTGGGTCCTTTCTTGGATTAACCCACTCTATGCCCGGAGATTTGGGCGTG
CCCCCGCAAGACTGCTAGCCGAGTAGCGTTGGGTTGCGAAAGGCCTTGTGGTACTGCCTGATAGGG
TGCTTGCGAGTGCCCCGGGAGGTCTCGTAGACCGTGCACCATGAGCACGAATCCTAAACCTCAAAG
ACAAACCAAAAGAAACACCAACCGCCGCCCACAGGACGTTAAGTTCCCGGGCGGTGGCCAGATCGT
TGGCGGGGTGTACTTGTTGCCGCGCAGGGGCCCCAGAGTGGGTGTGCGCGCGACGAGAAAGACCTC
GGAGCGGTCCCAGCCGCGTGGGAGGCGCCAACCTATCCCCAAGGTTAGGCGCACCACCGGCCGTT

SEQ ID NO. 105 (FR19,11a)
CTCTACTGTCACAGAGAGGGATATACGAACAGAGGAATCCATYTATCTGGCTTGTCAATTGCCCGA
AGAGGCCCGGAAGGCCATCAAATCACTGACAGAGACTATACGTGGGCGGCCCGATGGAAAACAG
CAAGGGCCAGGCCTGCGGATACAGGCGTTGCCGCGCAAGCGGGGTATTCACCACAAGCTTGGGGAA
CACCATGACTTGTTACATCAAAGCCAAGGCGGCTTGTAAAGCCGCTGGCATTGTTGACCCAGTGAT
GCTCGTGTGCGGCGACGACCTAGTGGTCATCTCAGAAAGCAAGGGGGTGGAGGAGGACCAACGAGA
CCTACGANTC

SEQ ID NO. 2 (BNL1, 1d)
MSTNPKPQRKTKRNTNRRPXXXXXXPGGGQIVGGVYLLPRRGPRXGVRATRKTSERSQPRGRRQPIP
KAXRXEGRSWAQPGYPWPLYGNEGCGWAXWLLSPRGSRPNWGP

SEQ ID NO. 4 (BNL1, 1d)
DGVNYATGNLPGCSFSIFLLALLSCLTVPXTAHEVRNASGVYHVTNDCSNSSIIYEMDGMIMHYPG
CVPCVREDNHLRCWMALTPTLAVKXASVPTXAIRRHVDLLVGXXTFCSAMYVXDLCGSVFLAGQLF
TFSPRMHHTTQECNCSI

SEQ ID NO. 6 (BNL2, 1d)
MSTNPKPQRKTKRNTNRRPQDVKXPGGGQIVGGVYLLPRRGPRLGVRATRKTSERSQPRDRRQPIP
KARQSDGXXWAQPGHPWPLYGNEGCGWAGWLLSPRGSRPSWGP

SEQ ID NO. 8 (BNL2, 1d)
DGVNYATGNLPGCSFSIFLLAFLSCLTVPTTAHEVRNASGVYHLTNDCSNSSIIYEMSGMILHAPG
CVPCVRENNSSRCWMXLTPTLAVKDANVPTAAIRRHVDLLVGTAAFRSAMYVGDLCGSVFLVGQLF
TFSPRLYHTTQECNCSI

SEQ ID NO. 10 (CAM1078, 1e)
MSTNPKPQRKTKRNTNRRPQDVKFPGGGQIVGGVYVLPRRGPRLGVRAARKTSERSQPRGRRQPIE
KERRPEGR

SEQ ID NO. 12 (FR2, 1f)
MSTNPKPQRKTKRNTNRRPQDVKFPGGGQIVGGVYLLPRRGPRLGVRATRKTSERSQPRGRRQPIP
KARRPEGRSWAQPGYPWPLYANEGCGWAGWLLSPRGSRPSWGPNDPRRRSRNLGKVIDTLTCGFAD
LMGYIPLVGAPLGGASRTLXHGVRVLXGGVXXXXXNLXGCSXXIFLLXLLSCLTVPTSAYEVHSTT
DGYHVTNDCSNGSIVYEAKDIILHTPGXVPCIREGNISRCWVPLTPTLAARIANAPIDEVRRHVDL
LVGAAVFCSAMYIGDLCGGVFLVGQLFTFTSRRHWT
VQDCNCSIYSGHITGHXXX

SEQ ID NO. 14 (BNL3, 2e)
MSTNPKPQRKTKRNTNRRPQDVKFPGGGQIVGGVYLLPRRGPRLGVRATRKTSERSQPRGRRQPIP
KDRXATGRSWGRPGYPWPLYGNEGLGWAGWLLSPRGSRPSWG

SEQ ID NO. 16 (BNL3, 2e)
TCXXADLMGYXPVVGAPVGGXARALAXGVRVLEDGINYXIGNLPGCSFSIFXLALLSCVTVPVSXV
EVKNTSQAYMATNDCSNNSIVWQLKDAVLHVPGCVPCENSSGRFHCWIPISPNIAVSKPGALTKGL
RRRIDAVVMSATLCSALYVGDVCGAVMIAAQAFIVAPKRHYFVQECNCSIYPGHITGHRMA

Fig. 3L

SEQ ID NO. 18 (FR4, 2f)
MSTNPKPQRKTKRNTNRRPQDVKFPGGGQIVGGVYLLPRRGPRLGVRAPRKTSERSQPRGRRQPIP
KDRRATGKSWGRPGYPWPLYGNEGLGWAGWLLSPRGSRPSWGPNDPRHRSRNLGKVIDTLTCGFXD
LMGYIPVVGAPVGGVARALAHGVRVLEDGINYATGNLPGCSFSIFLLALLSCITVPVSAIQVKNNS
HFYMATNDCANDSIVWQLRDAVLHVPGCVPCERSGNRTFCWTAVSPNVAVSRPGALTRGLRAHIDT
IVMSATLCSALYIGDLCGAVMIAAQVAVVSPQYHTFVQECNCSIYPGHITGHRMX

SEQ ID NO. 20 (BNL4, 2g)
DGVNYATGNLPGCSFSIFLLALLSCVTVPVSAVQVKNTSTMYMATNDCSNNSIIWQMQGAVLHVPG
CVPCELQGNKSRCWIPVTPNVAVNQPGALTRGLRTHIDTIVMVATLCSALYIGDVCGAVMIAAQVV
IVSPQHHNFSQDCNCSI

SEQ ID NO. 22 (BNL5, 2h)
MSTNPKPQRKTKRNTNRRPQDVKFPGGGRSLAEYTCARRGKLRRSSMG

SEQ ID NO. 24 (BNL5, 2h)
DGINYATGNLPGCSFSIFLLALLSCLTVPASAVQVKNTSHSYMVTNDCSNSSIVWQLKDAVLHVPG
CVPCERHCNQSRCWIPVTPNVAVSQPGALTRGLRTHIDTIVASATVCSALYVGDFCGAVMLVSQFF
MISPQHHIFVQDCNCSI

SEQ ID NO. 26 (BNL6, 2i)
DGINYATGNLPGCSFSIFLLALLSCITVPVSAVQVANRSGSYMVTNDCSNSSIVWQLEEAVLHVPG
CVPCEWKDNTSRCWIPVTPNIAVSQPGAXTKGLRTHIDIIVASATFCSALYV

SEQ ID NO. 28 (BNL7, 4k)
MSTNPKPQRKTKRNTNRRPMDVKFPGGGQIVGGVYLLPRRGPRLGVRATRKTSERSQPRGRRQPIP
KARRSEGRSWAQPGYPWPLYGNEGCGWAXWLLSPRGSRPSWGPNDPRRRSR

SEQ ID NO. 30 (BNL7, 4k)
DGINFATGNLPGCSFSIFLLALLSCLTVPASAINYRNVSGIYYVTNDCPNSSIVYEADHHILHLPG
CVPCVREGNQSRCWVALTPTVAAPYIGAPLESLRSHVDLMVGAATVCSALYIGDXCXGLFLVGQMF
SFRPRRHWTTQDCNCSI

SEQ ID NO. 32 (BNL8, 4k)
DGINYATGNLPGCSFSIFLLALLSCLTVPASAINYRNTSGIYHVTNDCPNSSIVYEADHHILHLPG
CVPCVRTGNQSRCWVALTPTVAAPYIGAPLESLRSHVDLMVGAATVCSALYIGDLCGGLFLVGQMF
SFRPRRHWTAQDCNCSI

SEQ ID NO. 34 (BNL9, 4k)
DGINYATGNLPGCSFSIFLLALLSCLTVPASAINYHNTSGIYHITNDCPNSSIVYEADHHILHLPG
CVPCVRVGNQSSCWVALTPTIAAPYIGAPLESLRSHVDLMVGAATVCSALYIGDLCGGAFLVGQMF
SFRPRRHWTTQDCNCSI

SEQ ID NO. 36 (BNL10, 4k)
DGINYATGNIPGCXFSIFLXALLSCLTVPASATNYRNVSGIYHVTNDCPNSSIVYEADHHILALPG
CVPCVRVGNQSRCWVALTPTVAAPYTAAPLESLRSHVDLMVGAATVCSALYIGXLCGGLFLVGQMF
SXQPRRHWTTQDCNCSI

SEQ ID NO. 38 (BNL11, 4k)
DGINYATGXLPGCSFSIFLLALLSCLTVPASATNYRNVSGIYHVTNDCPNSSIVFEADHHILHLPG
CVPCVKEGNHSRCWVALTPTVAAPYIGAPLESLRSHVDVMVGAATVCSALYIGDLCGGLFLVGQMF
SFRPRRHWTTQECNCSI

SEQ ID NO. 40 (BNL12, 4l)
DGINYATGNLPGCSFSIFILALLSCLTVPASAQHYRNVSGIYHVTNDCPNSSIVYESDHHILHLPG
CVPCVKTGNTSRCWVALTPTVAAPILSAPLMSVRRHVDLMVGAATLSSALYVGDLCGGAFLVGQMF
TFQPRRHWTVQDCNCSI

Fig.3M

SEQ ID NO. 46 (VN13, 7a)

MSTLPKPQRKTKRNTNRRPQDVKFPGGGQIVGGVYLLPRRGPRLGVRATRKTSERSQPRGRRQPIP
KVRHQTGRTWAQPGYPWPLYGNEGCGWAGWLLSPXGSRPNWGPNDPRXRSRNLGKVIDTLTXXFAD
LIEYI

SEQ ID NO. 44 (VN4, 7c)

MSTLPKPQRKTKRNTIRRPQDVKFPGGGQIVGGVYLLPRRGPRLGVRATRKTSERSQPRGRRQPIP
KVRHQTGRTWAQPGYPWPLYGNEGCGWAGWLLSPRGSRPNWGPNDPRRRSRNLGKVIDTLTCGFAD
LMGYIPVVGAPXGGVAXALAHGVXXIEDXVNYATXNLPXXSXSIXLLALLSCLTTPASAAHYTNKS
GLYHLTNDCPNSSIVYEAETLILHLPGCVPCVKXXNQSRCWVQASPTLAVPNASTPVTGFRKHVDI
MVGAAAFCSAMYVGDLCGGLFLVGQLFTLRPRMHQVVQECNCSIYTGHITGHRMA

SEQ ID NO. 48 (VN12, 7d)

MSTLPKPQRKTKRNTNRRPMDVKFPGGGQIVGGVYLLPRRGPRLGVRATRKTSERSQARGRRQPIP
KVRQNQGRTWAQPGYPWPLYGNEGCGWAGWLLSPRGSRPDWXPNDPRXRSRNLGKVIDTLTCGFAD
LMEYIPVVGAPLGGVAAELXHGVRAIEDGINYATGNLPGCSFSIFXLALLSCLTTPASALNYANKS
GLYHLTNDCPNSSIVYEANGMILHLPGCVPCVKTGNLTKCWLSASPTLAVQNASVSIRGVREHVDL
LVGAAAFCSAMYVGDLCGGLFLVGQLFTFRPRMYFIAQDCNCSIYAGHITGHRMA

SEQ ID NO. 42 (FR1, 9a)

MSTLPKPQRKTKRNTNRRPMDVKFPGGGQIVGGVYLLPRRGPRLGVRATRKTSERSQPRGRRQPIP
KVRQPTGRSWGQPGYPWPLYGNEGCGWAGWLLSPRGSRPNWGPNDPRRRSRNLGKVIDTLTXXLAD
LMGYIPVLGGPLGGVAAALAHGVRAIEDGVNYATGNLPGCSFSIFLLALLSCLTTPASAIQVKNAS
GIYHLTNDCSNNSIVFEAETMILHLPGCVPCIKAGNESRCWLPVSPTLAVPNSSVPIHGFRRHVDL
LVGAAAFCSAMYIGDLCGSIILVGQLFTFRPKYHQVTQDCNCSXNXGHVTGHRMA

SEQ ID NO. 50 (NE98, 10a)

MSTLPKPQRKTKRNTNXRPQDVKFPGGGQIVGGVYVLPRRGPQLGVRAVRKTSERSQPRSRRQPIP
RARRTEGRSWAQPGYPWPLYGNEGCGWAGWLLSPRGSRPSWGPNDPRRR

SEQ ID NO. 52 (NE98, 10a)

DGINFATGNLPGCSFSIFLLALFSCLLTPTAGLEYRNASGLYMVTNDCSNGSIVYEAGDIILHLPG
CVPCVRSGNTSRCWIPVSXTVAVKSPCAATASLRTHVDMMVXAATLCSALYVGDLCGALFLXGQGF
SWRHRQHWTVQDCNCSI

SEQ ID NO. 54 (BNL1,1d)

STVTENDIRVEESIYQCCDLAPEARKAIKSLTERLYIGGXLTNSKGQNCGYRRCRASGVLTTSCGN
TLTCYLKARAACRAAKLRDCTMLVCGDDLVVICESAGVEEDAANLRA

SEQ ID NO. 56 (BNL2,1d)

STVTENDIRTEXSIYQCCDLAXEARKAIKSLTERLYVGGPLTNSKGQNCGYRRCRASGVLTTSCGN
TLTCYLKARAACRAAKLQDCTMLVCGDDLVVICESAGVEEDAANLRV

SEQ ID NO. 58 (FR17,1d)

STVTENDIRVEESIYQCCDLAPEARKAIKSLTERLYIGGPLTNSKGQNCGYRRCRASGVLTTSCGN
TLTCYLKARAACRAAKLQDCTMLVCGDDLVVICESXGVEEDAANLRV

Fig. 3N

SEQ ID NO. 60 (CAM1078,1e)

MSTNPKPQRKTKRNTNRRPQDVKFPGGGQIVGGVYVLPRRGPRLGVRAARKTSERSQPRGRRQPIP
KERRPEGRSWAQPGYPWPLYGNEGCGWAGXLLSPRGSRPSWGPTDPRRRSRNLGKVIDTLTCXFAD
LMGYIP

SEQ ID NO. 62 (CAM1078,1e)

STVTEADIRTEESIYQCCDLHPEARVAIKSLTERLYVGGPLTNSKGENCGYRRCRASGVLTTSCGN
TLTCYIKALAACRAAKLQDCTMLVCGDDLVVICESVGTQEDAASLRA

SEQ ID NO. 64 (FR2, 1f)

STVTESDIRTEESIYQCCDLDPEARKAIRSLTERLYIGGPLTNSKGQNCGYRRCRASGVLTTSCGN
TLTCYIKARAACRAAKLQDCSMLVCGDDLVVICEIEGXXEDPSXXXX

SEQ ID NO. 66 (FR16,1g)

MSTNPKPQRKTKRNINRRPQDVKFPGGGQIVGGVYLLPRRGPRLGVRATRKTSERSQPRGRRQPIP
KARRSEGRSWAQPGYPWPLYGNEGMGWAGWLLSPHGSRPSWGPSDPRRRSRNLGKVIDTLTCGFAD
LMGYIPLVGAPLGGVARALAQGFRDL

SEQ ID NO. 68 (FR16,1g)

XXVTESDIRVEXSIYQCCDLAPEARVAIKSLTERLYVGGPLTNSKGQNCGYRRCRASGVLTTSCGN
TLTCYLKAAAACRAAKLRECTMLVCGDDLVVICESAGVQEDAASXXX

SEQ ID NO. 70 (BNL3,2e)

STVTERDIXTEESIYQACSLPEQARTAIHSLTERLYVGGPMMNSKGQSCGYRHCRASGVLTTSMGN
TITCYIKALAACKAAGIVAPTMLVCGDDLVVISESQGVEEDDRNLXX

SEQ ID NO. 72 (FR4, 2f)

STVTERDIRTEESIYLACSLPEQARTAIHSLTERLYVGGPMMNSKGQSCGYRRCRASGVLTTSMGN
TITCYVKALAACKAAGIVAPTMLVCGDDLVVISESQGAEEDERNLRV

SEQ ID NO. 74 (BNL5,2h)

STVAERDIRTEESIYLACSLPEQARTAIHSLTERLYVGGPMMNSKGQSCGYRRCRASGVLTTSMGN
TITCYVKALAACKAAGIVAPTMLVCGDDLVIISESQGTEEDERNLRV

SEQ ID NO. 76 (FR13,2k)

MSTNPKPQRKTKRNTNRRPQDVKFPGGGQIVGGVYLLXCRXPRXXXCATXKTXEQSQPRGRRQPIP
KDRXTTGKSWGRPGYPWPLYGNEGLGWAGWLLSPRGSRPSWGPTDPRHRSRNLGKVIDTLTXGFXD
LMGYIPVVGAPVXGVARALAHGVRVLEDGINYETGNLPGCSFSISLLALLSITXPVSAVEIKNTXN
TYMVTNDCSNXSITWQLXXAVLHVPGCVPCEREGNSSRCWIPVTPXVXVSRPGALTEGLRSHIDTI
VASATFCSALYIGDVCGAIMIAAQVVIVSPEHHHFVQDCNCSIYPGHITGPRMX

SEQ ID NO. 78 (FR13,2k)

STVTERDIRVEESVYLSCSLPEEARAAIHSLTERLYVGGPMQNSKGQSCGYRRCRASGVLTTSMGN
TLTCYLKAQAACRAAGIVAPTMLVCGDDLVVISESQGTERDENNLRP

Fig. 30

SEQ ID NO. 80 (FR18,21)

STVTERDIRNEESIFLACSLPEEARTVIHSLTERLYIGGPMMNSKGQSCGYRRCRASGVFTTSMGN
TITCYVKAMAACRAAGIDAPTMLVCGDDLVVISESQGTEEDFRNLRV

SEQ ID NO. 82 (PAK64,3g)

STVTEQDIRVEEEIYQCCDLEPEARRAIKSLTERLYVGGPMFNSKGLKCGYRRCRASGVLPTSYGN
TITCYIKARAAARAAGLQDPSFLVCGDDLVVVAESCXVDEEDRAALR

SEQ ID NO. 84 (BNL8,4k)

STVTEKDIRPEEEVYQCCDLEPEARKVITALTERLYVGGPMHNSKGDLCGYRRCRASGVYTTSFGN
TLTCYLKASAAIRAAGLRDCTMLVCGDDLVVIAESDGVEEDNRALXA

SEQ ID NO. 86 (BNL12,4l)

STVTEKDIRVEEEIYQCCDLXPEARKAISALTEXLYLGGPMYNSKGELCGYRRCRASGVYTTSFGN
TVTCYLKATAATRAAGLKDCTMLVCGDDLVVIAESEGVEEDSQPLRA

SEQ ID NO. 88 (EG81,4m)

STVTERDIRVEEEVYQCCDLEPEARKAISALTERLYVGGPMFNSKGDLCGYRRCRASGVYTTSFGN
TLTCYLKATAATRAAGLKDCTMLVCGDDLVVIAESDGVDEDRRALQA

SEQ ID NO. 90 (VN13,7a)

STVTERDVQTEHDIYQCCKLEPAARTAITSLTDRLYXGGPMXNSKGQACGYRRCRASGVLTTILAN
TLTCYLKAQAACRAAGLKDFDMLVCGDDLVVISESLGVSEDTSALRA

SEQ ID NO. 92 (VN4,7c)

STVTERDIXTEHDIYQCCQLDPVARKAITSLTERLYCXGPMMNSRGQSCGYRRCRASGVLTTSLGN
TLTCYLKAQAACRAAKLKNYDMLVCGDDLVVIAESGGVSEDVDALRA

SEQ ID NO. 94 (VN12,7d)

SSVTERDIRTEHDIYQCCQLDPVARKAITSLTERLYCGGPMYNSRGQSCGYRRCRASGVFTTSLGN
TMTCYLKAQAACRAXXLKNFDMLVCGDDLVVIAESGGVPEDAGALRV

SEQ ID NO. 96 (FR1,9a)

STVTGRDIRTEXDIYLSCQLDPEARKAIKSLTERLYVGGPMYNSKGQLCGQRRCRASGVLPTSMGN
TITCFLKATAACRAAGFTDYDMLVCGDDLVVVTESAGVNEDIANLRA

SEQ ID NO. 98 (NE98,10a)

STVTEQDIRVELSIFQACDLKDEARRVITSLTERLYCGGPMFNSKGQHCGYRRCRASGVLPTSFGN
TITCYIKAKAATKAAGIKNPSFLVCGDDLVVIAESAGIDEDKSALRA

SEQ ID NO. 100 (FR14,11a)

STVTERDIRTEESIYLSCQLPEEARKAIKSLTERLYVGGPMENSKGQACGYRRCRASGVFTTSLGN
TMTCYIKAKAACKAAGIVDPVMLVCGDDLVVISESKGVEEDQRDLRV

Fig. 3P

Figure 3 - continued

SEQ ID NO. 102 (FR15,11a)

STVTERDIRTEESIXXACQLPEEARKAIKSLTERLYVGGPMENSKGQACGYRRCRASGVFTTSLGN
TMTCYIKAXAACKXAGIVDPVMLVCGDDLVVISESKGVEEDQRDLXX

SEQ ID NO. 104 (FR19,11a)

MSTNFKPQRQTKRNTNRRPQDVKFPGGGQIVGGVYLLPRRGPRVGVRATRKTSERSQPRGRRQPIP
KVRRTTGR

SEQ ID NO. 106 (FR19,11a)

STVTERDIRTEESXYLACQLPEEARKAIKSLTERLYVGGPMENSKGQACGYRRCRASGVFTTSLGN
TMTCYIKAKAACKAAGIVDPVMLVCGDDLVVISESKGVEEDQRDLRX

Fig. 4A Core/E1 amino acid alignment

| Isolate | Type | SEQ ID | 1                                                       50 |
|---------|------|--------|-----------------------------------------------------------|
|         |      |        | MSTNPKPQKKNKRNTNRRPQDVKFPGGGQIVGGVYLLPRRGPRLGVRATR |
| HCV-1   | 1a   | 229    | ------------------------------------------------- |
| HCV-J   | 1b   | 230    | -----R-T----------------------------------------X- |
| BNL1    | 1d   | 2      | -----R-T-------XXXXX------------------------------ |
| BNL2    | 1d   | 6      | -----R-T----------------------------X------------- |
| CAM1078 | 1e   | 10/60  | -----R-T---------------------------V-------------- |
| FR2     | 1f   | 12     | -----R-T-----I------------------------------------ |
| FR16    | 1g   | 66     | -----R-T------------------------------------------ |
| HC-J6   | 2a   | 231    | -----R-T------------------------------------------ |
| HC-J8   | 2b   | 232    | -----R-T------------------------------------------ |
| CH610   | 2c   | 233    | -----R-T------------------------------------------ |
| NE92    | 2d   | 234    | -----R-T------------------------------------------ |
| BNL3    | 2e   | 14     | -----R-T------------------------------------------ |
| FR4     | 2f   | 18     | -----R-T---------------------------------------P-- |
| FR13    | 2k   | 76     | -----R-T-----------------------------XC-X-XXXC-X-- |
| EB1     | 3a   | 247    | ----L-R-T---I----------------------------V------C- |
| NZL1    | 3a   | 248    | ----L-R-T---I----------------------------V-------- |
| HCV-TR  | 3b   | 235    | ----L-RQT---L-N--------------------------V-------- |
| GB358   | 4c   | 249    | -----R-T-------M---------------------------------- |
| DK13    | 4d   | 236    | -----R-T-------M---------------------------------- |
| CAM600  | 4e   | 237    | -----R-T-------M---------------------------------- |
| GB809   | 4e   | 238    | ----L-R-T-----M---------------------------------- |
| HPCCOREEZA | 4? | 250   | -----R-T----T--------------------------------G--- |
| HPCCOREZB | 4?  | 251    | ---T-R-T-------M---------------------------------- |
| HPCCOREZC | 4?  | 252    | -----R-T-------M---------------------------------- |
| GB724   | 4?   | 253    | -----R-T-------M---------------------------------- |
| BNL7    | 4k   | 28     | -----R-T----T------------------------------------- |
| BE95    | 5a   | 239    | -----R-T-------M---------------------------------- |
| HK2     | 6a   | 240    | ----L-R-T---------------------------M------------- |
| VN13    | 7a   | 46     | ----L-R-T----I------------------------------------ |
| VN4     | 7c   | 44     | ----L-R-T------------------------------------------ |
| VN12    | 7d   | 48     | ----L-R-T-------M---------------------------------- |
| FR1     | 9a   | 42     | ----L-R-T----X-------------------------V---------- |
| NE98    | 10a  | 50     | ----L-R-T-------------------------------------Q--- |
| FR19    | 11a  | 104    | ------RQT------------------------------V------V--- |

Fig. 4B

```
                              51                                                  Core-V                                 100
                              KTSERSQPRGRRQPIPK ARRPEGRTWA QPGYPWPLYGNECGWAGWLLSP
Isolate      Type   SEQ ID
HCV-1        1a     229       ----------------  ----------  --------------------
HCV-J        1b     230       ----------------  ----------  ------M-------------
BNL1         1d     2         ----------------  -X-X----S-  --------------------
BNL2         1d     6         ---D------------  --QSD-XX--  --------X-----X-----
CAM1078      1e     10/60     ----------------  ------H---  --------------------
FR2          1f     12        ------E---------  --------S-  ------A-------------
FR16         1g     66        ----------------  --------S-  --------------------
HCJ6         2a     231       ----------------  D--ST-KS-GK ----------L---M-----
HCJ8         2b     232       ----------------  D--ST-KS-GK ----------L---------
CH610        2c     233       ----------------  D--TT-KS-GR ----------L---------
NE92         2d     234       ----------------  D--TT-KS-GK ----------L---------
BNL3         2e     14        ----------------  D--XAT-S-GR ----------L---------
FR4          2f     18        ----------------  D--AT-KS-GR ----------L---------
FR13         2k     76        --X-Q-----------  D-XTT-KS-GR ----------L---------
EB1          3a     247       ----------------  --------S-  --------------------
NZL1         3a     248       ----------------  --------S-  --------------------
HCV-TR       3b     235       ---KQ-HL--------  --SR----S-  ----------K---L-----
GB358        4c     249       ----------------  --------S-  --------------------
DK13         4d     236       ----------------  --QL----S-  --------------------
CAM600       4d     237       ----------------  --------T-  --------------------
GB809        4e     238       ----------------  --------S-  --------------------
BNL7         4k     28        ----------------  --------S-  --------------------
HPCCOREEZA   4?     250       ----------------  --------S-  --------------------
HPCCOREEZB   4?     251       ----------------  --------S-  ------F-------------
HPCCOREEZC   4?     252       ----------------  --------S-  --------------------
GB724        4?     253       ----------------  ------A-S-  ----------A---------
BE95         5a     239       ----------------  --Q-T-S-G-  --------------X-----
HK2          6a     240       ----------------  --Q-Q---H-  --------------------
VN13         7a     46        --V-HQT---------  --------S-  --------------------
VN4          7c     44        --V-HQT---------  --------S-  ----------K---------
VN12         7d     48        --V-QNQ---------  --------S-  ----------A---------
FR1          9a     42        --V-Q-T---------  S-G-----S-  ----------A---------
NE98         10a    50        ---S------------  R---T---S-  --------------------
FR19         11a    104       ----------------  --V--TT---  --------------------
```

Fig. 4C

| Isolate | Type | SEQ ID | 101 RGSRPSWGPTDPRRRSRNLGKVIDTLTCGFADLMGYIPLVGAPLGGAARA 150 |
|---|---|---|---|
| HCV1 | 1a | 229 | ------------------------------------------------- |
| HCV-J | 1b | 230 | -------N----------------------------------------- |
| BNL1 | 1d | 2 | ------------------------------------------------- |
| BNL2 | 1d | 6 | ------------------------------------------------- |
| CAM1078 | 1e | 10/60 | ----------------------------X-------------------- |
| FR2 | 1f | 12 | H-------N-----S---------------------------------S-T |
| FR16 | 1g | 66 | ------------------------------------------------V- |
| HC-J6 | 2a | 231 | --------N-----H---V------------------------V----V- |
| HC-J8 | 2b | 232 | --------T-----H---R-I----------------------V----V- |
| CH610 | 2c | 233 | --------------H--------------------------------V-V- |
| NE92 | 2d | 234 | --------------H-----------------------------V----V- |
| BNL3 | 2e | 14 | SEQ ID NO: 16 |
| FR4 | 2f | 18 | --------N-----H------------------XX------X-V-----V- |
| FR13 | 2k | 76 | --------------------------------------------V--X--- |
| HCV-TR | 3b | 235 | --------N-----F----------------X-X----------VX-V--- |
| GB116 | 4c | 241 | ------------------------------------V-----V------V- |
| DK13 | 4d | 236 | --------------------------------------------V----V- |
| CAM600 | 4e | 237 | --X-X---N---X---------------------------------V--V- |
| GB809 | 4e | 238 | --X-----N----------------------------------V----V- |
| G22 | 4f | 242 | --------N----------------------------------V----V- |
| GB549 | 4g | 243 | --------N----------------------------------V----V- |
| GB438 | 4h | 244 | ---D-X-N---X-----------------------------V----V- |
| BNL7 | 4k | 28 | --------N----------------------------------V----V- |
| BE95 | 5a | 239 | --------N-----K----------------------------G-I-V--- |
| HK2 | 6a | 240 | --------H---------------------------------V--V-A- |
| VN13 | 7a | 46 | X-------N-----X---------------XX---IE----X--V-X--- |
| VN4 | 7c | 44 | --------N----------------------------V----V------- |
| VN12 | 7d | 48 | --------N---X-----------------E------V---V-AE |
| FR1 | 9a | 42 | --------N-----------------------XXL---V----V-X--- |
| NE98 | 10a | 50 | --------N--------------------XXL------VL-G---V-A- |

Fig. 4D

| isolate | Type | SEQ ID | 151 LAHGVRVLEDGVNYATGNLPGCSFSIFLLALLSCLTVPASA | V1 YQVRNSTGL 200 |
|---|---|---|---|---|
| HCV1 | 1a | 229 | ---------------------------------------- | ---------- |
| HCV-J | 1b | 230 | ---------------------------------------- | I---E--VS-I |
| BNL1 | 1d | 4 | ---------------------------------------- | ---E--AS-V |
| BNL2 | 1d | 8 | ---------------------------------------- | ---E--AS-V |
| FR2 | 1f | 12 | -X-----XG--XXXXX--X--XX---X- | XT-HE--AS-V |
| FR16 | 1g | 66 | --Q-F-D- | TT-HE--AS-V |
| HC-J6 | 2a | 231 | -------F-------------------------------- | T---E-HST-DG |
| HC-J8 | 2b | 232 | -------I-------------------------------- | I-T-V--AE-K-ISTG |
| CH610 | 2c | 233 | -------I-------------------------------- | -V-V--VE---ISSS |
| S83 | 2c | 254 | --------------------------S------------- | IS-V--VE-K-TSTS |
| NE92 | 2d | 234 | -------I-------------------------------- | VE-KDTGDS |
| BNL3 | 2e | 16 | --X----I--X---------X------------------- | V-GL--K-TSSS |
| FR4 | 2f | 18 | -------I-------------------------------- | V-XVE-K-TSQA |
| BNL4 | 2g | 20 | -------I-------------------------------- | -V-I--K-NSHF |
| BNL5 | 2h | 24 | -------I-------------------------------- | -V-V--K-TSTM |
| BNL6 | 2i | 26 | -------I-------------------------------- | -V--K-TSHS |
| FR13 | 2k | 76 | -------I--------E----------------------- | I--V--V-A-RS-S |
| BR36 | 2k | 255 | -------I------------------------/I-X-V-- | VEIK-TXNT |
| HCV-TR | 3a | 235 | -----A-G---------------------F---------- | LEW--TS-- |
| Z4 | 3b | 256 | ---------------------------------------- | C---GLEYT-TS-- |
| GB809-4 | 4a | 257 | -----AV--I------------------------------ | EHY--AS-I |
| Z1 | 4a | 258 | -----AV--I------------------------------ | EHY--AS-I |
| GB116 | 4b | 241 | -E---AV--I-------S---------------------- | VHY--AS-V |
| GB215 | 4c | 259 | ---------------------------------------- | T--VNY--AS-V |
| GB358 | 4c | 260 | -----AV--I------------------------------ | IHY--AS-V |
| DK13 | 4d | 236 | ---L-----I------------------------------ | VNY--AS-I |
| CAM600 | 4e | 237 | ---AV----I------------------------------ | -NY--S-V |
| GB809-2 | 4e | 238 | ---AV----I------------------------------ | T--VNY--AS-I |
| CAMG22 | 4f | 261 | ---AV----I------------------------------ | GVNY--AS-V |
| CAMG27 | 4f | 262 | ---AV----I------------------------------ | VHYH-TS-I |
| GB549 | 4g | 243 | ---AV----I---------V-------------------- | VHYH-TS-I |
| GB438 | 4h | 244 | ---AV----I---------R-------------------- | QHY--IS-I |
| BNL7 | 4k | 30 | ---I-F---I------------------------------ | QHY--AS-I |
| BNL8 | 4k | 32 | ---------I------------------------------ | INY--VS-I |
| BNL9 | 4k | 34 | ---------I------------------------------ | INY--TS-I |
| BNL10 | 4k | 36 | ---------I-----------X------------------ | INYH-TS-I |
|  |  |  |  | TNY--VS-I |

Fig. 4E

```
BNL11   4k   38                                                    -I----X----------   ------------------   ---TNY--VS-I
BNL12   41   40                                                    --I--------------   -----------I------   ---QHY--VS-I
BE95    5a   239                                                   -----------------   -----------I------   ---VPY--AS-I
BE100   5a   263                                                   -----------------   ------------------   ---VPY--AS-I
HK2     6a   240   ----AI----------   ----I--X----XX-X---   -T-   ---LTYG--S--
VN4     7c   44    -----XXI--X------   --I--X-----X------   -T-   ---AHYT-KS--
VN12    7d   48    --X----AI--------   ----I-------------   -T-   ---LNYA-KS--
FR1     9a   42    -------AI--------   ----------X-------   -T-   ---I--K-AS-I
NE98    10a  52    ---I-F-----------   ------------------   ---F---LT-TAGLEY--AS-
```

Fig. 4F

| Isolate | Type | SEQ ID | V1 20 YHV TNDCPNSSI | V2 VYEAADAILHT | PGCVPC | V3 VREGNASRCWVAM | TPTVA | V4 250 TRD |
|---|---|---|---|---|---|---|---|---|
| HCV-1 | 1a | 229 | YHVTNDCPNSSI | VYEAADAILHT | PGCVPC | VREGNASRCWVAM | TPTVA | TRD |
| HCV-J | 1b | 230 | ---------- | ----S---M-M- | ------ | -----S-F----L | ---L- | A-N |
| BNL1 | 1d | 4 | ---L------ | ----S---I-MDGM-M-Y | ------ | -----D-HL---M-L | ---L- | VKX |
| BNL2 | 1d | 8 | ---L------ | ----S---I-MSGM---A | ------ | -----N-S----MXL | ---L- | VK- |
| FR2 | 1f | 12 | ---------- | ----S-G---K-I---- | --X--- | -----I----PL--- | -L-A- | I |
| HC-J6 | 2a | 231 | -M-------- | ----T-D-TWQLQA-V-V | ------ | EKV-T---IPVS-N- | VQQ |  |
| HC-J8 | 2b | 232 | -YA------- | ----S-N-TWQLT--V-L | ------ | ENDNGTLH-IQV-N- | VKH |  |
| CH610 | 2c | 233 | -M-------- | ----S---WQLEG-V-- | ------ | EQI-----PVS-N- | I-Q |  |
| S83 | 2c | 254 | -MP------- | ----S---WQLEG-V-- | ------ | E-TA-V----PVA-NL | ISQ |  |
| NE92 | 2d | 234 | -M-------- | ----Q---WQLR--V-V | ------ | EEK-I---IPVS-NI | VSQ |  |
| BNL3 | 2e | 16 | -MA------- | ----S-N-WQLX--V-V | ------ | ENSSGRFH-IPIS-NI | VSK |  |
| FR4 | 2f | 18 | -MA------- | ----A-D-WQLR--V-V | ------ | E-S--RTF-T-VS-N- | VSR |  |
| BNL4 | 2g | 20 | -MA------- | ----S-N-IWQMQG-V-V | ------ | ELQ-K---IPV-N- | VNQ |  |
| BNL5 | 2h | 24 | -M-------- | ----S---WQLK--V-V | ------ | E-HQ-Q---IPV-N- | VSQ |  |
| BNL6 | 2i | 26 | -M-------- | ----S---WQLEE-V-- | ------ | EWKD-T---IPV-NI | VSQ |  |
| FR13 | 2k | 76 | -M-------- | ----S-X-TWQLXX-V- | ------ | E---S---IPV-X- | XVSR |  |
| BR36 | 3a | 255 | -VL------- | ----S---D-V---- | ----I- | -QD-T-T-TPV--- | VKY |  |
| HCV-TR | 3b | 235 | -VL------- | ----S-G----E-V-- | ----L- | TT--Q-S-TTVST- | V-T |  |
| Z4 | 4a | 256 | --I------- | --------DHH---L | ------ | -MT-T---TPV--- | VAH |  |
| GB809-4 | 4a | 257 | --I------- | ----V---TDHH---L | ------ | -A--V---TPV--- | AVS |  |
| Z1 | 4b | 258 | --I------- | ----T---TEHH-M-L | ------ | -TE-T----PL--- | APY |  |
| GB116 | 4c | 241 | --I------- | --------DYH---L | ------ | ---V--Q---L--- | APY |  |
| GB215 | 4c | 259 | ---------- | --------DHH---L | ------ | ---V--Q-----LS | APY |  |
| GB358 | 4c | 260 | ---------- | --------TEHH---L | ------ | ---V--Q-----L- | APY |  |
| DK13 | 4d | 236 | ---------- | --------TDYH---L | ------ | ---K-T----SL-- | AQH |  |
| CAM600 | 4e | 237 | --I------- | ----A---TENH---L | ------ | ---T--Q-----L- | SPY |  |
| GB809-2 | 4e | 238 | --I------- | ----A---TDNH---L | ------ | --KT--Q-----L- | SPY |  |
| CAMG22 | 4f | 261 | -L-------- | ----F---VHH---L | ------ | ---T--Q-----I-L | APH |  |
| CAMG27 | 4f | 262 | --I------- | ----F---EHH---L | ------ | ---T--Q-----PL | APH |  |
| GB549 | 4g | 243 | ---------- | --------DHH-M-L | ------ | ---T--T-----PL | APY |  |
| GB438 | 4h | 244 | ---------- | --------DHH-M-L | ------ | ---V--V-----IPL | VPY |  |
| BNL7 | 4k | 30 | -Y-------- | --------DHH---L | ------ | ---T--Q-----L- | APY |  |
| BNL8 | 4k | 32 | ---------- | --------DHH---L | ------ | ---T--Q-----L- | APY |  |
| BNL9 | 4k | 34 | --I------- | --------DHH---L | ------ | ---V--Q-S---L- | I-APY |  |
| BNL10 | 4k | 36 | ---------- | --------DHH-AL | ------ | ---V--Q-----L- | APY |  |
| BNL11 | 4k | 38 | ---------- | ----F---DHH---L | ------ | ---K-----H----L | APY |  |

Fig. 4G

```
BNL12   41  ----   ----   -SDHH---L------KT--T----L-----API
GB724   40  --I-   ---V-  -TDHH---L---------T--V-----TPV----AVS
BE95   246  ----   -----  -DNL----A---------MT--V----QI----LSAPS
BE100  239  ----   -----  -D-L----A---------KD-V----QI----LSAPS
BE100  263  ----   -----  -DAM----L---L---VDDR-T--H--V----L-IPN
HK2    240  --L-   -----  -ETL----L---------KXX-Q----QAS--L-VPN
VN4     44  --L-   -----  -NGM----L---------KT--LTK--LSAS--L-VQN
VN12    48  --L-   -----  -ETM----L---------IKA--E---LPVS--L-VPN
FR1     42  --L-   -S-N-F ------------------
NE98    52  -M--   -S-G-  -G-I----L---------S---T----IPVSX---VKS
```

*Fig. 4H*

Fig. 4I

| | | |
|---|---|---|
| BNL12 | 41 | LSA-LMSV---V--M--A---S------------GA-------M---Q----- |
| GB724 | 40 | VDA-LESF---V--M--A----V-----------GA-------M---Q----- |
| BE95 | 246 | LGAVTAP---AV-Y-A-G-A---------A----AL-------M--YR--Q-A- |
| BE100 | 239 | FGAVTAP---AV-Y--G-A---------A----AL-------M--YR--Q-A- |
| HK2 | 263 | AST---GF---V---A-A-VV-S--I-----L--A--------------Q--- |
| VN4 | 240 | AST-V-GF-K-V-IM--A-AF---M---------GL-------LR--M-QV |
| VN12 | 44 | ASVSIRGV-E-V-----A-AF---M---------GL-------R---MYEI |
| FR1 | 48 | SSV-IHGF---V----A-AF---M-I--------II-------R-KY-QV |
| NE98 | 42 | PCAATAS--T-V-MM-XA-------------AL--X--G-SWRH-Q--- |
| | 52 | |

Fig. 4J

| Isolate | Type | SEQ ID | V5 301 TQGCNCSIYPGHITGHRMA 319 |
|---|---|---|---|
| HCV-1 | 1a | 229 | TQGCNCSIYPGHITGHRMA |
| HCV-J | 1b | 230 | V-D---------VS----- |
| BNL1 | 1d | 4 | --E---------------- |
| BNL2 | 1d | 8 | --E---------------- |
| FR2 | 1f | 12 | V-D------S-----XXX |
| HC-J6 | 2a | 231 | V-D------T-------- |
| HC-J8 | 2b | 232 | --E------Q-------- |
| CH610 | 2c | 233 | V-E-----------X |
| S83 | 2c | 254 | V-D-------------- |
| NE92 | 2d | 234 | V-E-------R-------- |
| BNL3 | 2e | 16 | V-E----------------- |
| FR4 | 2f | 18 | V-E-----------X |
| BNL4 | 2g | 20 | S-D----------------- |
| BNL5 | 2h | 24 | V-D----------------- |
| FR13 | 2k | 76 | V-D----L----P--X |
| BR36 | 3a | 255 | V-T----LS---- |
| HCV-TR | 3b | 235 | V-T-----VS---- |
| Z4 | 4a | 256 | --E---T------ |
| GB809-4 | 4a | 257 | --D---T------ |
| Z1 | 4b | 258 | --D---VS---- |
| GB116 | 4c | 241 | --D--A-V---- |
| GB215 | 4c | 259 | --D--A-V---G-- |
| GB358 | 4c | 260 | --D--A-V---- |
| DK13 | 4d | 236 | --D---T------ |
| CAM600 | 4e | 237 | --D---T------ |
| GB809 | 4e | 238 | --E--A------ |
| CAMG22 | 4f | 261 | --D---T------ |
| CAMG27 | 4f | 262 | --E--------- |
| GB549 | 4g | 243 | --D---D------ |
| GB438 | 4h | 244 | --D---V------ |
| BNL7 | 4k | 30 | A-D---------- |
| BNL8 | 4k | 32 | --D---------- |
| BNL9 | 4k | 34 | --D---------- |
| BNL10 | 4k | 36 | --D---------- |
| BNL11 | 4k | 38 | --E---------- |
| BNL12 | 4l | 40 | V-D---------- |

*Fig. 4K*

| | | |
|---|---|---|
| GB724 | 4x  246 | --D-------T------- |
| BE95  | 5a  239 | V-N----S--V------- |
| BE100 | 5a  263 | V-D----S--V---Q--- |
| HK2   | 6a  240 | V-D----T--V------- |
| VN4   | 7c   44 | V-E----T---------- |
| VN12  | 7d   48 | A-D----A---------- |
| FR1   | 9a   42 | --D----XNX--V----- |
| NE98  | 10a  52 | V-D--------------- |

Fig. 5A NS5B nucleotide alignment

```
IsolateType SEQ
ID           793 27981
HCV-1la264   CTCCACAGTCACTGAGAGCGACATCCGTACGGAGGAGGCAATCTACCAAT
HCV-J1b265   ---A--G-------------AT-----------T-----AT---T-----
BE901b266N   -A----------------C----A--------GTT-----T---T-----
BNL11d53     ---G-------T------------AT-------GTC-----AT-----A-
BNL21d55     ---G-------T------A----------T---C---RAT----------
FR171d57     ---G-------T------A----------T---GTC----AT--------
CAM10781e61  ---A--G--------AGCT---T-----A--A-------T-C---A----
FR21f63N     -A-----------------------T--T------A-------T-C----
FR161g67     NNNNNNN-------------------T--T-------GTC----RT---T-
HC-J62a267   ---A----C--------------A-------A-G--T----TC--A--T-GGG
HC-J82b268   ---A----C--------G--------AA-A--A--AT-C--A--T--GG
BNL32e69     ---G---------------A--T--AA--N--T----T-C--A----GG
FR42f71      ---A--C----------A-----G--T--AA-A--T-----T-C--A---TGG
BNL52h73     ---A-------G-G-----A--------A-G--C-----T-C--T---TTG
FR132k77A    -----------------------A--A-----A-AGTT--A---T-CG-T--T-TG-
r*R182179    ---A--------------G-------G----A-G-AT----T-C--A-T--TGG
T13a269      ---A--T----------ACAG-----A-GGT---A----AG--A------
T93b270      ---T--T------------ACAT-----A-G----------AG--A----
PAK643g81    ---T--T---------ACAG--T----A-GGTA--A--A-A---A-----
```

Fig.5B

| IsolateTypeSEQ ID | | | | | | | | | | |
|---|---|---|---|---|---|---|---|---|---|---|
| 79327981 | | | | | | | | | | |
| GB484c271 | ---- | -T- | -A- | -C- | -A-AG | ---- | ---- | A-GGTC | ---- | ---AGG | ---T- | -G- |
| GB1164c272 | ---- | -T- | -A- | -C- | -A-AG | ---- | ---- | -A-GGTC | ---- | --AGG-A | --T- | -G- |
| GB2154c273 | ---- | -T- | -A- | -C- | -A-AA | ---- | ---- | -A-GGTC | ---- | --AGG-A | --T- | -G- |
| GB3584c274 | ---- | -T- | -A- | -C- | -A-AG | ---- | ---- | -A-GGTC | ---- | --AGG-A | --T- | -G- |
| GB8094e275 | ---- | -T- | -G- | ---- | ---A- | ---- | ---- | -AAGGTC | --A- | -A-A-G- | ---T- | -G- |
| GB5494g276 | ---- | -G- | -G- | -C- | -A--G | --T- | ---- | -A-G--C | ---- | ---A-AG | ---- | -G- |
| BNL84k83 | ---- | -T- | -A- | -C- | -A-AG | ---- | ---- | -A-GC-C | ---- | --A-AGG | ---T- | -G- |
| BNL124l85 | ---- | -G- | -G- | ---- | -A-AG | ---- | ---- | -A-GGTC | ---- | ---A-AG | ---T- | ---- |
| EG814m87 | ---- | -C- | -A- | -C- | -A---G | ---- | ---- | -A-GGTC | ---- | ---AGG- | --T- | -G- |
| CHR185a277 | ---- | -G- | -C- | -T- | -C-ACAT | ---- | ---- | -AATG- | --T- | -A--T-T | ---T- | ---- |
| VN137a89 | --A- | ---- | ---- | ---A | ---C- | --TG | ---- | -AG--- | ---- | -C-T-AC | ---- | -G- |
| VN47c91 | ---- | -G- | ---- | ---- | ---C- | ---- | ---- | --RC-C | ---- | -C-C-AC | ---- | ---- |
| VN127d93 | ---- | -T- | -C- | ---- | -G--- | --C- | -T- | --C--T | --AC | -C-C-AC | ---T- | -G- |
| FR19a95A | ---- | ---- | ---- | ---- | -G-G- | -C-- | ---- | ---A-- | -C-A | -ACNA-AC | --T- | -TG- |
| NE9810a97 | ---- | ---T | ---- | ---- | ---CAG | ---- | ---- | -A-GGTA | -ACTTT | -C---TT- | -GG |
| FR141la99 | ---- | ---T | -C- | ---- | ---A- | ---- | -G- | ---A- | -G--A- | -A--AT-C | ---T- | -TG- |
| FR1511a101 | ---- | ---- | -T- | ---- | ---A- | ---- | ---- | ---A- | -A- | -A--AT-C | ---- | ---- |
| FR1911a105 | ---- | -T- | -T- | ---- | ---A- | ---G | -T- | -A--A- | ---A- | -AT-C | ---Y- | -T-TGG |

Fig.5C

| IsolateTypeSEQ ID | 7982 8031 |
|---|---|
| HCV-11a264 | GTTGTGACCTCGACCCCCAAGCCCGCGTGGCCATCAAGTCCCTCACCGAG |
| HCV-J1b265 | ---------T-G-C-----G-----A-GCA-----A-G---A----A--- |
| BE901b266 | ---------T-G-C-----G-G---A-ACA-----A-----G-----A--- |
| BNL1d53 | ---------T-G-C-----G-G---T----AA-----A-----G------- |
| BNL21d55 | ---------T-G-C----YG-G-------AA-----A-----G------- |
| FR171d57 | -C-------T-G-C-----G-G-------AA-----A-----G------- |
| CAM10781e61 | -C----------GC-------G----A-T-A-------A------- |
| FR21f63 | -C-----T--A--------G-G---T---AA-----A-G----------- |
| FR161g67 | -C---------G-C-----G-G---T----A-----A-----G-----T- |
| HC-J62a267 | -C-------TC-T-GCC-GAGG-G----A-ACT-----AC-C---A--G-T--- |
| HC-J82b268 | -C-------TCT--GCCT-AAG-------A-AACT-T---AC-C---G------T--- |
| BNL32e69 | -C-------TC-T-ACC-GAG--G---A-AACT-----AC-C--AT-G--T--- |
| FR42f71 | -CC------CTC-T-ACC-GAG--G-------GACT-----AC-T--AT-A--T--- |
| BNL52h73 | -CC------CTC-T-ACC-GAG----------AACT-----AC-T--AT-G--T--- |
| FR132k77 | -CC------TCA--TCC-GAGG-G--------A--CT-----AC-C---A--A--T--- |
| FR182179 | -CC------CTCGT-GCC-GAGG-G-------GACT-T-----AC-T--G----T--- |
| T13a269 | -C-------A--T--A--GG-G---A-GAGA-TG---TCC-----G------- |
| T93b270 | -C----------T--G--AG-G--T--GAA--G----GCG-T-----A------- |
| PAK643g81 | -----------T---G--GG-G--TA-ACG----A------G----G--A |

Fig.5D

```
IsolateTypeSEQ
ID
79828031
GB484c271      -------------G--G----G-------------AA----A--T-CCG----A--A---
GB1164c272     -------------G--G----G-------------AGA--A--T-CCG----A--A---
GB2154c273     -------------G--G----G-------------AA--TA--T-CCG----A--A---
GB3584c274     -------------G--G----G-------------AA---A--T-CTG----A--A---
GB8094e275     ----------T--G--G----G-------------AA--TA--AGCCG----A--A---
GB5494g276     -C---C-------G--G----G-------------AA--TG--ATCCG----A--G--A
BNL84k83       -------------G--G----G------T------AA--TT--T-CCG----A--A
BNL124185      -------------G--R----G-------------AAA--A--ATCCG----A-------
EG814m87       --------T----G--G---AG-G-----------AA---A--ATCCG----G-------
CHR185a277CA-TGT--T-GC-G--TG-G--T--G-T----A--ACG----A----C-A
VN137a89-C---A-GT-G--G----GC---A--GACA----CA--G--T--T--C
VN47c91-C---CC-A--T-----GGTG--A---AA----T--T-CA--T--G--T---
VN127d93-C---CC-AT-A--T--GGT---A--GAAA----T-CA--T--T--T---
FR19a95CC--CC-G-------AG-G-----GAAA---A----T------T---
NE9810a97CC------A-GGA-G-G--TA-GAG--TG--A-CT---A-----G---
FR1411a99C----C-AT-GCCTGAAG--G-------GAAA-------T--A--G--A---
FR1511a101C-----C-AT-GCC-GAAG-G------GAA----------T--A--A--G--A---
FR1911a103C-----C-AT-GCC-GAAG-G------GAA-------A--A--G--A---
```

Fig.5E

```
IsolateTypeSEQ
ID
       8032 8081
HCV-1la264AGGCTTTTATGTTGGGGCCCCTCTTACCAATTCAAGGGGGAGAACTGCGG
HCV-J1b265C-------------C-----T--C--G--T------G-A----C-------
BE901b266C---------A-C-----T--C--G--T--------A----C-------T--
BNL11d53C-----G---CA-C----------Y--A-----------AA--AC--------
BNL21d55C-----G--C--C-----------C--A-----------A---C---------
FR171d57C-----G---A-C-----------C--A-----C-----AA--C---------
CAM10781e61-------G--C--C-----C-----G--CT-G---------AA--------
FR21f63--------A---------------T--C--G--A--C-------AA---C-----
FR161g67C-----A-----C----------C-----C-----C----AA--AC--------
HC-J62a267--A-----C--G--A--G--CA-GTT---CAGC-A-----CC---C------
HC-J82b268--A-----C--A--A--G--CA-G--A--CAGC-AA----C-ATC-------
BNL32e69--A--C--C--A--A--G--CA-G-TG--CAGC-AA----C-ATC---------
FR42f71--A-----C--G--A--G--CA-G-TG--CAGC-AA----C--TC----------
BNL52h73--A-----C--A--A--G--CA-G-TG--CAGC-A-----AC--TC--------
FR132k77-----G--C--G--A--T--CA-GCAG--CAGC-A-----C-ATC---------
FR182l79--A--C--CA-A--C--G--GA-G-TG--CAGC-AA----CC--TC-----T--
T13a269C----------CTGC--------A-GTT---CAGC-A-----CCC-A--T----
T93b270C-----G---CA-C--A--T--CA-GTA---CAGT-A----CAGC-G--------
PAK643g81C---------C------A--T--CA-GTT---CAGC-A-----CTC--A----
```

Fig. 5F

```
IsolateTypeSEQ
ID              80328081
GB484c271--A--C--C--G--C--T---CA-GCAT--CAGC-A---A--CCTG----
GB1164c272--A--C--C--G--C--T---CA-GCAT--CAGC----A--CCTG----
GB2154c273--A--C--C-----G--C--T---CA-GCAT--AGC-AA--A--CCTG----
GB3584c274--A--C-----G--C--T---CA-GCAT--CAGC-A---A--CCTG--T--
GB8094e275--A--C--C--G--C--T---CA-GCAT--CAGC-A---A--CCTT----
GB5494g276--A--C--C--G--C-----T--CA-GTA---C--C-A-----CCTA----
BNL84k83---A--C--C--G--C-----CA-GCA---CAGC-A---A--CCTT--T--
BNL124185--R--C--CT-G--C------CA-GTAT--CAGC-AA-------CT----
EG814m87---A--C-----G--C--T---CA-GTTT--CAGC-A---A--CCTA--T--
CHR185a277C-C--G--CTG-----A----CA-GTAT--CAGC-A---C-AC-A--T--
VN137a89C-AT-G--CTNC--T--T---CA-GTNT--C--T-AA--TC-GCA--T--
VN47c91C----G---CTGC--W---G--CA-G-TG---C--CC-T--TC-ATCA--T--
VN127d93C----G--CTGC--C------CA-GTA----C--TC-A--TC--TCA--T--
FR19a95----C---------C--------A-GTA---C---A----CC-ACT---T--
NE9810a97C-------CTG---T--T---A-GTT---CAGC-A---AC-AC------
FR1411a99--A--A--C--G--C------GA-GGAA--CAGC-A---CC--GCT----
FR1511a101--A--A--C--G--C------GA-GGAA--CAGC-AA--CC--GC----
FR1911a105--A--C-----G--C------GA-GGAA--CAGC-A----CC--GC----
```

Fig.5G

| IsolateType | SEQ ID |
|---|---|
| | 80828131 |

```
HCV-11a264 CTATCGCAGGTGCCGCGGCGAGCGGCGTACTGACAACTAGCTGTGGTAACA
HCV-J1b265T------------C----------A--T------G-------G----C---C----
BE901b266----------C-A------------A------------G------G-C----C----T-
BNL11d53-----C---TC--------------C------G---T--C----------C--------
BNL21d55-------TC-------T--------T------G----C-C----------C--------
FR171d57----C---TC----------------C------G------T--C---------T-----
CAM10781e61----------------A----T--C-----CT-----------C----C--------
FR21f63----C------C-A----T-A-------------C---G---------------C--C--
FR161g67----------C-------T------T-------T----G---T--------C-------
HC-J62a267G---CA-GC-T----------C---G-G-T--C------ATG--G------
HC-J82b268---CA-GC-T----------A--T--TT-C--C--ATG--G--T-
BNL32e69A---CA-GCAT-----------C----A--G--C--C--C--TATG--G--T-
FR42f71A---CA-GC-T----------T------A--G--C--C--C--TATG--G------
BNL52h73T---CA-AC-T-----------C-----A--G--C--C--C-----ATG--G--T-
FR132k77A---CA-GC-C-----------C-----G--G--C--C--C-----ATG--G--T-
FR182l79A---CA-GC-T--------T-------G--GT-C--C---------ATG--C--T-
T13a269T------------C-------T--C--T-A---C---C-T--C------TC---C-----
T93b270------------C-C-----C---------------------CT--C-T-----TC--C--T-
PAK643g81A-----------C-T-----T------T----T---C--C--------AC------T-
```

Fig.5H

```
IsolateTypeSEQ
ID                    8082 8131
GB484c271G------------A--T------A-----------CTAC--C--C-------TC--G-----
GB1164c272G-------------A------T------------CTAC--C--C-------TC--G-----
GB2154c273G-------------A-------------A-----CTAC--C--C-------TC--G-----
GB3584c274G-------------A-------------A-----CTAC--C--C-------TC--G-----
GB8094e275G----------------A----------A------TAC--C--C-------TC--G-----
GB5494g276GC-A--G------T--A-----------------G-CTAC--C--C-----TC--G-----
BNL84k83G------G--A----------A--------------CTAC--G--C-------TC--A-----
BNL124185G-------G------------------------A-GTAC--C--A--T-TC--G--------
EGB14m87----C--------------------A--------------CTAC--C--C-------TC--A-----
CHR185a277T-----------T--A--------------C-----CT--C--C-------TATG--C---
VN137a89A----C--T-------A-G--C--T--------CT-----C--C--T-CTG--CC--T-
VN47c91A----C--T--------------A--C--T----------G--C--C--G----TG--C--T-
VN127d93G---C--------------------G--T--T--T--CT-C--C--A------TG--C---
FR19a95TC-A---C-A---------A--A-----A----CC--C--A----ATG---------
NE9810a97T--C----C-C----T--T--G--G--AC--C--C-------TC--G-----
FR1411a99A---A-GC-T--------------A---------G--T-C--C--C--A---TG--G-----
FR1511a101A--A-GC-T----------------------G----T-C--C--A----TG--G-----
FR1911a105A--CA-GC-T-----------------A-----G----T-C--C--A----TG--G-----
```

Fig. 5I

Fig. 5J

```
IsolateTypeSEQ
ID                    8132 8181
GB484c271--A---G--G-----C-----A----TCA--C--TATCAA---G--G-------G
GB1164c272--A---G--G-----TC----A----TCA--C--TATCA----G--G-------G
GB2154c273--A---G--G-----TC----A----TCA--C--ATCA-G--GT---------G
GB3584c274--A---G--G-----C-----A----TCA--C--TATCA---G--G-------G
JB8094e275--AA--G--G-----G-----------C-T---------ATCA-G--T--G---A
GB5494g276--TG-A--G-----T--TC---------GTT--G--TAC-A-G----------T--G
BNL84k83---A---G--G-----C-----A----TCA--T--TAT-A---G----------G
BNL124185--AG-G--C-----TC-T---------ACC----TACCA-G--T-----C--A
EG814m87---A---G--C-----C----------AC--C--TACCA----G--C--C--G
CHR185a277--A-G--G-----G---------T----TTTA--CT----A------AA---
VN137a89---T---G--------------T-G--A--T-A---G--A--CA----T--C----G
VN47c91---------A---A----TT-G--A--A-AA----G---A-G--A---AA---
VN127d93---A-G--A-----C-G-----T-A---G-T---A-G--A--RAA---
FR19a95----A------A-----T-C-G-----AACC--C--T--C---A--C--CT-T
NE9810a97--AA-----C--T-------A--AAA---TACCAA--T--C--AA-T
FR1411a99--A-G-----T-------A--TAAA--G--T---AA----T--CA-T
FR1511a101--A-G-----T--------------AAR----T---AA--Y-T-CA-T
FR1911a105--A-G-----T-------A----AA---G--T----AA----T--CA-T
```

Fig. 5K

```
IsolateTypeSEQ
ID                      818 8231
HCV-11a264CAGGACTGCACCATGCTCGTGTGTGGCGACGACTTAGTCGTTATCTGTGA
HCV-J1b265----------G--------AAC--A----C-T------------------
BE901b266----------G------------C--G----C-T-----------------
BNL11d53-G----------------------C--G--T--C-T-----------------
BNL21d55---------------G-------C--A----C-T-----------------
FR171d57-----------------A-----C--A----C-T-----------------
CAM10781e61--------------------------C--------C-------------C--
FR21f63-------T---T-A------C-----------C-T------G-----------
FR161g67-G---A----A----------------------C-C-------C--------
HC-J62a267ATT-CGCC---A-------G--A--C------T-----G--T--C----CA--
hC-J82b268GT----CCTGTT---T-G---------A----C-G------C----CA--
BNL32e69GT--C-CC-------G--------C----------T---C----T--C----CA--
FR42f71GTT-C-CC----G---------G----T--C-G--T--C----CA--
BNL52h73GTT-CTCC---G------G--T--------TC-G---A-C-----C----CA--
FR132k77GTT-CACC---A------G----------------C-G------C----CA--
FR182l79G-C-C-CC---A---T-G--A---------------C-G------C----CA--
T13a269--G-A---CCGGA-T-T---C--C--A--T--TC-G----AG-GGC---
T93b270A--A---CCAT-TT-C--T--C--C--A---T--G---G--A-C---
PAK643g81--A---CCAT-AT-C--T--C--C--A--T--T--G---G--AG-GGC---
```

Fig. 5L

Fig. 5M

```
IsolateType SEQ
ID                    8  2 3 2 8271
HCV-11a264 AAGCGCGGGGGTCCAGGAGGACGCGGCGAGCCTGAGAGCC
HCV-J1b265 G--T------AAC-------T----GC---AC----- 
BE901b266  ---------AAC---A-----------------AC---T-
BNL11d53 G--T------A---G----A--------A--AC---T-
BNL21d55 G---------A---G-------------A--AC---T-
FR171d57 G--T--R--A---G-----------T--A--AC---T-
CAM10781e61 G--T-TA---AC------------T------------C-
FR21f63 G-T--A----N---N----TC--T-- 
FR161g67 G--T---------------T--T--A---
HC-J62a267 G----CA----AC-G--------A-CG--A------
HC-J82b268 G---CAA---TAA-G--------A-CGA-A------T
BNL32e69 G--TCA----A---G--------ACCG--A------
FR42f71 G--TCA------CTG-------A-CGA-A-------T-
BNL52h73 G--TCA---AAC-G----T-A-CG--A-------T-
FR132k77 G--TCA---ACTG--AG-----A-AAC-A-----C-T
FR182l79 G--TCA-----AC-G--------A-CGA-AT-----T-
T13a269 G----AT--C--G-T-----TAGA--AGC------
T93b270 ---TGC--C--G--------AGA--AGCT---C----
PAK643g81 G--TTGC-KC--TG-T-----G-ATAG-GCAGC
```

Fig.5N

```
IsolateTypeSEQ
ID                  82328271
GB484c271G----AT--C--AG--------AAACGACC---CG-------
GB1164c272-----AT--C--AG--------AAACGAGC---CG-------
GB2154c273G----AT--C--AG--------AAACGAGC---CG----T--
GB3584c274G----AT--C--TG--------AAACGAGC---CG-------
GB8094e275G----GT--C--TG--------AAACGANC---CG----T--
GB5494g276G----GC--C--AG--------T--AAGAGC---CC-------
BNL84k83G------AT--C--AG--------TAACCGAGC---CCN------
BNL12418SG-----A---C--AG--------TT-CCAACC---CC-------
EG814m87G------AT--C--GG-C-------CGCCGAGC---CCA---T--
CHR185a277G---CA-----ACG--C------TAAA--------------
VN137a89G--TTT-------TC----------A-TAGTGCA---C----T--
VN47c91G---T-GA--A----TCT-----T--TT-ACGC----C----A--
VN127d93G-----GA--A-----CT-----T---C-G-GC-----C---T--
FR19a95G---T--T--A-----A-C------TATC-T-A-----C------
NE9810a97G-T--A-----A--G-T-----AA-AGCGC-T------T--
FR141la99-----AA------------GG---------CA-CG-GA---AC---T--
FR151la101G----AA-----------AG---------CA-CGAGA---AC-----
FR191la105----AA-----------GG---------CAACGAGA---AC--NT-
```

Fig. 6A  NS5B amino acid alignment

| Isolate | Type | SEQ ID | 2645 STVTESDIRTEEAIYQCCDLDPQARVAIKSLTERLYVGGPLTNSRGENCG 2694 |
|---|---|---|---|
| HCV-1 | 1a | 278 | -----N----------S-------A-E--Q--R----------------K-Q--- |
| HCV-J | 1b | 279 | ----------------------H-D--A---N----------------K----- |
| 2TY4 | 1c | 280 | -----N---V--S-------A-E--K---------I--X--------K-Q--- |
| BNL1 | 1d | 54 | -----N------XS------AXE--K-----------------------K-Q--- |
| BNL2 | 1d | 56 | -----N---V--S-------A-E--K------I---------------K-Q--- |
| FR17 | 1d | 58 | -----A----------S-------H-E-------I---------------K----- |
| CAM1078 | 1e | 62 | ----------------S-------E-K--R---------------------K-Q--- |
| FR2 | 1f | 64 | --XX-------V-XS-----A-E-------------------------K-Q--- |
| FR16 | 1g | 68 | -----R----------S--RA-S-PEE-HT--H-------MF---K-QT- |
| HC-J6 | 2a | 281 | -----R----------S---A-S-PQE--TV-H-------M---K-QS- |
| HC-J8 | 2b | 282 | ----------------S-S-PEE---T---H-------M---K-QS- |
| ARG8 | 2c | 283 | -----R----------S--LA-S-PE---T--H-------ML--K-QT- |
| NE92 | 2d | 284 | -----R---X------S---A-S-PE---T--H-------MM--K-QS- |
| BNL3 | 2e | 70 | -----R----------S--LA-S-PE---T--H-------MM--K-QS- |
| FR4 | 2f | 72 | ----A-R---------S--LA-S-PE---T--H-------MM--K-QS- |
| BNL5 | 2h | 74 | -----R---V--SV-LS-S-PEE--A--H-------MQ--K-QS- |
| FR13 | 2k | 78 | -----R---N--S-FLA-S-PEE--TV-H----I---MM--K-QS- |
| FR18 | 2l | 80 | -----R---N--S-FLA-S-PEE--TV-H----I---MM--K-QS- |
| BR34 | 3a | 285 | -----------------------E-E--K--SA-----C---MF--K-AQ- |
| BR36 | 3a | 286 | -----H----------E-------E-E--K----------C---MF--K-AQ- |
| BR33 | 3a | 287 | -----------------------E-E--K---R----C---MF--K-AQ- |
| T9 | 3b | 288 | -----------V--E---------------------I---MY--K-LQ- |
| PAK64 | 3g | 82 | -----Q---V--E-------E-E--R------------MF--K-LK- |

Fig. 6B

| | | | | | | | | |
|---|---|---|---|---|---|---|---|---|
| GB48 | 4c | 289 | ------ | -K---V--EV- | ----- | -E--E--K--TA- | ----- | -MH--K--DL- |
| GB116 | 4c | 290 | ------ | -K---V--EV- | ----- | -E--E--R--TA- | ----- | -MH---DL- |
| GB215 | 4c | 291 | ------ | -K---V--EV- | ----- | -E--E--KV-TA- | ----- | -MH--K--DL- |
| GB358 | 4c | 292 | ------ | -K---V--EV- | ----- | -E--E--KV-TA- | ----- | -MH--K--DL- |
| GB809 | 4e | 293 | ------ | -R--KV--EV- | ----- | -E--E--KV-AA- | ----- | -MH--K--DL- |
| CAMG22 | 4f | 294 | ------ | -R---V--EV- | ----- | -E-ET--KV-SA- | ----- | -MH---DL- |
| GB549 | 4g | 295 | ------ | -R----E- | ----- | -E--E--KV-SA- | ----- | -MY--K--DL- |
| GB438 | 4h | 296 | ------ | -R---V--E- | ----- | -E--E--KV-SA- | -K--- | -MY--K--DL- |
| CAR4/12054 | 4i | 297 | P----- | -R--X-V--EV- | -N | EXDX-KV-NA- | ----- | -MH--K--DL- |
| CAR1/501 | 4j | 298 | ------ | ---X-R---GEV- | -V--- | -E--E--K--TA- | ----- | -MF--K--DL- |
| EG13 | 4? | 299 | ------ | ------ | -N--- | -E--E--K--TA- | ----- | -MH--K--DL- |
| BNL8 | 4k | 84 | ------ | -K---P--EV- | ----- | -E--E--K--SA- | -X--L--- | -MY--K--L- |
| BNL12 | 4l | 86 | ------ | -K---V--E- | ----- | -X-E--K--SA- | ----- | -MF--K--DL- |
| EG81 | 4m | 88 | ------ | -R---V--EV- | ----- | -E--E--K--SA- | ----- | -MF--K--DL- |
| BE95 | 5a | 300 | ------ | -H---M---S- | -S--- | -Q-E--A--R- | -Q---C--- | -MY--K--QQ |
| CHR18 | 5a | 301 | ------ | -H---M---S- | -SLY- | -Q-E---R- | -Q---C--- | -MY--K--QQ |
| VN13 | 7a | 90 | ------ | -R-VQ---HD- | ----- | -K-E-A--T--T- | -D--X--- | -MX--K--QA- |
| VN4 | 7c | 92 | ------ | -R--X---HD- | -Q--- | ---V--K--T- | ----- | -MM---QS- |
| VN12 | 7d | 94 | -S---- | -R------ | -HD- | -Q----V--K--T- | -CX--- | -MM---QS- |
| FR1 | 9a | 96 | ------ | ---GR----XD- | -LS-Q- | ---E---K-- | -C--- | -MY---QL- |
| NE98 | 10a | 98 | ------ | -Q---V-LS-F-A- | -KDE--RV-T- | ----- | -MF--K--QH- |
| FR14 | 11a | 100 | ------ | -R------S--LS-Q-PEE--K- | ----- | ----- | -ME--K--QA- |
| FR15 | 11a | 102 | ------ | -R-----S-XXA-Q-PEE--K- | ----- | ----- | -ME--K--QA- |
| FR19 | 11a | 106 | ------ | -R-----SX-LA-Q-PEE--K- | ----- | ----- | -ME--K--QA- |

Fig. 6C

| Isolate | Type | SEQ ID | 2695 YRRCRASGVLTTSCGNTLTCYIKARAACRAAGLQDCTMLVCGDDLVVICE 2744 |
|---|---|---|---|
| HCV-1 | 1a | 278 | -------------------------------------------------- |
| HCV-J | 1b | 279 | ----------------------L--T----K------------N----- |
| 2TY4 | 1c | 280 | -------------------------L-------R---------------- |
| BNL1 | 1d | 54 | ----------------------L------K-R------------------ |
| BNL2 | 1d | 56 | -----------------------L-----K-------------------- |
| FR17 | 1d | 58 | -----------------------L-----K-------------------- |
| CAM1078 | 1e | 62 | -----------------------L-----K-------------------- |
| FR2 | 1f | 64 | ------------------------------K----------------S-- |
| FR16 | 1g | 68 | ----------------------L-A----K-RE----------------- |
| HC-J6 | 2a | 281 | -----------------M---------V-L---K---IIAP-------S- |
| HC-J8 | 2b | 282 | -----------------M-I---------L---K---IV-PV------S- |
| ARG8 | 2c | 283 | ---------A-------M-----------V---N---IVAP--------- |
| NE92 | 2d | 284 | -----------------M-I---------V-Q-K---IIAP-------S- |
| BNL3 | 2e | 70 | --H--------------M-I---------V---K---IVAP-------S- |
| FR4 | 2f | 72 | -----------------M-I---------V---K---IVAP-------S- |
| BNL5 | 2h | 74 | -----------------M-I---------L-Q-K---IVAP-------S- |
| FR13 | 2k | 78 | -----------------M-I---------V---------IVAP-----S- |
| FR18 | 2l | 80 | ---------F-------M-F-I-------V-M-----IDAP-------S- |
| BR34 | 3a | 285 | -----------------P-F-I-------T-A----T-A----RNPDF----VA- |
| BR36 | 3a | 286 | -----------------P-F-I-------T------T-AK---RSPDF----VA- |
| BR33 | 3a | 287 | -----------------P-F-I-------T------T-AK---RNPDF----VA- |
| T9 | 3b | 288 | -----------------P--------------K-S---K-PSF----VS- |
| PAK64 | 3g | 82 | -----------------P-Y-I-------------A------PSF----VA- |

Fig. 6D

| | | | | | | | | |
|---|---|---|---|---|---|---|---|---|
| GB48 | 4c | 289 | - | -Y- | -F- | -L- | -S- | IK- | -R- | -A- |
| GB116 | 4c | 290 | - | -Y- | -F- | -L- | -S- | -I- | -R- | -A- |
| GB215 | 4c | 291 | - | -Y- | -F- | -L- | -S- | -I-S | -R- | -A- |
| GB358 | 4c | 292 | - | -Y- | -F- | -L- | -S- | -I- | -R-Y | -A- |
| GB809 | 4e | 293 | - | -Y- | -F- | -M- | -L- | -S- | -I- | -K- | -A- |
| CAMG22 | 4f | 294 | - | -Y- | -F- | -M- | -FL- | -T- | -TK | -A- |
| GB549 | 4g | 295 | Q- | -Y- | -F- | -V- | -L- | -V- | -T- | -KG-S | -A- |
| GB438 | 4h | 296 | L- | -Y- | -F- | -V- | -L- | -T- | -T- | -K- | -S- |
| CAR4/1205 | 4i | 297 | I- | -Y- | -F- | -L- | -T- | -T- | -K- | -A- |
| CAR1/501 | 4j | 298 | Q- | -Y- | -F- | -L- | -T- | -T- | -K- | -S- |
| EG13 | 4? | 299 | - | -F- | -F- | -L- | -T- | -I- | -R- | |
| BNL8 | 4k | 84 | - | -Y- | -F- | -L- | -S- | -I- | -R- | -A- |
| BNL12 | 4l | 86 | - | -Y- | -F- | -V- | -L- | -T- | -K- | -A- |
| EG81 | 4m | 88 | - | -Y- | -F- | -L- | -T- | -T- | -K- | -A- |
| BE95 | 5a | 300 | - | -F- | -M- | -M- | -L-S | -R-R | -L- | -A- |
| CHR18 | 5a | 301 | - | -F- | -M- | -M- | -L-S | -K- | -L- | -S- |
| VN13 | 7a | 90 | - | ILA | -L- | -Q- | | -K- | -FD- | -A- |
| VN4 | 7c | 92 | - | -L- | -L- | -L- | -Q- | -K- | -KNYD | -A- |
| VN12 | 7d | 94 | - | -F- | -M- | -I- | -FL- | -Q- | -XK- | -KNFD | -A- |
| FR1 | 9a | 96 | Q- | -P- | -M- | -I- | -FL- | -T- | -FT- | -YD | -VT- |
| NE98 | 10a | 98 | - | -P- | -F- | -I- | -T- | -K- | -TK- | -IKNPSF | -A- |
| FR14 | 11a | 100 | - | -F- | -L- | -M- | -K- | -K- | -IV-PV | -S- |
| FR15 | 11a | 102 | - | -F- | -L- | -M- | -X- | -KX- | -IV-PV | -S- |
| FR19 | 11a | 106 | - | -F- | -L- | -M- | -K- | -K- | -IV-PV | -S- |

Fig. 6E

| Isolate | Type | SEQ ID | 2745 SAGVQEDAASLRA 2757 |
|---|---|---|---|
| HCV-1 | 1a | 278 | ------------- |
| HCV-J | 1b | 279 | ---T-----A--- |
| BE90 | 1b | 302 | ---T-------V- |
| BNL1 | 1d | 54 | ----E---N---- |
| BNL2 | 1d | 56 | ----E---N--V- |
| FR17 | 1d | 58 | -X--E---N--V- |
| CAM1078 | 1e | 62 | -V-T--------- |
| FR2 | 1f | 64 | IE-XX--PS---- |
| FR16 | 1g | 68 | ------------- |
| HC-J6 | 2a | 281 | -Q-TE--ERN--- |
| HC-J8 | 2b | 282 | -Q-NE--ERN--- |
| NE92 | 2d | 284 | -Q-TE--ERN--- |
| BNL3 | 2e | 70 | -Q--E--DRN--- |
| FR4 | 2f | 72 | -Q-AE--ERN--V |
| BNL5 | 2h | 74 | -Q-TE--ERN--V |
| FR13 | 2k | 78 | -Q-TER-ENN--P |
| FR18 | 2l | 80 | -Q-TE--ENN--V |
| GR34 | 3a | 285 | -Q-TE--ERN--V |
| BR36 | 3a | 286 | ------------- |
| BR33 | 3a | 287 | ------------- |
| T9 | 3b | 288 | -C--E--R-A--- |
| PAK64 | 3g | 82 | -CX-D-EDRAALR |

*Fig. 6F*

| | | | | |
|---|---|---|---|---|
| GB48 | 4c | 289 | -D--E--- | KRP-G- |
| GB116 | 4c | 290 | -D--E--- | KRA-G- |
| GB215 | 4c | 291 | -D--E--- | KRA-GV |
| GB358 | 4c | 292 | -D--E--- | KRA-G- |
| GB809 | 4e | 293 | -G--E--- | KRX-G- |
| CAMG22 | 4f | 294 | -D--E--- | RRA-G- |
| GB549 | 4g | 295 | -G--E--- | -RA--- |
| GB438 | 4h | 296 | -G--E--- | -RA--- |
| CAR4/12054 | 4i | 297 | -I--ID-- | KQA--T |
| CAR1/501 | 4j | 298 | ----E--- | PXTX-P |
| BNL8 | 4k | 84 | -D--E--- | NRA-X- |
| BNL12 | 4l | 86 | -E--E--- | SQP--- |
| EG81 | 4m | 88 | -D--D--- | RRA-Q- |
| BE95 | 5a | 300 | -Q--TH-- | E---- |
| CHR18 | 5a | 301 | -Q--TH-- | K---- |
| VN13 | 7a | 90 | -L--S--- | TSA--- |
| VN4 | 7c | 92 | -G--S--- | VDA--- |
| VN12 | 7d | 94 | -G--P--- | GA---V |
| FR1 | 9a | 96 | ---N--- | I-N--- |
| NE98 | 10a | 98 | ---ID--- | KSA--- |
| FR14 | 11a | 100 | -K--E--- | QRD--V |
| FR15 | 11a | 102 | -K--E--- | QRD--- |
| FR19 | 11a | 106 | -K--E--- | QRD--- |

SEQUENCES OF HEPATITIS C VIRUS GENOTYPES AND THEIR USE AS PROPHYLACTIC, THERAPEUTIC AND DIAGNOSTIC AGENTS

This is a divisional of application Ser. No. 08/836,075, filed Apr. 21, 1997, pending, which is a 371 U.S. national phase of PCT/EP95/04155, filed Oct. 23, 1995.

The invention relates to new sequences of hepatitis C virus (HCV) genotypes and their use as prophylactic, therapeutic and diagnostic agents.

The present invention relates to new genomic nucleotide sequences and amino acid sequences corresponding to the coding region of these genomes. The invention relates to new HCV types and subtypes sequences which are different from the known HCV types and subtypes sequences. More particularly, the present invention relates to new HCV type 7 sequences, new HCV type 9 sequences, new HCV types 10 and new HCV type 11 sequences. Also the present invention relates to new HCV type 1 sequences of subtypes 1d, 1e, 1f and 1g; new HCV type 2 sequences of subtypes 2e, 2f, 2g, 2h, 2i, 2k and 2l; new HCV type 3 sequences of subtype 3g, new HCV type 4 sequences of subtypes 4k, 4l and 4m; a process for preparing them, and their use for diagnosis, prophylaxis and therapy.

The technical problem underlying the present invention is to provide new HCV sequences from until now unknown HCV types and/or subtypes. More particularly, the present invention provides new type-specific sequences of the Core, the E1 and the NS5 regions of new HCV types 7, 9, 10 and 11, as well as of new variants (subtypes) of HCV types 1, 2, 3 and 4. These new HCV sequences are useful to diagnose the presence of HCV type 1, and/or type 2, and/or type 3, and/or type 4, and/or type 7, and/or type 9, and/or type 10, and/or type 11 genotypes or serotypes in a biological sample. Moreover, the availability of these new type-specific sequences can increase the overall sensitivity of HCV detection and should also prove to be useful for prophylactic and therapeutic purposes.

Hepatitis C viruses (HCV) have been found to be the major cause of non-A, non-B hepatitis. The sequences of cDNA clones covering the complete genome of several prototype isolates have been determined (Kato et al., 1990; Choo et al., 1991; Okamoto et al., 1991; Okamoto et al., 1992). Comparison of these isolates shows that the variability in nucleotide sequences can be used to distinguish at least 2 different genotypes, type 1 (HCV-1 and HCV-J) and type 2 (HC-J6 and HC-J8), with an average homology of about 68%. Within each type, at least two subtypes exist (e.g. represented by HCV-1 and HCV-J), having an average homology of about 79%. HCV genomes belonging to the same subtype show average homologies of more than 90% (Okamoto et al., 1992). However, the partial nucleotide sequence of the NS5 region of the HCV-T isolates showed at most 67% homology with the previously published sequences, indicating the existence of yet another HCV type (Mori et al., 1992). Parts of the 5' untranslated region (UR), core, NS3, and NS5 regions of this type 3 have been published, further establishing the similar evolutionary distances between the 3 major genotypes and their subtypes (Chan et al., 1992). Type 4 was subsequently discovered (Stuyver et al., 1993b; Simmonds et al., 1993a; Bukh et al., 1993; Stuyver et al., 1994a). As well as type 5 (Stuyver et al., 1993b; Simmonds et al., 1993c; Bukh et al., 1993; Stuyver et al., 1994b), and type 6 HCV groups (Bukh et al., 1993; Simmonds et al., 1993c). An overview of the present state of the art regarding HCV genotypes is given in Table 3. The nomenclature system proposed by the inventors of the present application has now been accepted by scientists worldwide (Simmonds et al., 1994).

The aim of the present invention is to provide new HCV nucleotide and amino acid sequences enabling the detection of HCV infection.

Another aim of the present infection is to provide new nucleotide and amino acid HCV sequences enabling the classification of infected biological fluids into different serological groups.

Another aim of the present invention is to provide new nucleotide and amino acid HCV sequences ameliorating the overall HCV detection rate.

Another aim of the present invention is to provide new HCV sequences, useful for the design of HCV prophylactic or therapeutic vaccine compositions.

Another aim of the present invention is to provide a pharmaceutical composition consisting of antibodies raised against the polypeptides encoded by these new HCV sequences, for therapy or diagnosis.

All the aims of the present invention are met by the following embodiments of the present invention.

The present invention relates more particularly to an HCV polynucleic acid, having a nucleotide sequence which is unique to a heretofore unidentified HCV type or subtype which is different from HCV subtypes 1a, 1b, 1c, 2a, 2b, 2c, 2d, 3a, 3b, 3c, 3d, 3f, 4a, 4b, 4c, 4d, 4e, 4f, 4g, 4h, 4i, 4j, 5a or 6a, with said HCV subtypes being classified as in Table 3 by comparison of a part of the NS5 gene nucleotide sequence spanning positions 7932 to 8271, with said amino acid numbering being shown in Table 1, and with said polynucleic acid containing at least one nucleotide differing from said known HCV nucleotide sequences, or the complement thereof. The sequence of known HCV isolates may be found in any nucleotide sequence database known in the art (such as for instance the EMBL database).

The present invention thus also relates to a polynucleic acid having a nucleotide sequence which is unique to at least one of HCV subtypes 1d, 1e, 1f, 1g, 2e, 2f, 2g, 2h, 2i, 2k, 2l, 3g, 4k, 4l, 4m, 7a, 7c or 7d, with said HCV subtypes being classified as defined above.

The present invention thus also relates to a polynucleic acid having a nucleotide sequence which is unique to at least one of HCV types 9, 10 or 11, with said HCV types being classified as defined above.

It is to be noted that the nucleotide(s) difference in the polynucleic acids of the invention may involve an amino acid difference in the corresponding amino acid sequences encoded by said polynucleic acids. A composition according to the present invention may contain only polynucleic acid sequences or polynucleic acid sequences mixed with any excipient known in the art of diagnosis, prophylaxis or therapy.

According to a preferred embodiment, the present invention relates to a polynucleic acid encoding an HCV polyprotein comprising in its amino acid sequence at least one of the following amino acid residues:
I15, C38, V44, A49, Q43, P49, Q55, A58, S60 or D60, E68 or V68, H70, A71 or Q71or N71, D72, H81, H101, D106, S110, L130, I134, E135, L140, S148, T150 or E150, Q153, F155, D157, G160, E165, I169, F181, L186, T190, T192 or I192 or H192, I193, A195, S196, R197 or N197 or K197, Q199 or D199 or H199 or N199, F200 or T200, A208, I213, M216 or S216, N217 or S217 or G217 or K217, T218, I219, A222, Y223, I230, W231 or L231, S232 or H232 or A232, Q233, E235 L235, F236 or T236, F237, L240 or M240, A242, N244, N249, I250 or K250 or R250, A252 or C252, A254, I255 or V255, D256 or M256, E257, E260 or K260, R261, V268, S272 or R272, I285, G290 or F290, A291, A293 or L293 or W293, T294 or A294, S295 or H295, K296 or E296, Y297 or M297, I299 or Y299, I300, S301, P316, S2646, A2648, G2649, A2650, V2652, Q2653, H2656 or L2656, D2657, F2659, K2663 or Q2663, A2667 or V1667, D2677, L2681, M2686 or Q2686 or E2686, A2692 or K2692, H2697, I2707, L2708 or Y2708, A2709, A2719 or M2719, F2727, T2728 or D2728, E2729, F2730 or Y2730, I2741, I2745, V2746 or E2746 or L2746 or K2746, A2748, S2749 or P2749, R2750, E2751, D2752 or N2752 or S2752 or T2752 or V2752 or I2752 or Q2752, S2753 or D2753 or G2753, D2754, A2755, L2756 or Q2756, R2757,
with said notation being composed of a letter representing the amino acid residue by its one-letter code, and a number representing the amino acid numbering according to Kato et al. (1980), as shown in Table 1, or a part of said polynucleic acid which is unique to at least one of the HCV subtypes or types as defined in Table 5, and which contains at least one nucleotide differing from known HCV nucleotide sequences, or the complement thereof.

Each of the above-mentioned residues can be found in FIGS. 2, 4 or 6 showing the new amino acid sequences of the present invention aligned with known sequences of other types or subtypes of HCV for the Core/E1 region.

According to another preferred embodiment, the present invention relates to a polynucleic acid encoding a HCV polyprotein comprising in its amino acid sequence at least one amino acid sequence chosen from the following list:

| Sequence | SEQ ID NO |
|---|---|
| ARQSDGRSWAQ or ARRSEGRSWAQ as for subtype 1d | (SEQ ID NO 107 and 108) |
| ERRPEGRSWAQ as for subtype 1e | (SEQ ID NO 109) |
| ARRPEGRSWAQ as for subtype 1f | (SEQ ID NO 110) |
| DRRTTGKSWGR as for subtype 2k | (SEQ ID NO 111) |
| DRRATGRSWGR as for subtype 2e | (SEQ ID NO 112) |
| DRRATGKSWGR as for subtype 2f | (SEQ ID NO 113) |
| VRQPTGRSWGQ as for type 9 | (SEQ ID NO 114) |
| VRHQTGRTWAQ as for subtype 7a and 7c | (SEQ ID NO 115) |
| VRQNQGRTWAQ as for subtype 7d | (SEQ ID NO 116) |
| ARRTEGRSWAQ as for type 10 | (SEQ ID NO 117) |
| VRRTGRXXXX or VRRTTGRTWAQ as for type 11 | (SEQ ID NO 118 and 119) |
| HEVRNASGVYHV or HEVRNASGVYHL as for subtype 1d | (SEQ ID NO 120 and 121) |
| YEVHSTTDGYHV as for subtype 1f | (SEQ ID NO 122) |
| VEVKNTSQAYMA as for subtype 2e | (SEQ ID NO 123) |
| IQVKNNSHFYMA as for subtype 2f | (SEQ ID NO 124) |
| VQVKNTSTMYMA as for subtype 2g | (SEQ ID NO 125) |
| VQVKNTSHSYMV as for subtype 2h | (SEQ ID NO 126) |
| VQVANRSGSYMV as for subtype 2i | (SEQ ID NO 127) |
| VEIKNTXNTYVL or VEIKNTSNTYVL as for subtype 2k | (SEQ ID NO 128 and 129) |
| INYRNVSGIYYV or INYRNTSGIYHV or INYHNTSGIYHI or TNYRNVSGIYHV as for subtype 4k | (SEQ ID NO 130, 131, 132 or 133) |
| QHYRNVSGIYHV as for subtype 4l | (SEQ ID NO 134) |
| IQVKNASGIYHL as for type 9 | (SEQ ID NO 135) |
| AHYTNKSGLYHL as for subtype 7c | (SEQ ID NO 136) |
| LNYANKSGLYHL as for subtype 7d | (SEQ ID NO 137) |
| LEYRNASGLYMV as for type 10 | (SEQ ID NO 138) |
| IYEMDGMIMHY or IYEMSGMILHA as for subtype 1d | (SEQ ID NO 139 and 140) |
| VYEAKDIILHT as for subtype 1f | (SEQ ID NO 141) |
| VWQLXDAVLHV as for subtype 2e | (SEQ ID NO 142) |
| VWQLRDAVLHV as for subtype 2f | (SEQ ID NO 143) |

-continued

| | |
|---|---|
| IWQMQGAVLHV as for subtype 2g | (SEQ ID NO 144) |
| VWQLKDAVLHV as for subtype 2h | (SEQ ID NO 145) |
| VWQLEEAVLHV as for subtype 2i | (SEQ ID NO 146) |
| TWQLXXAVLHV as for subtype 2k | (SEQ ID NO 147) |
| VYEADHHILHL or VYEADHHILAL or VFEADHHILHL as for subtupe 4k | (SEQ ID NO 148, 149 and 150) |
| VYESDHHILHL as for subtype 4l | (SEQ ID NO 151) |
| VFEAETMILHL as for type 9 | (SEQ ID NO 152) |
| VYEAETLILHL as for subtype 7c | (SEQ ID NO 153) |
| VYEANGMILHL as for subtype 7d | (SEQ ID NO 154) |
| VYEAGDIILHL as for type 10 | (SEQ ID NO 155) |
| VREDNHLRCWMAL or VRENNSSRCWMAL as for subtype 1d | (SEQ ID NO 156 and 157) |
| IREGNISRCWVPL as for subtype 1f | (SEQ ID NO 158) |
| ENSSGRFHCWIPI as for subtype 2e | (SEQ ID NO 159) |
| ERSGNRTFCWTAV as for subtype 2f | (SEQ ID NO 160) |
| ELQGNKSRCWIPV as for subtype 2g | (SEQ ID NO 161) |
| ERHQNQSRCWIPV as for subtype 2h | (SEQ ID NO 162) |
| EWKDNTSRCWIPV as for subtype 2i | (SEQ ID NO 163) |
| EREGNSSRCWIPV as for subtype 2k | (SEQ ID NO 164) |
| VREGNQSRCWVAL or VRTGNQSRCWVAL or VRVGNQSSCWVAL or VRVGNQSRCWVAL or VKEGNHSRCWVAL as for subtype 4k | (SEQ ID NO: 165, 166, 167, 168 or 169) |
| VKTGNTSRCWVAL as for subtype 4l | (SEQ ID NO 170) |
| IKAGNESRCWLPV as for type 9 | (SEQ ID NO 171) |
| VKEGNQSRCWVQA as for subtype 7c | (SEQ ID NO 172) |
| VKXXNLTKCWLSA as for subtype 7d | (SEQ ID NO 173) |
| VRSGNTSRCWIPV as for type 10 | (SEQ ID NO 174) |
| VKNASVPTAA or VKDANVPTAA as for subtype 1d | (SEQ ID NO 175 and 176) |
| ARIANAPIDE as for subtype 1f | (SEQ ID NO 177) |
| VSKPGALTKG as for subtype 2e | (SEQ ID NO 178) |
| VSRPGALTRG as for subtype 2f | (SEQ ID NO 179) |
| VNQPGALTRG as for subtype 2g | (SEQ ID NO 180) |
| VSQPGALTRG as for subtype 2h | (SEQ ID NO 181) |
| VSQPGALTKG as for subtype 2i | (SEQ ID NO 182) |
| VSRPGALTEG as for subtype 2k | (SEQ iD NO 183) |
| APYIGAPLES or APYTAAPLES as for subtype 4k | (SEQ ID NO 184 and 185) |
| APILSAPLMS as for subtype 4l | (SEQ ID NO 186) |
| VPNSSVPIHG as for type 9 | (SEQ ID NO 187) |
| VPNASTPVTG as for subtype 7c | (SEQ ID NO 188) |
| VQNASVSIRG as for subtype 7d | (SEQ ID NO 189) |
| VKSPCAATAS as for type 10 | (SEQ ID NO 190) |
| SPRMHHTTQE or SPRLYHTTQE as for subtype 1d | (SEQ ID NO 191 and 192) |
| TSRRHWTVQD as for subtype 1f | (SEQ ID NO 193) |

-continued

| | |
|---|---|
| APKRHYFVQE as for subtype 2e | (SEQ ID NO 194) |
| SPQYHTFVQE as for subtype 2f | (SEQ ID NO 195) |
| SPQHHNFSQD as for subtype 2g | (SEQ ID NO 196) |
| SPQHHIFVQD as for subtype 2h | (SEQ ID NO 197) |
| SPEHHHFVQD as for subtype 2k | (SEQ ID NO 198) |
| RPRRHWTTQD or RPRRHWTAQD or QPRRHWTTQD or RPRRHWTTQE as for subtype 4k | (SEQ ID NO 199, 200, 201 or 202) |
| QPRRHWTVQD as for subtype 4l | (SEQ ID NO 203) |
| RPKYHQVTQD as for type 9 | (SEQ ID NO 204) |
| RPRMHQVVQE as for subtype 7c | (SEQ ID NO 205) |
| RPRMYEIAQD as for subtype 7d | (SEQ ID NO 206) |
| RHRQHWTVQD as for type 10 | (SEQ ID NO 207) | or a part of said polynucleic acid which is unique to at least one of the HCV subtypes or types as defined Table 5, and which contains at least one nucleotide differing from known HCV nucleotide sequences, or the complement thereof.

Using the 5' non-coding LiPA system (Stuyver et al., 1993) and a new core LiPA system including multiple probes for subtypes 1a, 1b, 1c, 2a, 2b or 2c derived from the core region (Stuyver et al., 1995), samples from the Benelux, Cameroon, France and Vietnam were selected because of their aberrant reactivities (isolates CAM1078, FR2, FR1, VN4, VN12, VN13, NE98). Some samples were, together with many other samples, sequenced as a control for typing. Sequencing results, however, indicated the discovery of new subtypes (isolates BNL1, BNL2, BNL3, FR4, BNL4, BNL5, BNL6, BNL7, BNL8, BNL9, BNL10, BNL11 and BNL12). Nucleotide sequences in the core and E1 regions which have not yet been reported before, were analyzed in the frame of the invention. Genomic sequences of subtype 1d, 1e, 1f, 1g 2e, 2f, 2g, 2h, 2i, 2k, 2l, 3g, 4k, 4l, 4m, 7a, 7c, 7d and types 9, 10 and 11 isolates are reported for the first time in the present invention. The NS5B region was also analyzed.

The term "polynucleic acid" refers to a single-stranded or double-stranded nucleic acid sequence which may contain at least 5 contiguous nucleotides in common with the complete nucleotide sequence (e.g. at least 6, 7, 8, 9, 10, 11, 12, 13, 14, 15, 16, 17, 18, 19, 20, 21, 22, 23, 24, 25, 30, 35, 40, 45, 50, 60, 75 or more contiguous nucleotides). A polynucleic acid which is up till about 100 nucleotides in length is often also referred to as an oligonucleotide. A polynucleic acid may consist of deoxyribonucleotides or ribonucleotides, nucleotide analogues or modified nucleotides, or may have been adapted for therapeutic purposes. A polynucleic acid may also comprise a double stranded cDNA clone which can be used for cloning purposes, or for in vivo therapy, or prophylaxis.

The oligonucleotides according to the present invention, used as primers or probes may also contain or consist of nucleotide analogous such as phosphorothioates (Matsukura et al., 1987), alkylphosphoriates (Miller et al., 1979) or peptide nucleic acids (Nielsen et al., 1991; Nielsen et al., 1993) or may contain interculating agents (Asseline et al., 1984).

As most other variations or modifications introduced into the original DNA sequences of the invention these variations will neccissitate adaptions with respect to the conditions under which the oligonucleotide should be used to obtain the required specificty and sensitivity. However the eventual results will be essentially the same as those obtained with the unmodified oligonucleotides.

The introduction of these modifications may be advantageous in order to positivily influence characteristics such as hybridization kinetics, reversibility of the hybrid-formation, biological stability of the oligonucleotide molecules, etc.

The polynucleic acids of the invention may be comprised in a composition of any kind. Said composition may be for diagnostic, therapeutic or prophylactic use.

The expression "sequences which are unique to an HCV type or subtype" refers to sequences which are not shared by any other type or subtype of HCV, and can thus be used to uniquely detect that HCV type or subtype. Sequence variability is demonstrated in the present invention between the newly found HCV types and subtypes (see Table 5) and the known HCV types and subtypes (see Table 3), and it is therefore from these regions of sequence variability in particular that type- or subtypes-specific polynucleic acids, oligonucleotides, polypeptides and peptides may be obtained. The term type- or subtypes-specific refers to the fact that a sequence is unique to that HCV type or subtype involved.

The expression "nucleotides corresponding to" refers to nucleotides which are homologous or complementary to an indicated nucleotide sequence or region within a specific HCV sequence.

The term "coding region" corresponds to the region of the HCV genome that encodes the HCV polyprotein. In fact, it comprises the complete genome with the exception of the 5' untranslated region and 3' untranslated region.

The term "HCV polyprotein" refers to the HCV polyprotein of the HCV-J isolate (Kato et al., 1990). The adenine residue at position 330 (Kato et al., 1990) is the first residue of the ATG codon that initiates the long HCV polyprotein of 3010 amino acids in HCV-J and other type 1b isolates, and of 3011 amino acids in HCV-1 and other type 1a isolates, and of 3033 amino acids in type 2 isolates HC-J6 and HC-J8 (Okamoto et al., 1992).

This adenine is designated as position 1 at the nucleic acid level, and this methionine is designated as position 1 at the amino acid level, in the present invention. As type 1a isolates contain 1 extra amino acid in the NS5A region, coding sequences of type 1a and 1b have identical numbering in the Core, E1, NS3, and NS4 region, but will differ in the NS5B region as indicated in Table 1. Type 2 isolates have 4 extra amino acids in the E2 region, and 17 or 18 extra amino acids in the NS5 region compared to type 1 isolates, and will differ in numbering from type 1 isolates in the NS3/4 region and NS5b regions as indicated in Table 1. Similar insertions compared with type 1 (but of a different size) can also be observed in type 3a sequences which affect the numbering of type 3a amino acids accordingly. Other insertions or deletions may be readily observed in type1,2, 3, 4, 5, 6, 7, 8, 9, 10 and 11 sequences after alignment withknown HCV sequences.

More preferably the definition of HCV types is concluded from the classification of HCV isolates according to their nucleotide distances calculated as detailed below:

(1) based on phylogenetic analysis of nucleic acid sequences in the NS5B region between nucleotides 7935 and 8274 (Choo et al., 1991) or 8261 and 8600 (Kato et al., 1990) or 8342 and 8681 (Okamoto et al., 1991), isolates belonging to the same HCV type show nucleotide distances of less than 0.34, usually less than 0.33, and more usually of less than 0.32, and isolates belonging to the same subtype show

TABLE 1

| | Region | Positions described in the present invention* | Positions described for HCV-J (Kato et al., 1990) | Positions described for HCV-1 (Choo et al., 1991) | Positions described for HC-J6, HC-J8 (Okamoto et al., 1992) |
|---|---|---|---|---|---|
| Nucleotides | NS5B | 8023/8235 | 8352/8564 | 8026/8238 | 8433/8645 |
| | | 7932/8271 | 8261/8600 | 7935/8274 | 8342/8681 |
| | | coding region of present invention | 330/9359 | 1/9033 | 342/9439 |
| Amino Acids | NS5B | 2675/2745 | 2675/2745 | 2676/2746 | 2698/2768 |
| | | 2645/2757 | 2645/2757 | 2646/2758 | 2668/2780 |

Comparison of the HCV nucleotide and amino acid numbering system used in the present invention (*) with the numbering used for other prototype isolates. For example, 8352/8564 indicates the region designated by the numbering from nucleotide 8352 to nucleotide 8564 as described by Kato et al. (1990). Since the numbering system of the present invention starts at the polyprotein initiation site, the 329 nucleotides of the 5' untranslated region described by Kato et al. (1990) have to be substracted,and the corresponding region is numbered from nucleotide 8023 ('8352-329') to 8235 ('8564-329').

The term "genotype" as used in the present invention refers to both types and/or subtypes.

The term "HCV type" corresponds to a group of HCV isolates of which the complete genome shows more than 73% preferably more than 74% homology at the nucleic acid level, or of which the NS5 region between nucleotide positions 7932 and 8271 shows more than 75.4% homology at the nucleic acid level, or of which the complete HCV polyprotein shows more than 78% homology at the amino acid level, or of which the NS5 region between amino acids at positions 2645 and 2757 shows more than 80% homology at the amino acid level, to polyproteins of the other isolates of the group, with said numbering beginning at the first ATG codon or first methionine of the long HCV polyprotein of the HCV-J isolate (Kato et al., 1990). Isolates belonging to different types of HCV exhibit homologies, over the complete genome, of less than 74%, preferably less than 73%, at the nucleic acid level and less than 78% at the amino acid level. Isolates belonging to the same type usually show homologies of about 90 to 99% at the nucleic acid level and 95 to 96% at the amino acid level when belonging to the same subtype, and those belonging to the same type but different subtypes preferably show homologies of about 76% to 82% (more particularly of about 77% to 80%) at the nucleic acid level and 85–86% at the amino acid level.

nucleotide distances of less than 0.135, usually of less than 0.13, and more usually of less than 0.125, usually ranging between 0.0003 and 0.1151, and consequently isolates belonging to the same type but different subtypes show nucleotide distances ranging from 0.135 to 0.34, usually ranging from 0.1384 to 0.2977, and more usually ranging from 0.15 to 0.32, and isolates belonging to different HCV types show nucleotide distances greater than 0.34, usually greater that 0.35, and more usually of greater than 0.358, more usually ranging from 0.3581 to 0.6670.

(2) based on phylogenetic analysis of nucleic acid sequences in the core/E1 region between nucleotides 378 and 957, isolates belonging to the same HCV type show nucleotide distances of less than 0.38, usually of less than 0.37, and more usually of less than 0.364, and isolates belonging to the same subtype show nucleotide distances of less than 0.17, usually of less than 0.16, and more usually of less than 0.15, more usually less than 0.135, more usually less than 0.134, and consequently isolates belonging to the same type but different subtypes show nucleotide distances ranging from 0.15 to 0.38, usually ranging from 0.16 to 0.37, and more usually ranging from 0.17 to 0.36, more usually ranging from 0.133 to 0.379, and isolates belonging to different HCV types show nucleotide distances greater than 0.34, 0.35, 0.36, usually more than 0.365, and more usually of greater than 0.37,

TABLE 2

| | | Molecular evolutionary distances | | |
|---|---|---|---|---|
| Region | core/E1 579 bp | E1 384 bp | NS5B 340 bp | NS5B 222 bp |
| Isolates* | 0.0017–0.1347 | 0.0026–0.2031 | 0.0003–0.1151 | 0.000–0.1323 |
| | (0.0750 ± 0.0245) | (0.0969 ± 0.0289) | (0.0637 ± 0.0229) | (0.0607 ± 0.0205) |
| Subtypes* | 0.1330–0.3794 | 0.1645–0.4869 | 0.1384–0.2977 | 0.117–0.3538 |
| | (0.2786 ± 0.0363) | (0.3761 ± 0.0433) | (0.2219 ± 0.0341) | (0.2391 ± 0.0399) |

TABLE 2-continued

| | Molecular evolutionary distances | | | |
|---|---|---|---|---|
| Region | core/E1 579 bp | E1 384 bp | NS5B 340 bp | NS5B 222 bp |
| Types* | 0.3479–0.6306 (0.4703 ± 0.0525) | 0.4309–0.9561 (0.6308 ± 0.0928) | 0.3581–0.6670 (0.4994 ± 0.0495) | 0.3457–0.7471 (0.5295 ± 0.0627) |

*Figures created by the PHYLIP program DNADIST are expressed as minimum to maximum (average ± standard deviation). Phylogenetic distances for isolates belonging to the same subtype ('isolates'), to different subtypes of the same type ('subtypes'), and to different types ('types') are given.

In a comparative phylogenetic analysis of available sequences, ranges of molecular evolutionary distances for different regions of the genome were calculated, based on 19,781 pairwise comparisons by means of the DNADIST program of the phylogeny inference package PHYLIP version 3.5c (Felsenstein, 1993). The results are shown in Table 2 and indicate that although the majority of distances obtained in each region fit with classification of a certain isolate, only the ranges obtained in the 340bp NS5B-region are non-overlapping and therefore conclusive. However, as was performed in the present invention, it is preferable to obtain sequence information from at least 2 regions before final classification of a given isolate.

Designation of a number to the different types of HCV and HCV nomenclature is based on chronological discovery of the different types. The numbering system used in the present invention might still fluctuate according to international conventions or guidelines. For example, "type 4" might be changed into "type 5" or "type 6". Also the arbitrarily chosen border distances between types and subtypes and isolates may still be subject to change according to international guidelines or conventions. Therefore types 7a, 8a, 8b, 9a may for example be designated 6b, 6c, 6d, and 6d in the future; and type 10a which shows relatedness with genotype 3 may be denoted 3 g instead of 10a.

The term "subtype" corresponds to a group of HCV isolates of which the complete polyprotein shows a homology of more than 90% both at the nucleic acid and amino acid levels, or of which the NS5 region between nucleotide positions 7932 and 8271 shows a homology of more than 90% at the nucleic acid level to the corresponding parts of the genomes of the other isolates of the same group, with said numbering beginning with the adenine residue of the initiation codon of the HCV polyprotein. Isolates belonging to the same type but different subtypes of HCV show homologies of more than 74% at the nucleic acid level and of more than 78% at the amino acid level.

It is to be understood that extremely variable regions such as the E1, E2 and NS4 regions will exhibit lower homologies than the average homology of the complete genome of the polyprotein.

Using these criteria, HCV isolates can be classified into at least 11 types. Several subtypes can clearly be distinguished in types 1, 2, 3, 4 and 7: 1a, 1b, 1c, 1d, 1e, 1f, 1g, 2a, 2b, 2c, 2d, 2e, 2f, 2g, 2h, 2i, 2k, 2l, 3a, 3b, 3c, 3d, 3f, 3g, 4a, 4b, 4c, 4d, 4e, 4f, 4g, 4h, 4i, 4j, 4k, 4l, 4m, 7a, 7c, and 7d based on homologies of the 5' UR and coding regions. An overview of most of the reported isolates and their proposed classification according to the typing system of the present invention as well as other proposed classifications is presented in Table 3.

TABLE 3

HCV CLASSIFICATION

| | OKAMOTO | MORI | CHA | NAKAO | PROTOTYPE |
|---|---|---|---|---|---|
| 1a | I | I | Pt | GI | HCV-1, HCV-H, HC-J1 |
| 1b | II | II | KI | GII | HCV-J, HCV-BK, HCV-T, HC-JK1, HC-J4, HCV-CHINA |
| 1c | | | | | HC-G9 |
| 2a | III | III | K2a | GIII | HC-J6 |
| 2b | IV | IV | K2b | GIII | HC-J8 |
| 2c | | | | | S83, ARG6, ARG8, I10, T983 |
| 2d | | | | | NE92 |
| 3a | V | V | K3 | GIV | BR36, BR56, HD10, N2L1, BR33, Ta, E-b1 |
| 3b | | VI | K3 | GIV | HCV-TR, Tb, NE137 |
| 3c | | | | | NE48 |
| 3d | | | | | NE274 |
| 3e | | | | | NE145 |
| 3f | | | | | NE125 |
| 4a | | | | | Z4, GB809-4 |
| 4b | | | | | Z1 |
| 4c | | | | | GB116, GB358, GB215, Z6, Z7 |
| 4d | | | | | DK13 |
| 4e | | | | | GB809-2, CAM600, CAM736 |
| 4f | | | | | CAM622, CAM627 |
| 4g | | | | | GB549 |
| 4h | | | | | GB438 |
| 4i | | | | | CAR4/1205 |

TABLE 3-continued

HCV CLASSIFICATION

| OKA-MOTO | MORI | CHA | NAKAO | PROTOTYPE |
|---|---|---|---|---|
| 4j | | | | CAR1/905 |
| 5a | | | GV | SA3, SA4, SA1, SA7, SA11, BE95 |
| 6a | | | | HK1, HK2, HK3, HK4, VN11 |

Overview of the known HCV types and subtypes classified according to the different authors.

The term "complement" refers to a nucleotide sequence which is complementary to an indicated sequence and which is able to hybridize to the indicated sequences.

The composition of the invention can comprise many combinations. By way of example, the composition of the invention can comprise:

two (or more) nucleic acids from the same region or, two nucleic acids (or more), respectively from different regions, for the same isolate or for different isolates, or nucleic acids from the same regions and from at least two different regions (for the same isolate or for different isolates).

The present invention relates particularly to a polynucleic acid as defined above having a sequence selected from any of SEQ ID NO 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103 to 105, or a part of said polynucleic acid which is unique to any of the HCV subtypes or types as defined in Table 5, and which contains at least one nucleotide differing from known HCV polynucleic acids, or the complement thereof.

The present invention relates more particularly to a polynucleic acid as defined 5 above, which codes for the 5' UR, the Core/E1, the NS4 or the NS5B region or a part thereof.

More particularly, the present invention relates to a polynucleic acid as defined above which is a cDNA sequence.

Also included within the present invention are sequence variants of the polynucleic acids as selected from any of the nucleotide sequences as given in any of the above given SEQ ID numbers with said sequence variants containing either deletion and/or insertions of one or more nucleotides, especially insertions or deletions of 1 or more codons, mainly at the extremities of oligonucleotides (either 3' or 5'), or substitutions of some non-essential nucleotides (i.e. nucleotides not essential to discriminate between different genotypes of HCV) by others (including modified nucleotides an/or inosine), for example, a type 1 or 2 sequence might be modified into a type 7 sequence by replacing some nucleotides of the type 1 or 2 sequence with type-specific nucleotides of type 7 as shown in for instance FIG. 1 and 2.

Particularly preferred variant polynucleic acids of the present invention include also sequences which hybridise under stringent conditions with any of the polynucleic acid sequences of the present invention. Particularly, sequences which show a high degree of homology (similarity) to any of the polynucleic acids of the invention as described above. Particularly sequences which are at least 80%, 85%, 90%, 95% or more homologous to said polynucleic acid sequences of the invention. Preferably said sequences will have less than 20%, 15%, 10%, or 5% variation of the original nucleotides of said polynucleic acid sequence.

Polynucleic acid sequences according to the present invention which are homologous to the sequences as represented by a SEQ ID NO can be characterized and isolated according to any of the techniques known in the art, such as amplification by means of sequence-specific primers, hybridization with sequence-specific probes under more or less stringent conditions, serological screening methods or via the LiPA typing system.

Other preferred variant polynucleic acids of the present invention include sequences which are redundant as a result of the degeneracy of the genetic code compared any of the above-given polynucleic acids of the present invention. These variant polynucleic acid sequences will thus encode the same amino acid sequence as the polynucleic acids they are derived from.

Also included within the scope of the present invention are 5' non-coding region sequences which can be readily obtained from type 1 subtype 1d, 1e, 1f or 1g isolates; type 2 subtype 2e, 2f, 2g, 2h, 2i, 2k or 2l isolates; type 3 subtype 3g isolates; type 4 subtype 4k, 4l or 4m isolates; type 7 subtype 7a, 7c or 7d isolates, type 9, type 10 or type 11 isolates discribed herein. Such sequences may contain type or subtype-specific motifs which can be employed for type and/or subtype-specific hybridization assays, e.g. such as described by Stuyver et al. (1993).

Polynucleic acid sequences of the genomes indicated above from regions not yet depicted in the present examples, figures and sequence listing can be obtained by any of the techniques known in the art, such as amplification techniques using suitable primers from the sequences of these new genomes given in FIG. 1 of the present invention.

The present invention also relates to an oligonucleotide primer comprising part of a polynucleic acid as defined above, with said primer being able to act as a primer for specifically amplifying the nucleic acid of a certian HCV isolate belonging to the genotype from which the primer is derived.

The term "primer" refers to a single stranded DNA oligonucleotide sequence capable of acting as a point of initiation for synthesis of a primer extension product which is complementary to the nucleic acid strand to be copied. The length and the sequence of the primer must be such that they allow to prime the synthesis of the extension products. Preferably the primer is about 5–50 nucleotides. Specific length and sequence will depend on the complexity of the required DNA or RNA targets, as well as on the conditions of primer use such as temperature and ionic strength.

The fact that amplification primers do not have to match exactly with corresponding template sequence to warrant proper amplification is amply documented in the literature (Kwok et al., 1990).

The amplification method used can be either polymerase chain reaction (PCR; Saiki et al., 1988), ligase chain reaction (LCR; Landgren et al., 1988; Wu & Wallace, 1989; Barany, 1991), nucleic acid sequence-based amplification (NASBA; Guatelli et al., 1990; Compton, 1991), transcription-based amplification system (TAS; Kwoh et al., 1989), strand displacement amplification (SDA; Duck, 1990; Walker et al., 1992) or amplification by means of Qβ replicase (Lizardi et al., 1988; Lomeli et al., 1989) or any other suitable method to amplify nucleic acid molecules using primer extension. During amplification, the amplified products can be conveniently labelled either using labelled primers or by incorporating labelled nucleotides. Labels may be isotopic ($^{32}$P, $^{35}$S, etc.) or non-isotopic (biotin, digoxigenin, etc.). The amplification reaction is repeated between 20 and 70 times, advantageously between 25 and 45 times.

The present invention also relates to an oligonucleotide probe comprising part of a polynucleic acid as defined above, with said probe being able to act as a hybridization probe for specific detection and/or classification into types and/or subtypes of an HCV nucleic caid containing said nucleotide sequence, with said probe being possibly labelled or attached to a solid substrate.

The term "probe" refers to single stranded sequence-specific oligonucleotides which have a sequence which is complementary to the target sequence of the HCV genotype(s) to be detected.

Preferably, these probes are about 5 to 50 nucleotides long, more preferably from about 10 to 25 nucleotides.

The term "solid support" can refer to any substrate to which an oligonucleotide probe can be coupled, provided that it retains its hybridization characteristics and provided that the background level of hybridization remains low. Usually the solid substrate will be a microtiter plate, a membrane (e.g. nylon or nitrocellulose) or a microsphere (bead). Prior to application to the membrane or fixation it may be convenient to modify the nucleic acid probe in order to facilitate fixation or improve the hybridization efficiency. Such modifications may encompass homopolymer tailing, coupling with different reactive groups such as aliphatic groups, $NH_2$ groups, SH groups, carboxylic groups, or coupling with biotin or haptens.

The present invention also relates to a diagnostic kit for use in determining the genotype of HCV, said kit comprising a primer as defined above.

The present invention also relates to a diagnostic kit for use in determining the genotype of HCV, said kit comprising a probe as defined above.

The present invention also relates to a diagnostic kit as defined above, wherein said probe(s) is(are) attached to a solid substrate.

The present invention also relates to a diagnostic kit as defined above, wherein a range of said probes is attached to specific locations on a solid substrate.

The present invention also relates to a diagnostic kit as defined above, wherein said solid support is a membrane strip and said probes are coupled to the membrane in the form of parallel lines.

The present invention also relates to a method for the detection of HCV nucleic acids present in a biological sample, comprising:
(i) possibly extracting sample nucleic acid,
(ii) amplifying the nucleic acid with at least one primer as defined above,
(iii) detecting the amplified nucleic acids.

The present invention also relates to a method for the detection of HCV nucleic acids present in a biological sample, comprising:
(i) possibly extracting sample nucleic acid,
(ii) possibly amplifying the nucleic acid with at least one primer as defined above, or with a universal HCV primer,
(iii) hybridizing the nucleic acids of the biological sample, possibly under denatured conditions, at appropriate conditions with one or more probes as defined above, with said probes being preferably attached to a solid substrate,
(iv) possibly washing at appropriate conditions,
(v) detecting the hybrids formed.

The present invention also relates to a method for detecting the presence of one or more HCV genotypes present in a biological sample, comprising:
(i) possibly extracting sample nucleic acid,
(ii) specifically amplifying the nucleic acid with at least one primer as defined above,
(iii) detecting said amplified nucleic acids.

The present invention also relates to a method for detecting the presence of one or more HCV genotypes present in a biological sample, comprising:
(i) possibly extracting sample nucleic acid,
(ii) possibly amplifying the nucleic acid with at least one primer as defined above or with a universal HCV primer,
(iii) hybridizing the nucleic acids of the biological sample, possibly under denatured conditions, at appropriate conditions with one or more probes as defined above, with said probes being preferably attached to a solid substrate,
(iv) possibly washing at appropriate conditions,
(v) detecting the hybrids formed,
(vi) inferring the presence of one or more HCV genotypes present from the observed hybridization pattern.

The present invention also relates to a method as defined above, wherein said probes are further characterized as defined above.

The present invention also relates to a method as defined above, wherein said nucleic acids are labelled during or after amplification.

Preferably, this technique could be performed in the 5' non-coding, Core or NS5B region.

The term "nucleic acid" can also be referred to as analyte strand and corresponds to a single- or double-stranded nucleic acid molecule. This analyte strand is preferentially positive- or negative stranded RNA, cDNA or amplified cDNA.

The term "biological sample" refers to any biological sample (tissue or fluid) containing HCV nucleic acid sequences and refers more particularly to blood serum or plasma samples.

The term "universal HCV primer" refers to oligonucleotide sequences complementary to any of the conserved regions of the HCV genome.

The expression "appropriate" hybridization and washing conditions are to be understood as stringent and are generally known in the art (e.g. Maniatis et al., Molecular Cloning: A Laboratory Manual, New York, Cold Spring Harbor Laboratory, 1982).

However, according to the hybridization solution (SSC, SSPE, etc.), these probes should be hybridized at their appropriate temperature in order to attain sufficient specificity.

The term "labelled" refers to the use of labelled nucleic acids. This may include the use of labelled nucleotides incorporated during the polymerase step of the amplification such as illustrated by Saiki et al. (1988) or Bej et al. (1990) or labelled primers, or by any other method known to the person skilled in the art.

The process of the invention comprises the steps of contacting any of the probes as defined above, with one of the following elements:
 either a biological sample in which the nucleic acids are made available for hybridization,
 or the purified nucleic acids contained in the biological sample or a single copy derived from the purified nucleic acids, or an amplified copy derived from the purified nucleic acids, with said elements or with said probes being attached to a solid substrate.

The expression "inferring the presence of one or more HCV genotypes present from the observed hybridization pattern" refers to the identification of the presence of HCV genomes in the sample by analyzing the pattern of binding of a panel of oligonucleotide probes. Single probes may provide useful information concerning the presence or absence of HCV genomes in a sample. On the other hand, the variation of the HCV genomes is dispersed in nature, so rarely is any one probe able to identify uniquely a specific HCV genome. Rather, the identity of an HCV genotype may be inferred from the pattern of binding of a panel of oligonucleotide probes, which are specific for (different) segments of the different HCV genomes. Depending on the choice of these oligonucleotide probes, each known HCV genotype will correspond to a specific hybridization pattern upon use of a specific combination of probes. Each HCV genotype will also be able to be discriminated from any other HCV genotype amplified with the same primers depending on the choice of the oligonucleotide probes. Comparison of the generated pattern of positively hybridizing probes for a sample containing one or more unkown HCV sequences to a scheme of expected hybridization patterns, allows one to clearly infer the HCV genotypes present in said sample.

The present invention thus relates to a method as defined above, wherein one or more hybridization probes are selected from any of SEQ ID NO 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103 or 105 or sequence variants thereof as defined above.

In order to distinguish the amplified HCV genomes from each other, the target polynucleic acids are hybridized to a set of sequence-specific DNA probes targetting HCV genotypic regions (unique regions) located in the HCV polynucleic acids.

Most of these probes target the most type- or subtype-specific regions of HCV genotypes, but some can be caused to hybridize to more than one HCV genotype.

According to the hybridization solution (SSC, SSPE, etc.), these probes should be stringently hybridized at their appropriate temperature in order to attain sufficient specificity. However, by slightly modifying the DNA probes, either by adding or deleting one or a few nucleotides at their extremities (either 3' or 5'), or substituting some non-essential nucleotides (i.e. nucleotides not essential to discriminate between types) by others (including modified nucleotides or inosine) these probes or variants thereof can be caused to hybridize specifically at the same hybridization conditions (i.e. the same temperature and the same hybridization solution). Also changing the amount (concentration) of probe used may be beneficial to obtain more specific hybridization results. It should be noted in this context, that probes of the same length, regardless of their GC content, will hybridize specifically at approximately the same temperature in TMACl solutions (Jacobs et al., 1988).

Suitable assay methods for purposes of the present invention to detect hybrids formed between the oligonucleotide probes and the nucleic acid sequences in a sample may comprise any of the assay formats known in the art, such as the conventional dot-blot format, sandwich hybridization or reverse hybridization. For example, the detection can be accomplished using a dot blot format, the unlabelled amplified sample being bound to a membrane, the membrane being incorporated with at least one labelled probe under suitable hybridization and wash conditions, and the presence of bound probe being monitored.

An alternative and preferred method is a "reverse" dot-blot format, in which the amplified sequence contains a label. In this format, the unlabelled oligonucleotide probes are bound to a solid support and exposed to the labelled sample under appropriate stringent hybridization and subsequent washing conditions. It is to be understood that also any other assay method which relies on the formation of a hybrid between the nucleic acids of the sample and the oligonucleotide probes according to the present invention may be used.

According to an advantageous embodiment, the process of detecting one or more HCV genotypes contained in a biological sample comprises the steps of contacting amplified HCV nucleic acid copies derived from the biological sample, with oligonucleotide probes which have been immobilized as parallel lines on a solid support.

According to this advantageous method, the probes are immobilized in a Line Probe Assay (LiPA) format. This is a reverse hybridization format (Saiki et al., 1989) using membrane strips onto which several oligonucleotide probes (including negative or positive control oligonucleotides) can be conveniently applied as parallel lines.

The invention thus also relates to a solid support, preferably a membrane strip, carrying on its surface, one or more probes as defined above, coupled to the support in the form of parallel lines.

The LiPA is a very rapid and user-friendly hybridization test. Results can be read after 4 hours. after the start of the amplification. After amplification during which usually a non-isotopic label is incorporated in the amplified product, and alkaline denaturation, the amplified product is contacted with the probes on the membrane and the hybridization is carried out for about 1 to 1,5 h hybridized polynucleic acid is detected. From the hybridization pattern generated, the HCV type can be deduced either visually, but preferably using dedicated software. The LiPA format is completely compatible with commercially available scanning devices, thus rendering automatic interpretation of the results very reliable. All those advantages make the LiPA format liable for the use of HCV detection in a routine setting. The LiPA format should be particularly advantageous for detecting the presence of different HCV genotypes.

The present invention also relates to a method for detecting and identifying novel HCV genotypes, different from the known HCV genomes, comprising the steps of:

determining to which HCV genotype the nucleotides present in a biological sample belong, according to the process as defined above, in the case of observing a sample which does not generate a hybridization pattern compatible with those defined in Table 3, sequencing the portion of the HCV genome sequence corresponding to the aberrantly hybridizing probe of the new HCV genotype to be determined.

The present invention also relates to a method for preparing a polynucleic acid according to the present invention. These methods include any method known in the art for preparing polynucleic acids (e.g. the phosphodiester method for synthesizing oligonucleotides as described by Agarwal et al. 1972, Agnew. Chem. Int. Ed. Engl. 11:451, the phosphotriester method of Hsiung et al. 1979, Nucleic Acid Res. 6:1371, or the automated diethylphosphoramidite method of Baeucage et al. 1981, Tetrahedron Letters 22:1859–1862.). Alternatively, the polynucleic acids of the present invention may be isolated fragments of naturally occuring or cloned DNA or RNA. In addition, the oligonucleotides according to the present invention may be synthesized automatically on commercial instruments sold by a variety of manufacturers.

The present invention particularly also relates to a polypeptide having an amino acid sequence encoded by a polynucleic acid as defined above, or a part thereof which is unique to at least one of the HCV subtypes or types as defined in Table 5, and which contains at least one amino acid differing from any of the known HCV types or subtypes, or an analog thereof being substantially homologous and biologically equivalent.

The term 'polypeptide' refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogues of an amino acid (including, for example, unnatural amino acids, PNA, etc.), polypeptides with substituted linkages, as well as other modifications known in the art, both naturally occurring and non-naturally occurring.

The term "unique" is referred above.

By "biologically equivalent" as used throughout the specification and claims, it is meant that the compositions are immunogenically equivalent to the proteins (polypeptides) or peptides of the invention as defined above and below.

By "substantially homologous" as used throughout the ensuing specification and claims to describe proteins and peptides, it is meant a degree of homology in the amino acid sequence to the proteins or peptides of the invention. Preferably the degree of homology is in excess of 90, preferably in excess of 95, with a particularly preferred group of proteins being in excess of 99 homologous with the proteins or peptides of the invention.

The term "analog" as used throughout the specification or claims to describe the proteins or peptides of the present invention, includes any protein or peptide having an amino acid residue sequence substantially identical to a sequence specifically shown herein in which one or more residues have been conservatively substituted with a biologically equivalent residue. Examples of conservative substitutions include the substitution of one-polar (hydrophobic) residue such as isoleucine, valine, leucine or methionine for another, the substitution of one polar (hydrophillic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. Examples of allowable mutations acccording to the present inevntion can be found in Table 4.

The phrase "conservative substitution" also includes the use of a chemically derivatized residue in place of a non-derivatized residue provided that the resulting protein or peptide is biologically equivalent to theprotein or peptide of the invention.

"Chemical derivative" refers to a protein or peptide having one or more residues chemically derivatized by reaction of a functional side group. Examples of such derivatized molecules, include but are not limited to, those molecules in which free amino groups have been derivatized to form amine hydrochlorides, p-toluene sulfonyl groups, carbobenzoxy groups, t-butyloxycarbonyl groups, chloracetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as chemical derivatives are those proteins or peptides which contain one or more naturally-occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. The proteins or peptides of the present invention also include any protein or peptide having one or more additions and/or deletions or residues relative to the sequence of a peptide whose sequence is shown herein, so long as the peptide is biologically equivalent to the proteins or peptides of the invention.

It is to be noted that, at the level of the amino acid sequence, at least one amino acids difference (with respect to known HCV amino acid sequences) is sufficient to be part of the invention, which means that the polypeptides of the invention correspond to polynucleic acids having at least one nucleotide difference (with known HCV polynucleic acid sequences) involving an amino acid difference in the encoded polyprotein.

As the NS4 and the Core regions are known to contain several epitopes, for example characterized in patent application EP-A-0 489 968, and as the E1 protein is expected to be subject to immune attack as part of the viral envelope and expected to contain epitopes, the NS4, Core and E1 epitopes of the new types and subtypes disclosed herein will consistently differ from the epitopes present in previously known genotypes. This is examplified by the type-specificity of NS4 synthetic peptides as described in Simmonds et al. (1993c) and Stuyver et al. (1993b) and PCT/EP 94/01323 and the type-specificity of recombinant E1 proteins as described in Maertens et al. (1994).

The peptides according to the present invention contain preferably at least 3, preferably 4, 5 contiguous HCV amino acids, 6, 7 preferably however at least 8 contiguous HCV amino acids, at least 10 or at least 15 (for instance at least 9, 10, 11, 12, 13, 14, 15, 16, 17, 19, 20, 21, 22, 23, 24, 25, 30, 35, 40, 45, 50 or more amino acids).

TABLE 4

| Amino acids | Synonymous groups |
| --- | --- |
| Ser (S) | Ser, Thr, Gly, Asn |
| Arg (R) | Arg, His, Lys, Glu, Gln |
| Leu (L) | Leu; Ile, Met, Phe, Val, Tyr |
| Pro (P) | Pro, Ala, Thr, Gly |
| Thr (T) | Thr, Pro, Ser, Ala, Gly, His, Gln |
| Ala (A) | Ala, Pro, Gly, Thr |
| Val (V) | Val, Met, Ile, Tyr, Phe, Leu, Val |
| Gly (G) | Gly, Ala, Thr, Pro, Ser |
| Ile (I) | Ile, Met, Leu, Phe, Val, Ile, Tyr |
| Phe (F) | Phe, Met, Tyr, Ile, Leu, Trp, Val |
| Tyr (Y) | Tyr, Phe, Trp, Met, Ile, Val, Leu |
| Cys (C) | Cys, Ser, Thr, Met |
| His (H) | His, Gln, Arg, Lys, Glu, Thr |
| Gln (Q) | Gln, Glu, His, Lys, Asn, Thr, Arg |
| Asn (N) | Asn, Asp, Ser, Gln |
| Lys (K) | Lys, Arg, Glu, Gln, His |
| Asp (D) | Asp, Asn, Glu, Gln |
| Glu (E) | Glu, Gln, Asp, Lys, Asn, His, Arg |
| Met (M) | Met, Ile, Leu, Phe, Val |

Overview of the amino acid substitutions which could form the basis of analogs (muteins) as defined above The polypeptides of the invention, and particularly the fragments, can be prepared by classical chemical synthesis.

The synthesis can be carried out in homogeneous solution or in solid phase.

For instance, the synthesis technique in homogeneous solution which can be used is the one described by Houben-weyl in the book entitled "Methode der organischen chemie" (Method of organic chemistry) edited by E. Wunsh, vol. 15-I et II. THIEME, Stuttgart 1974.

The polypeptides of the invention can also be prepared in solid phase according to the methods described by Atherton and Shepard in their book entitled "Solid phase peptide synthesis" (IRL Press, Oxford, 1989).

The polypeptides according to this invention can be prepared by means of recombinant DNA techniques as described by Maniatis et al., Molecular Cloning: A Laboratory Manual, New York, Cold Spring Harbor Laboratory, 1982).

The present invention relates particularly to a polypeptide as defined above, comprising in its amino acid sequence at least one of the following amino acid residues: I15, C38, V44, A49, Q43, P49, Q55, A58, S60 or D60, E68 or V68, H70 , A71 or Q71 or N71, D72, H81, H101, D106, S110, L130, I134, E135, L140, S148, T150 or E150, Q153, F155, D157, G160, E165, I169, F181, L186, T190, T192 or I192 or H192, I193 , A195, S196, R197 or N197 or K197, Q199 or D199 or H199, N199, F200 or T200, A208, I213, M216 or S216, N217 or S217 or G217 or K217, T218, I219, A222, Y223, I230, W231 or L231, S232 or H232 or A232, Q233, E235 or L235, F236 or T236, F237, L240 or M240, A242, N244, N249, I250 or K250 or R250, A252 or C252, A254, I255 or V255, D256 or M256, E257, E260 or K260, R261, V268, S272 or R272, I285, G290 or F290, A291, A293 or L293 or W293, T294 or A294, S295, H295, K296 or E296, Y297 or M297, I299 or Y299, I300, S301, P316, S2646, A2648, G2649, A2650, V2652, Q2653, H2656 or L2656, D2657, F2659, K2663 or Q2663, A2667 or V2667, D2677, L2681, M2686 or Q2686 or E2686, A2692 or K2692, H2697, I2707, L2708 or Y2708, A2709, A2719 or M2719, F2727, T2728 or D2728, E2729, F2730 or Y2730, I2741, I2745, V2746 or E2746 or L2746 or K2746, A2748, S2749 or P2749, R2750, E2751, D2752 or N2752 or S2752 or T2752 or V2752 or I2752 or Q2752, S2753 or D2753 or G2753, D2754, A2755, L2756 or Q2756, or R2757, with said notation being composed of a letter representing the amino acid residue by its one-letter code, and a number representing the amino acid numbering according to Kato et al., 1990 as shown in Table 1 (see also the numbering in FIGS. 2, 4 and 6), or a part thereof which is unique to at least one of the HCV subtypes or types as defined in Table 5, and which contains at least one amino acid differing from any of the known HCV types or subtypes, or an analog thereof being substantially homologous and biologically equivalent to said polypeptide or part thereof.

These unique amino acid residues can be deduced from aligning the new HCV amino acid sequences as given in FIG. 3 to all known HCV sequences. An alignment with the new sequences as represented in SEQ ID NO 1 to 106 is given in for instance FIGS. 2, 4 and 6. It should be clear that the alignments given in these figures may be completed with all known HCV sequences to illustrate that any of the above-given unique residues is indeed unique for at least one of the new HCV sequences of the present invention.

Within the group of unique and new amino acid residues of the present invention, unique residues may be found which are specific for the following new types (subtypes) of HCV according to the HCV classification system used in the present invention: type 1 subtype 1d, 1e, 1f or 1g isolates; type 2 subtype 2e, 2f, 2g, 2h, 2i, 2k or 2l isolates; type 3 subtype 3g isolates; type 4 subtype 4k, 4l or 4m isolates; type 7 subtype 7a, 7c or 7d isolates, type 9, type 10 or type 11 isolates. In order to obtain these residues the alignments given in FIGS. 2, 4 and 6 may be used to deduce the type- and or subtype-specificity of any of the unique residues given above.

For example T190 (detected in subtype 1d) refers to a threonine at position 190 (see FIG. 2). In other sequences only a serine (S90) or exceptionally an alanine (A190 in type 10a) can be detected.

The polypeptides according to this embodiment of the invention may be possibly labelled, or attached to a solid substrate, or coupled to a carrier molecule such as biotin, or mixed with a proper adjuvant all known in the art and according to the intended use (diagnostic, therapeutic or prophylactic).

The present invention also relates to a polypeptide as defined above, comprising in its amino acid sequence at least one of the sequences repesented by SEQ ID NO107 to 207 as listed above, or a part thereof which is unique to at least one of the HCV subtypes or types as defined in Table 5, or an analog thereof being substantially homologous and biologically equivalent to said polypeptide or part thereof.

The present invention relates also to a polypeptide having an amino acid sequence as represented in any of SEQ ID NO 1 to 106, or a part thereof which is unique to at least one of the HCV subtypes or types as defined in Table 5, or an analog thereof being substantially homologous and biologically equivalent to said polypeptide or part thereof.

The variable region in the core protein (V-CORE in FIG. 2) has been shown to be useful for serotyping (Machida et al., 1992). The sequence of the type 1 subtype 1d, 1e, 1f or 1g sequence; type 2 subtype 2e, 2f, 2g, 2h, 2i, 2k and 2l sequence; type 3 subtype 3g; type 4, subtype 4k, 4l or 4m sequence; type 7 (subtype 7a, 7c and 7d sequences), 9, 10 or 11 sequences of the present invention show type-specific features in this region. The peptide from amino acid 68 to 78 (V-core region) shows the following unique sequence for the sequences of the present invention (see FIG. 2):

```
ARQSDGRSWAQ or ARRSEGRSWAQ as for subtype 1d  (SEQ ID NO 107 and 108)

ERRPEGRSWAQ as for subtype 1e               (SEQ ID NO 109)

ARRPEGRSWAQ as for subtype 1f               (SEQ ID NO 110)

DRRTTGKSWGR as for subtype 2k               (SEQ ID NO 111)

DRRATGRSWGR as for subtype 2e               (SEQ ID NO 112)

DRRATGKSWGR as for subtype 2f               (SEQ ID NO 113)
```

-continued

| | |
|---|---|
| VRQPTGRSWGQ as for type 9 | (SEQ ID NO 114) |
| VRHQTGRTWAQ as for subtype 7a and 7c | (SEQ ID NO 115) |
| VRQNQGRTWAQ as for subtype 7d | (SEQ ID NO 116) |
| ARRTEGRSWAQ as for type 10 | (SEQ ID NO 117) |
| VRRTTGRXXXX or VRRTTGRTWAQ as for type 11 | (SEQ ID NO 118 and 119) |

Five type-specific variable regions (V1 to V5) can be identified after aligning E1 amino acid sequences of the genotypes of the present invention to the genotypes already known, as shown in FIG. 2.

```
Region V1 encompasses amino acids 192 to 203, this is the amino-terminal 10

-continued

| | |
|---|---|
| VYEANGMILHL as for subtype 7d | (SEQ ID NO 154) |
| VYEAGDIILHL as for type 10. | (SEQ ID NO 155) |

Region V3 encompasses the amino acids 230 to 242. The following unique V3 region sequences can be deduced from FIG. 2:

| | |
|---|---|
| VREDNHLRCWMAL or VRENNSSRCWMAL as for subtype 1d | (SEQ ID NO 156 and 157) |
| IREGNISRCWVLP as for subtype 1f | (SEQ ID NO 158) |
| ENSSGRFHCWIPI as for subtype 2e | (SEQ ID NO 159) |
| ERSGNRTFCWTAV as for subtype 2f | (SEQ ID NO 160) |
| ELQGNKSRCWIPV as for subtype 2g | (SEQ ID NO 161) |
| ERHQNQSRCWIPV as for subtype 2h | (SEQ ID NO 162) |
| EWKDNTSRCWIPV as for subtype 2i | (SEQ ID NO 163) |
| EREGNSSRCWIPV as for subtype 2k | (SEQ ID NO 164) |
| VREGNQSRCWVAL or VRTGNQSRCWVAL or VRVGNQSSCWVAL or VRVGNQSRCWVAL or VKEGNHSRCWVAL as for subtype 4k | (SEQ ID NO 165, 166, 167, 168 or 169) |
| VKTGNTSRCWVAL as for subtype 4l | (SEQ ID NO 170) |
| IKAGNESRCWLPV as for type 9 | (SEQ ID NO 171) |
| VKXXNQSRCWVQA as for subtype 7c | (SEQ ID NO 172) |
| VKTGNLTKCWLSA as for subtype 7d | (SEQ ID NO 173) |
| VRSGNTSRCWIPV as for type 10 | (SEQ ID NO 174) |

Region V4 encompasses the amino acids 248 to 257. The following unique V4 region sequences can be deduced from FIG. 2:

| | |
|---|---|
| VKNASVPTAA or VKDANVPTAA as for subtype 1d | (SEQ ID NO 175 and 176) |
| ARIANAPIDE as for subtype 1f | (SEQ ID NO 177) |
| VSKPGALTKG as for subtype 2e | (SEQ ID NO 178) |
| VSRPGALTRG as for subtype 2f | (SEQ ID NO 179) |
| VNQPGALTRG as for subtype 2g | (SEQ ID NO 180) |
| VSQPGALTRG as for subtype 2h | (SEQ ID NO 181) |
| VSQPGALTKG as for subtype 2i | (SEQ ID NO 182) |
| VSRPGALTEG as for subtype 2k | (SEQ ID NO 183) |
| APYIGAPLES or APYTAAPLES as for subtype 4k | (SEQ ID NO 184 and 185) |
| APILSAPLMS as for subtype 4l | (SEQ ID NO 186) |
| VPNSSVPIHG as for type 9 | (SEQ ID NO 187) |
| VPNASTPVTG as for subtype 7c | (SEQ ID NO 188) |
| VQNASVSIRG as for subtype 7d | (SEQ ID NO 189) |
| VKSPCAATAS as for type 10 | (SEQ ID NO 190) |

Region V5 encompasses the amino acids 294 to 303. The following unique V5 region peptides can be deduced from FIG. 2:

| | |
|---|---|
| SPRMHHTTQE or SPRLYHTTQE as for subtype 1d | (SEQ ID NO 191 and 192) |
| TSRRHWTVQD as for subtype 1f | (SEQ ID NO 193) |
| APKRHYFVQE as for subtype 2e | (SEQ ID NO 194) |
| SPQYHTFVQE as for subtype 2f | (SEQ ID NO 195) |

-continued

```
SPQHHNFSQD as for subtype 2g                                                              (SEQ ID NO 196)

SPQHHIFVQD as for subtype 2h                                                              (SEQ ID NO 197)

SPEHHHFVQD as for subtype 2k                                                              (SEQ ID NO 198)

RPRRHWTTQD or RPRRHWTAQD or QPRRHWTTQD or RPRRHWTTQE as for subtype 4k                    (SEQ ID NO 199,
                                                                                           200, 201 or 202)

QPRRHWTVQD as for subtype 4l                                                              (SEQ ID NO 203)

RPKYHQVTQD as for type 9                                                                  (SEQ ID NO 204)

RPRMHQVVQE as for subtype 7c                                                              (SEQ ID NO 205)

RPRMYEIAQD as for subtype 7d                                                              (SEQ ID NO 206)

RHRQHWTVQD as for tvoe 10                                                                 (SEQ ID NO 207)
```

The above given list of peptides are particularly useful for treatment and vaccine and diagnostic development.

Also comprised in the present invention is any synthetic peptide (see below) or polypeptide containing at least an epitope derived from the above-defined peptides in their peptidic chain. Also comprised within the present invention is any synthetic peptide or polypeptide comprising at least 6, 7, 8, or 9 contiguous amino acids derived from the above-defined peptides in their peptidic chain.

As used herein, 'epitope' or 'antigenic determinant' means an amino acid sequence that is immunoreactive. Generally an epitope consists of at least 3 to 4 amino acids, and more usually, consists of at least 5 or 6 amino acids, sometimes the epitope consists of about 7 to 8, or even about 10 amino acids.

The present invention particularly relates to any peptide (see below) or polypeptide contained in any of the amino acid sequences as represented in SEQ ID NO 2, 4, 7, 9, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104 or 106 (see Table 5 and FIG. 3, Examples section).

The present invention also relates to a recombinant polypeptide encoded by a polynucleic acid as defined above, or a part thereof which is unique to any of the HCV subtypes or types as defined in Table 5, or an analog thereof being substantially homologous and biologically equivalent to said polypeptide.

The present invention also relates to a recombinant expression vector comprising a polynucleic acid or a part thereof as defined above, operably linked to prokaryotic, eukaryotic or viral transcription and translation control elements.

In general said recombinant vector will comprise a vector sequence, an appropriate prokaryotic, eukaryotic or viral promoter sequence followed by the nucleotide sequences as defined above, with said recombinant vector allowing the expression of any one of the polypeptides as defined above in a prokaryotic, or eukaryotic host or in living mammals when injected as naked DNA, and more particularly a recombinant vector allowing the expression of any of the new HCV sequences of the invention spanning particularly the following amino acid positions:

a polypeptide starting in the region between positions I and 10 and ending at any position in the region between positions 70 and 420, more particularly a polypeptide spanning positions 1 to 70, 1 to 85, positions 1 to 120, positions 1 to 150, positions 1 to 191, or positions 1 to 200, for expression of the Core protein, and a polypeptide spanning positions 1 to 263, positions 1 to 326, positions 1 to 383, or positions 1 to 420 for expression of the Core and E1 protein;

a polypeptide starting at any position in the region between positions 117 and 192, and ending at any position in the region between positions 263 and 420, for expression of E1, or forms that have the hydrophobic region deleted (positions 264 to 293 plus or minus 8 amino acids);

a polypeptide starting at any position in the region between positions 1556 and 1688, and ending at any position in the region between positions 1739 and 1764, for expression of NS4, more particularly ;a polypeptide starting at position 1658 and ending at position 1711, for expression of NS4a antigen, and more particularly, a polypeptide starting at position 1712 and ending in the region between positions 1743 and 1972 (for instance 1712–1743, 1712–1764, 1712–1782, 1712–1972, 1712–1782, 1712–1902), for expression of NS4b antigen or parts thereof.

Any other HCV vector construction known in the art may also be used for the recombinant polypeptides of the present invention.

Also any of the known purification methods for recombinant proteins may be used for the production of the recombinant polypeptides of the present invention, particularly the HCV recombinant polypeptide purification methods as disclosed in PCT/EP 95/03031 in name of Innogenetics N.V.

The term "vector" may comprise a plasmid, a cosmid, a phage, or a virus or a transgenic animal. Particularly useful for vaccine development may be BCG or adenoviral vectors, as well as avipox recombinant viruses.

The present invention also relates to a method for the production of a recombinant polypeptide as defined above, comprising:

transformation of an appropriate cellular host with a recombinant vector, in which a polynucleic acid or a part thereof according to as defined above has been inserted under the control of appropriate regulatory elements, culturing said transformed cellular host under conditions enabling the expression of said insert, and, harvesting said polypeptide.

The term 'recombinantly expressed' used within the context of the present invention refers to the fact that the proteins of the present invention are produced by recombinant expression methods be it in prokaryotes, or lower or higher eukaryotes as discussed in detail below.

The term 'lower eukaryote' refers to host cells such as yeast, fungi and the like. Lower eukaryotes are generally (but not necessarily) unicellular. Preferred lower eukaryotes are yeasts, particularly species within *Saccharomyces, Schizosaccharomyces, Kluveromyces, Pichia* (e.g. *Pichia pastoris*), *Hansenula* (e.g. *Hansenula polymorpha*), *Yarowia, Schwaniomyces, Schizosaccharomyces, Zygosaccharomyces* and the like. *Saccharomyces cerevisiae, S. carlsbergensis* and *K. lactis* are the most commonly used yeast hosts, and are convenient fungal hosts.

The term 'prokaryotes' refers to hosts such as *E.coli, Lactobacillus, Lactococcus, Salmonella, Streptococcus, Bacillus subtilis* or *Streptomyces*. Also these hosts are contemplated within the present invention.

The term 'higher eukaryote' refers to host cells derived from higher animals, such as mammals, reptiles, insects, and the like. Presently preferred higher eukaryote host cells are derived from Chinese hamster (e.g. CHO), monkey (e.g. COS and Vero cells), baby hamster kidney (BHK), pig kidney (PK15), rabbit kidney 13 cells (RK13), the human osteosarcoma cell line 143 B, the human cell line HeLa and human hepatoma cell lines like Hep G2, and insect cell lines (e.g. *Spodoptera frugiperda*). The host cells may be provided in suspension or flask cultures, tissue cultures, organ cultures and the like. Alternatively the host cells may also be transgenic animals.

The term 'recombinant polynucleotide or nucleic acid' intends a polynucleotide or nucleic acid of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

The term 'recombinant host cells', 'host cells', 'cells', 'cell lines', 'cell cultures', and other such terms denoting microorganisms or higher eukaryotic cell lines cultured as unicellular entities refer to cells which can be or have been, used as recipients for a recombinant vector or other transfer polynucleotide, and include the progeny of the original cell which has been transfected. It is understood that the progeny of a single parental cell may not necessarily be completely identical in morphology or in genomic or total DNA complement as the original parent, due to natural, accidental, or deliberate mutation.

The term 'replicon' is any genetic element, e.g., a plasmid, a chromosome, a virus, a cosmid, etc., that behaves as an autonomous unit of polynucleotide replication within a cell; i.e., capable of replication under its own control.

The term 'vector' is a replicon further comprising sequences providing replication and/or expression of a desired open reading frame.

The term 'control sequence' refers to polynucleotide sequences which are necessary to effect the expression of coding sequences to which they are ligated. The nature of such control sequences differs depending upon the host organism; in prokaryotes, such control sequences generally include promoter, ribosomal binding site, splicing sites and terminators; in eukaryotes, generally, such control sequences include promoters, splicing sites, terminators and, in some instances, enhancers. The term 'control sequences' is intended to include, at a minimum, all components whose presence is necessary for expression, and may also include additional components whose presence is advantageous, for example, leader sequences which govern secretion.

The term 'promoter' is a nucleotide sequence which is comprised of consensus sequences which allow the binding of RNA polymerase to the DNA template in a manner such that mRNA production initiates at the normal transcription initiation site for the adjacent structural gene.

The expression 'operably linked' refers to a juxtaposition wherein the components so described are in a relationship permitting them to function in their intended manner. A control sequence 'operably linked' to a coding sequence is ligated in such a way that expression of the coding sequence is achieved under conditions compatible with the control sequences.

The segment of the HCV cDNA encoding the desired sequence inserted into the vector sequence may be attached to a signal sequence. Said signal sequence may be that from a non-HCV source, e.g. the IgG or tissue plasminogen activator (tpa) leader sequence for expression in mammalian cells, or the à-mating factor sequence for expression into yeast cells, but particularly preferred constructs according to the present invention contain signal sequences appearing in the HCV genome before the respective start points of the proteins.

A variety of vectors may be used to obtain recombinant expression of HCV single or specific oligomeric envelope proteins of the present invention. Lower eukaryotes such as yeasts and glycosylation mutant strains are typically transformed with plasmids, or are transformed with a recombinant virus. The vectors may replicate within the host independently, or may integrate into the host cell genome.

Higher eukaryotes may be transformed with vectors, or may be infected with a recombinant virus, for example a recombinant vaccinia virus. Techniques and vectors for the insertion of foreign DNA into vaccinia virus are well known in the art, and utilize, for example homologous recombination. A wide variety of viral promoter sequences, possibly terminator sequences and poly(A)-addition sequences, possibly enhancer sequences and possibly amplification sequences, all required for the mammalian expression, are available in the art. Vaccinia is particularly preferred since vaccinia halts the expression of host cell proteins. Vaccinia is also very much preferred since it allows the expression of f.i. E1 and E2 proteins of HCV in cells or individuals which are immunized with the live recombinant vaccinia virus. For vaccination of humans the avipox and Ankara Modified Virus (AMV) are particularly useful vectors.

Also known are insect expression transfer vectors derived from baculovirus *Autographa californica* nuclear polyhedrosis virus (AcNPV), which is a helper-independent viral expression vector. Expression vectors derived from this system usually use the strong viral polyhedrin gene promoter to drive the expression of heterologous genes. Different vectors as well as methods for the introduction of heterologous DNA into the desired site of baculovirus are available to the man skilled in the art for baculovirus expression. Also different signals for posttranslational modification recognized by insect cells are known in the art.

The present invention also relates to a host cell transformed with a recombinant vector as defined above.

The present invention also relates to a method for detecting antibodies to HCV present in a biological sample, comprising:

(i) contacting the biological sample to be analysed for the presence of HCV with a polypeptide as defined above,
(ii) detecting the immunological complex formed between said antibodies and said polypeptide.

The present invention also relates to a method for HCV typing, comprising:

(i) contacting the biological sample to be analysed for the presence of HCV with a polypeptide as defined above,
(ii) detecting the immunological complex formed between said antibodies and said polypeptide.

The present invention also relates to a diagnostic kit for use in detecting the presence of HCV, said kit comprising at least one polypeptide as defined above, with said polypeptide being preferably bound to a solid support.

The present invention also relates to a diagnostic kit for HCV typing, said kit comprising at least one polypeptide as defined above, with said polypeptide being preferably bound to a solid support.

The present invention also relates to diagnostic kit according as defined above, said kit comprising a range of said polypeptides which are attached to specific locations on a solid substrate.

The present invention also relates to a diagnostic kit as defined above, wherein said solid support is a membrane strip and said polypeptides are coupled to the membrane in the form of parallel lines.

The immunoassay methods according to the present invention may utilize antigens from the different domains of the new and unique polypeptide sequences of the present invention that maintain linear (in case of peptides) and conformational epitopes (in case of polypeptides) recognized by antibodies in the sera from individuals infected with HCV. It is within the scope of the invention to use for instance single or specific oligomeric antigens, dimeric antigens, as well as combinations of single or specific oligomeric antigens. The HCVantigens of the present invention may be employed in virtually any assay format that employs a known antigen to detect antibodies. Of course, a format that denatures the HCV conformational epitope should be avoided or adapted. A common feature of all of these assays is that the antigen is contacted with the body component suspected of containing HCV antibodies under conditions that permit the antigen to bind to any such antibody present in the component. Such conditions will typically be physiologic temperature, pH and ionic strenght using an excess of antigen. The incubation of the antigen with the specimen is followed by detection of immune complexes comprised of the antigen.

Design of the immunoassays is subject to a great deal of variation, and many formats are known in the art. Protocols may, for example, use solid supports, or immunoprecipitation. Most assays involve the use of labeled antibody or polypeptide; the labels may be, for example, enzymatic, fluorescent, chemiluminescent, radioactive, or dye molecules. Assays which amplify the signals from the immune complex are also known; examples of which are assays which utilize biotin and avidin or streptavidin, and enzyme-labeled and mediated immunoassays, such as ELISA assays.

The immunoassay may be, without limitation, in a heterogeneous or in a homogeneous format, and of a standard or competitive type. In a heterogeneous format, the polypeptide is typically bound to a solid matrix or support to facilitate separation of the sample from the polypeptide after incubation. Examples of solid supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride (known as Immunolon™), diazotized paper, nylon membranes, activated beads, and Protein A beads. For example, Dynatech Immunolon™ 1 or Immunlon™ 2 microtiter plates or 0.25 inch polystyrene beads (Precision Plastic Ball) can be used in the heterogeneous format. The solid support containing the antigenic polypeptides is typically washed after separating it from the test sample, and prior to detection of bound antibodies. Both standard and competitive formats are know in the art.

In a homogeneous format, the test sample is incubated with the combination of antigens in solution. For example, it may be under conditions that will precipitate any antigen-antibody complexes which are formed. Both standard and competitive formats for these assays are known in the art.

In a standard format, the amount of HCV antibodies in the antibody-antigen complexes is directly monitored. This may be accomplished by determining whether labeled anti-xenogeneic (e.g. anti-human) antibodies which recognize an epitope on anti-HCV antibodies will bind due to complex formation. In a competitive format, the amount of HCV antibodies in the sample is deduced by monitoring the competitive effect on the binding of a known amount of labeled antibody (or other competing ligand) in the complex.

Complexes formed comprising anti-HCV antibody (or in the case of competitive assays, the amount of competing antibody) are detected by any of a number of known techniques, depending on the format. For example, unlabeled HCV antibodies in the complex may be detected using a conjugate of anti-xenogeneic Ig complexed with a label (e.g. an enzyme label).

In an immunoprecipitation or agglutination assay format the reaction between the HCV antigens and the antibody forms a network that precipitates from the solution or suspension and forms a visible layer or film of precipitate. If no anti-HCV antibody is present in the test specimen, no visible precipitate is formed.

There currently exist three specific types of particle agglutination (PA) assays. These assays are used for the detection of antibodies to various antigens when coated to a support. One type of this assay is the hemagglutination assay using red blood cells (RBCs) that are sensitized by passively adsorbing antigen (or antibody) to the RBC. The addition of specific antigen antibodies present in the body component, if any, causes the RBCs coated with the purified antigen to agglutinate.

To eliminate potential non-specific reactions in the hemagglutination assay, two artificial carriers may be used instead of RBC in the PA. The most common of these are latex particles. However, gelatin particles may also be used. The assays utilizing either of these carriers are based on passive agglutination of the particles coated with purified antigens.

The HCV antigens of the present invention comprised of conformational epitopes will typically be packaged in the form of a kit for use in these immunoassays. The kit will normally contain in separate containers the native HCV antigen, control antibody formulations (positive and/or negative), labeled antibody when the assay format requires the same and signal generating reagents (e.g. enzyme substrate) if the label does not generate a signal directly. The native HCV antigen may be already bound to a solid matrix or separate with reagents for binding it to the matrix. Instructions (e.g. written, tape, CD-ROM, etc.) for carrying out the assay usually will be included in the kit.

Immunoassays that utilize the native HCV antigen are useful in screening blood for the preparation of a supply from which potentially infective HCV is lacking. The method for the preparation of the blood supply comprises the following steps. Reacting a body component, preferably blood or a blood component, from the individual donating blood with HCV polypeptides of the present invention to allow an immunological reaction between HCV antibodies, if any, and the HCV antigen. Detecting whether anti-HCV antibody—HCV antigen complexes are formed as a result of the reacting. Blood contributed to the blood supply is from donors that do not exhibit antibodies to the native HCV antigens.

In cases of a positive reactivity to the HCV antigen, it is preferable to repeat the immunoassay to lessen the possibility of false positives. For example, in the large scale screening of blood for the production of blood products (e.g. blood transfusion, plasma, Factor VII, immunoglobulin, etc.) 'screening' tests are typically formatted to increase sensitivity (to insure no contaminated blood passes) at the expense of specificity; i.e. the false-positive rate is increased. Thus, it is typical to only defer for further testing those donors who are 'repeatedly reactive'; i.e. positive in two or more runs of the immunoassay on the donated sample. However, for confirmation of HCV-positivity, the 'confirmation' tests are typically formatted to increase specificity (to insure that no false-positive samples are confirmed) at the expense of sensitivity.

The solid phase selected can include polymeric or glass beads, nitrocellulose, microparticles, microwells of a reaction tray, test tubes and magnetic beads. The signal generating compound can include an enzyme, a luminescent compound, a chromogen, a radioactive element and a chemiluminescent compound. Examples of enzymes include alkaline phosphatase, horseradish peroxidase and beta-galactosidase. Examples of enhancer compounds include biotin, anti-biotin and avidin. Examples of enhancer compounds binding members include biotin, anti-biotin and avidin. In order to block the effects of rheumatoid factor-like substances, the test sample is subjected to conditions sufficient to block the effect of rheumatoid factor-like substances. These conditions comprise contacting the test sample with a quantity of anti-human IgG to form a mixture, and incubating the mixture for a time and under conditions sufficient to form a reaction mixture product substantially free of rheumatoid factor-like substance.

The present invention particularly relates to an immunoassay format in which the polypeptides (or peptides) of the invention are coupled to a membrane in the form of parallel lines. This assay format is particularly advantageous for HCV typing purposes.

The present invention also relates to a pharmaceutical composition comprising at least one (recombinant) polypeptides as defined above and a suitable excipient, diluent or carrier.

The present invention also relates to a method of preventing HCV infection, comprising administering the pharmaceutical composition as defined above to a mammal in effective amount to stimulate the production of protective antibody or protective T-cell response.

The present invention relates to the use of a composition as defined above in a method for preventing HCV infection.

The present invention further relates to a vaccine for immunizing a mammal against HCV infection, comprising at least one (recombinant) polypeptide as defined above, in a pharmaceutically acceptable carrier.

The term 'immunogenic' refers to the ability of a substance to cause a humoral and/or cellular response, whether alone or when linked to a carrier, in the presence or absence of an adjuvant. 'Neutralization' refers to an immune response that blocks the infectivity, either partially or fully, of an infectious agent. A 'vaccine' is an immunogenic composition capable of eliciting protection against HCV, whether partial or complete. A vaccine may also be useful for treatment of an individual, in which case it is called a therapeutic vaccine.

The term 'therapeutic' refers to a composition capable of treating HCV infection.

The term 'effective amount' refers to an amount of epitope-bearing polypeptide sufficient to induce an immunogenic response in the individual to which it is administered, or to otherwise detectably immunoreact in its intended system (e.g., immunoassay). Preferably, the effective amount is sufficient to effect treatment, as defined above. The exact amount necessary will vary according to the application. For vaccine applications or for the generation of polyclonal antiserum/antibodies, for example, the effective amount may vary depending on the species, age, and general condition of the individual, the severity of the condition being treated, the particular polypeptide selected and its mode of administration, etc. It is also believed that effective amounts will be found within a relatively large, non-critical range. An appropriate effective amount can be readily determined using only routine experimentation. Preferred ranges of proteins for prophylaxis of HCV disease are 0.01 to 100 $\mu$g/dose, preferably 0.1 to 50 $\mu$g/dose. Several doses may be needed per individual in order to achieve a sufficient immune response and subsequent protection against HCV disease.

The present invention also relates to a vaccine as defined above, comprising at least one (recombinant) polypeptide as defined above, with said polypeptide being unique for at least one of the subtypes or types as defined above.

Said vaccine compositions may include prophylactic as well as therapeutic vaccine compositions.

Pharmaceutically acceptable carriers include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers; and inactive virus particles. Such carriers are well known to those of ordinary skill in the art.

Preferred adjuvants to enhance effectiveness of the composition include, but are not limited to: aluminim hydroxide (alum), N-acetyl-muramyl-L-threonyl-D-isoglutamine (thr-MDP) as found in U.S. Pat. No. 4,606,918, N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (MTP-PE) and RIBI, which contains three components extracted from bacteria, monophosphoryl lipid A, trehalose dimycolate, and cell wall skeleton (MPL+TDM+CWS) in a 2% squalene/Tween 80 emulsion. Any of the 3 components MPL, TDM or CWS may also be used alone or combined 2 by 2. Additionally, adjuvants such as Stimulon (Cambridge Bioscience, Worcester, Mass.).

Immunogenic compositions used as vaccines comprise a 'sufficient amount' or 'an immunologically effective amount' of the proteins of the present invention, as well as any other of the above mentioned components, as needed. 'Immunologically effective amount', means that the administration of that amount to an individual, either in a single dose or as part of a series, is effective for treatment, as defined above. This amount varies depending upon the health and physical condition of the individual to be treated, the taxonomic group of individual to be treated (e.g. non-human primate, primate, etc.), the capacity of the individual's immune system to synthesize antibodies, the degree of protection desired, the formulation of the vaccine, the treating doctor's assessment of the medical situation, the strain of infecting HCV, and other relevant factors. It is expected that the amount will fall in a relatively broad range that can be determined through routine trials. Usually, the amount will vary from 0.01 to 1000 $\mu$g/dose, more particularly from 0.1 to 100 $\mu$g/dose.

The proteins of the invention may also serve as vaccine carriers to present homologous (e.g. T cell epitopes or B cell epitopes fromfor istance the core,E1, E2, NS2, NS3, NS4 or NS5 regions) or heterologous (non-HCV) haptens, in the same manner as Hepatitis B surface antigen (see European Patent Application 174,444). In this use, envelope proteins provide an immunogenic carrier capable of stimulating an immune response to haptens or antigens conjugated to the aggregate. The antigen may be conjugated either by conventional chemical methods, or may be cloned into the gene encoding E1 and/or E2 at a location corresponding to a hydrophilic region of the protein. Such hydrophylic regions include the V1 region (encompassing amino acid positions 191 to 202), the V2 region (encompassing amino acid positions 213 to 223), the V3 region (encompassing amino acid positions 230 to 242), the V4 region (encompassing amino acid positions 230 to 242), the V5 region (encompassing amino acid positions 294 to 303) and the V6 region (encompassing amino acid positions 329 to 336). Another useful location for insertion of haptens is the hydrophobic region (encompassing approximately amino acid positions 264 to 293). It is shown in the present invention that this region can be deleted without affecting the reactivity of the deleted E1 protein with antisera. Therefore, haptens may be inserted at the site of the deletion.

The immunogenic compositions are conventionally administered parenterally, typically by injection, for example, subcutaneously or intramuscularly. Additional formulations suitable for other methods of administration include oral formulations and suppositories. Dosage treatment may be a single dose schedule or a multiple dose schedule. The vaccine may be administered in conjunction with other immunoregulatory agents.

The administration of the immunogen(s) of the present invention may be for either a prophylactic or therapeutic purpose. When provided prophylactically, the immunogen(s) is provided in advance of any exposure to HCV or in advance of any symptom of any symptoms due to HCV infection. The prophylactic administration of the immunogen serves to prevent or attenuate any subsequent infection of HCV in a mammal. When provided therapeutically, the immunogen(s) is provided at (or shortly after) the onset of the infection or at the onset of any symptom of infection or disease caused by HCV. The therapeutic administration of the immunogen(s) serves to attenuate the infection or disease.

In addition to use as a vaccine, the compositions can be used to prepare antibodies to HCV (E1) proteins. The antibodies can be used directly as antiviral agents. To prepare antibodies, a host animal is immunized using the E1 proteins native to the virus particle bound to a carrier as described above for vaccines. The host serum or plasma is collected following an appropriate time interval to provide a composition comprising antibodies reactive with the (E1) protein of the virus particle. The gamma globulin fraction or the IgG antibodies can be obtained, for example, by use of saturated ammonium sulfate or DEAE Sephadex, or other techniques known to those skilled in the art. The antibodies are substantially free of many of the adverse side effects which may be associated with other anti-viral agents such as drugs.

The present invention also relates particularly to a peptide corresponding to an amino acid sequence encoded by at least one of the HCV genomic sequences as defined above, with said peptide being unique to any of the HCV subtypes or types as defined in Table 5, and which contains at least one amino acid differing from any of the known HCV types or subtypes, or an analog thereof being substantially homologous and biologically equivalent.

The present invention relates particularly to a peptide comprising at least one unique epitope of the new sequences of the invention as represented in SEQ ID NO 1 to 106.

The present invention relates also particularly to a peptide comprising in its sequence a unique amino acid residue of the invention as defined above.

The present invention relates particularly to a peptide which is biotinylated as explained in WO 93/18054.

All the embodiments (immunoassay formats, vaccines, compositions, uses, etc.) illustrated for the polypeptides of the invention as above also relate to the peptides of the invention.

The present invention also relates to a method for detecting antibodies to HCV present in a biological sample, comprising:

(i) contacting the biological sample to be analysed for the presence of HCV with a peptide as defined above, (ii) detecting the immunological ccomplex formed between said antibodies and said peptide.

The present invention also relates to a method for HCV typing, comprising:

(i) contacting the biological sample to be analysed for the presence of HCV with a peptide as defined above, (ii) detecting the immunological ccomplex formed between said antibodies and said peptide.

The present invention also relates to a diagnostic kit for use in detecting the presence of HCV, said kit comprising at least one peptide as defined above, with said peptide being preferably bound to a solid support.

The present invention also relates to a diagnostic kit for HCV typing, said kit comprising at least one peptide as defined above, with said peptide being preferably bound to a solid support.

The present invention also relates to a diagnostic kit as defined above, wherein said peptides are selected from the following:

at least one NS4 peptide, at least one NS4 peptide and at least one Core peptide, at least one NS4 peptide and at least one Core peptide and at least one E1 peptide, at least one NS4 peptide and at least one E1 peptide.

The present invention also relates to a diagnostic kit as defined above, said kit comprising a range of said peptides which are attached to specific locations on a solid substrate.

The present invention also relates to a diagnostic kit as defined above, wherein said solid support is a membrane strip and said peptides are coupled to the membrane in the form of parallel lines.

The present invention also relates to a pharmaceutical composition comprising at least one as defined above and a suitable excipient, diluent or carrier.

the present invention also relates to a method of preventing HCV infection, comprising administering the pharmaceutical composition as defined above to a mammal in effective amount to stimulate the production of protective antibody or protective T-cell response.

The present invention also relates to the use of a composition as defined above in a method for preventing HCV infection.

The present invention also relates to a vaccine for immunizing a mammal against HCV infection, comprising at least one peptide as defined above, in a pharmaceutically acceptable carrier.

The present invention relates also to a vaccine as defined above, comprising at least one peptide as defined above, with said peptide being unique for at least one of the subtypes or types as defined in Table 5.

The present invention relates to an antibody raised upon immunization with at least one polypeptide or peptide as defined above, with said antibody being specifically reactive with any of said polypeptides or peptides, and with said antibody being preferably a monoclonal antibody.

The monoclonal antibodies of the invention can be produced by any hybridoma liable to be formed according to classical methods from splenic cells of an animal, particularly from a mouse or rat, immunized against the HCV polypeptides according to the invention as defined above on the one hand, and of cells of a myeloma cell line on the other hand, and to be selected by the ability of the hybridoma to produce the monoclonal antibodies recognizing the polypeptides which has been initially used for the immunization of the animals.

The antibodies involved in the invention can be labelled by an appropriate label of the enzymatic, fluorescent, or radioactive type.

The monoclonal antibodies according to this preferred embodiment of the invention may be humanized versions of mouse monoclonal antibodies made by means of recombinant DNA technology, departing from parts of mouse and/or human genomic DNA sequences coding for H and L chains or from cDNA clones coding for H and L chains.

Alternatively the monoclonal antibodies according to this preferred embodiment of the invention may be human monoclonal antibodies. These antibodies according to the present embodiment of the invention can also be derived from human peripheral blood lymphocytes of patients infected with HCV type 1 subtype 1d, 1e, 1f or 1g, HCV type 2 subtype 2e, 2f, 2g, 2h, 2i, 2k or 2l; HCV type 3, subtype 3g; HCV type 4 subtype 4k, 4l or 4m; and/or HCV type 7 (subtypes 7a, 7c or 7d), 9, 10 or 11, or vaccinated against HCV. Such human monoclonal antibodies are prepared, for instance, by means of human peripheral blood lymphocytes (PBL) repopulation of severe combined immune deficiency (SCID) mice (for recent review, see Duchosal et al. 1992) or by screening Eppstein Barr-virus-transformed lymphocytes of infected or vaccinated individuals for the presence of reactive B-cells by means of the antigens of the present invention.

The invention also relates to the use of the proteins of the invention, muteins thereof, or peptides derived therefrom for the selection of recombinant antibodies by the process of repertoire cloning (Persson et al., 1991).

Antibodies directed to peptides derived from a certain genotype may be used either for the detection of such HCV genotypes, or as therapeutic agents.

The present invention relates also to a method for detecting HCV antigens present in a biological sample, comprising:
(i) contacting said biological sample with an antibody as defined above,
(ii) detecting the immune compleexes formed between said HCV antigens and said antibody.

The present invention relates also to a method for HCV typing, comprising:
(i) contacting said biological sample with an antibody as defined above,
(ii) detecting the immune compleexes formed between said HCV antigens and said antibody.

The present invention relates also to a diagnostic kit for use in detecting the presence of HCV, said kit comprising at least one antibody as defined above, with said antibody being preferably bound to a solid support.

The present invention relates also to a diagnostic kit for HCV typing, said kit comprising at least one antibody as defined above, with said antibody being preferably bound to a solid support.

The present invention relates also to a diagnostic kit as defined above, said kit comprising a range of said antibodies which are attached to specific locations on a solid substrate.

The present invention relates also to a pharmaceutical composition comprising at least one antibody as defined above and a suitable excipient, diluent or carrier.

The present invention relates also to a method of preventing or treating HCV infection, comprising administering the pharmaceutical composition as defined above to a mammal in effective amount.

The present invention relates also to the use of a composition as defined above in a method for preventing or treating HCV infection.

The genotype may also be detected by means of a type-specific antibody as defined above, which may also be linked to any polynucleotide sequence that can afterwards be amplified by PCR to detect the immune complex formed (Immuno-PCR, Sano et al., 1992).

Any publications or patent applications referred to herein are incorporated by reference. The following examples illustrate aspects of the invention but are in no way intended to limit the scope thereof.

FIGURE LEGENDS

Figure Legends

FIG. 1

Alignment of the nucleotide sequences of the Core/E1 region of some of the isolates of the newly identified types and subtypes of the present invention, with other known prototype isolates of subtypes.

FIG. 2

Alignment of the amino acid sequences of the Core/E1 region of some of the isolates of the newly identified types and subtypes of the present invention, with other known prototype isolates of subtypes.

FIG. 3

Nucleotide and amino acid sequences obtained from the new HCV isolates of the present invention (SEQ ID NO 1 to 106).

FIG. 4

Alignment of the amino acid sequences of the Core/E1 region of some of the isolates of the newly identified types and subtypes of the present invention, with other known prototype isolates of subtypes.

FIG. 5

Alignment of the nucleotide sequences of the NS5b region of some of the isolates of the newly identified types and subtypes of the present invention, with other known prototype isolates of subtypes.

FIG. 6

Alignment of the amino acid sequences of the NS5b region of some of the isolates of the newly identified types and subtypes of the present invention, with other known prototype isolates of subtypes.

Table 5

Overview of the new subtypes and types of the present invention and the regions sequenced. The subtypes between barckets have been replaced by the non-bracketed subtypes following the classification of Tokita et al. (1994).

EXAMPLES

Serum Samples.

Serum samples from Cameroonian blood donors (CAM) were screened for HCV antibodies with Innotest HCV Ab III, and confirmed by INNO-LIA HCV III (Innogenetics, Antwerp, Belgium). Serum samples from patients with chronic hepatitis C infection were obtained from various centers in the Benelux countries (BNL), from France (FR), from Pakistan (PAK), from Egypt (EG), and from Vietnam (VN).

Samples from the Benelux, Cameroon, France and Vietnam were selected because of their aberrant reactivities (isolates CAM1078, FR2, FR1, VN4, VN12, VN13, NE98 and others (see Table 5)).

cPCR, LiPA, Cloning and Sequencing.

RNA isolation, cDNA synthesis, PCR, cloning, and LiPA genotyping using biotinylated 5' UR amplification products were performed as described (Stuyver et al., 1994c). The 5' UR, the Core/E1, and the NS5B PCR products were used for direct sequencing. The sequence of the universal 5' UR primers HCPr95, HCPr96, HCPr98, and HCPr29, were described previously (Stuyver et al. 1993b). The following primers were also described (Stuyver et al. 1994c): HCPr41, a sense primer for the amplification of the Core region; HCPr52 and HCPr54 for amplification of the Core/E1 region; and HCPr206 and HCPr207 for amplication of a 340-bp NS5B region.

Serum samples BNL1, BNL2, BNL3, BNL4, BNL5, BNL6, BNL7, BNL8, BNL9, BNL10, BNL11, BNL12, CAM1078, FR2, FR16, FR4, FR13, VN13, VN4, VN12, FR1, NE98, and FR19 were analyzed in the Core/E1 region by direct sequencing. Serum samples BNL1, BNL2, FR17, CAM1078, FR2, FR16, BNL3, FR4, BNL5, FR13, FR18, PAK64, BNL8, BNL12, EG81, VN13, VN4, VN12, FR1, NE98, FR14, FR15, and FR19 were also analyzed in the NS5B region by direct sequencing. Partial 5' UR, Core, E1, and NS5B sequences were obtained. The length of the obtained sequences is sufficient to classify the obtained sequences into new types or subtypes, based on the phylogenetic distances to known sequences. The following sequences could be obtained (nucleotide sequences have odd-numbered SEQ ID NO., amino acid sequences have even-numbered SEQ ID NO.): SEQ ID NO 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103 and 105. The amino acid sequences deduced therefrom are given in SEQ ID NO 2, 4, 7, 9, 12, 14, 16, 18, 20, 22, 24, 26, 28, 30, 32, 34, 36, 38, 40, 42, 44, 46, 48, 50, 20 52, 54, 56, 58, 60, 62, 64, 66, 68, 70, 72, 74, 76, 78, 80, 82, 84, 86, 88, 90, 92, 94, 96, 98, 100, 102, 104 and 106. Table 5 gives an overview of these sequences.

TABLE 5

| Type | Isolate | Nucleotide sequence position | | |
|---|---|---|---|---|
| 1d | BNL1 | 1–310 (SEQ ID NO.1) | 478–925 (SEQ ID NO.3) | 7932–8271 (SEQ ID NO.53) |
| 1d | BNL2 | 1–310 (SEQ ID NO.5) | 478–925 (SEQ ID NO.7) | 7932–8271 (SEQ ID NO.55) |
| 1d | FR17 | | | 7932–8271(SEQ ID NO.57) |
| 1e | CAM1078 | 1–223 (SEQ ID NO.9) | (−238)–414 (SEQ ID NO.59) | 7932–8271 (SEQ ID NO.61) |
| 1f | FR2 | 1–950 (SEQ ID NO.11) | | 7932–8271 (SEQ ID NO.63) |
| 1g | FR16 | (−15)–816 (SEQ ID NO.65) | | 7932–8271 (SEQ ID NO.67) |
| 2e | BNL3 | 1–310 (SEQ ID NO.13) | 478–957 (SEQ ID NO.15) | 7932–8271 (SEQ ID NO.69) |
| 2f | FR4 | 1–957 (SEQ ID NO 17) | | 7932–8271 (SEQ ID NO.71) |
| 2g | BNL4 | | 478–925 (SEQ ID NO.19) | |
| 2h | BNL5 | 1–310 (SEQ ID NO.21) | 478–925 (SEQ ID NO.23) | 7932–8271 (SEQ ID NO.73) |
| 2i | BNL6 | | 478–833 (SEQ ID NO.25) | |
| 2k | FR13 | (−238)–957 (SEQ ID NO.75) | | 7932–8271 (SEQ ID NO.77) |
| 2l | FR18 | | | 7932–8271 (SEQ ID NO.79) |
| 3g | PAK64 | | | 7932–8271 (SEQ ID NO.81) |
| 4k | BNL7 | 1–310 (SEQ ID NO.27) | 478–925 (SEQ ID NO.29) | |
| 4k | BNL8 | | 478–925 (SEQ ID NO.31) | 7932–8271 (SEQ ID NO.83) |
| 4k | BNL9 | | 478–925 (SEQ ID NO.33) | |
| 4k | BNL10 | | 478–925 (SEQ ID NO.35) | |
| 4k | BNL11 | | 478–925 (SEQ ID NO.37) | |
| 4l | BNL12 | | 478–925 (SEQ ID NO.39) | 7932–8271 (SEQ ID NO.85) |
| 4m | EG81 | | | 7932–8271 (SEQ ID NO.87) |
| 7a (8b) | VN13 | 1–413 (SEQ ID NO.45) | | 7932–8271 (SEQ ID NO.89) |
| 7c (8a) | VN4 | 1–957 (SEQ ID NO.43) | | 7932–8271 (SEQ ID NO.91) |
| 7d (9a) | VN12 | 1–957 (SEQ ID NO.47) | | 7932–8271 (SEQ ID NO.93) |
| 9a (7a) | FR1 | 1–957 (SEQ ID NO.41) | | 7932–8271 (SEQ ID NO.95) |
| 10a | NE98 | 1–310 (SEQ ID NO.49) | 478–925 (SEQ ID NO.51) | 7932–8271 (SEQ ID NO.97) |
| 11a | FR14 | | | 7932–8266 (SEQ ID NO.99) |
| 11a | FR15 | | | 7932–8271 (SEQ ID NO.101) |
| 11a | FR19 | (−238)–223 (SEQ ID NO.103) | | 7932–8271 (SEQ ID NO.105) |
| | | Amino acid sequence position | | |
| 1d | BNL1 | 1–103 (SEQ ID NO.2) | 159–308 (SEQ ID NO.4) | 2645–2757 (SEQ ID NO.54) |
| 1d | BNL2 | 1–103 (SEQ ID NO.6) | 159–308 (SEQ ID NO.8) | 2645–2757 (SEQ ID NO.56) |
| 1d | FR17 | | | 2645–2757 (SEQ ID NO.58) |
| 1e | CAM1078 | 1–74 (SEQ ID NO.10) | 1–138 (SEQ ID NO.60) | 2645–2757 (SEQ ID NO.62) |
| 1f | FR2 | 1–316 (SEQ ID NO.12) | | 2645–2757 (SEQ ID NO.64) |
| 1g | FR16 | 1–158 (SEQ ID NO.66) | | 2645–2757 (SEQ ID NO.68) |
| 2e | BNL3 | 1–103 (SEQ ID NO.14) | 159–317 (SEQ ID NO.16) | 2645–2757 (SEQ ID NO.70) |
| 2f | FR4 | 1–317 (SEQ ID NO.18) | | 2645–2757 (SEQ ID NO.72) |
| 2g | BNL4 | | 159–308 (SEQ ID NO.20) | |
| 2h | BNL5 | 1–103 (SEQ ID NO.22) | 159–308 (SEQ ID NO.24) | 2645–2757 (SEQ ID NO.74) |
| 2i | BNL6 | | 159–277 (SEQ ID NO.26) | |
| 2k | FR13 | 1–316 (SEQ ID NO.76) | | 2645–2757 (SEQ ID NO.78) |
| 2l | FR18 | | | 2645–2757 (SEQ ID NO.80) |
| 3g | PAK64 | | | 2645–2757 (SEQ ID NO.82) |
| 4k | BNL7 | 1–103 (SEQ ID NO.28) | 159–308 (SEQ ID NO.30) | |
| 4k | BNL8 | | 159–308 (SEQ ID NO.32) | 2645–2757 (SEQ ID NO.84) |
| 4k | BNL9 | | 159–308 (SEQ ID NO.34) | |
| 4k | BNL10 | | 159–308 (SEQ ID NO.36) | |
| 4k | BNL11 | | 159–308 (SEQ ID NO.38) | |
| 4l | BNL12 | | 159–308 (SEQ ID NO.40) | 2645–2757 (SEQ ID NO.86) |
| 4m | EG81 | | | 2645–2757 (SEQ ID NO.88) |

TABLE 5-continued

| Type | Isolate | Nucleotide sequence position | | |
|------|---------|------|------|------|
| 7a | (8b) VN13 | 1–137 (SEQ ID NO.46) | | 2645–2757 (SEQ ID NO.90) |
| 7c | (8a) VN4 | 1–317 (SEQ ID NO.44) | | 2645–2757 (SEQ ID NO.92) |
| 7d | (9a) VN12 | 1–317 (SEQ ID NO.48) | | 2645–2757 (SEQ ID NO.94) |
| 9a | (7a) FR1 | 1–317 (SEQ ID NO.42) | | 2645–2757 (SEQ ID NO.96) |
| 10a | NE98 | 1–103 (SEQ ID NO.50) | 159–308 (SEQ ID NO.52) | 2645–2757 (SEQ ID NO.98) |
| 11a | FR14 | | | 2645–2755 (SEQ ID NO.100) |
| 11a | FR15 | | | 2645–2757 (SEQ ID NO.102) |
| 11a | FR19 | 1–74 (SEQ ID NO.104) | | 2645–2757 (SEQ ID NO.106) |

Phylogenetic Analysis.

Previously published sequences were taken from the EMBL/Genbank database. Alignments were created using the program HCVALIGN (Stuyver et al. 1994c). Sequences were presented in a sequential format to the Phylogeny Inference Package (PHYLIP) version 3.5c (public domain program freely available from the University of Washington, Seattle, USA). Distance matrices were produced by DNA-DIST using the Kimura 2-parameter setting and further analyzed in NEIGHBOR, using the neighbor-joining setting. The program DRAWTREE was used to create graphic outputs.

Identification of New Subtypes

These analyses indicated the clustering of BNL1, BNL2, CAM 1078, FR2, FR16, and FR17 with type 1 isolates, yet neither of these sequences clustered together with any of the known type 1 subtypes 1a, 1b, or 1c. BNL1, BNL2, and FR17 clearly clustered together and could be assigned a new type 1 subtype 1d, while CAM1078 could be classified into another new subtype 1e, FR2 could be classified into another type 1 subtype 1f, and FR16 could be classified into yet another type 1 subtype 1g. Interestingly, all 3 type 1d isolates (BNL1, BNL2, and FR17) and 1g isolate FR16 were obtained from patients of Moroccan ethnic origin who resided in Europe.

Another group of isolates showed homology to other type 2 sequences, but none of the isolates BNL3, FR4, BNL4, BNL5, BNL6, FR13, or FR18 could be classified into one of the known type 2 subtypes 2a, 2b, 2c (Bukh et al., 1993), or 2d (Stuyver et al., 1994c). Based on the phylogenetic distances to other type 2 isolates and to other isolates of the group, each of these isolates could be classified into a new type 2 subtype. BNL3 was assigned subtype 2e, FR4 subtype 2f, BNL4 subtype 2g, BNL5 subtype 2h, and BNL6 could be classified into yet another type 2 subtype 2i. If the previously published isolate HN4 is classified as 2j, FR13 and FR18 may be classified into new type 2 subtypes 2k and 2l. However, the possibility that FR13 and FR18 could belong to subtypes 2g or 2i has not yet been ruled out. Definite classification can be obtained by determining the NS5B sequences of isolates BNL4 and BNL6, belonging to subtypes 2g and 2i, respectively.

Isolate PAK64 showed homology to type 3 sequences, but could not be classified into one of the known type 3 subtypes 3a to f. Based on the phylogenetic distances to other type 3 isolates, PAK64 could be classified into a new type 3 subtype. PAK64 was assigned subtype 3g. However, the possibility that PAK64 belongs to a known type 3 subtype can not be strictly ruled out since only one region of the genome has been sequenced. Definite classification can be obtained by determining the Core/E1 sequences of isolate PAK64 after amplification with primerHcPr52 and HcPr54.

Among the Benelux and Egyptian samples that were analyzed, some sequences clustered with the previously identified type 4 subtypes 4c and 4d. However, BNL7, BNL8, BNL9, BNL10, BNL11, BNL12, and EG81 clustered into new subtypes of type 4. Isolates BNL7, BNL8, BNL9, BNL10, and BNL11 clustered again separately from BNL12 and EG81 into a new subtype 4k. This subtype was the predominant subtype in the Benelux countries. BNL12 and EG81 also segregated into separate subtypes. BNL12 was assigned to another new subtype 4l and EG81 was assigned to yet another new subtype 4m.

Identification of New HCV Major Types

Isolates FR1, VN4, VN12, VN13, NE98, FR14, FR15, and FR19 did not cluster with any of the known 6 major types of HCV. VN4, VN12, and VN13 were very distantly related to genotype 6, but phylogenetic analysis indicated that these isolates should be assigned new major types. VN13, VN4 and VN12 were related at the subtype level and assigned type 7a, 7c, and 7d, respectively. FR1 was not related to any known isolate and was assigned genotype 9a. NE98 shows a distant relatedness to type 3 sequences, yet phylogenetic analysis suggested classification into a new major type 10a. Depending on international guidelines for assigning type and subtype levels, NE98 may also be classified into an additional type 3 subtype. FR14, FR15, and FR19 show a very distant relatedness to type 2 sequences, yet phylogenetic analysis indicated thes isolates to be classified into a new major type 11, all belonging to the same subtype designated 11a. Depending on international guidelines for assigning type and subtype levels, FR14, FR15, and FR19 may also be classified into an additional type 2 subtype.

REFERENCES

Barany F (1991). Genetic disease detection and DNA amplification using cloned thermostable ligase. Proc Natl Acad Sci USA 88: 189–193.

Bej A, Mahbubani M, Miller R, Di Cesare J, Haff L, Atlas R (1990) Mutiplex PCR amplification and immobilized capture probes for detection of bacterial pathogens and indicators in water. Mol Cell Probes 4: 353–365.

Bukh J, Purcell R, Miller R (1992). Sequence analysis of the 5' noncoding region of hepatitis C virus. Proc Natl Acad Sci USA 89: 4942–4946.

Bukh J, Purcell R, Miller R (1993). At least 12 genotypes of hepatitis C virus predicted by is sequence analysis of the putative E1 gene of isolates collected worldwide. Proc. Natl. Acad. Sci. USA 90,8234–8238.

Cha T, Beal E, Irvine B, Kolberg J, Chien D, Kuo G, Urdea M (1992) At least five related, but distinct, hepatitis C viral genotypes exist. Proc Natl Acad Sci USA 89:7144–7148.

Chan S-W, Simmonds P, McOmish F, Yap P, Mitchell R, Dow B, Follett E (1991) Serological responses to infection with three different types of hepatitis C virus. Lancet 338:1991.

Chan S-W, McOmish F, Holmes E, Dow B, Peutherer J, Follett E, Yap P, Simmonds P (1992) Analysis of a new hepatitis C virus type and its phylogenetic relationship to existing variants. J Gen Virol 73:1131–1141.

Chomczynski P, Sacchi N (1987) Single step method of RNA isolation by acid guanidinium thiocyanate-phenol-chloroform extraction. Anal Biochem 162:156–159.

Choo Q, Richman K, Han J, Berger K, Lee C, Dong C, Gallegos C, Coit D, Medina-Selby A, Barr P, Weiner A, Bradley D, Kuo G, Houghton M (1991) Genetic organization and diversity of the hepatitis C virus. Proc Natl Acad Sci USA 88:2451–2455.

Compton J (1991). Nucleic acid sequence-based amplification. Nature, 350: 91–92.

Duchosal A, Eming S, Fisher P (1992) Immunization of hu-PBL-SCID mice and the resue of human monoclonal Fab fragments through combinatorial libraries. Nature 355:258–262.

Duck P (1990). Probe amplifier system based on chimeric cycling oligonucleotides. Biotechniques 9, 142–147.

Guatelli J, Whitfield K, Kwoh D, Barringer K, Richman D, Gengeras T (1990) Isothermal, in vitro amplification of nucleic acids by a multienzyme reaction modeled after retroviral replication. Proc Natl Acad Sci USA 87: 1874–1878.

Hijikata M, Kato N, Ootsuyama Y, Nakagawa M, Shimotohmo K (1991) Gene mapping of the putative structural region of the hepatitis C virus genome by in vitro processing analysis. Proc Natl Acad Sci USA 88, 5547–5551.

Jacobs K, Rudersdorf R, Neill S, Dougherty J, Brown E, Fritsch E (1988) The thermal stability of oligonucleotide duplexes is sequence independent in tetraalkylammonium salt solutions: application to identifying recombinant DNA clones. Nucl Acids Res 16:4637–4650.

Kato N, Hijikata M, Ootsuyama Y, Nakagawa M, Ohkoshi S, Sugimura T, Shimotohno K (1990) Molecular cloning of the human hepatitis C virus genome from Japanese patients with non-A, non-B hepatitis. Proc Natl Acad Sci USA 87:9524–9528.

Kwoh D, Davis G, Whitfield K, Chappelle H, Dimichele L, Gingeras T (1989). Transcription-based amplification system and detection of amplified human immunodeficiency virus type 1 with a bead-based sandwich hybridization format. Proc Natl Acad Sci USA, 86: 1173–1177.

Kwok S, Kellogg D, McKinney N, Spasic D, Goda L, Levenson C, Sinisky J, (1990). Effects of primer-template mismatches on the polymerase chain reaction: Human immunodeficiency views type 1 model studies. Nucl. Acids Res., 18: 999.

Landgren U, Kaiser R, Sanders J, Hood L (1988). A ligase-mediated gene detection technique. Science 241:1077–1080.

Lizardi P, Guerra C, Lomeli H, Tussie-Luna I, Kramer F (1988) Exponential amplification of recombinant RNA hybridization probes. Bio/Technology 6:1197–1202.

Lomeli H, Tyagi S, Printchard C, Lisardi P, Kramer F (1989) Quantitative assays based on the use of replicatable hybridization probes. Clin Chem 35: 1826–1831.

Machida A, Ohnuma H, Tsuda F, Munekata E, Tanaka T, Akahane Y, Okamoto H, Mishiro S (1992) Hepatology 16, 886–891.

Maniatis T, Fritsch E, Sambrook J (1982) Molecular cloning: a laboratory manual. Cold Spring Harbor Laboratory Press, Cold Spring Harbor, N.Y.

Mori S, Kato N, Yagyu A, Tanaka T, Ikeda Y, Petchclai B, Chiewsilp P, Kurimura T, Shimotohno K (1992) A new type of hepatitis C virus in patients in Thailand. Biochem Biophys Res Comm 183:334–342.

Okamoto H, Okada S, Sugiyama Y, Kurai K, lizuka H, Machida A, Miyakawa Y, Mayumi M (1991) Nucleotide sequence of the genomic RNA of hepatitis C virus isolated from a human carrier: comparison with reported isolates for conserved and divergent regions. J Gen Virol 72:2697–2704.

Okamoto H. Kurai K, Okada S, Yamamoto K, Lizuka H, Tanaka T, Fukuda S, Tsuda F,

Mishiro S (1992) Full-length sequences of a hepatitis C virus genome having poor homology to reported isolates: comparative study of four distinct genotypes. Virology 188:331–341.

Persson M, Caothien R, Burton D (1991). Generation of diverse high-affinity human monoclonal antibodies by repertoire cloning. Proc Natl Acad Sci USA 89:2432–2436.

Saiki R, Gelfand D, Stoffel S, Scharf S, Higuchi R, Horn G, Mullis K, Erlich H (1988). Primer-directed enzymatic amplification of DNA with a thermostable DNA polymerase. Science 239:487–491.

Saiki R, Walsh P, Levenson C, Erlich H (1989) Genetic analysis of amplified DNA with immobilized sequence-specific oligonucleotide probes (1989) Proc Natl Acad Sci USA 86:6230–6234.

Sano T, Smith C, Cantor C (1992) Immuno-PCR: very sensitive antigen detection by means of specific antibody-DNA conjugates. Science 258:120–122.

Simmonds P, McOmsh F, Yap P, Chan S, Lin C, Dusheiko G, Saeed A, Holmes E (1993a), Sequence variability in the 5' non-coding region of hepatitis C virus: identification of a new virus type and restrictions on sequence diversity. J Gen Virology, 74:661–668.

Stuyver L, Rossau R, Wyseur A, Duhamel M, Vanderborght B, Van Heuverswyn H, Maertens G (1993b) Typing of hepatitis C virus (HCV) isolates and characterization of new (sub)types using a Line Probe Assay. J Gen Virology, 74: 1093–1102.

Tokita et al. (1994) Hepatitis C virus vraiants from Vietnam are classifiable into the seventh, eighth, and ninth major genetic groups. Proc. Natl. Acad. Sci, 91: 11022–11026.

Walker G, Little M, Nadeau J, Shank D (1992). Isothermal in vitro amplification of DNA by a restriction enzyme/DNA polymerase system. Proc Natl Acad Sci USA 89:392–396.

Wu D, Wallace B (1989). The ligation amplification reaction (LAR)—amplification of specific DNA sequences using sequential rounds of template-dependent ligation. Genomics 4:560–569.

Miller P, Yano J, Yano E, Carroll C, Jayaram K, Ts'o P (1979) Nonionic nucleic acid analogues. Synthesis and characterization of dideoxyribonucleoside methylphosphonates. Biochemistry 18(23):5134–43.

Nielsen P, Egholm M, Berg R, Buchardt 0 (1991) Sequence-selective recognition of DNA by strand displacement with a thymine-substituted polyamide. Science 254 (5037):1497–500.

Nielsen P, Egholm M, Berg R, Buchardt 0 (1993) Sequence specific inhibition of DNA restriction enzyme cleavage by PNA. Nucleic-Acids-Res. 21(2):197–200.

Asseline U, Delarue M, Lancelot G, Toulme F, Thuong N (1984) Nucleic acid-binding molecules with high affinity and base sequence specificity: intercalating agents covalently linked to oligodeoxynucleotides. Proc. Natl. Acad. Sci. USA 81(11):3297–301.

Matsukura M, Shinozuka K, Zon G, Mitsuya H, Reitz M, Cohen J, Broder S (1987) Phosphorothioate analogs of oligodeoxynucleotides: inhibitors of replication and cytopathic effects of human immunodeficiency virus. Proc. Natl. Acad. Sci. USA 84(21):7706–10.

Maertens, G., Ducatteeuw, A., Stuyver, L., Vandeponseele, P., Venneman, A., Wyseur, A., Bosman, F., Heijtink, R. & de Martynoff, G. (1994) Low prevalence of anti-E1 antibodies reactive to recombinant type 1b E1 envelope protein in type 2, 3, and 4 sera, but high prevalence in subtypes 1a and 1b. In: Viral Hepatitis and Liver Disease, Proceedings of the International Symposium on Viral Hepatitis and Liver Disease (Eds. Nishioka, K., Suzuki, H., Mishiro, S., and Oda, T.), pp 314–316, Springer-Verlag Tokyo.

Simmonds, P., Rose, K. A., Graham, S., Chan, S.-W., McOmish, F., Dow, B. C., Follett, E. A. C., Yap, P. L., & Marsden, H. (1993b) Mapping of serotype-specific, immunodominant epitopes in the NS4 region of hepatitis C virus (HCV): Use of type-specific peptides to serologically discriminate infections with HCV type 1, 2, and 3. *J. Clin. Microbiol.* 31, 1493–1503.

Simmonds, P., Holmes, E. C., Cha, T.-A., Chan, S.-W., McOmish, F., Irvine, B., Beall, E., Yap, P.L., Kolberg, J., & Urdea, M. S. (1993c) *J. Gen. Virol.* 74, 2391–2399.

Stuyver, L., Van Arnhem, W., Wyseur, A. & Maertens, G. (1994) Cloning and phylogenetic analysis of the Core, E2, and NS314 regions of hepatitis C virus type 5a. Biochem. Biophys. Res. Comm. 202, 1308–1314.

Simmonds, P., Alberti, A., Alter, H., Bonino, F., Bradley, D. W., Brechot, C., Brouwer, J., Chan, S.-W., Chayama K., Chen, D.-S., Choo, Q.-L., Colombo, M., Cuypers, T., Date, T., Dusheiko, G., Esteban, J.l., Fay, O., Hadziyannis, S., Han, J., Hatzakis, A., Holmes, E. C., Hotta, H., Houghton, M., Irvine, B., Kohara, M., Kolberg, J. A., Kuo, G., Lau, J. Y. N., Lelie, P. N., Maertens, G., McOmish, F., Miyamura, T., Mizokami, M., Nomoto, A., Prince A.M., Reesink, H.W., Rice, C., Roggendorf, M., Schalm, S., Shikata, T., Shimotohno, K., Stuyver, L, Trépo, C., Weiner, A., Yap, P. L. & Urdea, M. S. (1994) A proposed system for the nomenclature of hepatitis C virus genotypes. *Hepatology* 19, 1321–1324.

Stuyver, L., Van Arnhem, W., Wyseur, A., DeLeys, R. & Maertens, G. (1993a) Analysis of the putative E1 envelope and NS4a epitope regions of HCV type 3. Biochem. Biophys. Res. Comm. 192, 635–641.

Stuyver, L., Rossau, R., Wyseur, A., Duhamel, M., Vanderborght, B., Van Heuverswyn, H. & Maertens, G. (1993b) Typing of hepatitis C virus isolates and characterization of new subtypes using a line probe assay. J. Gen Virol. 74, 1093–1102.

Stuyver, L., Wyseur, A., Van Arnhem, W., Rossau, R., Delaporte, E., Dazza, M.-C., Van Doom, L.-J., Kleter, B. & Maertens, G. (1994a) The use of a line probe assay as a tool to detect new types or subtypes of hepatitis C virus. In: Viral Hepatitis and Liver Disease, Proceedings of the International Symposium on Viral Hepatitis and Liver Disease (Eds. Nishioka, K., Suzuki, H., Mishiro, S., and Oda, T.), pp 317–319, Springer-Verlag Tokyo.

Stuyver, L., Van Arnhem, W., Wyseur, A. & Maertens, G. (1994b) Cloning and Phylogenetic analysis of the Core, E2, and NS3/4 regions of the hepatitis C virus type 5a. Biochem. Biophys. Res. Comm. 202,1308–1314.

Stuyver, L., Van Arnhem, W., Wyseur, A., Hernandez, F., Delaporte, E., & Maertens, G. (1994c) Classification of hepatitis C viruses based on phylogenetics analysis of the E1 and NS5B regions and identification of 5 new subtypes. Proc. Natl. Acad. Sci. USA 91.

Stuyver et al. (1995) Hepatitis C virus genotyping by means of 5'-UR/core line probe assays and molecular analysis of untypeable samples. Virus Reasearch (in press).

SEQUENCE LISTING

<160> NUMBER OF SEQ ID NOS: 302

<210> SEQ ID NO 1
<211> LENGTH: 327
<212> TYPE: DNA
<213> ORGANISM: hepatitis C virus
<220> FEATURE:
<221> NAME/KEY: misc_feature
<222> LOCATION: (66)..(72)
<223> OTHER INFORMATION: n represents any nucleotide
<220> FEATURE:
<221> NAME/KEY: misc_feature
<222> LOCATION: (130)..(131)
<223> OTHER INFORMATION: n represents any nucleotide
<220> FEATURE:
<221> NAME/KEY: misc_feature
<222> LOCATION: (285)..(285)
<223> OTHER INFORMATION: n represents any nucleotide

<400> SEQUENCE: 1

```
atgagcacga atcctaaacc tcaaagaaaa accaaacgta acaccaaccg ccgccctcak      60
ggsgtnnnnn nnccgggtgg cggtcagatc gttggtggag tttacctgtt gccgcgcagg     120
ggccccaggn ngggtgtgcg cgcgactagg aagacttccg agcggtcaca acctcgtggc     180
aggcgacagc ctatccccaa ggctcgycgg yccgagggca ggtcctgggc tcagcccggg     240
tatccttggc ccctctatgg caatgagggc tgcgggtggg cgggntggct cctgtcccccc     300 cgcggctctc ggcccaattg gggcccc                                         327
```

-continued

```
<210> SEQ ID NO 2
<211> LENGTH: 109
<212> TYPE: PRT
<213> ORGANISM: hepatitis C virus
<220> FEATURE:
<221> NAME/KEY: MISC_FEATURE
<222> LOCATION: (20)..(24)
<223> OTHER INFORMATION: Xaa represents any amino acid
<220> FEATURE:
<221> NAME/KEY: MISC_FEATURE
<222> LOCATION: (44)..(44)
<223> OTHER INFORMATION: Xaa represents any amino acid
<220> FEATURE:
<221> NAME/KEY: MISC_FEATURE
<222> LOCATION: (69)..(69)
<223> OTHER INFORMATION: Xaa represents any amino acid
<220> FEATURE:
<221> NAME/KEY: MISC_FEATURE
<222> LOCATION: (95)..(95)
<223> OTHER INFORMATION: Xaa represents any amino acid
<220> FEATURE:
<221> NAME/KEY: MISC_FEATURE
<222> LOCATION: (71)..(71)
<223> OTHER INFORMATION: Xaa represents any amino acid

<400> SEQUENCE: 2

Met Ser Thr Asn Pro Lys Pro Gln Arg Lys Thr Lys Arg Asn Thr Asn
1               5                   10                  15

Arg Arg Pro Xaa Xaa Xaa Xaa Xaa Pro Gly Gly Gly Gln Ile Val Gly
            20                  25                  30

Gly Val Tyr Leu Leu Pro Arg Arg Gly Pro Arg Xaa Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Xaa Arg Xaa Glu Gly Arg Ser Trp Ala Gln Pro Gly
65                  70                  75                  80

Tyr Pro Trp Pro Leu Tyr Gly Asn Glu Gly Cys Gly Trp Ala Xaa Trp
                85                  90                  95

Leu Leu Ser Pro Arg Gly Ser Arg Pro Asn Trp Gly Pro
            100                 105

<210> SEQ ID NO 3
<211> LENGTH: 447
<212> TYPE: DNA
<213> ORGANISM: hepatitis C virus
<220> FEATURE:
<221> NAME/KEY: misc_feature
<222> LOCATION: (327)..(328)
<223> OTHER INFORMATION: n represents any nucleotide

<400> SEQUENCE: 3
gacggcgtga actatgcaac agggaacttg cccggttgct ctttctctat cttcctcttg      60
gctttgctgt cctgcttgac ggttccaack accgctcacg aggtgcgcaa cgcatccggg     120
gtgtatcatg tcaccaacga ctgttccaac tcgagcatca tctatgagat ggacggtatg     180
atcatgcact acccagggtg cgtgccctgc gttcgggagg ataaccatct ccgctgctgg     240
atggcgctca cccccacgct tgcggtcaaa aaygctagtg tccccactrc ggcaatccga     300
cgtcacgtcg acttgcttgt tggggnncc acgttctgtt ccgctatgta cgtgggrgac     360
cttttgcggt ctgtcttcct cgctggccag ctattcacct tttcaccccg catgcaccat     420
acaacgcagg agtgcaactg ctcaatc                                         447

<210> SEQ ID NO 4
<211> LENGTH: 149
```

```
<212> TYPE: PRT
<213> ORGANISM: hepatitis C virus
<220> FEATURE:
<221> NAME/KEY: MISC_FEATURE
<222> LOCATION: (30)..(30)
<223> OTHER INFORMATION: Xaa represents any amino acid
<220> FEATURE:
<221> NAME/KEY: MISC_FEATURE
<222> LOCATION: (91)..(91)
<223> OTHER INFORMATION: Xaa represents any amino acid
<220> FEATURE:
<221> NAME/KEY: MISC_FEATURE
<222> LOCATION: (97)..(97)
<223> OTHER INFORMATION: Xaa represents any amino acid
<220> FEATURE:
<221> NAME/KEY: MISC_FEATURE
<222> LOCATION: (109)..(110)
<223> OTHER INFORMATION: Xaa represents any amino acid
<220> FEATURE:
<221> NAME/KEY: MISC_FEATURE
<222> LOCATION: (119)..(119)
<223> OTHER INFORMATION: Xaa represents any amino acid

<400> SEQUENCE: 4

Asp Gly Val Asn Tyr Ala Thr Gly Asn Leu Pro Gly Cys Ser Phe Ser
1               5                   10                  15

Ile Phe Leu Leu Ala Leu Leu Ser Cys Leu Thr Val Pro Xaa Thr Ala
            20                  25                  30

His Glu Val Arg Asn Ala Ser Gly Val Tyr His Val Thr Asn Asp Cys
        35                  40                  45

Ser Asn Ser Ser Ile Ile Tyr Glu Met Asp Gly Met Ile Met His Tyr
    50                  55                  60

Pro Gly Cys Val Pro Cys Val Arg Glu Asp Asn His Leu Arg Cys Trp
65                  70                  75                  80

Met Ala Leu Thr Pro Thr Leu Ala Val Lys Xaa Ala Ser Val Pro Thr
                85                  90                  95

Xaa Ala Ile Arg Arg His Val Asp Leu Leu Val Gly Xaa Xaa Thr Phe
            100                 105                 110

Cys Ser Ala Met Tyr Val Xaa Asp Leu Cys Gly Ser Val Phe Leu Ala
        115                 120                 125

Gly Gln Leu Phe Thr Phe Ser Pro Arg Met His His Thr Thr Gln Glu
    130                 135                 140

Cys Asn Cys Ser Ile
145

<210> SEQ ID NO 5
<211> LENGTH: 327
<212> TYPE: DNA
<213> ORGANISM: hepatitis C virus
<220> FEATURE:
<221> NAME/KEY: misc_feature
<222> LOCATION: (70)..(70)
<223> OTHER INFORMATION: n represents any nucleotide
<220> FEATURE:
<221> NAME/KEY: misc_feature
<222> LOCATION: (222)..(223)
<223> OTHER INFORMATION: n represents any nucleotide

<400> SEQUENCE: 5
atgagcacga atcctaaacc tcaaagaaaa accaaacgta acaccaaccg ccgcccacag      60
gacgtcaagn tcccgggtgg tggtcagatc gttggtggag tttacctgtt gccgcgcagg     120
ggccccaggt tgggtgtgcg cgcgaccagg aagacttccg agcggtcgca gcctcgtgac     180
aggcgacagc ctattcctaa ggctcgccag tccgatggca gnncctgggc tcagccaggg     240
```

```
catccctggc ccctctatgg caatgagggc tgcggatggg cgggatggct cctgtccccc    300
cgcggctctc ggcccagttg gggcccc                                        327
```

<210> SEQ ID NO 6
<211> LENGTH: 109
<212> TYPE: PRT
<213> ORGANISM: hepatitis C virus
<220> FEATURE:
<221> NAME/KEY: MISC_FEATURE
<222> LOCATION: (24)..(24)
<223> OTHER INFORMATION: Xaa represents any amino acid
<220> FEATURE:
<221> NAME/KEY: MISC_FEATURE
<222> LOCATION: (74)..(74)
<223> OTHER INFORMATION: Xaa represents any amino acid
<220> FEATURE:
<221> NAME/KEY: MISC_FEATURE
<222> LOCATION: (75)..(75)
<223> OTHER INFORMATION: Xaa represents any amino acid

<400> SEQUENCE: 6

```
Met Ser Thr Asn Pro Lys Pro Gln Arg Lys Thr Lys Arg Asn Thr Asn
1               5                   10                  15

Arg Arg Pro Gln Asp Val Lys Xaa Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Asp Arg Arg Gln Pro
    50                  55                  60

Ile Pro Lys Ala Arg Gln Ser Asp Gly Xaa Xaa Trp Ala Gln Pro Gly
65                  70                  75                  80

His Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro
            100                 105
```

<210> SEQ ID NO 7
<211> LENGTH: 447
<212> TYPE: DNA
<213> ORGANISM: hepatitis C virus

<400> SEQUENCE: 7

```
gacggcgtga actatgcaac agggaatttg cctggttgct ctttctctat cttcctctta    60
gcttttctgt cctgcttgac ggttccaact accgctcatg aggtgcgcaa cgcatccggg   120
gtatatcatc tcaccaatga ctgttccaac tcgagcatca tctatgagat gagtggtatg   180
atcttgcacg ccccagggtg tgtgccctgc gttcgggaga caactcttc tcgttgctgg    240 atgccrctca ccccacgct tgcggtcaaa acgctaatg tccctactgc ggcaatccga     300
cgccatgtcg acttgctggt tgggacagcc gcgtttcgtt ccgctatgta cgtggggggac  360 ctctgcggat ccgtcttcct tgtcggccag ctattcacct tttcaccccg cttgtaccat   420
acaacacagg agtgcaactg ctcaatc                                       447
```

<210> SEQ ID NO 8
<211> LENGTH: 149
<212> TYPE: PRT
<213> ORGANISM: hepatitis C virus
<220> FEATURE:
<221> NAME/KEY: MISC_FEATURE
<222> LOCATION: (82)..(82)
<223> OTHER INFORMATION: Xaa represents any amino acid -continued

```
<400> SEQUENCE: 8

Asp Gly Val Asn Tyr Ala Thr Gly Asn Leu Pro Gly Cys Ser Phe Ser
1               5                   10                  15

Ile Phe Leu Leu Ala Phe Leu Ser Cys Leu Thr Val Pro Thr Thr Ala
            20                  25                  30

His Glu Val Arg Asn Ala Ser Gly Val Tyr His Leu Thr Asn Asp Cys
        35                  40                  45

Ser Asn Ser Ser Ile Ile Tyr Glu Met Ser Gly Met Ile Leu His Ala
    50                  55                  60

Pro Gly Cys Val Pro Cys Val Arg Glu Asn Asn Ser Ser Arg Cys Trp
65                  70                  75                  80

Met Xaa Leu Thr Pro Thr Leu Ala Val Lys Asp Ala Asn Val Pro Thr
                85                  90                  95

Ala Ala Ile Arg Arg His Val Asp Leu Leu Val Gly Thr Ala Ala Phe
                100                 105                 110

Arg Ser Ala Met Tyr Val Gly Asp Leu Cys Gly Ser Val Phe Leu Val
            115                 120                 125

Gly Gln Leu Phe Thr Phe Ser Pro Arg Leu Tyr His Thr Thr Gln Glu
    130                 135                 140

Cys Asn Cys Ser Ile
145

<210> SEQ ID NO 9
<211> LENGTH: 223
<212> TYPE: DNA
<213> ORGANISM: hepatitis C virus

<400> SEQUENCE: 9
atgagcacga atcctaaacc tcaaagaaaa accaaaagaa acaccaaccg ccgcccacag     60
gacgtcaagt tcccgggcgg tggccagatc gttggtggag tctacgtgct accgcgcagg    120
ggccctagat tgggtgtgcg cgcagcgcgg aagacttcgg agcggtcgca acctcgtggg    180
aggcgccaac ctattcccaa ggagcgccga cccgagggca ggt                      223

<210> SEQ ID NO 10
<211> LENGTH: 74
<212> TYPE: PRT
<213> ORGANISM: hepatitis C virus

<400> SEQUENCE: 10

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Val Leu Pro Arg Arg Gly Pro Arg Leu Gly Val Arg Ala
        35                  40                  45

Ala Arg Lys Thr Ser Glu Arg Ser Gln Pro Arg Gly Arg Arg Gln Pro
    50                  55                  60

Ile Pro Lys Glu Arg Arg Pro Glu Gly Arg
65                  70

<210> SEQ ID NO 11
<211> LENGTH: 957
<212> TYPE: DNA
<213> ORGANISM: hepatitis C virus
<220> FEATURE:
<221> NAME/KEY: misc_feature
<222> LOCATION: (454)..(454)
```

```
<223> OTHER INFORMATION: n represents any nucleotide
<220> FEATURE:
<221> NAME/KEY: misc_feature
<222> LOCATION: (476)..(476)
<223> OTHER INFORMATION: n represents any nucleotide
<220> FEATURE:
<221> NAME/KEY: misc_feature
<222> LOCATION: (489)..(501)
<223> OTHER INFORMATION: n represents any nucleotide
<220> FEATURE:
<221> NAME/KEY: misc_feature
<222> LOCATION: (510)..(510)
<223> OTHER INFORMATION: n represents any nucleotide
<220> FEATURE:
<221> NAME/KEY: misc_feature
<222> LOCATION: (522)..(523)
<223> OTHER INFORMATION: n represents any nucleotide
<220> FEATURE:
<221> NAME/KEY: misc_feature
<222> LOCATION: (540)..(540)
<223> OTHER INFORMATION: n represents any nucleotide
<220> FEATURE:
<221> NAME/KEY: misc_feature
<222> LOCATION: (678)..(678)
<223> OTHER INFORMATION: n represents any nucleotide
<220> FEATURE:
<221> NAME/KEY: misc_feature
<222> LOCATION: (951)..(957)
<223> OTHER INFORMATION: n represents any nucleotide

<400> SEQUENCE: 11
atgagcacga atcctaaacc tcaaagaaaa accaaacgca acaccaaccg ccgcccacag      60
gacgttaaat tcccgggtgg ggggcagatc gtgggtggag tttacttgtt gccgcgcagg     120
ggccccaggt tgggtgtgcg cgcgacgagg aagacttccg agcggtcgca acctcgcgga     180
aggcgacagc ctatcccaa ggctcgccga cccgagggca ggtcctgggc tcagcctggg      240
tacccatggc ccctctatgc taacgagggc tgcggatggg cgggatggct cctgtcccct     300
cgcggctccc gtcctagctg ggccccaat gaccccgac gtagatcacg caatttgggt      360
aaggtcatcg ataccctaac gtgtggcttc gccgatctca tggggtacat tccgctcgtc     420
ggcgcccccc taggggggcgc ttccagaacc ctgncacatg gtgtccgggt cctgggaggc     480
ggcgtgatnn nnnnnnnnnn naaccttccn ggttgctctt tnnctatctt cctcttggcn     540
ttactctctt gcctcacagt ccccacctct gcctatgagg tgcacagcac aaccgatggc     600
taccatgtca ctaatgactg ttccaacggc agcatcgtat atgaggcaaa ggacatcatc     660
cttcacacgc ctgggtgngt gccctgcata cgggaaggca atatctcccg ttgctgggta     720
ccgctcaccc ccacgctcgc agcgcggatc gcgaacgctc ccatcgatga ggtgcggcgt     780
cacgtcgacc tcctcgtggg ggcagccgtg ttctgctcag ccatgtacat tgggaccctt     840
tgtgggggcg tcttcctcgt tgggcaattg ttcacccttca cgtcccggcg gcattggacg     900
gtgcaggact gtaattgttc catttactct ggccacataa cgggccaccg nnnnnnn      957

<210> SEQ ID NO 12
<211> LENGTH: 319
<212> TYPE: PRT
<213> ORGANISM: hepatitis C virus
<220> FEATURE:
<221> NAME/KEY: MISC_FEATURE
<222> LOCATION: (152)..(152)
<223> OTHER INFORMATION: Xaa represents any amino acid
<220> FEATURE:
<221> NAME/KEY: MISC_FEATURE
<222> LOCATION: (159)..(159)
<223> OTHER INFORMATION: Xaa represents any amino acid
<220> FEATURE:
<221> NAME/KEY: MISC_FEATURE
```

-continued

```
<222> LOCATION: (163)..(163)
<223> OTHER INFORMATION: Xaa represents any amino acid
<220> FEATURE:
<221> NAME/KEY: MISC_FEATURE
<222> LOCATION: (164)..(167)
<223> OTHER INFORMATION: Xaa represents any amino acid
<220> FEATURE:
<221> NAME/KEY: MISC_FEATURE
<222> LOCATION: (170)..(170)
<223> OTHER INFORMATION: Xaa represents any amino acid
<220> FEATURE:
<221> NAME/KEY: MISC_FEATURE
<222> LOCATION: (174)..(175)
<223> OTHER INFORMATION: Xaa represents any amino acid
<220> FEATURE:
<221> NAME/KEY: MISC_FEATURE
<222> LOCATION: (180)..(180)
<223> OTHER INFORMATION: Xaa represents any amino acid
<220> FEATURE:
<221> NAME/KEY: MISC_FEATURE
<222> LOCATION: (226)..(226)
<223> OTHER INFORMATION: Xaa represents any amino acid
<220> FEATURE:
<221> NAME/KEY: MISC_FEATURE
<222> LOCATION: (317)..(319)
<223> OTHER INFORMATION: Xaa represents any amino acid

<400> SEQUENCE: 12

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Ser Trp Ala Gln Pro Gly
65                  70                  75                  80

Tyr Pro Trp Pro Leu Tyr Ala Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ser Arg Thr Leu Xaa His Gly Val Arg Val Leu Xaa Gly
145                 150                 155                 160

Gly Val Xaa Xaa Xaa Xaa Asn Leu Xaa Gly Cys Ser Xaa Xaa Ile
                165                 170                 175

Phe Leu Leu Xaa Leu Leu Ser Cys Leu Thr Val Pro Thr Ser Ala Tyr
            180                 185                 190

Glu Val His Ser Thr Thr Asp Gly Tyr His Val Thr Asn Asp Cys Ser
        195                 200                 205

Asn Gly Ser Ile Val Tyr Glu Ala Lys Asp Ile Ile Leu His Thr Pro
    210                 215                 220

Gly Xaa Val Pro Cys Ile Arg Glu Gly Asn Ile Ser Arg Cys Trp Val
225                 230                 235                 240

Pro Leu Thr Pro Thr Leu Ala Ala Arg Ile Ala Asn Ala Pro Ile Asp
                245                 250                 255

Glu Val Arg Arg His Val Asp Leu Leu Val Gly Ala Ala Val Phe Cys
            260                 265                 270
```

```
Ser Ala Met Tyr Ile Gly Asp Leu Cys Gly Gly Val Phe Leu Val Gly
        275                 280                 285

Gln Leu Phe Thr Phe Thr Ser Arg Arg His Trp Thr Val Gln Asp Cys
        290                 295                 300

Asn Cys Ser Ile Tyr Ser Gly His Ile Thr Gly His Xaa Xaa Xaa
305                 310                 315
```

<210> SEQ ID NO 13
<211> LENGTH: 310
<212> TYPE: DNA
<213> ORGANISM: hepatitis C virus
<220> FEATURE:
<221> NAME/KEY: misc_feature
<222> LOCATION: (208)..(208)
<223> OTHER INFORMATION: n represents any nucleotide
<220> FEATURE:
<221> NAME/KEY: misc_feature
<222> LOCATION: (210)..(210)
<223> OTHER INFORMATION: n represents any nucleotide

<400> SEQUENCE: 13

```
atgagcacaa atcctaaacc tcaaagaaaa accaaaagaa ataccaaccg ccgcccacag     60
gacgtcaagt tcccgggcgg cggccagatc gttggcggag tttacttgtt gccgcgcagg   120
ggccccagat tgggtgtgcg cgcgacgaga aagacttctg aacggtccca gccacgtgga   180
aggcgccagc ccatccctaa agatcggngn gccactggca ggtcctgggg acgtccagga   240
tatccctggc ccctgtatgg gaacgagggg ctcggctggg caggatggct cctgtccccc   300
cgaggctctc                                                           310
```

<210> SEQ ID NO 14
<211> LENGTH: 108
<212> TYPE: PRT
<213> ORGANISM: hepatitis C virus
<220> FEATURE:
<221> NAME/KEY: MISC_FEATURE
<222> LOCATION: (70)..(70)
<223> OTHER INFORMATION: Xaa represents any amino acid

<400> SEQUENCE: 14

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Asp Arg Xaa Ala Thr Gly Arg Ser Trp Gly Arg Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly
            100                 105
```

<210> SEQ ID NO 15
<211> LENGTH: 579
<212> TYPE: DNA
<213> ORGANISM: hepatitis C virus
<220> FEATURE:
<221> NAME/KEY: misc_feature
<222> LOCATION: (9)..(9)

```
<223> OTHER INFORMATION: n represents any nucleotide
<220> FEATURE:
<221> NAME/KEY: misc_feature
<222> LOCATION: (11)..(11)
<223> OTHER INFORMATION: n represents any nucleotide
<220> FEATURE:
<221> NAME/KEY: misc_feature
<222> LOCATION: (33)..(33)
<223> OTHER INFORMATION: n represents any nucleotide
<220> FEATURE:
<221> NAME/KEY: misc_feature
<222> LOCATION: (63)..(63)
<223> OTHER INFORMATION: n represents any nucleotide
<220> FEATURE:
<221> NAME/KEY: misc_feature
<222> LOCATION: (79)..(79)
<223> OTHER INFORMATION: n represents any nucleotide
<220> FEATURE:
<221> NAME/KEY: misc_feature
<222> LOCATION: (116)..(116)
<223> OTHER INFORMATION: n represents any nucleotide
<220> FEATURE:
<221> NAME/KEY: misc_feature
<222> LOCATION: (155)..(155)
<223> OTHER INFORMATION: n represents any nucleotide
<220> FEATURE:
<221> NAME/KEY: misc_feature
<222> LOCATION: (194)..(194)
<223> OTHER INFORMATION: n represents any nucleotide
<220> FEATURE:
<221> NAME/KEY: misc_feature
<222> LOCATION: (272)..(272)
<223> OTHER INFORMATION: n represents any nucleotide

<400> SEQUENCE: 15
acgtgcggnt ntgccgacct catggggtac atncccgttg tcggcgcccc ggtgggcggg      60
gtngccaggg ccctcgcgna tggcgtgcgg gtcctggagg acgggataaa ttatgnaaca     120
gggaacctcc ctggttgctc cttttctatc ttctngttgg ctcttctgtc ttgtgtcacc     180
gtgcctgtct ctgncgttga ggtcaaaaat accagtcagg cctatatggc aaccaacgac     240
tgctccaaca acagcatcgt atggcaattg gnggacgcgg tgcttcatgt tcctggatgt     300 gtccctgcg agaatagctc cggtcggttc cactgttgga tcccgatctc gcccaacata     360
gccgtgagca aacctggtgc tctcaccaag ggactgcggg cacgcattga tgccgtcgtg     420
atgtccgcca ccctctgctc tgccctgtac gtgggagatg tgtgcggcgc agtgatgata     480
gctgcacagg ctttcatcgt ggcaccgaag cgccattact tcgtccagga atgcaattgc     540
tccatatacc caggccacat tacaggtcat cgcatggcg                            579

<210> SEQ ID NO 16
<211> LENGTH: 193
<212> TYPE: PRT
<213> ORGANISM: hepatitis C virus
<220> FEATURE:
<221> NAME/KEY: MISC_FEATURE
<222> LOCATION: (3)..(4)
<223> OTHER INFORMATION: Xaa represents any amino acid
<220> FEATURE:
<221> NAME/KEY: MISC_FEATURE
<222> LOCATION: (11)..(11)
<223> OTHER INFORMATION: Xaa represents any amino acid
<220> FEATURE:
<221> NAME/KEY: MISC_FEATURE
<222> LOCATION: (21)..(21)
<223> OTHER INFORMATION: Xaa represents any amino acid
<220> FEATURE:
<221> NAME/KEY: MISC_FEATURE
<222> LOCATION: (27)..(27)
<223> OTHER INFORMATION: Xaa represents any amino acid
<220> FEATURE:
<221> NAME/KEY: MISC_FEATURE
```

-continued

```
<222> LOCATION: (39)..(39)
<223> OTHER INFORMATION: Xaa represents any amino acid
<220> FEATURE:
<221> NAME/KEY: MISC_FEATURE
<222> LOCATION: (52)..(52)
<223> OTHER INFORMATION: Xaa represents any amino acid
<220> FEATURE:
<221> NAME/KEY: MISC_FEATURE
<222> LOCATION: (65)..(65)
<223> OTHER INFORMATION: Xaa represents any amino acid
<220> FEATURE:
<221> NAME/KEY: MISC_FEATURE
<222> LOCATION: (91)..(91)
<223> OTHER INFORMATION: Xaa represents any amino acid

<400> SEQUENCE: 16

Thr Cys Xaa Xaa Ala Asp Leu Met Gly Tyr Xaa Pro Val Val Gly Ala
1               5                   10                  15

Pro Val Gly Gly Xaa Ala Arg Ala Leu Ala Xaa Gly Val Arg Val Leu
            20                  25                  30

Glu Asp Gly Ile Asn Tyr Xaa Thr Gly Asn Leu Pro Gly Cys Ser Phe
        35                  40                  45

Ser Ile Phe Xaa Leu Ala Leu Leu Ser Cys Val Thr Val Pro Val Ser
    50                  55                  60

Xaa Val Glu Val Lys Asn Thr Ser Gln Ala Tyr Met Ala Thr Asn Asp
65                  70                  75                  80

Cys Ser Asn Asn Ser Ile Val Trp Gln Leu Xaa Asp Ala Val Leu His
                85                  90                  95

Val Pro Gly Cys Val Pro Cys Glu Asn Ser Ser Gly Arg Phe His Cys
            100                 105                 110

Trp Ile Pro Ile Ser Pro Asn Ile Ala Val Ser Lys Pro Gly Ala Leu
        115                 120                 125

Thr Lys Gly Leu Arg Ala Arg Ile Asp Ala Val Val Met Ser Ala Thr
    130                 135                 140

Leu Cys Ser Ala Leu Tyr Val Gly Asp Val Cys Gly Ala Val Met Ile
145                 150                 155                 160

Ala Ala Gln Ala Phe Ile Val Ala Pro Lys Arg His Tyr Phe Val Gln
                165                 170                 175

Glu Cys Asn Cys Ser Ile Tyr Pro Gly His Ile Thr Gly His Arg Met
            180                 185                 190

Ala

<210> SEQ ID NO 17
<211> LENGTH: 957
<212> TYPE: DNA
<213> ORGANISM: hepatitis C virus
<220> FEATURE:
<221> NAME/KEY: misc_feature
<222> LOCATION: (956)..(957)
<223> OTHER INFORMATION: n represents any nucleotide

<400> SEQUENCE: 17
atgagcacaa atcctaaacc tcaaagaaaa actaaaagaa acactaaccg tcgcccacag      60
gacgttaagt tcccgggcgg cggccagatc gttggcggag tttacttgtt gccgcgcagg     120
ggccccaggt tgggtgtgcg cgcgccaagg aagacttctg aacggtccca gccacgtgga     180
aggcgccagc ccatcccaaa agatcggcgc gccactggca agtcctgggg acgtccagga     240
tacccttggc ccctgtacgg gaacgagggc ctcggctggg cagggtggct cctgtccccc     300
cggggctctc gcccctcgtg gggcccaaac gacccccggc acaggtcacg caacttgggt     360
```

-continued

```
aaggtcatcg ataccctcac gtgtggcttt gscgacctca tggggtacat acctgtcgtc    420
ggcgccctg tgggcggcgt tgccagagcc ctcgcgcatg gcgtgcgggt cctggaggac    480
gggataaatt atgcaacagg aacttgccc ggttgctcct tttctatctt cttgctggct    540
ctcttgtctt gtatcaccgt gcccgtgtct gccatacagg ttaagaacaa cagccacttc    600
tacatggcga ctaatgactg tgccaatgac agcatcgtct ggcagctcag ggacgcggtg    660
ctccatgttc ctggatgtgt ccctgtgag aggtcaggta ataggacctt ctgttggaca    720
gcggtctcgc ccaacgtggc tgtgagccga cctggtgctc tcactagagg tctgcgggct    780
cacattgata ccatcgtgat gtccgccacc ctctgctctg ccctatacat aggggaccta    840
tgcggcgctg tgatgatagc agcgcaagtt gccgtcgtct caccgcaata ccatactttt    900
gtccaggaat gcaactgctc catataccca ggccatatca caggacatcg aatggnn     957
```

```
<210> SEQ ID NO 18
<211> LENGTH: 319
<212> TYPE: PRT
<213> ORGANISM: hepatitis C virus
<220> FEATURE:
<221> NAME/KEY: MISC_FEATURE
<222> LOCATION: (131)..(131)
<223> OTHER INFORMATION: Xaa represents any amino acid
<220> FEATURE:
<221> NAME/KEY: MISC_FEATURE
<222> LOCATION: (319)..(319)
<223> OTHER INFORMATION: Xaa represents any amino acid
```

<400> SEQUENCE: 18

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Pro Arg Lys Thr Ser Glu Arg Ser Gln Pro Arg Gly Arg Arg Gln Pro
    50                  55                  60

Ile Pro Lys Asp Arg Arg Ala Thr Gly Lys Ser Trp Gly Arg Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Asn Asp Pro
            100                 105                 110

Arg His Arg Ser Arg Asn Leu Gly Lys Val Ile Asp Thr Leu Thr Cys
        115                 120                 125

Gly Phe Xaa Asp Leu Met Gly Tyr Ile Pro Val Val Gly Ala Pro Val
    130                 135                 140

Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Ile Thr Val Pro Val Ser Ala Ile
            180                 185                 190

Gln Val Lys Asn Asn Ser His Phe Tyr Met Ala Thr Asn Asp Cys Ala
        195                 200                 205

Asn Asp Ser Ile Val Trp Gln Leu Arg Asp Ala Val Leu His Val Pro
    210                 215                 220

Gly Cys Val Pro Cys Glu Arg Ser Gly Asn Arg Thr Phe Cys Trp Thr

-continued

```
                225                 230                 235                 240
Ala Val Ser Pro Asn Val Ala Val Ser Arg Pro Gly Ala Leu Thr Arg
                    245                 250                 255
Gly Leu Arg Ala His Ile Asp Thr Ile Val Met Ser Ala Thr Leu Cys
                260                 265                 270
Ser Ala Leu Tyr Ile Gly Asp Leu Cys Gly Ala Val Met Ile Ala Ala
            275                 280                 285
Gln Val Ala Val Ser Pro Gln Tyr His Thr Phe Val Gln Glu Cys
        290                 295                 300
Asn Cys Ser Ile Tyr Pro Gly His Ile Thr Gly His Arg Met Xaa
305                 310                 315

<210> SEQ ID NO 19
<211> LENGTH: 447
<212> TYPE: DNA
<213> ORGANISM: hepatitis C virus

<400> SEQUENCE: 19
gacggggtaa attatgcaac agggaatctg cctggttgct ctttctctat cttcttgttg      60
gctcttctgt cttgtgtcac cgtgcctgtc tctgccgtgc aggttaagaa caccagtacc    120
atgtacatgg caaccaatga ctgttccaac aacagcatca tctggcaaat gcagggcgcg    180
gtgcttcatg ttcctggatg tgtcccgtgt gagttgcagg gcaataagtc ccggtgctgg    240
ataccggtca ctcccaacgt ggctgtgaac cagcccggcg ccctcactag gggcttgcgg    300
acgcacattg acaccatcgt gatggtcgct acgctctgtt ctgcactcta catcggggac    360
gtgtgtggcg cggtgatgat agctgctcag gttgtcattg tctcgccgca acatcacaac    420
ttttcccagg attgcaattg ttccatc                                        447

<210> SEQ ID NO 20
<211> LENGTH: 149
<212> TYPE: PRT
<213> ORGANISM: hepatitis C virus

<400> SEQUENCE: 20

Asp Gly Val Asn Tyr Ala Thr Gly Asn Leu Pro Gly Cys Ser Phe Ser
1               5                   10                  15
Ile Phe Leu Leu Ala Leu Leu Ser Cys Val Thr Val Pro Val Ser Ala
            20                  25                  30
Val Gln Val Lys Asn Thr Ser Thr Met Tyr Met Ala Thr Asn Asp Cys
        35                  40                  45
Ser Asn Asn Ser Ile Ile Trp Gln Met Gln Gly Ala Val Leu His Val
    50                  55                  60
Pro Gly Cys Val Pro Cys Glu Leu Gln Gly Asn Lys Ser Arg Cys Trp
65                  70                  75                  80
Ile Pro Val Thr Pro Asn Val Ala Val Asn Gln Pro Gly Ala Leu Thr
                85                  90                  95
Arg Gly Leu Arg Thr His Ile Asp Thr Ile Val Met Val Ala Thr Leu
            100                 105                 110
Cys Ser Ala Leu Tyr Ile Gly Asp Val Cys Gly Ala Val Met Ile Ala
        115                 120                 125
Ala Gln Val Val Ile Val Ser Pro Gln His His Asn Phe Ser Gln Asp
    130                 135                 140
Cys Asn Cys Ser Ile
145
```

```
<210> SEQ ID NO 21
<211> LENGTH: 310
<212> TYPE: DNA
<213> ORGANISM: hepatitis C virus

<400> SEQUENCE: 21
atgagcacaa atcctaaacc tcaaagaaaa accaaaagaa acactaaccg ccgcccacag      60
gacgttaagt tcccgggcgg tggccagatc gttggcggag tatacttgtt gccgcgcagg     120
ggcccccggt tgggtgtgcg cgcgacgagg aaaacttccg aacggtccca gccacgtggg     180
aggcgccagc ccatccctaa agatcggcgc tccactggca atcctgggg acgtccagga     240 taccttggc ccctgtatgg gaacgagggc cttggttggg caggatggct cttgtcccct     300
cgaggctctc                                                            310

<210> SEQ ID NO 22
<211> LENGTH: 48
<212> TYPE: PRT
<213> ORGANISM: hepatitis C virus

<400> SEQUENCE: 22

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Arg Ser Leu Ala
            20                  25                  30

Glu Tyr Thr Cys Ala Arg Arg Gly Lys Leu Arg Arg Ser Ser Met Gly
        35                  40                  45

<210> SEQ ID NO 23
<211> LENGTH: 447
<212> TYPE: DNA
<213> ORGANISM: hepatitis C virus

<400> SEQUENCE: 23
gacgggataa actacgcaac agggaatctg cccggttgct cctttctat cttcttgctg       60 gccttgctat cctgtctcac tgtgccggcg tccgctgtgc aggtcaagaa caccagccac     120
tcttatatgg tgaccaatga ttgctcaaac agcagcattg tctggcagct taaggatgct     180
gtgcttcacg tccctggatg tgttccatgt gagaggcacc aaaatcagtc tcgctgctgg     240
atacctgtga cacccaatgt ggccgtgagc caacctggcg cgctcaccag gggtttgcgg     300
acgcacattg acaccatcgt tgcgtctgct accgtctgct cagctttgta tgtgggcgac     360
ttctgcggcg cagtgatgtt ggtctctcaa ttttttcatga tctcccctca gcaccacatc     420
ttcgtccagg attgcaactg ctcgata                                        447

<210> SEQ ID NO 24
<211> LENGTH: 149
<212> TYPE: PRT
<213> ORGANISM: hepatitis C virus

<400> SEQUENCE: 24

Asp Gly Ile Asn Tyr Ala Thr Gly Asn Leu Pro Gly Cys Ser Phe Ser
1               5                   10                  15

Ile Phe Leu Leu Ala Leu Leu Ser Cys Leu Thr Val Pro Ala Ser Ala
            20                  25                  30

Val Gln Val Lys Asn Thr Ser His Ser Tyr Met Val Thr Asn Asp Cys
        35                  40                  45

Ser Asn Ser Ser Ile Val Trp Gln Leu Lys Asp Ala Val Leu His Val
```

-continued

```
              50                  55                  60
Pro Gly Cys Val Pro Cys Glu Arg His Gln Asn Gln Ser Arg Cys Trp
65                  70                  75                  80

Ile Pro Val Thr Pro Asn Val Ala Val Ser Gln Pro Gly Ala Leu Thr
                85                  90                  95

Arg Gly Leu Arg Thr His Ile Asp Thr Ile Val Ala Ser Ala Thr Val
            100                 105                 110

Cys Ser Ala Leu Tyr Val Gly Asp Phe Cys Gly Ala Val Met Leu Val
            115                 120                 125

Ser Gln Phe Phe Met Ile Ser Pro Gln His His Ile Phe Val Gln Asp
        130                 135                 140

Cys Asn Cys Ser Ile
145

<210> SEQ ID NO 25
<211> LENGTH: 356
<212> TYPE: DNA
<213> ORGANISM: hepatitis C virus

<400> SEQUENCE: 25
gacgggataa actatgcaac agggaacctg cctggttgct cctttctat cttcttactg      60 gccctgcttt cttgcatcac cgtgccggtc tctgccgtgc aagttgcgaa ccgcagtggt    120
tcttacatgg tgaccaatga ttgctcgaac agcagcatcg tttggcagct cgaggaggcc    180
gtccttcacg tccctggatg tgttcccttg gagtggaagg acaacacctc ccgctgctgg    240
ataccggtca cccctaacat cgctgtgagc caacctggcg cgcttaccaa gggcctgcgg    300
acacatattg acatcattgt cgcgtccgcc acgttctgct ctgccttgta tgtggg        356

<210> SEQ ID NO 26
<211> LENGTH: 118
<212> TYPE: PRT
<213> ORGANISM: hepatitis C virus
<220> FEATURE:
<221> NAME/KEY: MISC_FEATURE
<222> LOCATION: (95)..(95)
<223> OTHER INFORMATION: Xaa represents any amino acid

<400> SEQUENCE: 26

Asp Gly Ile Asn Tyr Ala Thr Gly Asn Leu Pro Gly Cys Ser Phe Ser
1               5                   10                  15

Ile Phe Leu Leu Ala Leu Leu Ser Cys Ile Thr Val Pro Val Ser Ala
            20                  25                  30

Val Gln Val Ala Asn Arg Ser Gly Ser Tyr Met Val Thr Asn Asp Cys
        35                  40                  45

Ser Asn Ser Ser Ile Val Trp Gln Leu Glu Glu Ala Val Leu His Val
    50                  55                  60

Pro Gly Cys Val Pro Cys Glu Trp Lys Asp Asn Thr Ser Arg Cys Trp
65                  70                  75                  80

Ile Pro Val Thr Pro Asn Ile Ala Val Ser Gln Pro Gly Ala Xaa Thr
                85                  90                  95

Lys Gly Leu Arg Thr His Ile Asp Ile Ile Val Ala Ser Ala Thr Phe
            100                 105                 110

Cys Ser Ala Leu Tyr Val
        115

<210> SEQ ID NO 27
<211> LENGTH: 310
```

```
<212> TYPE: DNA
<213> ORGANISM: hepatitis C virus
<220> FEATURE:
<221> NAME/KEY: misc_feature
<222> LOCATION: (283)..(284)
<223> OTHER INFORMATION: n represents any nucleotide

<400> SEQUENCE: 27
atgagcacga atcctaaacc tcaaagaaaa accaaacgta acaccaaccg ccgccccatg    60
gacgttaagt tcccgggtgg tggccagatc gttggcggag tttacttgtt gccgcgcagg   120
ggccccaggt tgggtgtgcg cgcgactcgg aagacttcgg agcggtcgca acctcgtggg   180
agacgccaac ctatccccaa ggcgcgtcga tccgagggaa ggtcctgggc acagccagga   240
tatccatggc tctctttacgg taatgagggt tgcgggtggg cannatggct cttgtccccc   300
cgcggttctc                                                          310

<210> SEQ ID NO 28
<211> LENGTH: 117
<212> TYPE: PRT
<213> ORGANISM: hepatitis C virus
<220> FEATURE:
<221> NAME/KEY: MISC_FEATURE
<222> LOCATION: (95)..(95)
<223> OTHER INFORMATION: Xaa represents any amino acid

<400> SEQUENCE: 28

Met Ser Thr Asn Pro Lys Pro Gln Arg Lys Thr Lys Arg Asn Thr Asn
1               5                   10                  15

Arg Arg Pro Met Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Xaa Trp
                85                  90                  95

Leu Leu Ser Pro Arg Gly Ser Arg Pro Ser Trp Gly Pro Asn Asp Pro
            100                 105                 110

Arg Arg Arg Ser Arg
        115

<210> SEQ ID NO 29
<211> LENGTH: 447
<212> TYPE: DNA
<213> ORGANISM: hepatitis C virus

<400> SEQUENCE: 29
gacgggatca attttgcaac agggaacctc ccgggttgct cctttttctat cttcctcttg    60 gcactcctct cgtgcctgac tgtccccgct tcggccatca actatcgcaa tgtctcgggc   120
atttactatg tcaccaatga ttgcccgaat tcaagcatag tgtatgaggc cgaccatcac   180
atcttgcacc tccaggttg cgtgccctgc gtgagagagg ggaatcagtc acgttgctgg   240
gtagccctta cccctaccgt cgcagcgcca tacatcggcg cgccacttga gtctctacgg   300
agtcatgtgg acttgatggt gggggccgcc actgtttgtt cagcccttta catcggggat   360
ttrtgtggyg gcttgttcct agtcggtcag atgttctctt ccgaccaag gcgccactgg   420
```
actactcaag attgcaattg ttccatc 447

<210> SEQ ID NO 30
<211> LENGTH: 149
<212> TYPE: PRT
<213> ORGANISM: hepatitis C virus
<220> FEATURE:
<221> NAME/KEY: MISC_FEATURE
<222> LOCATION: (121)..(121)
<223> OTHER INFORMATION: Xaa represents any amino acid
<220> FEATURE:
<221> NAME/KEY: MISC_FEATURE
<222> LOCATION: (123)..(123)
<223> OTHER INFORMATION: Xaa represents any amino acid

<400> SEQUENCE: 30

Asp Gly Ile Asn Phe Ala Thr Gly Asn Leu Pro Gly Cys Ser Phe Ser
1               5                   10                  15

Ile Phe Leu Leu Ala Leu Leu Ser Cys Leu Thr Val Pro Ala Ser Ala
            20                  25                  30

Ile Asn Tyr Arg Asn Val Ser Gly Ile Tyr Tyr Val Thr Asn Asp Cys
        35                  40                  45

Pro Asn Ser Ser Ile Val Tyr Glu Ala Asp His His Ile Leu His Leu
    50                  55                  60

Pro Gly Cys Val Pro Cys Val Arg Glu Gly Asn Gln Ser Arg Cys Trp
65                  70                  75                  80

Val Ala Leu Thr Pro Thr Val Ala Ala Pro Tyr Ile Gly Ala Pro Leu
                85                  90                  95

Glu Ser Leu Arg Ser His Val Asp Leu Met Val Gly Ala Ala Thr Val
            100                 105                 110

Cys Ser Ala Leu Tyr Ile Gly Asp Xaa Cys Xaa Gly Leu Phe Leu Val
        115                 120                 125

Gly Gln Met Phe Ser Phe Arg Pro Arg Arg His Trp Thr Thr Gln Asp
    130                 135                 140

Cys Asn Cys Ser Ile
145

<210> SEQ ID NO 31
<211> LENGTH: 447
<212> TYPE: DNA
<213> ORGANISM: hepatitis C virus

<400> SEQUENCE: 31
gacgggatca attatgcaac aggaaccttt cccggttgct cttttctctat cttcctcttg      60 gcactcctct cgtgcctgac tgttcccgct tcggccatta actaccgcaa cacctcgggc     120
atctaccacg tcaccaatga ctgcccgaac tcgagcatag tttatgaggc cgaccaccac     180
atcttgcacc ttccaggttg cgtgccctgc gtgagaactg ggaatcagtc acgttgctgg     240
gtggccctta ctcctaccgt cgcagcgcca tacatcggcg caccgcttga gtctctgcgg     300
agtcatgtgg atctgatggt ggggctgcc actgtttgct cagcccttta catcggggat      360
ttgtgtggcg gcttgttctt ggttggtcag atgttttctt ccgaccacg acgccactgg      420 actgcccagg attgcaattg ttctatc                                           447

<210> SEQ ID NO 32
<211> LENGTH: 149
<212> TYPE: PRT
<213> ORGANISM: hepatitis C virus

<400> SEQUENCE: 32

```
Asp Gly Ile Asn Tyr Ala Thr Gly Asn Leu Pro Gly Cys Ser Phe Ser
1               5                   10                  15

Ile Phe Leu Leu Ala Leu Leu Ser Cys Leu Thr Val Pro Ala Ser Ala
            20                  25                  30

Ile Asn Tyr Arg Asn Thr Ser Gly Ile Tyr His Val Thr Asn Asp Cys
        35                  40                  45

Pro Asn Ser Ser Ile Val Tyr Glu Ala Asp His His Ile Leu His Leu
    50                  55                  60

Pro Gly Cys Val Pro Cys Val Arg Thr Gly Asn Gln Ser Arg Cys Trp
65                  70                  75                  80

Val Ala Leu Thr Pro Thr Val Ala Ala Pro Tyr Ile Gly Ala Pro Leu
                85                  90                  95

Glu Ser Leu Arg Ser His Val Asp Leu Met Val Gly Ala Ala Thr Val
                100                 105                 110

Cys Ser Ala Leu Tyr Ile Gly Asp Leu Cys Gly Gly Leu Phe Leu Val
            115                 120                 125

Gly Gln Met Phe Ser Phe Arg Pro Arg Arg His Trp Thr Ala Gln Asp
        130                 135                 140

Cys Asn Cys Ser Ile
145
```

<210> SEQ ID NO 33
<211> LENGTH: 447
<212> TYPE: DNA
<213> ORGANISM: hepatitis C virus

<400> SEQUENCE: 33

```
gacgggatta ttatgcaac agggaatctt cccggttgct ccttttctat cttcctcttg      60
gcacttctct cgtgcctgac tgtccccgct tcggccatta actaccacaa cacctcgggc     120
atctatcata tcaccaacga ctgcccgaat tcaagcatag tgtatgaggc cgaccatcac     180
atcttgcatc tcccaggttg cgtgccctgc gtgagagtgg ggaatcagtc gagttgctgg     240
gtggccctta cccctaccat cgcagcgcca tacatcggcg caccgcttga gtccttgcgg     300
agtcatgtgg atctgatggt gggggcggcc actgtctgtt cagccctta catcggggat      360
ttgtgtggcg gtcgttctt ggttggtcag atgttctctt ccgaccacg gcgccactgg       420
accacccaag attgcaactg ctccatc                                         447
```

<210> SEQ ID NO 34
<211> LENGTH: 149
<212> TYPE: PRT
<213> ORGANISM: hepatitis C virus

<400> SEQUENCE: 34

```
Asp Gly Ile Asn Tyr Ala Thr Gly Asn Leu Pro Gly Cys Ser Phe Ser
1               5                   10                  15

Ile Phe Leu Leu Ala Leu Leu Ser Cys Leu Thr Val Pro Ala Ser Ala
            20                  25                  30

Ile Asn Tyr His Asn Thr Ser Gly Ile Tyr His Ile Thr Asn Asp Cys
        35                  40                  45

Pro Asn Ser Ser Ile Val Tyr Glu Ala Asp His His Ile Leu His Leu
    50                  55                  60

Pro Gly Cys Val Pro Cys Val Arg Val Gly Asn Gln Ser Ser Cys Trp
65                  70                  75                  80

Val Ala Leu Thr Pro Thr Ile Ala Ala Pro Tyr Ile Gly Ala Pro Leu
```

-continued

```
                85                  90                  95
Glu Ser Leu Arg Ser His Val Asp Leu Met Val Gly Ala Ala Thr Val
            100                 105                 110

Cys Ser Ala Leu Tyr Ile Gly Asp Leu Cys Gly Gly Ala Phe Leu Val
            115                 120                 125

Gly Gln Met Phe Ser Phe Arg Pro Arg His Trp Thr Thr Gln Asp
        130                 135                 140

Cys Asn Cys Ser Ile
145

<210> SEQ ID NO 35
<211> LENGTH: 447
<212> TYPE: DNA
<213> ORGANISM: hepatitis C virus

<400> SEQUENCE: 35
gacgggatca attatgcaac aggaatatt cccggttgct cyttttctat cttccttytg      60
gcacttctct cgtgtctgac tgtccccgct tcggccacta actatcgcaa cgtctcgggc    120
atctaccatg tcaccaatga ctgcccgaat tcaagcatag tgtatgaggc cgaccatcac    180
atcttagcac ttccaggttg cgtgccctgc gtgagagtgg ggaaccagtc acgctgctgg    240
gtggccctta cccctaccgt cgcagcgcca tacaccgcgg cgccgcttga gtccctgcgg    300
agtcatgtgg atctgatggt gggagctgcc actgtttgtt cagcccttta catcggggay    360
ttgtgtggcg gcttgttctt ggttggtcag atgttctctt tycagcctcg gcgccactgg    420
actacccagg attgcaattg ttccatc                                        447

<210> SEQ ID NO 36
<211> LENGTH: 149
<212> TYPE: PRT
<213> ORGANISM: hepatitis C virus
<220> FEATURE:
<221> NAME/KEY: MISC_FEATURE
<222> LOCATION: (14)..(14)
<223> OTHER INFORMATION: Xaa represents any amino acid
<220> FEATURE:
<221> NAME/KEY: MISC_FEATURE
<222> LOCATION: (20)..(20)
<223> OTHER INFORMATION: Xaa represents any amino acid
<220> FEATURE:
<221> NAME/KEY: MISC_FEATURE
<222> LOCATION: (120)..(120)
<223> OTHER INFORMATION: Xaa represents any amino acid
<220> FEATURE:
<221> NAME/KEY: MISC_FEATURE
<222> LOCATION: (134)..(134)
<223> OTHER INFORMATION: Xaa represents any amino acid

<400> SEQUENCE: 36

Asp Gly Ile Asn Tyr Ala Thr Gly Asn Ile Pro Gly Cys Xaa Phe Ser
1               5                   10                  15

Ile Phe Leu Xaa Ala Leu Leu Ser Cys Leu Thr Val Pro Ala Ser Ala
            20                  25                  30

Thr Asn Tyr Arg Asn Val Ser Gly Ile Tyr His Val Thr Asn Asp Cys
        35                  40                  45

Pro Asn Ser Ser Ile Val Tyr Glu Ala Asp His His Ile Leu Ala Leu
    50                  55                  60

Pro Gly Cys Val Pro Cys Val Arg Val Gly Asn Gln Ser Arg Cys Trp
65                  70                  75                  80

Val Ala Leu Thr Pro Thr Val Ala Ala Pro Tyr Thr Ala Ala Pro Leu
                85                  90                  95
```

-continued

Glu Ser Leu Arg Ser His Val Asp Leu Met Val Gly Ala Ala Thr Val
            100                 105                 110

Cys Ser Ala Leu Tyr Ile Gly Xaa Leu Cys Gly Gly Leu Phe Leu Val
            115                 120                 125

Gly Gln Met Phe Ser Xaa Gln Pro Arg Arg His Trp Thr Thr Gln Asp
        130                 135                 140

Cys Asn Cys Ser Ile
145

<210> SEQ ID NO 37
<211> LENGTH: 447
<212> TYPE: DNA
<213> ORGANISM: hepatitis C virus

<400> SEQUENCE: 37
gacgggatta attatgcaac agggaayctc cccggttgct cttttctat cttcctcttg      60
gcacttctct cgtgcctgac tgtccccgct tcggccacca actaccgcaa tgtctcgggc     120
atttaccatg tcaccaatga ctgcccgaat tcaagcatag tgtttgaggc cgaccatcac     180
atcttgcacc ttccaggatg cgtgccctgc gtgaaagagg gaaatcattc acgctgctgg     240
gtggcccttaa ccctaccgt cgcagcgcca tacatcggcg cgccacttga gtctctacgg     300
agtcatgtgg atgtgatggt gggggctgcc actgtttgtt cagcccttta catcggggat     360
ctgtgcggtg gcttgttcct ggttggtcag atgttctctt ccgaccacg gcgccactgg     420
actacccagg aatgcaattg ttccatc                                         447

<210> SEQ ID NO 38
<211> LENGTH: 149
<212> TYPE: PRT
<213> ORGANISM: hepatitis C virus
<220> FEATURE:
<221> NAME/KEY: MISC_FEATURE
<222> LOCATION: (9)..(9)
<223> OTHER INFORMATION: Xaa represents any amino acid

<400> SEQUENCE: 38

Asp Gly Ile Asn Tyr Ala Thr Gly Xaa Leu Pro Gly Cys Ser Phe Ser
1               5                   10                  15

Ile Phe Leu Leu Ala Leu Leu Ser Cys Leu Thr Val Pro Ala Ser Ala
            20                  25                  30

Thr Asn Tyr Arg Asn Val Ser Gly Ile Tyr His Val Thr Asn Asp Cys
        35                  40                  45

Pro Asn Ser Ser Ile Val Phe Glu Ala Asp His His Ile Leu His Leu
    50                  55                  60

Pro Gly Cys Val Pro Cys Val Lys Glu Gly Asn His Ser Arg Cys Trp
65                  70                  75                  80

Val Ala Leu Thr Pro Thr Val Ala Ala Pro Tyr Ile Gly Ala Pro Leu
                85                  90                  95

Glu Ser Leu Arg Ser His Val Asp Val Met Val Gly Ala Ala Thr Val
            100                 105                 110

Cys Ser Ala Leu Tyr Ile Gly Asp Leu Cys Gly Gly Leu Phe Leu Val
            115                 120                 125

Gly Gln Met Phe Ser Phe Arg Pro Arg Arg His Trp Thr Thr Gln Glu
        130                 135                 140

Cys Asn Cys Ser Ile
145

```
<210> SEQ ID NO 39
<211> LENGTH: 447
<212> TYPE: DNA
<213> ORGANISM: hepatitis C virus

<400> SEQUENCE: 39
gacgggatca attatgcaac agggaacctc cccggttgct ctttctctat cttcatcctg      60
gcacttctct cgtgcctgac tgtcccggcc tcggctcagc attatcggaa tgtctcgggc     120
atttaccacg tcaccaacga ctgcccgaac tccagcatag tgtatgagtc cgaccatcac     180
atcttacacc taccagggtg tgtaccctgt gtgaagactg gaacacttc gcgctgctgg      240 gtggccttaa cacctaccgt ggccgcgccc atactttcgg ctccacttat gtccgtacgg     300
cggcatgtgg atctgatggt gggtgcagct accctatcgt ctgccctcta cgttggagac     360
ctctgcgggg gtgccttcct agtggggcag atgttcacct ccagccgcg tcgccactgg      420 actgtccaag actgcaactg ttccatc                                         447

<210> SEQ ID NO 40
<211> LENGTH: 149
<212> TYPE: PRT
<213> ORGANISM: hepatitis C virus

<400> SEQUENCE: 40

Asp Gly Ile Asn Tyr Ala Thr Gly Asn Leu Pro Gly Cys Ser Phe Ser
1               5                   10                  15

Ile Phe Ile Leu Ala Leu Leu Ser Cys Leu Thr Val Pro Ala Ser Ala
            20                  25                  30

Gln His Tyr Arg Asn Val Ser Gly Ile Tyr His Val Thr Asn Asp Cys
        35                  40                  45

Pro Asn Ser Ser Ile Val Tyr Glu Ser Asp His His Ile Leu His Leu
    50                  55                  60

Pro Gly Cys Val Pro Cys Val Lys Thr Gly Asn Thr Ser Arg Cys Trp
65                  70                  75                  80

Val Ala Leu Thr Pro Thr Val Ala Ala Pro Ile Leu Ser Ala Pro Leu
                85                  90                  95

Met Ser Val Arg Arg His Val Asp Leu Met Val Gly Ala Ala Thr Leu
            100                 105                 110

Ser Ser Ala Leu Tyr Val Gly Asp Leu Cys Gly Gly Ala Phe Leu Val
        115                 120                 125

Gly Gln Met Phe Thr Phe Gln Pro Arg Arg His Trp Thr Val Gln Asp
    130                 135                 140

Cys Asn Cys Ser Ile
145

<210> SEQ ID NO 41
<211> LENGTH: 957
<212> TYPE: DNA
<213> ORGANISM: hepatitis C virus
<220> FEATURE:
<221> NAME/KEY: misc_feature
<222> LOCATION: (383)..(383)
<223> OTHER INFORMATION: n represents any nucleotide
<220> FEATURE:
<221> NAME/KEY: misc_feature
<222> LOCATION: (924)..(924)
<223> OTHER INFORMATION: n represents any nucleotide
<220> FEATURE:
<221> NAME/KEY: misc_feature
<222> LOCATION: (387)..(387)
<223> OTHER INFORMATION: n represents any nucleotide
```

```
<220> FEATURE:
<221> NAME/KEY: misc_feature
<222> LOCATION: (928)..(928)
<223> OTHER INFORMATION: n represents any nucleotide

<400> SEQUENCE: 41
atgagcacac ttccaaaacc ccaaagaaaa accaaaagaa atactaaccg tcgccctatg      60
gacgtcaagt tcccgggcgg cggccagatc gttggtggag tttacttgtt gccgcgcagg    120
ggccctcgtt tgggtgtgcg cgcgacgaga agacctccg aacggtccca gcctagaggc     180
aggcgccagc ccataccaaa ggtacgccag ccgacaggcc gtagctgggg tcaacccggc    240 taccccttggc cccttttatgg caacgagggc tgcggatggg cgggatggct cctgtccccc    300
cgcgggtctc gtcctaattg ggccccaac gaccccggc gaaggtcccg caacttgggt      360
aaggtcatcg ataccttac atncggncta gccgacctca tggggtacat ccctgtccta     420
ggagggccgc ttggcggcgt tgcggctgcc ctggcgcatg gcgttagggc aatcgaggac    480
ggggtcaatt acgcaacagg gaatcttcct ggttgctcct tttctatctt cctcttagca    540
ctgttatcgt gcctcactac accagcctca gcaattcaag tcaagaacgc tctgggatc    600 taccatctta ccaatgactg ctcgaacaac agcatcgttt ttgaggcgga gaccatgata    660
ctgcatcttc caggttgtgt cccatgtatc aaggcgggga atgagtcacg atgttggctc    720
cctgtctccc ccaccttagc cgtccccaac tcatcagtgc aatccacgg gtttcgccga    780 cacgtagacc tcctcgttgg ggcagcggca ttttgttcgg ccatgtacat cggagacctc    840
tgtggtagca taatcttggt agggcagctt tttactttca ggcctaagta ccatcaggtt    900
acccaggatt gtaactgctc tatnaacnct ggccacgtca cgggacacag gatggca       957
```

```
<210> SEQ ID NO 42
<211> LENGTH: 319
<212> TYPE: PRT
<213> ORGANISM: hepatitis C virus
<220> FEATURE:
<221> NAME/KEY: MISC_FEATURE
<222> LOCATION: (128)..(129)
<223> OTHER INFORMATION

```
Arg Arg Arg Ser Arg Asn Leu Gly Lys Val Ile Asp Thr Leu Thr Xaa
        115                 120                 125
Xaa Leu Ala Asp Leu Met Gly Tyr Ile Pro Val Leu Gly Gly Pro Leu
    130                 135                 140
Gly Gly Val Ala Ala Leu Ala His Gly Val Arg Ala Ile Glu Asp
145             150                 155                 160
Gly Val Asn Tyr Ala Thr Gly Asn Leu Pro Gly Cys Ser Phe Ser Ile
                165                 170                 175
Phe Leu Leu Ala Leu Leu Ser Cys Leu Thr Thr Pro Ala Ser Ala Ile
            180                 185                 190
Gln Val Lys Asn Ala Ser Gly Ile Tyr His Leu Thr Asn Asp Cys Ser
        195                 200                 205
Asn Asn Ser Ile Val Phe Glu Ala Glu Thr Met Ile Leu His Leu Pro
    210                 215                 220
Gly Cys Val Pro Cys Ile Lys Ala Gly Asn Glu Ser Arg Cys Trp Leu
225                 230                 235                 240
Pro Val Ser Pro Thr Leu Ala Val Pro Asn Ser Ser Val Pro Ile His
                245                 250                 255
Gly Phe Arg Arg His Val Asp Leu Leu Val Gly Ala Ala Ala Phe Cys
            260                 265                 270
Ser Ala Met Tyr Ile Gly Asp Leu Cys Gly Ser Ile Ile Leu Val Gly
        275                 280                 285
Gln Leu Phe Thr Phe Arg Pro Lys Tyr His Gln Val Thr Gln Asp Cys
    290                 295                 300
Asn Cys Ser Xaa Asn Xaa Gly His Val Thr Gly His Arg Met Ala
305                 310                 315

<210> SEQ ID NO 43
<211> LENGTH: 957
<212> TYPE: DNA
<213> ORGANISM: hepatitis C virus
<220> FEATURE:
<221> NAME/KEY: misc_feature
<222> LOCATION: (446)..(446)
<223> OTHER INFORMATION: n represents any nucleotide
<220> FEATURE:
<221> NAME/KEY: misc_feature
<222> LOCATION: (467)..(467)
<223> OTHER INFORMATION: n represents any nucleotide
<220> FEATURE:
<221> NAME/KEY: misc_feature
<222> LOCATION: (470)..(470)
<223> OTHER INFORMATION: n represents any nucleotide
<220> FEATURE:
<221> NAME/KEY: misc_feature
<222> LOCATION: (483)..(483)
<223> OTHER INFORMATION: n represents any nucleotide
<220> FEATURE:
<221> NAME/KEY: misc_feature
<222> LOCATION: (500)..(500)
<223> OTHER INFORMATION: n represents any nucleotide
<220> FEATURE:
<221> NAME/KEY: misc_feature
<222> LOCATION: (513)..(514)
<223> OTHER INFORMATION: n represents any nucleotide
<220> FEATURE:
<221> NAME/KEY: misc_feature
<222> LOCATION: (520)..(520)
<223> OTHER INFORMATION: n represents any nucleotide
<220> FEATURE:
<221> NAME/KEY: misc_feature
<222> LOCATION: (531)..(531)
<223> OTHER INFORMATION: n represents any nucleotide

<400> SEQUENCE: 43
```

-continued

```
atgagcacac ttccaaaacc ccaaagaaaa accaaaagaa acaccatccg ccgcccacag      60
gacgtcaagt tcccgggtgg cggccagatc gttggtggag tctacttgct gccgcgcagg     120
ggcccgcgct tgggtgtgcg cgcgacgaga aagacttctg aacggtccca gcccagaggt     180
aggcgccaac caatacccaa agtgcgccac caaacgggcc gtacctgggc ccagcccggg     240 taccctggc ctctttatgg aaatgagggc tgtggttggg caggctggct cctgtccccc      300
cgcggctctc gcccaaattg gggcccaaac gaccccggc ggaggtcccg caacttgggt      360
aaagtcatcg acaccttac ttgcggcttc gccgacctca tggggtatat ccctgtcgta      420
ggcgctccgw tgggaggcgt cgcggnggcc ttggcgcatg gggtcanggn catcgaggac     480
ggngtaaatt acgcaacagn gaatcttccc ggnngctctn tctctatctt nctcttggca    540
cttctctcgt gccttacaac accagcctcc gcggcgcatt ataccaacaa gtctggcctg     600
taccatctca ccaacgactg ccccaacagc agcatcgttt atgaggcgga gacactgatt     660
ttgcacttgc ctgggtgtgt accttgtgtg aagrtgraca atcaatcccg gtgctgggtg     720
caggcctccc cgaccctggc agtgccgaac gcgtctacgc cagtcaccgg gttccgcaaa     780
catgtggaca tcatggtggg cgctgccgcg ttctgttcag ctatgtatgt ggggacctg      840 tgcgggggcc ttttcctcgt tggacagctc ttcacgctca ggcctcggat gcatcaggtt     900
gtccaggagt gtaactgttc catctacaca gggcatatca ctggacaccg aatggca       957
```

<210> SEQ ID NO 44
<211> LENGTH: 319
<212> TYPE: PRT
<213> ORGANISM: hepatitis C virus
<220> FEATURE:
<221> NAME/KEY: MISC_FEATURE
<222> LOCATION: (144)..(144)
<223> OTHER INFORMATION: Xaa represents any amino acid
<220> FEATURE:
<221> NAME/KEY: MISC_FEATURE
<222> LOCATION: (149)..(149)
<223> OTHER INFORMATION: Xaa represents any amino acid
<220> FEATURE:
<221> NAME/KEY: MISC_FEATURE
<222> LOCATION: (156)..(157)
<223> OTHER INFORMATION: Xaa represents any amino acid
<220> FEATURE:
<221> NAME/KEY: MISC_FEATURE
<222> LOCATION: (161)..(161)
<223> OTHER INFORMATION: Xaa represents any amino acid
<220> FEATURE:
<221> NAME/KEY: MISC_FEATURE
<222> LOCATION: (167)..(167)
<223> OTHER INFORMATION: Xaa represents any amino acid
<220> FEATURE:
<221> NAME/KEY: MISC_FEATURE
<222> LOCATION: (171)..(172)
<223> OTHER INFORMATION: Xaa represents any amino acid
<220> FEATURE:
<221> NAME/KEY: MISC_FEATURE
<222> LOCATION: (174)..(174)
<223> OTHER INFORMATION: Xaa represents any amino acid
<220> FEATURE:
<221> NAME/KEY: MISC_FEATURE
<222> LOCATION: (232)..(233)
<223> OTHER INFORMATION: Xaa represents any amino acid
<220> FEATURE:
<221> NAME/KEY: MISC_FEATURE
<222> LOCATION: (177)..(177)
<223> OTHER INFORMATION: Xaa represents any amino acid

<400> SEQUENCE: 44

Met Ser Thr Leu Pro Lys Pro Gln Arg Lys Thr Lys Arg Asn Thr Ile
1               5                  10                  15

Arg Arg Pro Gln Asp Val Lys Phe Pro Gly Gly Gln Ile Val Gly
            20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
50                  55                  60

Ile Pro Lys Val Arg His Gln Thr Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Asn Trp Gly Pro Asn Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Val Val Gly Ala Pro Xaa
130                 135                 140

Gly Gly Val Ala Xaa Ala Leu Ala His Gly Val Xaa Xaa Ile Glu Asp
145                 150                 155                 160

Xaa Val Asn Tyr Ala Thr Xaa Asn Leu Pro Xaa Xaa Ser Xaa Ser Ile
                165                 170                 175

Xaa Leu Leu Ala Leu Leu Ser Cys Leu Thr Thr Pro Ala Ser Ala Ala
            180                 185                 190

His Tyr Thr Asn Lys Ser Gly Leu Tyr His Leu Thr Asn Asp Cys Pro
            195                 200                 205

Asn Ser Ser Ile Val Tyr Glu Ala Glu Thr Leu Ile Leu His Leu Pro
210                 215                 220

Gly Cys Val Pro Cys Val Lys Xaa Xaa Asn Gln Ser Arg Cys Trp Val
225                 230                 235                 240

Gln Ala Ser Pro Thr Leu Ala Val Pro Asn Ala Ser Thr Pro Val Thr
                245                 250                 255

Gly Phe Arg Lys His Val Asp Ile Met Val Gly Ala Ala Ala Phe Cys
            260                 265                 270

Ser Ala Met Tyr Val Gly Asp Leu Cys Gly Gly Leu Phe Leu Val Gly
            275                 280                 285

Gln Leu Phe Thr Leu Arg Pro Arg Met His Gln Val Val Gln Glu Cys
            290                 295                 300

Asn Cys Ser Ile Tyr Thr Gly His Ile Thr Gly His Arg Met Ala
305                 310                 315

<210> SEQ ID NO 45
<211> LENGTH: 413
<212> TYPE: DNA
<213> ORGANISM: hepatitis C virus
<220> FEATURE:
<221> NAME/KEY: misc_feature
<222> LOCATION: (302)..(302)
<223> OTHER INFORMATION: n represents nucleotide
<220> FEATURE:
<221> NAME/KEY: misc_feature
<222> LOCATION: (340)..(340)
<223> OTHER INFORMATION: n represents nucleotide
<220> FEATURE:
<221> NAME/KEY: misc_feature
<222> LOCATION: (384)..(384)
<223> OTHER INFORMATION: n represents nucleotide

<400> SEQUENCE: 45

```
atgagcacac ttcctaaacc tcaaagaaaa accaaacgaa acaccaaccg tcgcccacag     60
```

-continued

```
gacgtcaagt tcccgggtgg cggtcagatc gttggtggag tttacttgtt gccgcgcagg      120
ggccctcgtt tgggtgtgcg cgcgacgagg aaaacttctg aacggtccca gcccagggt       180 agacgccaac ctataccgaa ggtgcgtcac caaacgggcc gtacctgggc tcaacccggg      240 taccctggc ctctttatgg gaatgagggt tgtggctggg cagggtggct cctgtccccc       300
cncggctctc gccctaattg gggccctaat gaccccggn ggaggtcccg caacctgggt       360
aaggtcatcg ataccttac ttgnggsttc gccgacctca tagagtacat tcc             413
```

<210> SEQ ID NO 46
<211> LENGTH: 137
<212> TYPE: PRT
<213> ORGANISM: hepatitis C virus
<220> FEATURE:
<221> NAME/KEY: MISC_FEATURE
<222> LOCATION: (101)..(101)
<223> OTHER INFORMATION: Xaa represents any amino acid
<220> FEATURE:
<221> NAME/KEY: MISC_FEATURE
<222> LOCATION: (114)..(114)
<223> OTHER INFORMATION: Xaa represents any amino acid
<220> FEATURE:
<221> NAME/KEY: MISC_FEATURE
<222> LOCATION: (128)..(129)
<223> OTHER INFORMATION: Xaa represents any amino acid

<400> SEQUENCE: 46

Met Ser Thr Leu Pro Lys Pro Gln Arg Lys Thr Lys Arg Asn Thr Asn
 1               5                  10                  15

Arg Arg Pro Gln Asp Val Lys Phe Pro Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Val Arg His Gln Thr Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Xaa Gly Ser Arg Pro Asn Trp Gly Pro Asn Asp Pro
            100                 105                 110

Arg Xaa Arg Ser Arg Asn Leu Gly Lys Val Ile Asp Thr Leu Thr Xaa
        115                 120                 125

Xaa Phe Ala Asp Leu Ile Glu Tyr Ile
    130                 135

<210> SEQ ID NO 47
<211> LENGTH: 957
<212> TYPE: DNA
<213> ORGANISM: hepatitis C virus
<220> FEATURE:
<221> NAME/KEY: misc_feature
<222> LOCATION: (324)..(324)
<223> OTHER INFORMATION: n represents any nucleotide
<220> FEATURE:
<221> NAME/KEY: misc_feature
<222> LOCATION: (340)..(340)
<223> OTHER INFORMATION: n represents any nucleotide
<220> FEATURE:
<221> NAME/KEY: misc_feature
<222> LOCATION: (455)..(455)
<223> OTHER INFORMATION: n represents any nucleotide

<400> SEQUENCE: 47

-continued

```
atgagcacac ttccaaaacc ccaaagaaaa accaaaagaa acacaaaccg tcgcccaatg      60
gatgtcaagt tcccgggcgg cggtcagatc gttggtggag tctacttgtt accgcgcagg     120
ggcccacgtt tgggtgtgcg cgcgacgagg aagacttcgg aacggtccca ggccagaggt     180
aggcgccaac caatacccaa ggtgcgccag aaccaaggcc gaacctgggc tcagcctggg     240 taccctggc ccctttatgg aacgagggc tgcggctggg cggggtggct cttgtcccc        300 cgtggctctc gcccggactg gggncccaat gaccccggn ggaggtcccg caacctgggt     360
aaggtcatcg acaccctcac ttgcggcttc gccgacctca tggagtacat ccctgtcgtt     420
ggcgcccccc ttggaggcgt tgcggcggaa ctggnacatg gtgtcagggc catcgaggac     480
gggataaact atgcaacagg gaatcttcct ggttgctctt tctctatctt ccwcttggca     540
cttctctcgt gcctcaccac gcctgcctcc gcactaaact atgctaacaa gtctgggctg     600
tatcatctaa ccaatgactg ccccaatagc agcattgtgt atgaggcgaa tggcatgatc     660
ctgcatctcc cgggttgcgt ccctgcgtg aagaccggca acctgaccaa gtgttggctg      720
tcggcctccc cgacattggc ggtgcagaat gcgtcggtgt ccatcagggg tgtccgcgag     780
cacgtggacc tcttggtggg tgctgctgcg ttctgctctg ccatgtacgt gggcgactta     840
tgcggtgggc tctttctcgt tgggcagttg ttcacgttca gacccaggat gtatgagatc     900
gcccaggact gcaactgttc catctatgca ggccacatca ctgggcaccg gatggcg       957
```

<210> SEQ ID NO 48
<211> LENGTH: 319
<212> TYPE: PRT
<213> ORGANISM: hepatitis C virus
<220> FEATURE:
<221> NAME/KEY: MISC_FEATURE
<222> LOCATION: (108)..(108)
<223> OTHER INFORMATION: Xaa represents any amino acid
<220> FEATURE:
<221> NAME/KEY: MISC_FEATURE
<222> LOCATION: (114)..(114)
<223> OTHER INFORMATION: Xaa represents any amino acid
<220> FEATURE:
<221> NAME/KEY: MISC_FEATURE
<222> LOCATION: (152)..(152)
<223> OTHER INFORMATION: Xaa represents any amino acid
<220> FEATURE:
<221> NAME/KEY: MISC_FEATURE
<222> LOCATION: (178)..(178)
<223> OTHER INFORMATION: Xaa represents any amino acid

<400> SEQUENCE: 48

```
Met Ser Thr Leu Pro Lys Pro Gln Arg Lys Thr Lys Arg Asn Thr Asn
1               5                   10                  15

Arg Arg Pro Met Asp Val Lys Phe Pro Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Ala Arg Gly Arg Arg Gln Pro
    50                  55                  60

Ile Pro Lys Val Arg Gln Asn Gln Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Asp Trp Xaa Pro Asn Asp Pro
            100                 105                 110

Arg Xaa Arg Ser Arg Asn Leu Gly Lys Val Ile Asp Thr Leu Thr Cys
```

-continued

```
                115                 120                 125
Gly Phe Ala Asp Leu Met Glu Tyr Ile Pro Val Val Gly Ala Pro Leu
    130                 135                 140
Gly Gly Val Ala Ala Glu Leu Xaa His Gly Val Arg Ala Ile Glu Asp
145                 150                 155                 160
Gly Ile Asn Tyr Ala Thr Gly Asn Leu Pro Gly Cys Ser Phe Ser Ile
                165                 170                 175
Phe Xaa Leu Ala Leu Leu Ser Cys Leu Thr Thr Pro Ala Ser Ala Leu
            180                 185                 190
Asn Tyr Ala Asn Lys Ser Gly Leu Tyr His Leu Thr Asn Asp Cys Pro
            195                 200                 205
Asn Ser Ser Ile Val Tyr Glu Ala Asn Gly Met Ile Leu His Leu Pro
    210                 215                 220
Gly Cys Val Pro Cys Val Lys Thr Gly Asn Leu Thr Lys Cys Trp Leu
225                 230                 235                 240
Ser Ala Ser Pro Thr Leu Ala Val Gln Asn Ala Ser Val Ser Ile Arg
                245                 250                 255
Gly Val Arg Glu His Val Asp Leu Leu Val Gly Ala Ala Ala Phe Cys
            260                 265                 270
Ser Ala Met Tyr Val Gly Asp Leu Cys Gly Gly Leu Phe Leu Val Gly
            275                 280                 285
Gln Leu Phe Thr Phe Arg Pro Arg Met Tyr Glu Ile Ala Gln Asp Cys
    290                 295                 300
Asn Cys Ser Ile Tyr Ala Gly His Ile Thr Gly His Arg Met Ala
305                 310                 315
```

<210> SEQ ID NO 49
<211> LENGTH: 309
<212> TYPE: DNA
<213> ORGANISM: hepatitis C virus

<400> SEQUENCE: 49

```
atgagcacac ttcctaaacc acaaagaaaa accaaaagaa acaccaaccc cggccacagg      60
acgttaagtt cccaggcggc ggtcagatcg ttggtggagt ttacgtgcta ccacgcaggg     120
gccccccagtt gggtgtgcgt gcagtgcgca agacttccga gcggtcgcaa cctcgcagta   180
ggcgccaacc catccccagg gcgcgccgaa ccgagggcag gtcctgggct cagcccgggt    240
acccttggcc cctatatggg aatgagggct gcgggtgggc aggtggctc ctgtccccgc     300
gcggctctc                                                            309
```

<210> SEQ ID NO 50
<211> LENGTH: 115
<212> TYPE: PRT
<213> ORGANISM: hepatitis C virus
<220> FEATURE:
<221> NAME/KEY: MISC_FEATURE
<222> LOCATION: (17)..(17)
<223> OTHER INFORMATION: Xaa represents any amino acid

<400> SEQUENCE: 50

```
Met Ser Thr Leu Pro Lys Pro Gln Arg Lys Thr Lys Arg Asn Thr Asn
1               5                   10                  15
Xaa Arg Pro Gln Asp Val Lys Phe Pro Gly Gly Gly Gln Ile Val Gly
            20                  25                  30
Gly Val Tyr Val Leu Pro Arg Arg Gly Pro Gln Leu Gly Val Arg Ala
        35                  40                  45
```

-continued

```
Val Arg Lys Thr Ser Glu Arg Ser Gln Pro Arg Ser Arg Arg Gln Pro
         50                  55                  60

Ile Pro Arg Ala Arg Arg Thr Glu Gly Arg Ser Trp Ala Gln Pro Gly
 65              70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Asn Asp Pro
            100                 105                 110

Arg Arg Arg
        115

<210> SEQ ID NO 51
<211> LENGTH: 447
<212> TYPE: DNA
<213> ORGANISM: hepatitis C virus

<400> SEQUENCE: 51
gacggaatta atttcgcaac agggaattta cctggttgct ctttctctat cttccttctg      60
gctttgttct catgcttgct tacacccaca gccgggctgg agtaccgtaa tgcctccgga     120
ctctacatgg taactaacga ctgcagtaac ggtagtatct tgtatgaggc cggggatatt     180
atcctccact acctggctg tgtcccctgc gtacgctctg caatacatc aagatgctgg      240 atccctgtga gcccyaccgt cgccgtgaag tcgccctgcg ccgccaccgc ctctctccgc     300
acgcacgtgg atatgatggt gggrgcggcc accctatgct cagctctcta cgtaggagac     360
ctttgtggag cgctatttct tgtygggcag gggttctcat ggagacatcg ccagcattgg     420
actgtccagg actgcaactg ttccatc                                         447

<210> SEQ ID NO 52
<211> LENGTH: 149
<212> TYPE: PRT
<213> ORGANISM: hepatitis C virus
<220> FEATURE:
<221> NAME/KEY: MISC_FEATURE
<222> LOCATION: (85)..(85)
<223> OTHER INFORMATION: Xaa represents Pro
<220> FEATURE:
<221> NAME/KEY: MISC_FEATURE
<222> LOCATION: (108)..(108)
<223> OTHER INFORMATION: Xaa represents Gly
<220> FEATURE:
<221> NAME/KEY: MISC_FEATURE
<222> LOCATION: (128)..(128)
<223> OTHER INFORMATION: Xaa represents Val

<400> SEQUENCE: 52

Asp Gly Ile Asn Phe Ala Thr Gly Asn Leu Pro Gly Cys Ser Phe Ser
 1               5                  10                  15

Ile Phe Leu Leu Ala Leu Phe Ser Cys Leu Leu Thr Pro Thr Ala Gly
             20                  25                  30

Leu Glu Tyr Arg Asn Ala Ser Gly Leu Tyr Met Val Thr Asn Asp Cys
         35                  40                  45

Ser Asn Gly Ser Ile Val Tyr Glu Ala Gly Asp Ile Ile Leu His Leu
     50                  55                  60

Pro Gly Cys Val Pro Cys Val Arg Ser Gly Asn Thr Ser Arg Cys Trp
 65                  70                  75                  80

Ile Pro Val Ser Xaa Thr Val Ala Val Lys Ser Pro Cys Ala Ala Thr
                 85                  90                  95

Ala Ser Leu Arg Thr His Val Asp Met Met Val Xaa Ala Ala Thr Leu
            100                 105                 110
```

Cys Ser Ala Leu Tyr Val Gly Asp Leu Cys Gly Ala Leu Phe Leu Xaa
            115                 120                 125

Gly Gln Gly Phe Ser Trp Arg His Arg Gln His Trp Thr Val Gln Asp
    130                 135                 140

Cys Asn Cys Ser Ile
145

<210> SEQ ID NO 53
<211> LENGTH: 340
<212> TYPE: DNA
<213> ORGANISM: hepatitis C virus

<400> SEQUENCE: 53

| | | | | | | |
|---|---|---|---|---|---|---|
| ctcgacagtt | actgagaatg | acatccgtgt | cgaggaatca | atataccaat | gttgtgactt | 60 |
| ggcccccgag | gctcgcaagg | ccataaagtc | gctcaccgag | cggctgtaca | tcgggggccc | 120 |
| yctaaccaat | tcaaaaggac | agaactgcgg | ctaccgtcgg | tgccgcgcca | gcggcgtgct | 180 |
| gactaccagc | tgcggcaaca | ccctgacatg | ctacttgaaa | gccagagcgg | cctgtcgagc | 240 |
| tgcaaagctc | cgggactgca | ccatgctcgt | gtgcggggat | gaccttgtcg | ttatctgtga | 300 |
| gagtgcggga | gtcgaggaag | acgcggcgaa | cctacgagct | | | 340 |

<210> SEQ ID NO 54
<211> LENGTH: 113
<212> TYPE: PRT
<213> ORGANISM: hepatitis C virus
<220> FEATURE:
<221> NAME/KEY: MISC_FEATURE
<222> LOCATION: (40)..(40)
<223> OTHER INFORMATION: Xaa represents any amino acid

<400> SEQUENCE: 54

Ser Thr Val Thr Glu Asn Asp Ile Arg Val Glu Glu Ser Ile Tyr Gln
1               5                   10                  15

Cys Cys Asp Leu Ala Pro Glu Ala Arg Lys Ala Ile Lys Ser Leu Thr
            20                  25                  30

Glu Arg Leu Tyr Ile Gly Gly Xaa Leu Thr Asn Ser Lys Gly Gln Asn
        35                  40                  45

Cys Gly Tyr Arg Arg Cys Arg Ala Ser Gly Val Leu Thr Thr Ser Cys
    50                  55                  60

Gly Asn Thr Leu Thr Cys Tyr Leu Lys Ala Arg Ala Ala Cys Arg Ala
65                  70                  75                  80

Ala Lys Leu Arg Asp Cys Thr Met Leu Val Cys Gly Asp Asp Leu Val
                85                  90                  95

Val Ile Cys Glu Ser Ala Gly Val Glu Glu Asp Ala Ala Asn Leu Arg
            100                 105                 110

Ala

<210> SEQ ID NO 55
<211> LENGTH: 340
<212> TYPE: DNA
<213> ORGANISM: hepatitis C virus

<400> SEQUENCE: 55

| | | | | | | |
|---|---|---|---|---|---|---|
| ctcgacagtt | actgagaacg | acatccgtac | cgaggratca | atctatcaat | gttgtgactt | 60 |
| ggcccccygag | gcccgcaagg | ccataaagtc | gctcaccgag | cggctgtacg | tcggggccc | 120 |
| cctaaccaat | tcaaggggc | agaactgcgg | ctatcgtcgg | tgtcgcgcta | gcggcgtgct | 180 |

```
gaccaccagc tgcggcaaca ccctcacatg ctacttgaaa gccagggcgg cctgtcgagc      240
tgcaaagctc caggactgca cgatgctcgt gtgcggagac gaccttgtcg ttatctgtga      300
gagcgcggga gtcgaggagg acgcggcgaa cctacgagtc                            340
```

<210> SEQ ID NO 56
<211> LENGTH: 113
<212> TYPE: PRT
<213> ORGANISM: hepatitis C virus
<220> FEATURE:
<221> NAME/KEY: MISC_FEATURE
<222> LOCATION: (12)..(12)
<223> OTHER INFORMATION: Xaa represents any amino acid
<220> FEATURE:
<221> NAME/KEY: MISC_FEATURE
<222> LOCATION: (22)..(22)
<223> OTHER INFORMATION: Xaa represents any amino acid

<400> SEQUENCE: 56

```
Ser Thr Val Thr Glu Asn Asp Ile Arg Thr Glu Xaa Ser Ile Tyr Gln
 1               5                  10                  15

Cys Cys Asp Leu Ala Xaa Glu Ala Arg Lys Ala Ile Lys Ser Leu Thr
            20                  25                  30

Glu Arg Leu Tyr Val Gly Gly Pro Leu Thr Asn Ser Lys Gly Gln Asn
        35                  40                  45

Cys Gly Tyr Arg Arg Cys Arg Ala Ser Gly Val Leu Thr Thr Ser Cys
    50                  55                  60

Gly Asn Thr Leu Thr Cys Tyr Leu Lys Ala Arg Ala Ala Cys Arg Ala
65                  70                  75                  80

Ala Lys Leu Gln Asp Cys Thr Met Leu Val Cys Gly Asp Asp Leu Val
                85                  90                  95

Val Ile Cys Glu Ser Ala Gly Val Glu Glu Asp Ala Ala Asn Leu Arg
            100                 105                 110

Val
```

<210> SEQ ID NO 57
<211> LENGTH: 340
<212> TYPE: DNA
<213> ORGANISM: hepatitis C virus

<400> SEQUENCE: 57

```
ctcgacagtt actgagaacg acattcgtgt cgaggaatca atctaccagt gctgtgactt      60 ggccccgag gccgcaagg ccataaagtc gctcaccgag cggctgtata tcggggtcc       120 cctaaccaac tcaaaagggc agaactgcgg ctaccgtcgg tgccgcgcca gcggcgtgct     180
gactaccagc tgcggtaata ccctcacatg ttacttgaaa gccagggcgg cctgtcgagc     240
tgcgaagctc caggactgca caatgctcgt gtgcggagac gaccttgtcg ttatctgtga     300
gagtgcrgga gtcgaggagg atgcggcgaa cctacgagtc                           340
```

<210> SEQ ID NO 58
<211> LENGTH: 113
<212> TYPE: PRT
<213> ORGANISM: hepatitis C virus
<220> FEATURE:
<221> NAME/KEY: MISC_FEATURE
<222> LOCATION: (102)..(102)
<223> OTHER INFORMATION: Xaa represents any amino acid

<400> SEQUENCE: 58

```
Ser Thr Val Thr Glu Asn Asp Ile Arg Val Glu Glu Ser Ile Tyr Gln
 1               5                  10                  15
```

```
Cys Cys Asp Leu Ala Pro Glu Ala Arg Lys Ala Ile Lys Ser Leu Thr
        20                  25                  30

Glu Arg Leu Tyr Ile Gly Gly Pro Leu Thr Asn Ser Lys Gly Gln Asn
        35                  40                  45

Cys Gly Tyr Arg Arg Cys Arg Ala Ser Gly Val Leu Thr Thr Ser Cys
        50                  55                  60

Gly Asn Thr Leu Thr Cys Tyr Leu Lys Ala Arg Ala Ala Cys Arg Ala
65                  70                  75                  80

Ala Lys Leu Gln Asp Cys Thr Met Leu Val Cys Gly Asp Asp Leu Val
                85                  90                  95

Val Ile Cys Glu Ser Xaa Gly Val Glu Glu Asp Ala Ala Asn Leu Arg
                100                 105                 110

Val

<210> SEQ ID NO 59
<211> LENGTH: 652
<212> TYPE: DNA
<213> ORGANISM: hepatitis C virus
<220> FEATURE:
<221> NAME/KEY: misc_feature
<222> LOCATION: (524)..(524)
<223> OTHER INFORMATION: n represents any nucleotide
<220> FEATURE:
<221> NAME/KEY: misc_feature
<222> LOCATION: (625)..(625)
<223> OTHER INFORMATION: n represents any nucleotide

<400> SEQUENCE: 59
cgtacagcct ccaggacccc ccctcccggg agagccatag tggtctgcgg aaccggtgag      60
tacaccggaa ttgccaggac gaccgggtcc tttcttggat caacccgctc aatgcctgga     120
gatttgggcg tgcccccgca agactgctag ccgagtagtg ttgggtcgcg aaaggccttg     180
tggtactgcc tgatagggtg cttgcgagtc ccccggagg tctcgtagac cgtgcaccat      240
gagcacgaat cctaaacctc aaagaaaaac caaagaaac accaaccgcc gcccacagga      300
cgtcaagttc ccgggcggtg gccagatcgt tggtggagtc tacgtgctac cgcgcagggg     360
ccctagattg ggtgtgcgcg cagcgcggaa gacttcggag cggtcgcaac ctcgtgggag     420
gcgccaacct attcccaagg agcgccgacc cgagggcagg tcctgggcgc agcccgggta     480
cccctggccc ctctatggta acgagggctg cgggtgggca ggtngctcc tgtcccctcg      540 cggctcccgt cctagttggg gtcctactga ccccgggcgt aggtcacgca atttgggtaa     600
ggtcatcgat accctcacgt gttngttcgc cgacctcatg gggtacatac cg            652

<210> SEQ ID NO 60
<211> LENGTH: 138
<212> TYPE: PRT
<213> ORGANISM: hepatitis C virus
<220> FEATURE:
<221> NAME/KEY: MISC_FEATURE
<222> LOCATION: (96)..(96)
<223> OTHER INFORMATION: Xaa represents any amino acid
<220> FEATURE:
<221> NAME/KEY: MISC_FEATURE
<222> LOCATION: (129)..(129)
<223> OTHER INFORMATION: Xaa represents any amino acid

<400> SEQUENCE: 60

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
```

```
                    20                  25                  30
Gly Val Tyr Val Leu Pro Arg Arg Gly Pro Arg Leu Gly Val Arg Ala
                35                  40                  45
Ala Arg Lys Thr Ser Glu Arg Ser Gln Pro Arg Gly Arg Arg Gln Pro
 50                  55                  60
Ile Pro Lys Glu Arg Arg Pro Glu Gly Arg Ser Trp Ala Gln Pro Gly
 65                  70                  75                  80
Tyr Pro Trp Pro Leu Tyr Gly Asn Glu Gly Cys Gly Trp Ala Gly Xaa
                85                  90                  95
Leu Leu Ser Pro Arg Gly Ser Arg Pro Ser Trp Gly Pro Thr Asp Pro
                100                 105                 110
Arg Arg Arg Ser Arg Asn Leu Gly Lys Val Ile Asp Thr Leu Thr Cys
                115                 120                 125
Xaa Phe Ala Asp Leu Met Gly Tyr Ile Pro
                130                 135
```

<210> SEQ ID NO 61
<211> LENGTH: 340
<212> TYPE: DNA
<213> ORGANISM: hepatitis C virus

<400> SEQUENCE: 61

```
ctcaacggtc actgaagctg atatccgaac agaggagtcc ataccaat gctgtgacct       60
gcaccccgaa gcacgtgtag ccatcaagtc tttgactgaa aggctgtacg tcggggggcc    120
cttgaccaat tcaaaagggg agaactgcgg ctatcgcaga tgccgtgcca gcggcgtctt    180
gacaaccagc tgcggcaaca ccctcacctg ctatatcaag gccctagcag cctgtagagc    240
tgccaagctc caggactgca ccatgctcgt ctgtggcgac gacctggtcg tgatctgcga    300
gagtgtaggg acccaggagg atgcggcgag cctgcgagcc                          340
```

<210> SEQ ID NO 62
<211> LENGTH: 113
<212> TYPE: PRT
<213> ORGANISM: hepatitis C virus

<400> SEQUENCE: 62

```
Ser Thr Val Thr Glu Ala Asp Ile Arg Thr Glu Glu Ser Ile Tyr Gln
 1               5                   10                  15
Cys Cys Asp Leu His Pro Glu Ala Arg Val Ala Ile Lys Ser Leu Thr
                20                  25                  30
Glu Arg Leu Tyr Val Gly Gly Pro Leu Thr Asn Ser Lys Gly Glu Asn
                35                  40                  45
Cys Gly Tyr Arg Arg Cys Arg Ala Ser Gly Val Leu Thr Thr Ser Cys
 50                  55                  60
Gly Asn Thr Leu Thr Cys Tyr Ile Lys Ala Leu Ala Ala Cys Arg Ala
 65                  70                  75                  80
Ala Lys Leu Gln Asp Cys Thr Met Leu Val Cys Gly Asp Asp Leu Val
                85                  90                  95
Val Ile Cys Glu Ser Val Gly Thr Gln Glu Asp Ala Ala Ser Leu Arg
                100                 105                 110
Ala
```

<210> SEQ ID NO 63
<211> LENGTH: 340
<212> TYPE: DNA
<213> ORGANISM: hepatitis C virus

```
<220> FEATURE:
<221> NAME/KEY: misc_feature
<222> LOCATION: (1)..(1)
<223> OTHER INFORMATION: n represents any nucleotide
<220> FEATURE:
<221> NAME/KEY: misc_feature
<222> LOCATION: (311)..(311)
<223> OTHER INFORMATION: n represents any nucleotide
<220> FEATURE:
<221> NAME/KEY: misc_feature
<222> LOCATION: (316)..(316)
<223> OTHER INFORMATION: n represents any nucleotide
<220> FEATURE:
<221> NAME/KEY: misc_feature
<222> LOCATION: (330)..(340)
<223> OTHER INFORMATION: n represents any nucleotide

<400> SEQUENCE: 63
ntcaacagtc actgagagtg atatccgtac agaggagtcc atctaccaat gctgtgatct      60 agacccgag gctcgcaagg ccataaggtc cctcacagag aggctttata tcggggtcc      120 cctgacaaac tcaaaagggc agaactgcgg ctaccgccga tgccgtgcaa gcggcgtcct    180
gacgactagc tgcggcaaca ccctcacctg ttacataaag gccagggcag cctgtcgagc    240
tgcgaagctc caggattgct caatgctcgt ctgtggcgac gaccttgtcg ttatctgcga    300
gatcgagggg ntccangagg atccgtcgan nnnnnnnnnn                          340

<210> SEQ ID NO 64
<211> LENGTH: 113
<212> TYPE: PRT
<213> ORGANISM: hepatitis C virus
<220> FEATURE:
<221> NAME/KEY: MISC_FEATURE
<222> LOCATION: (104)..(105)
<223> OTHER INFORMATION: Xaa represents any amino acid
<220> FEATURE:
<221> NAME/KEY: MISC_FEATURE
<222> LOCATION: (110)..(113)
<223> OTHER INFORMATION: Xaa represents any amino acid

<400> SEQUENCE: 64

Ser Thr Val Thr Glu Ser Asp Ile Arg Thr Glu Ser Ile Tyr Gln
1               5                   10                  15

Cys Cys Asp Leu Asp Pro Glu Ala Arg Lys Ala Ile Arg Ser Leu Thr
                20                  25                  30

Glu Arg Leu Tyr Ile Gly Gly Pro Leu Thr Asn Ser Lys Gly Gln Asn
            35                  40                  45

Cys Gly Tyr Arg Arg Cys Arg Ala Ser Gly Val Leu Thr Thr Ser Cys
        50                  55                  60

Gly Asn Thr Leu Thr Cys Tyr Ile Lys Ala Arg Ala Ala Cys Arg Ala
65                  70                  75                  80

Ala Lys Leu Gln Asp Cys Ser Met Leu Val Cys Gly Asp Asp Leu Val
                85                  90                  95

Val Ile Cys Glu Ile Glu Gly Xaa Xaa Glu Asp Pro Ser Xaa Xaa Xaa
            100                 105                 110

Xaa

<210> SEQ ID NO 65
<211> LENGTH: 831
<212> TYPE: DNA
<213> ORGANISM: hepatitis C virus
<220> FEATURE:
<221> NAME/KEY: misc_feature
<222> LOCATION: (779)..(779)
<223> OTHER INFORMATION: n represents any nucleotide
```

```
<400> SEQUENCE: 65
cgtagaccgt gcaccatgag cacgaatcct aaacctcaaa gaaaaaccaa acgtaacatc      60
aaccgccgcc cacaggacgt caagttcccg ggcggtggcc agatcgtcgg tggagtttac     120
ctgttgccgc gcaggggccc tagattgggt gtgcgcgcga ctaggaagac ttccgagcgg     180
tcgcaacctc gtgggaggcg acagcctatc cccaaggctc gccgatccga gggcaggtcc     240
tgggctcagc ccgggtaccc ttggcccctc tatggcaatg agggcatggg ttgggcaggg     300
tggctcctgt cccccatgg ctcccggcct agttggggcc cttcagaccc cggcgtagg     360 tcgcgtaatt tgggtaaggt catcgatacc ctcacatgcg gcttcgccga cctcatgggg     420
tacattccgc tcgtcggcgc ccccctaggg ggcgttgcca gggccctggc gcaaggcttc     480
cgggatctac cacgtcacca acgattgttc caatgggagc attgtgtatg aggcggaagg     540
catgatcatg catctccccg ggtgcgtgcc ctgcgttcgg gaaggtaata tctctcgttg     600
ctgggtaccg ttttccccca cgctcgcagc caggaatgct agcgtcccca ctcaggcaat     660
tcggcgacac gtcgacttgc ttgttggggc ggccacactc tgttctgcta tgtatgtggg     720
ggacctctgt gggtccgtct tcctcgtcgg ccaactgttc accttcacaw cccgccagna     780
ctacacagtg caagactgca attgttccat ctaccccggc catataacgg g              831

<210> SEQ ID NO 66
<211> LENGTH: 158
<212> TYPE: PRT
<213> ORGANISM: hepatitis C virus

<400> SEQUENCE: 66

Met Ser Thr Asn Pro Lys Pro Gln Arg Lys Thr Lys Arg Asn Ile Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Met Gly Trp Ala Gly Trp
                85                  90                  95

Leu Leu Ser Pro His Gly Ser Arg Pro Ser Trp Gly Pro Ser Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Val Ala Arg Ala Leu Ala Gln Gly Phe Arg Asp Leu
145                 150                 155

<210> SEQ ID NO 67
<211> LENGTH: 340
<212> TYPE: DNA
<213> ORGANISM: hepatitis C virus
<220> FEATURE:
<221> NAME/KEY: misc_feature
<222> LOCATION: (1)..(7)
<223> OTHER INFORMATION: n represents any nucleotide
<220> FEATURE:
```

```
<221> NAME/KEY: misc_feature
<222> LOCATION: (334)..(340)
<223> OTHER INFORMATION: n represents any nucleotide

<400> SEQUENCE: 67
nnnnnnngtc actgagagtg atatccgtgt cgaggartca atttaccaat gctgtgacct      60
ggcccccgag gctcgcgtag ccataaagtc gctcactgag cggctatatg tcggggcccc    120
tctcaccaac tcaaaaggac agaactgcgg ctatcgccgg tgccgtgcga gcggtgtgct    180
gactactagc tgcggtaaca ccctcacatg ctacctgaaa gccgccgcgg cctgtcgagc    240
tgcaaagctc cgggaatgca caatgctcgt gtgtggcgac gacctcgtcg ttatctgtga    300
gagtgcgggg gtccaggagg atgctgcaag cctnnnnnnn                          340

<210> SEQ ID NO 68
<211> LENGTH: 113
<212> TYPE: PRT
<213> ORGANISM: hepatitis C virus
<220> FEATURE:
<221> NAME/KEY: MISC_FEATURE
<222> LOCATION: (1)..(2)
<223> OTHER INFORMATION: Xaa represents any amino acid
<220> FEATURE:
<221> NAME/KEY: MISC_FEATURE
<222> LOCATION: (12)..(12)
<223> OTHER INFORMATION: Xaa represents any amino acid
<220> FEATURE:
<221> NAME/KEY: MISC_FEATURE
<222> LOCATION: (111)..(113)
<223> OTHER INFORMATION: Xaa represents any amino acid

<400> SEQUENCE: 68

Xaa Xaa Val Thr Glu Ser Asp Ile Arg Val Glu Xaa Ser Ile Tyr Gln
1               5                   10                  15

Cys Cys Asp Leu Ala Pro Glu Ala Arg Val Ala Ile Lys Ser Leu Thr
            20                  25                  30

Glu Arg Leu Tyr Val Gly Gly Pro Leu Thr Asn Ser Lys Gly Gln Asn
        35                  40                  45

Cys Gly Tyr Arg Arg Cys Arg Ala Ser Gly Val Leu Thr Thr Ser Cys
50                  55                  60

Gly Asn Thr Leu Thr Cys Tyr Leu Lys Ala Ala Ala Cys Arg Ala
65                  70                  75                  80

Ala Lys Leu Arg Glu Cys Thr Met Leu Val Cys Gly Asp Asp Leu Val
            85                  90                  95

Val Ile Cys Glu Ser Ala Gly Val Gln Glu Asp Ala Ala Ser Xaa Xaa
        100                 105                 110

Xaa

<210> SEQ ID NO 69
<211> LENGTH: 340
<212> TYPE: DNA
<213> ORGANISM: hepatitis C virus
<220> FEATURE:
<221> NAME/KEY: misc_feature
<222> LOCATION: (28)..(28)
<223> OTHER INFORMATION: n represents any nucleotide
<220> FEATURE:
<221> NAME/KEY: misc_feature
<222> LOCATION: (336)..(340)
<223> OTHER INFORMATION: n represents any nucleotide

<400> SEQUENCE: 69
ctcgacagtc acagagagag atataagnac tgaggagtcc ataaccagg cttgttcctt      60
```

```
acccgagcag gccagaactg ccatacactc attgactgag agactctacg taggagggcc      120
catgatgaac agcaaagggc aatcctgcgg atacaggcat tgccgcgcca gcggagtgct      180
caccaccagt atgggaata ccatcacgtg ctacatcaag gccctagcgg cttgtaaagc       240
agcaggaata gtgcccca ccatgctggt gtgcggcgat gacctagttg tcatctcaga       300
gagtcaggga gtcgaggagg acgaccggaa cctgannnnn                            340
```

<210> SEQ ID NO 70
<211> LENGTH: 113
<212> TYPE: PRT
<213> ORGANISM: hepatitis C virus
<220> FEATURE:
<221> NAME/KEY: MISC_FEATURE
<222> LOCATION: (9)..(9)
<223> OTHER INFORMATION: Xaa represents any amino acid
<220> FEATURE:
<221> NAME/KEY: MISC_FEATURE
<222> LOCATION: (112)..(113)
<223> OTHER INFORMATION: Xaa represents any amino acid

<400> SEQUENCE: 70

```
Ser Thr Val Thr Glu Arg Asp Ile Xaa Thr Glu Glu Ser Ile Tyr Gln
1               5                   10                  15

Ala Cys Ser Leu Pro Glu Gln Ala Arg Thr Ala Ile His Ser Leu Thr
            20                  25                  30

Glu Arg Leu Tyr Val Gly Gly Pro Met Met Asn Ser Lys Gly Gln Ser
        35                  40                  45

Cys Gly Tyr Arg His Cys Arg Ala Ser Gly Val Leu Thr Thr Ser Met
50                  55                  60

Gly Asn Thr Ile Thr Cys Tyr Ile Lys Ala Leu Ala Ala Cys Lys Ala
65                  70                  75                  80

Ala Gly Ile Val Ala Pro Thr Met Leu Val Cys Gly Asp Asp Leu Val
                85                  90                  95

Val Ile Ser Glu Ser Gln Gly Val Glu Glu Asp Asp Arg Asn Leu Xaa
            100                 105                 110

Xaa
```

<210> SEQ ID NO 71
<211> LENGTH: 340
<212> TYPE: DNA
<213> ORGANISM: hepatitis C virus

<400> SEQUENCE: 71

```
ctcaaccgtc acagagaggg atataagaac tgaggagtcc atatacctgg cctgctcctt      60
acccgagcag gcccggactg ccatacattc attaactgag agactttacg tgggagggcc     120
catgatgaac agcaaagggc agtcctgcgg atacaggcgt tgccgcgcta gcggagtgct     180
caccaccagt atgggaaca ccatcacgtg ttatgtgaaa gccctcgcag cttgtaaagc      240
tgcgggcatt gttgccccca cgatgctggt gtgcggcgat gacctggttg tcatctcaga    300
gagtcagggg gctgaggagg acgagcgaaa cctgagagtc                           340
```

<210> SEQ ID NO 72
<211> LENGTH: 113
<212> TYPE: PRT
<213> ORGANISM: hepatitis C virus

<400> SEQUENCE: 72

```
Ser Thr Val Thr Glu Arg Asp Ile Arg Thr Glu Glu Ser Ile Tyr Leu
1               5                   10                  15
```

```
Ala Cys Ser Leu Pro Glu Gln Ala Arg Thr Ala Ile His Ser Leu Thr
            20                  25                  30

Glu Arg Leu Tyr Val Gly Gly Pro Met Met Asn Ser Lys Gly Gln Ser
        35                  40                  45

Cys Gly Tyr Arg Arg Cys Arg Ala Ser Gly Val Leu Thr Thr Ser Met
    50                  55                  60

Gly Asn Thr Ile Thr Cys Tyr Val Lys Ala Leu Ala Ala Cys Lys Ala
65                  70                  75                  80

Ala Gly Ile Val Ala Pro Thr Met Leu Val Cys Gly Asp Asp Leu Val
                85                  90                  95

Val Ile Ser Glu Ser Gln Gly Ala Glu Glu Asp Glu Arg Asn Leu Arg
            100                 105                 110

Val
```

```
<210> SEQ ID NO 73
<211> LENGTH: 340
<212> TYPE: DNA
<213> ORGANISM: hepatitis C virus

<400> SEQUENCE: 73
ctcaacagtc gcggagagag acatcaggac cgaggagtcc atttaccttg cctgctcctt      60
acccgagcaa gcccgaactg ccatacattc attgactgag agactttacg taggagggcc     120
catgatgaac agcaagggac agtcctgcgg ttacagacgt tgccgcgcca gcggagtgct     180
caccaccagc atgggaaata ccatcacatg ctatgtgaag gcattagctg cctgcaaagc     240
tgcaggcatc gttgctccca cgatgctggt ttgtggcgac gatctggtca tcatctcaga     300
gagtcaggga accgaggagg atgagcggaa cctgagagtc                          340
```

```
<210> SEQ ID NO 74
<211> LENGTH: 113
<212> TYPE: PRT
<213> ORGANISM: hepatitis C virus

<400> SEQUENCE: 74

Ser Thr Val Ala Glu Arg Asp Ile Arg Thr Glu Glu Ser Ile Tyr Leu
1               5                   10                  15

Ala Cys Ser Leu Pro Glu Gln Ala Arg Thr Ala Ile His Ser Leu Thr
            20                  25                  30

Glu Arg Leu Tyr Val Gly Gly Pro Met Met Asn Ser Lys Gly Gln Ser
        35                  40                  45

Cys Gly Tyr Arg Arg Cys Arg Ala Ser Gly Val Leu Thr Thr Ser Met
    50                  55                  60

Gly Asn Thr Ile Thr Cys Tyr Val Lys Ala Leu Ala Ala Cys Lys Ala
65                  70                  75                  80

Ala Gly Ile Val Ala Pro Thr Met Leu Val Cys Gly Asp Asp Leu Val
                85                  90                  95

Ile Ile Ser Glu Ser Gln Gly Thr Glu Glu Asp Glu Arg Asn Leu Arg
            100                 105                 110

Val
```

```
<210> SEQ ID NO 75
<211> LENGTH: 1195
<212> TYPE: DNA
<213> ORGANISM: hepatitis C virus
<220> FEATURE:
<221> NAME/KEY: misc_feature
```

```
<222> LOCATION: (3)..(3)
<223> OTHER INFORMATION: n represents any nucleotide
<220> FEATURE:
<221> NAME/KEY: misc_feature
<222> LOCATION: (7)..(7)
<223> OTHER INFORMATION: n represents any nucleotide
<220> FEATURE:
<221> NAME/KEY: misc_feature
<222> LOCATION: (352)..(352)
<223> OTHER INFORMATION: n represents any nucleotide
<220> FEATURE:
<221> NAME/KEY: misc_feature
<222> LOCATION: (361)..(361)
<223> OTHER INFORMATION: n represents any nucleotide
<220> FEATURE:
<221> NAME/KEY: misc_feature
<222> LOCATION: (369)..(369)
<223> OTHER INFORMATION: n represents any nucleotide
<220> FEATURE:
<221> NAME/KEY: misc_feature
<222> LOCATION: (371)..(371)
<223> OTHER INFORMATION: n represents any nucleotide
<220> FEATURE:
<221> NAME/KEY: misc_feature
<222> LOCATION: (374)..(374)
<223> OTHER INFORMATION: n represents any nucleotide
<220> FEATURE:
<221> NAME/KEY: misc_feature
<222> LOCATION: (387)..(387)
<223> OTHER INFORMATION: n represents any nucleotide
<220> FEATURE:
<221> NAME/KEY: misc_feature
<222> LOCATION: (395)..(395)
<223> OTHER INFORMATION: n represents any nucleotide
<220> FEATURE:
<221> NAME/KEY: misc_feature
<222> LOCATION: (446)..(446)
<223> OTHER INFORMATION: n represents any nucleotide
<220> FEATURE:
<221> NAME/KEY: misc_feature
<222> LOCATION: (621)..(621)
<223> OTHER INFORMATION: n represents any nucleotide
<220> FEATURE:
<221> NAME/KEY: misc_feature
<222> LOCATION: (629)..(629)
<223> OTHER INFORMATION: n represents any nucleotide
<220> FEATURE:
<221> NAME/KEY: misc_feature
<222> LOCATION: (798)..(798)
<223> OTHER INFORMATION: n represents any nucleotide
<220> FEATURE:
<221> NAME/KEY: misc_feature
<222> LOCATION: (887)..(887)
<223> OTHER INFORMATION: n represents any nucleotide
<220> FEATURE:
<221> NAME/KEY: misc_feature
<222> LOCATION: (887)..(888)
<223> OTHER INFORMATION: n represents any nucleotide
<220> FEATURE:
<221> NAME/KEY: misc_feature
<222> LOCATION: (890)..(891)
<223> OTHER INFORMATION: n represents any nucleotide
<220> FEATURE:
<221> NAME/KEY: misc_feature
<222> LOCATION: (978)..(978)
<223> OTHER INFORMATION: n represents any nucleotide
<220> FEATURE:
<221> NAME/KEY: misc_feature
<222> LOCATION: (1194)..(1194)
<223> OTHER INFORMATION: n represents any nucleotide
<220> FEATURE:
<221> NAME/KEY: misc_feature
<222> LOCATION: (673)..(673)
<223> OTHER INFORMATION: n represents any nucleotide

<400> SEQUENCE: 75
cgnacancct ccaggccccc ccctcccggg agagccatag tggtctgcgg aaccggtgag     60
```

```
tacaccggaa ttgccgggaa gactgggtcc tttcttggat aaacccactc tatgcccggc    120
catttgggcg tgcccccgca agactgctar ccgagtagcg ttgggttgcg aaaggccttg    180
tggtactgcc tgatagggtg cttgcgagtg ccccggagg tctcgtagac cgtgcatcat     240
gagcacaaat cctaaacctc aagaaaaac caaaagaaac actaaccgcc gcccacagga     300
cgttaagttc ccggcggtg gccagatcgt tggcggagta tacttgttgc cntgcagggg     360
ncccaggtng ngtntatgcg caacgangaa gactnccgaa cagtcccagc cacgtgggag    420
gcgccagccc atcccgaaag atcggngcac cactggcaag tcctggggac gtccaggata    480
tccctggccc ctgtatggga acgagggcct cgggtgggca gggtggctcc tgtccccccg    540
gggctcccgc ccgtcatggg gccccacgga ccccggcat aggtcgcgca acttgggtaa     600
ggtcatcgat accctcacgt ncggctttnc cgacctcatg gggtacattc ccgtcgttgg    660
cgccccagta ggnggcgtcg ccagagctct cgcgcatggc gtgagagtcc tggaggacgg    720
gataaactat gaaacaggga acctcccgg ttgctctttc tctatctccc tccttgctct     780
tctgtcctga attaccgngc cagtttctgc tgtggaaatc aaaaacacca gmaacacata    840
catggtgact aacgactgtt caaacagyag catcacctgg cagcttnngn ncgcggtgct    900
tcacgttcct ggatgcgtcc cctgtgaacg agagggcaac agttcccggt gctggattcc    960
agtcacgccc racgtakncg tgagccgacc tggtgcccta accgagggtt tgcgatcgca   1020
catcgacacc atcgtagcgt ccgcaacatt ttgttctgcc ctctacatag gggatgtatg   1080
tggcgcgata atgatagctg cccaagtggt catcgtctcg ccggagcatc atcactttgt   1140
ccaggactgt aactgttcca tctacccggg ccacataacg gggcctcgta tgtng        1195
```

<210> SEQ ID NO 76
<211> LENGTH: 318
<212> TYPE: PRT
<213> ORGANISM: hepatitis C virus
<220> FEATURE:
<221> NAME/KEY: MISC_FEATURE
<222> LOCATION: (38)..(38)
<223> OTHER INFORMATION: Xaa represents any amino acid
<220> FEATURE:
<221> NAME/KEY: MISC_FEATURE
<222> LOCATION: (41)..(41)
<223> OTHER INFORMATION: Xaa represents any amino acid
<220> FEATURE:
<221> NAME/KEY: MISC_FEATURE
<222> LOCATION: (44)..(44)
<223> OTHER INFORMATION: Xaa represents any amino acid
<220> FEATURE:
<221> NAME/KEY: MISC_FEATURE
<222> LOCATION: (44)..(46)
<223> OTHER INFORMATION: Xaa represents any amino acid
<220> FEATURE:
<221> NAME/KEY: MISC_FEATURE
<222> LOCATION: (50)..(50)
<223> OTHER INFORMATION: Xaa represents any amino acid
<220> FEATURE:
<221> NAME/KEY: MISC_FEATURE
<222> LOCATION: (53)..(53)
<223> OTHER INFORMATION: Xaa represents any amino acid
<220> FEATURE:
<221> NAME/KEY: MISC_FEATURE
<222> LOCATION: (70)..(70)
<223> OTHER INFORMATION: Xaa represents any amino acid
<220> FEATURE:
<221> NAME/KEY: MISC_FEATURE
<222> LOCATION: (128)..(128)
<223> OTHER INFORMATION: Xaa represents any amino acid
<220> FEATURE:
<221> NAME/KEY: MISC_FEATURE
<222> LOCATION: (131)..(131)
<223> OTHER INFORMATION: Xaa represents any amino acid

```
<220> FEATURE:
<221> NAME/KEY: MISC_FEATURE
<222> LOCATION: (145)..(145)
<223> OTHER INFORMATION: Xaa represents any amino acid
<220> FEATURE:
<221> NAME/KEY: MISC_FEATURE
<222> LOCATION: (186)..(186)
<223> OTHER INFORMATION: Xaa represents any amino acid
<220> FEATURE:
<221> NAME/KEY: MISC_FEATURE
<222> LOCATION: (197)..(197)
<223> OTHER INFORMATION: Xaa represents any amino acid
<220> FEATURE:
<221> NAME/KEY: MISC_FEATURE
<222> LOCATION: (209)..(209)
<223> OTHER INFORMATION: Xaa represents any amino acid
<220> FEATURE:
<221> NAME/KEY: MISC_FEATURE
<222> LOCATION: (216)..(217)
<223> OTHER INFORMATION: Xaa represents any amino acid
<220> FEATURE:
<221> NAME/KEY: MISC_FEATURE
<222> LOCATION: (244)..(244)
<223> OTHER INFORMATION: Xaa represents any amino acid
<220> FEATURE:
<221> NAME/KEY: MISC_FEATURE
<222> LOCATION: (246)..(246)
<223> OTHER INFORMATION: Xaa represents any amino acid
<220> FEATURE:
<221> NAME/KEY: MISC_FEATURE
<222> LOCATION: (318)..(318)
<223> OTHER INFORMATION: Xaa represents any amino acid

<400> SEQUENCE: 76

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Xaa Cys Arg Xaa Pro Arg Xaa Xaa Xaa Cys Ala
        35                  40                  45

Thr Xaa Lys Thr Xaa Glu Gln Ser Gln Pro Arg Gly Arg Arg Gln Pro
    50                  55                  60

Ile Pro Lys Asp Arg Xaa Thr Thr Gly Lys Ser Trp Gly Arg Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg His Arg Ser Arg Asn Leu Gly Lys Val Ile Asp Thr Leu Thr Xaa
        115                 120                 125

Gly Phe Xaa Asp Leu Met Gly Tyr Ile Pro Val Val Gly Ala Pro Val
    130                 135                 140

Xaa Gly Val Ala Arg Ala Leu Ala His Gly Val Arg Val Leu Glu Asp
145                 150                 155                 160

Gly Ile Asn Tyr Glu Thr Gly Asn Leu Pro Gly Cys Ser Phe Ser Ile
                165                 170                 175

Ser Leu Leu Ala Leu Leu Ser Ile Thr Xaa Pro Val Ser Ala Val Glu
            180                 185                 190

Ile Lys Asn Thr Xaa Asn Thr Tyr Met Val Thr Asn Asp Cys Ser Asn
        195                 200                 205

Xaa Ser Ile Thr Trp Gln Leu Xaa Xaa Ala Val Leu His Val Pro Gly
    210                 215                 220

Cys Val Pro Cys Glu Arg Glu Gly Asn Ser Ser Arg Cys Trp Ile Pro
225                 230                 235                 240
```

Val Thr Pro Xaa Val Xaa Val Ser Arg Pro Gly Ala Leu Thr Glu Gly
              245             250                 255

Leu Arg Ser His Ile Asp Thr Ile Val Ala Ser Ala Thr Phe Cys Ser
              260                 265                 270

Ala Leu Tyr Ile Gly Asp Val Cys Gly Ala Ile Met Ile Ala Ala Gln
              275                 280                 285

Val Val Ile Val Ser Pro Glu His His His Phe Val Gln Asp Cys Asn
              290                 295                 300

Cys Ser Ile Tyr Pro Gly His Ile Thr Gly Pro Arg Met Xaa
305                 310                 315

<210> SEQ ID NO 77
<211> LENGTH: 340
<212> TYPE: DNA
<213> ORGANISM: hepatitis C virus

<400> SEQUENCE: 77
atccacagtc actgaaagag acatcagagt tgaagagtcc gtttatctgt cctgttcact     60
tcccgaggag gcccgagctg ccatacactc actaactgag aggctgtacg tgggaggtcc    120
catgcagaac agcaaggggc aatcctgcgg atacaggcgc tgccgcgcca gcgggtgct    180 caccactagc atgggaata ctctcacatg ctacttgaag gcccaggcgg cctgcagggc    240
cgcgggcatt gttgcaccca caatgctggt gtgtggcgac gacctggtcg tcatctcaga    300
gagtcagggg actgagaggg acgagaacaa cctgagacct                          340

<210> SEQ ID NO 78
<211> LENGTH: 113
<212> TYPE: PRT
<213> ORGANISM: hepatitis C virus

<400> SEQUENCE: 78

Ser Thr Val Thr Glu Arg Asp Ile Arg Val Glu Glu Ser Val Tyr Leu
1               5                   10                  15

Ser Cys Ser Leu Pro Glu Glu Ala Arg Ala Ala Ile His Ser Leu Thr
              20                  25                  30

Glu Arg Leu Tyr Val Gly Gly Pro Met Gln Asn Ser Lys Gly Gln Ser
          35                  40                  45

Cys Gly Tyr Arg Arg Cys Arg Ala Ser Gly Val Leu Thr Thr Ser Met
      50                  55                  60

Gly Asn Thr Leu Thr Cys Tyr Leu Lys Ala Gln Ala Ala Cys Arg Ala
65                  70                  75                  80

Ala Gly Ile Val Ala Pro Thr Met Leu Val Cys Gly Asp Asp Leu Val
              85                  90                  95

Val Ile Ser Glu Ser Gln Gly Thr Glu Arg Asp Glu Asn Asn Leu Arg
              100                 105                 110

Pro

<210> SEQ ID NO 79
<211> LENGTH: 340
<212> TYPE: DNA
<213> ORGANISM: hepatitis C virus

<400> SEQUENCE: 79
ctcaacagtc acggagaggg acatcaggaa tgaggagtcc atattcctgg cctgctcgtt     60
gcccgaggag gcccggactg tcatacattc gctcactgag agactctaca taggcggggcc    120

-continued

```
gatgatgaac agcaaaggcc agtcctgtgg atacaggcgt tgtcgcgcca gcggggtgtt      180
caccactagc atgggcaata ccatcacgtg ctatgtgaaa gccatggcag cttgcagagc      240
tgccgggatt gacgccccca caatgttggt atgtggcgac gacctggtgg tcatctcaga      300
gagtcagggg accgaggagg acgagcgaaa tctgagagtc                            340
```

<210> SEQ ID NO 80
<211> LENGTH: 113
<212> TYPE: PRT
<213> ORGANISM: hepatitis C virus

<400> SEQUENCE: 80

```
Ser Thr Val Thr Glu Arg Asp Ile Arg Asn Glu Ser Ile Phe Leu
1               5                   10                  15

Ala Cys Ser Leu Pro Glu Glu Ala Arg Thr Val Ile His Ser Leu Thr
                20                  25                  30

Glu Arg Leu Tyr Ile Gly Gly Pro Met Met Asn Ser Lys Gly Gln Ser
                35                  40                  45

Cys Gly Tyr Arg Arg Cys Arg Ala Ser Gly Val Phe Thr Thr Ser Met
                50                  55                  60

Gly Asn Thr Ile Thr Cys Tyr Val Lys Ala Met Ala Ala Cys Arg Ala
65              70                  75                  80

Ala Gly Ile Asp Ala Pro Thr Met Leu Val Cys Gly Asp Asp Leu Val
                85                  90                  95

Val Ile Ser Glu Ser Gln Gly Thr Glu Glu Asp Glu Arg Asn Leu Arg
                100                 105                 110

Val
```

<210> SEQ ID NO 81
<211> LENGTH: 340
<212> TYPE: DNA
<213> ORGANISM: hepatitis C virus

<400> SEQUENCE: 81

```
ctcttgactc tactgtcact gaacaggata tcagggtaga agaagaaata taccaatgtt      60
gtgaccttga gccggaggct agacgggcaa tcaaatcgct cacggaacgg ctttacgttg     120
gaggtcccat gttcaacagc aaggggctca aatgcggata tcgccgttgc cgtgctagcg     180
gtgtattgcc cactagctac ggtaatacaa tcacctgcta catcaaggcc agagcggctg     240
ctcgagctgc gggccttcaa gacccatcat tccttgtctg cggagatgat ttggtggtag     300
tggctgagag ttgcgkcgtt gatgaggagg atagggcagc                           340
```

<210> SEQ ID NO 82
<211> LENGTH: 113
<212> TYPE: PRT
<213> ORGANISM: hepatitis C virus
<220> FEATURE:
<221> NAME/KEY: MISC_FEATURE
<222> LOCATION: (103)..(103)
<223> OTHER INFORMATION: Xaa represents any amino acid

<400> SEQUENCE: 82

```
Ser Thr Val Thr Glu Gln Asp Ile Arg Val Glu Glu Glu Ile Tyr Gln
1               5                   10                  15

Cys Cys Asp Leu Glu Pro Glu Ala Arg Arg Ala Ile Lys Ser Leu Thr
                20                  25                  30

Glu Arg Leu Tyr Val Gly Gly Pro Met Phe Asn Ser Lys Gly Leu Lys
                35                  40                  45
```

```
Cys Gly Tyr Arg Arg Cys Arg Ala Ser Gly Val Leu Pro Thr Ser Tyr
        50                  55                  60

Gly Asn Thr Ile Thr Cys Tyr Ile Lys Ala Arg Ala Ala Arg Ala
 65              70              75                  80

Ala Gly Leu Gln Asp Pro Ser Phe Leu Val Cys Gly Asp Asp Leu Val
                85                  90                  95

Val Val Ala Glu Ser Cys Xaa Val Asp Glu Gly Asp Arg Ala Ala Leu
            100                 105                 110

Arg
```

<210> SEQ ID NO 83
<211> LENGTH: 340
<212> TYPE: DNA
<213> ORGANISM: hepatitis C virus
<220> FEATURE:
<221> NAME/KEY: misc_feature
<222> LOCATION: (336)..(336)
<223> OTHER INFORMATION: n represents any nucleotide

<400> SEQUENCE: 83

```
ctccactgta accgaaaagg acatcaggcc cgaggaagag gtctatcagt gttgtgacct     60
ggagcccgaa gctcgcaagg ttattaccgc cctcacagaa agactctacg tgggcggccc   120
catgcacaac agcaagggag acctttgtgg gtatcggaga tgccgcgcaa gcggcgtcta   180
cacgaccagc ttcggaaaca cactgacgtg ctacctcaaa gcctcagctg ctattagagc   240
ggcagggctg agagactgca ccatgctggt ttgcggtgac gacttggtcg tcatcgctga   300
gagcgatggc gtagaggagg ataaccgagc cctccnagcc                         340
```

<210> SEQ ID NO 84
<211> LENGTH: 113
<212> TYPE: PRT
<213> ORGANISM: hepatitis C virus
<220> FEATURE:
<221> NAME/KEY: MISC_FEATURE
<222> LOCATION: (112)..(112)
<223> OTHER INFORMATION: Xaa represents any amino acid
<220> FEATURE:
<221> NAME/KEY: misc_feature
<223> OTHER INFORMATION: Xaa represents any amino acid

<400> SEQUENCE: 84

```
Ser Thr Val Thr Glu Lys Asp Ile Arg Pro Glu Glu Val Tyr Gln
 1               5                  10                  15

Cys Cys Asp Leu Glu Pro Glu Ala Arg Lys Val Ile Thr Ala Leu Thr
                20                  25                  30

Glu Arg Leu Tyr Val Gly Gly Pro Met His Asn Ser Lys Gly Asp Leu
            35                  40                  45

Cys Gly Tyr Arg Arg Cys Arg Ala Ser Gly Val Tyr Thr Thr Ser Phe
        50                  55                  60

Gly Asn Thr Leu Thr Cys Tyr Leu Lys Ala Ser Ala Ala Ile Arg Ala
 65              70              75                  80

Ala Gly Leu Arg Asp Cys Thr Met Leu Val Cys Gly Asp Asp Leu Val
                85                  90                  95

Val Ile Ala Glu Ser Asp Gly Val Glu Glu Asp Asn Arg Ala Leu Xaa
            100                 105                 110

Ala
```

<210> SEQ ID NO 85

```
<211> LENGTH: 340
<212> TYPE: DNA
<213> ORGANISM: hepatitis C virus

<400> SEQUENCE: 85
ctccacggtg actgaaaagg acatcagggt cgaggaagag atctatcaat gttgtgacct      60
ggarcccgaa gcccgcaaag caatatccgc cctcacagag agrctctact tgggcggccc     120
catgtataac agcaaagggg agctctgcgg gtatcggagt gccgcgcga gcggagtgta     180 caccacaagt ttcgggaaca cagtgacctg ctatcttaag gccaccgcag ctaccagggc     240
tgcaggccta aaagactgca ccatgctggt ctgcggtgac gacttggtcg tcatcgccga     300
gagcgagggc gtagaggagg attcccaacc cctccgagcc                            340

<210> SEQ ID NO 86
<211> LENGTH: 113
<212> TYPE: PRT
<213> ORGANISM: hepatitis C virus
<220> FEATURE:
<221> NAME/KEY: MISC_FEATURE
<222> LOCATION: (21)..(21)
<223> OTHER INFORMATION: Xaa represents any amino acid
<220> FEATURE:
<221> NAME/KEY: MISC_FEATURE
<222> LOCATION: (34)..(34)
<223> OTHER INFORMATION: Xaa represents any amino acid

<400> SEQUENCE: 86

Ser Thr Val Thr Glu Lys Asp Ile Arg Val Glu Glu Ile Tyr Gln
1               5                   10                  15

Cys Cys Asp Leu Xaa Pro Glu Ala Arg Lys Ala Ile Ser Ala Leu Thr
                20                  25                  30

Glu Xaa Leu Tyr Leu Gly Gly Pro Met Tyr Asn Ser Lys Gly Glu Leu
            35                  40                  45

Cys Gly Tyr Arg Arg Cys Arg Ala Ser Gly Val Tyr Thr Thr Ser Phe
    50                  55                  60

Gly Asn Thr Val Thr Cys Tyr Leu Lys Ala Thr Ala Ala Thr Arg Ala
65                  70                  75                  80

Ala Gly Leu Lys Asp Cys Thr Met Leu Val Cys Gly Asp Asp Leu Val
                85                  90                  95

Val Ile Ala Glu Ser Glu Gly Val Glu Glu Asp Ser Gln Pro Leu Arg
            100                 105                 110

Ala

<210> SEQ ID NO 87
<211> LENGTH: 340
<212> TYPE: DNA
<213> ORGANISM: hepatitis C virus

<400> SEQUENCE: 87
ctccaccgta accgaaaggg acatcaggt cgaggaggag gtctatcagt gttgtgatct      60
ggagccagag gcccgcaagg caatatccgc cctcacggag agactctatg tgggcggtcc     120
catgtttaac agcaagggag acctatgtgg ctaccgcagg tgccgcgcaa gcggcgtcta     180
caccaccagc ttcggaaaca cactgacctg ctacctcaag gccacggccg ctaccagagc     240
ggccggcctg aaggattgca caatgctggt ttgcggggac gacctggtcg tcatcgcaga     300
gagcgatggc gtggacgagg accgccgagc cctccaagct                            340

<210> SEQ ID NO 88
```

-continued

```
<211> LENGTH: 113
<212> TYPE: PRT
<213> ORGANISM: hepatitis C virus

<400> SEQUENCE: 88

Ser Thr Val Thr Glu Arg Asp Ile Arg Val Glu Glu Val Tyr Gln
1               5                   10                  15

Cys Cys Asp Leu Glu Pro Glu Ala Arg Lys Ala Ile Ser Ala Leu Thr
            20                  25                  30

Glu Arg Leu Tyr Val Gly Gly Pro Met Phe Asn Ser Lys Gly Asp Leu
        35                  40                  45

Cys Gly Tyr Arg Arg Cys Arg Ala Ser Gly Val Tyr Thr Thr Ser Phe
    50                  55                  60

Gly Asn Thr Leu Thr Cys Tyr Leu Lys Ala Thr Ala Ala Thr Arg Ala
65                  70                  75                  80

Ala Gly Leu Lys Asp Cys Thr Met Leu Val Cys Gly Asp Asp Leu Val
                85                  90                  95

Val Ile Ala Glu Ser Asp Gly Val Asp Glu Asp Arg Arg Ala Leu Gln
            100                 105                 110

Ala

<210> SEQ ID NO 89
<211> LENGTH: 340
<212> TYPE: DNA
<213> ORGANISM: hepatitis C virus
<220> FEATURE:
<221> NAME/KEY: misc_feature
<222> LOCATION: (111)..(111)
<223> OTHER INFORMATION: n represents any nucleotide
<220> FEATURE:
<221> NAME/KEY: misc_feature
<222> LOCATION: (126)..(126)
<223> OTHER INFORMATION: n represents any nucleotide

<400> SEQUENCE: 89
ctcaacagtc acagagcgcg atgtccagac ggagcatgac atctaccagt gctgtaagtt      60
ggagcccgca gcacggacag ccatcacatc gcttactgac cgattgtact ncggtggtcc     120
catgtntaac tctaaaggtc aggcatgtgg ataccgtagg tgcagggcca gtggcgtctt     180
gaccaccatc ctggccaata tctctgacttg ctacttgaaa gctcaggcgg catgcagagc    240
tgccgggctg aaggactttg acatgttggt ctgcggagac gaccttgtcg ttatttcgga    300
gagtttgggg gtctcggagg acactagtgc actgcgagct                           340

<210> SEQ ID NO 90
<211> LENGTH: 113
<212> TYPE: PRT
<213> ORGANISM: hepatitis C virus
<220> FEATURE:
<221> NAME/KEY: MISC_FEATURE
<222> LOCATION: (37)..(37)
<223> OTHER INFORMATION: Xaa represents any amino acid
<220> FEATURE:
<221> NAME/KEY: MISC_FEATURE
<222> LOCATION: (42)..(42)
<223> OTHER INFORMATION: Xaa represents any amino acid

<400> SEQUENCE: 90

Ser Thr Val Thr Glu Arg Asp Val Gln Thr Glu His Asp Ile Tyr Gln
1               5                   10                  15

Cys Cys Lys Leu Glu Pro Ala Ala Arg Thr Ala Ile Thr Ser Leu Thr
            20                  25                  30
```

-continued

```
Asp Arg Leu Tyr Xaa Gly Gly Pro Met Xaa Asn Ser Lys Gly Gln Ala
        35                  40                  45

Cys Gly Tyr Arg Arg Cys Arg Ala Ser Gly Val Leu Thr Thr Ile Leu
    50                  55                  60

Ala Asn Thr Leu Thr Cys Tyr Leu Lys Ala Gln Ala Ala Cys Arg Ala
65                  70                  75                  80

Ala Gly Leu Lys Asp Phe Asp Met Leu Val Cys Gly Asp Asp Leu Val
                85                  90                  95

Val Ile Ser Glu Ser Leu Gly Val Ser Glu Asp Thr Ser Ala Leu Arg
            100                 105                 110

Ala
```

<210> SEQ ID NO 91
<211> LENGTH: 340
<212> TYPE: DNA
<213> ORGANISM: hepatitis C virus

<400> SEQUENCE: 91

```
ctcgacagtc accgagcgcg acatccrcac cgagcacgac atctaccaat gctgccaact     60
tgacccggtg gcacgcaagg ctattacatc tctgactgag cggctgtact gcggwgggcc    120
catgatgaac tcccgtggtc aatcatgtgg ataccgtagg tgccgagcca gtggcgtgct    180
caccacgagc ttgggcaata ccctaacatg ctatttgaaa gcacaagcag cgtgtagggc    240
agcaaagctc aaaaactatg acatgttagt ctgcggagac gatctagtcg ttatcgcgga    300
gagtggagga gtctctgagg atgttgacgc cctgcgagca                          340
```

<210> SEQ ID NO 92
<211> LENGTH: 113
<212> TYPE: PRT
<213> ORGANISM: hepatitis C virus
<220> FEATURE:
<221> NAME/KEY: MISC_FEATURE
<222> LOCATION: (9)..(9)
<223> OTHER INFORMATION: Xaa represents any amino acid
<220> FEATURE:
<221> NAME/KEY: MISC_FEATURE
<222> LOCATION: (38)..(38)
<223> OTHER INFORMATION: Xaa represents any amino acid

<400> SEQUENCE: 92

```
Ser Thr Val Thr Glu Arg Asp Ile Xaa Thr Glu His Asp Ile Tyr Gln
1               5                   10                  15

Cys Cys Gln Leu Asp Pro Val Ala Arg Lys Ala Ile Thr Ser Leu Thr
                20                  25                  30

Glu Arg Leu Tyr Cys Xaa Gly Pro Met Met Asn Ser Arg Gly Gln Ser
            35                  40                  45

Cys Gly Tyr Arg Arg Cys Arg Ala Ser Gly Val Leu Thr Thr Ser Leu
    50                  55                  60

Gly Asn Thr Leu Thr Cys Tyr Leu Lys Ala Gln Ala Ala Cys Arg Ala
65                  70                  75                  80

Ala Lys Leu Lys Asn Tyr Asp Met Leu Val Cys Gly Asp Asp Leu Val
                85                  90                  95

Val Ile Ala Glu Ser Gly Gly Val Ser Glu Asp Val Asp Ala Leu Arg
            100                 105                 110

Ala
```

<210> SEQ ID NO 93
<211> LENGTH: 340

```
<212> TYPE: DNA
<213> ORGANISM: hepatitis C virus

<400> SEQUENCE: 93
ctcctccgtc acggagcgtg acatccgcac tgaacacgac atctatcagt gctgccaatt      60
agatccggta gcacggaaag ccattacatc tcttactgag cggctgtact gcggcggccc     120
catgtacaac tctcgaggtc agtcatgtgg gtaccgcagg tgccgggcta gtggtgtctt     180
caccacaagc ttgggcaaca ccatgacatg ctacctgaag gctcaggcgg cttgtagggc     240
agcraagctc aaaaactttg acatgttggt ctgcggagac gacctagtcg ttattgctga     300
gagcggagga gtccctgagg atgccggggc cctgcgagtc                            340

<210> SEQ ID NO 94
<211> LENGTH: 113
<212> TYPE: PRT
<213> ORGANISM: hepatitis C virus
<220> FEATURE:
<221> NAME/KEY: MISC_FEATURE
<222> LOCATION: (81)..(81)
<223> OTHER INFORMATION: Xaa represents any amino acid

<400> SEQUENCE: 94

Ser Ser Val Thr Glu Arg Asp Ile Arg Thr Glu His Asp Ile Tyr Gln
1               5                   10                  15
Cys Cys Gln Leu Asp Pro Val Ala Arg Lys Ala Ile Thr Ser Leu Thr
            20                  25                  30
Glu Arg Leu Tyr Cys Gly Gly Pro Met Tyr Asn Ser Arg Gly Gln Ser
        35                  40                  45
Cys Gly Tyr Arg Arg Cys Arg Ala Ser Gly Val Phe Thr Thr Ser Leu
    50                  55                  60
Gly Asn Thr Met Thr Cys Tyr Leu Lys Ala Gln Ala Ala Cys Arg Ala
65                  70                  75                  80
Xaa Lys Leu Lys Asn Phe Asp Met Leu Val Cys Gly Asp Asp Leu Val
                85                  90                  95
Val Ile Ala Glu Ser Gly Gly Val Pro Glu Asp Ala Gly Ala Leu Arg
            100                 105                 110
Val

<210> SEQ ID NO 95
<211> LENGTH: 340
<212> TYPE: DNA
<213> ORGANISM: hepatitis C virus
<220> FEATURE:
<221> NAME/KEY: misc_feature
<222> LOCATION: (36)..(36)
<223> OTHER INFORMATION: n represents any nucleotide

<400> SEQUENCE: 95
atccacagtc acggggcgcg acatacgcac agaacnagac atttacctgt cctgccagct      60
cgacccagag gcccggaaag ccataaagtc tctcactgag aggctctatg tcggggggccc    120
tatgtacaac tcaaagggcc aactctgtgg tcaacgccga tgccgagcaa gcggagtact     180
ccccacaagc atgggtaaca ccatcacatg cttcctgaag gcaaccgccg cttgccgagc     240
agccggcttt acagattatg acatgttggt ctgcggagac gatttggttg tcgtaactga     300
gagtgctgga gtcaacgagg atatcgctaa cctgcgagcc                            340

<210> SEQ ID NO 96
<211> LENGTH: 113
```

```
<212> TYPE: PRT
<213> ORGANISM: hepatitis C virus
<220> FEATURE:
<221> NAME/KEY: MISC_FEATURE
<222> LOCATION: (12)..(12)
<223> OTHER INFORMATION: Xaa represents any amino acid

<400> SEQUENCE: 96

Ser Thr Val Thr Gly Arg Asp Ile Arg Thr Glu Xaa Asp Ile Tyr Leu
1               5                   10                  15

Ser Cys Gln Leu Asp Pro Glu Ala Arg Lys Ala Ile Lys Ser Leu Thr
            20                  25                  30

Glu Arg Leu Tyr Val Gly Gly Pro Met Tyr Asn Ser Lys Gly Gln Leu
        35                  40                  45

Cys Gly Gln Arg Arg Cys Arg Ala Ser Gly Val Leu Pro Thr Ser Met
    50                  55                  60

Gly Asn Thr Ile Thr Cys Phe Leu Lys Ala Thr Ala Ala Cys Arg Ala
65                  70                  75                  80

Ala Gly Phe Thr Asp Tyr Asp Met Leu Val Cys Gly Asp Asp Leu Val
                85                  90                  95

Val Val Thr Glu Ser Ala Gly Val Asn Glu Asp Ile Ala Asn Leu Arg
            100                 105                 110

Ala

<210> SEQ ID NO 97
<211> LENGTH: 340
<212> TYPE: DNA
<213> ORGANISM: hepatitis C virus

<400> SEQUENCE: 97
ctccactgtc actgagcagg acatcagggt agaactttcc atctttcagg cctgtgacct     60
caaggacgag gctaggaggg tgataacttc actcacggag cggctttact gtggtggtcc    120
tatgttcaac agcaagggac aacactgcgg ttaccgccgc tgccgtgcta gtgggtgct    180 acccaccagc ttcgggaaca caatcacctg ttacatcaaa gcaaaggcag ctaccaaagc    240
tgccggaatt aaaaatccat cattccttgt ctgcggagat gacttggtcg tgattgctga    300
gagtgcaggg atcgatgagg acaagagcgc cttgagagct                          340

<210> SEQ ID NO 98
<211> LENGTH: 113
<212> TYPE: PRT
<213> ORGANISM: hepatitis C virus

<400> SEQUENCE: 98

Ser Thr Val Thr Glu Gln Asp Ile Arg Val Glu Leu Ser Ile Phe Gln
1               5                   10                  15

Ala Cys Asp Leu Lys Asp Glu Ala Arg Arg Val Ile Thr Ser Leu Thr
            20                  25                  30

Glu Arg Leu Tyr Cys Gly Gly Pro Met Phe Asn Ser Lys Gly Gln His
        35                  40                  45

Cys Gly Tyr Arg Arg Cys Arg Ala Ser Gly Val Leu Pro Thr Ser Phe
    50                  55                  60

Gly Asn Thr Ile Thr Cys Tyr Ile Lys Ala Lys Ala Ala Thr Lys Ala
65                  70                  75                  80

Ala Gly Ile Lys Asn Pro Ser Phe Leu Val Cys Gly Asp Asp Leu Val
                85                  90                  95

Val Ile Ala Glu Ser Ala Gly Ile Asp Glu Asp Lys Ser Ala Leu Arg
```

Ala

<210> SEQ ID NO 99
<211> LENGTH: 340
<212> TYPE: DNA
<213> ORGANISM: hepatitis C virus

<400> SEQUENCE: 99

```
ctctaccgtc acagagaggg acatacggac agaagaatcc atctatctgt cttgtcaatt     60
gcctgaagag gcccggaaag ccattaaatc gctgacagag agactatacg tgggcggccc    120
gatggaaaac agcaagggcc aggcttgcgg atataggcgt tgccgcgcaa gcggggtatt    180
caccacaagc ttggggaaca ccatgacttg ttacatcaaa gctaaagcgg cttgtaaagc    240
cgctggcatt gtagacccgg tgatgctcgt gtgcggtgac gacctagtgg tcatctcaga    300
aagcaagggg gtggaggagg accagcggga cctacgagtc                          340
```

<210> SEQ ID NO 100
<211> LENGTH: 113
<212> TYPE: PRT
<213> ORGANISM: hepatitis C virus

<400> SEQUENCE: 100

```
Ser Thr Val Thr Glu Arg Asp Ile Arg Thr Glu Glu Ser Ile Tyr Leu
  1               5                  10                  15
Ser Cys Gln Leu Pro Glu Glu Ala Arg Lys Ala Ile Lys Ser Leu Thr
             20                  25                  30
Glu Arg Leu Tyr Val Gly Gly Pro Met Glu Asn Ser Lys Gly Gln Ala
         35                  40                  45
Cys Gly Tyr Arg Arg Cys Arg Ala Ser Gly Val Phe Thr Thr Ser Leu
     50                  55                  60
Gly Asn Thr Met Thr Cys Tyr Ile Lys Ala Lys Ala Ala Cys Lys Ala
 65                  70                  75                  80
Ala Gly Ile Val Asp Pro Val Met Leu Val Cys Gly Asp Asp Leu Val
                 85                  90                  95
Val Ile Ser Glu Ser Lys Gly Val Glu Glu Asp Gln Arg Asp Leu Arg
            100                 105                 110
Val
```

<210> SEQ ID NO 101
<211> LENGTH: 335
<212> TYPE: DNA
<213> ORGANISM: hepatitis C virus

<400> SEQUENCE: 101

```
ctccactgtc actgagagag acatacggac agaagaatcc atctayytgg cttgtcaatt     60
gcccgaagag gcccggaagg ccattaaatc actgacagag agactatacg tgggcggccc    120
gatggaaaac agcaaaggcc aggcctgcgg atataggcgt tgccgcgcaa gcggggtatt    180
caccacaagc ttggggaaca ccatgacttg ttacatcaag gccaargcag cttgtaaagc    240
ygctggcatt gttgacccgg tgatgctcgt gtgcggcgac gacctagtgg tcatctcaga    300
gagcaagggg gtagaggagg accagcgaga cctac                              335
```

<210> SEQ ID NO 102
<211> LENGTH: 113
<212> TYPE: PRT

```
<213> ORGANISM: hepatitis C virus
<220> FEATURE:
<221> NAME/KEY: MISC_FEATURE
<222> LOCATION: (15)..(16)
<223> OTHER INFORMATION: Xaa represents any amino acid
<220> FEATURE:
<221> NAME/KEY: MISC_FEATURE
<222> LOCATION: (75)..(75)
<223> OTHER INFORMATION: Xaa represents any amino acid
<220> FEATURE:
<221> NAME/KEY: MISC_FEATURE
<222> LOCATION: (80)..(80)
<223> OTHER INFORMATION: Xaa represents any amino acid
<220> FEATURE:
<221> NAME/KEY: MISC_FEATURE
<222> LOCATION: (112)..(113)
<223> OTHER INFORMATION: Xaa represents any amino acid

<400> SEQUENCE: 102
```

Ser Thr Val Thr Glu Arg Asp Ile Arg Thr Glu Ser Ile Xaa Xaa
1               5                   10                  15

Ala Cys Gln Leu Pro Glu Glu Ala Arg Lys Ala Ile Lys Ser Leu Thr
            20                  25                  30

Glu Arg Leu Tyr Val Gly Gly Pro Met Glu Asn Ser Lys Gly Gln Ala
        35                  40                  45

Cys Gly Tyr Arg Arg Cys Arg Ala Ser Gly Val Phe Thr Thr Ser Leu
    50                  55                  60

Gly Asn Thr Met Thr Cys Tyr Ile Lys Ala Xaa Ala Ala Cys Lys Xaa
65                  70                  75                  80

Ala Gly Ile Val Asp Pro Val Met Leu Val Cys Gly Asp Asp Leu Val
            85                  90                  95

Val Ile Ser Glu Ser Lys Gly Val Glu Glu Asp Gln Arg Asp Leu Xaa
            100                 105                 110

Xaa

```
<210> SEQ ID NO 103
<211> LENGTH: 461
<212> TYPE: DNA
<213> ORGANISM: hepatitis C virus

<400> SEQUENCE: 103
```
cgtacagcct ccaggacccc ccctcccggg agagccatag tggtctgcgg aaccggtgag    60
tacaccggaa ttgccgggaa gactgggtcc tttcttggat aacccactc tatgcccgga    120 gatttgggcg tgcccccgca agactgctag ccgagtagcg ttgggttgcg aaaggccttg    180
tggtactgcc tgatagggtg cttgcgagtg ccccggagg tctcgtagac cgtgcaccat    240
gagcacgaat cctaaacctc aaagacaaac caaagaaac accaaccgcc gcccacagga    300
cgttaagttc ccgggcggtg gccagatcgt tggcggggtg tacttgttgc cgcgcagggg    360
ccccagagtg ggtgtgcgcg cgacgagaaa gacctcggag cggtcccagc cgcgtgggag    420
gcgccaacct atccccaagg ttaggcgcac caccggccgt t                      461

```
<210> SEQ ID NO 104
<211> LENGTH: 74
<212> TYPE: PRT
<213> ORGANISM: hepatitis C virus

<400> SEQUENCE: 104
```

Met Ser Thr Asn Pro Lys Pro Gln Arg Gln Thr Lys Arg Asn Thr Asn
1               5                   10                  15

Arg Arg Pro Gln Asp Val Lys Phe Pro Gly Gly Gly Gln Ile Val Gly

```
                 20                  25                  30
Gly Val Tyr Leu Leu Pro Arg Arg Gly Pro Arg Val Gly Val Arg Ala
             35                  40                  45

Thr Arg Lys Thr Ser Glu Arg Ser Gln Pro Arg Gly Arg Arg Gln Pro
 50                  55                  60

Ile Pro Lys Val Arg Arg Thr Thr Gly Arg
 65                  70

<210> SEQ ID NO 105
<211> LENGTH: 340
<212> TYPE: DNA
<213> ORGANISM: hepatitis C virus
<220> FEATURE:
<221> NAME/KEY: misc_feature
<222> LOCATION: (338)..(338)
<223> OTHER INFORMATION: n represents any nucleotide

<400> SEQUENCE: 105
ctctactgtc acagagaggg atatacgaac agaggaatcc atytatctgg cttgtcaatt    60
gcccgaagag gcccggaagg ccatcaaatc actgacagag agactatacg tgggcggccc   120
gatggaaaac agcaagggcc aggcctgcgg atacaggcgt tgccgcgcaa gcggggtatt   180
caccacaagc ttggggaaca ccatgacttg ttacatcaaa gccaaggcgg cttgtaaagc   240
cgctggcatt gttgacccag tgatgctcgt gtgcggcgac gacctagtgg tcatctcaga   300
aagcaagggg gtggaggagg accaacgaga cctacgantc                         340

<210> SEQ ID NO 106
<211> LENGTH: 113
<212> TYPE: PRT
<213> ORGANISM: hepatitis C virus
<220> FEATURE:
<221> NAME/KEY: MISC_FEATURE
<222> LOCATION: (14)..(14)
<223> OTHER INFORMATION: Xaa represents any amino acid
<220> FEATURE:
<221> NAME/KEY: MISC_FEATURE
<222> LOCATION: (113)..(113)
<223> OTHER INFORMATION: Xaa represents any amino acid

<400> SEQUENCE: 106

Ser Thr Val Thr Glu Arg Asp Ile Arg Thr Glu Glu Ser Xaa Tyr Leu
 1               5                  10                  15

Ala Cys Gln Leu Pro Glu Glu Ala Arg Lys Ala Ile Lys Ser Leu Thr
             20                  25                  30

Glu Arg Leu Tyr Val Gly Gly Pro Met Glu Asn Ser Lys Gly Gln Ala
         35                  40                  45

Cys Gly Tyr Arg Arg Cys Arg Ala Ser Gly Val Phe Thr Thr Ser Leu
 50                  55                  60

Gly Asn Thr Met Thr Cys Tyr Ile Lys Ala Lys Ala Ala Cys Lys Ala
 65                  70                  75                  80

Ala Gly Ile Val Asp Pro Val Met Leu Val Cys Gly Asp Asp Leu Val
             85                  90                  95

Val Ile Ser Glu Ser Lys Gly Val Glu Glu Asp Gln Arg Asp Leu Arg
            100                 105                 110

Xaa

<210> SEQ ID NO 107
<211> LENGTH: 11
<212> TYPE: PRT
<213> ORGANISM: hepatitis C virus
```

```
<400> SEQUENCE: 107

Ala Arg Gln Ser Asp Gly Arg Ser Trp Ala Gln
    1               5                   10

<210> SEQ ID NO 108
<211> LENGTH: 11
<212> TYPE: PRT
<213> ORGANISM: hepatitis C virus

<400> SEQUENCE: 108

Ala Arg Arg Ser Glu Gly Arg Ser Trp Ala Gln
1               5                   10

<210> SEQ ID NO 109
<211> LENGTH: 11
<212> TYPE: PRT
<213> ORGANISM: hepatitis C virus

<400> SEQUENCE: 109

Glu Arg Arg Pro Glu Gly Arg Ser Trp Ala Gln
1               5                   10

<210> SEQ ID NO 110
<211> LENGTH: 11
<212> TYPE: PRT
<213> ORGANISM: hepatitis C virus

<400> SEQUENCE: 110

Ala Arg Arg Pro Glu Gly Arg Ser Trp Ala Gln
1               5                   10

<210> SEQ ID NO 111
<211> LENGTH: 11
<212> TYPE: PRT
<213> ORGANISM: hepatitis C virus

<400> SEQUENCE: 111

Asp Arg Arg Thr Thr Gly Lys Ser Trp Gly Arg
1               5                   10

<210> SEQ ID NO 112
<211> LENGTH: 11
<212> TYPE: PRT
<213> ORGANISM: hepatitis C virus

<400> SEQUENCE: 112

Asp Arg Arg Ala Thr Gly Arg Ser Trp Gly Arg
1               5                   10

<210> SEQ ID NO 113
<211> LENGTH: 11
<212> TYPE: PRT
<213> ORGANISM: hepatitis C virus

<400> SEQUENCE: 113

Asp Arg Arg Ala Thr Gly Lys Ser Trp Gly Arg
1               5                   10

<210> SEQ ID NO 114
<211> LENGTH: 11
<212> TYPE: PRT
<213> ORGANISM: hepatitis C virus

<400> SEQUENCE: 114
```

```
Val Arg Gln Pro Thr Gly Arg Ser Trp Gly Gln
1               5                   10

<210> SEQ ID NO 115
<211> LENGTH: 11
<212> TYPE: PRT
<213> ORGANISM: hepatitis C virus

<400> SEQUENCE: 115

Val Arg His Gln Thr Gly Arg Thr Trp Ala Gln
1               5                   10

<210> SEQ ID NO 116
<211> LENGTH: 11
<212> TYPE: PRT
<213> ORGANISM: hepatitis C virus

<400> SEQUENCE: 116

Val Arg Gln Asn Gln Gly Arg Thr Trp Ala Gln
1               5                   10

<210> SEQ ID NO 117
<211> LENGTH: 11
<212> TYPE: PRT
<213> ORGANISM: hepatitis C virus

<400> SEQUENCE: 117

Ala Arg Arg Thr Glu Gly Arg Ser Trp Ala Gln
1               5                   10

<210> SEQ ID NO 118
<211> LENGTH: 11
<212> TYPE: PRT
<213> ORGANISM: hepatitis C virus
<220> FEATURE:
<221> NAME/KEY: MISC_FEATURE
<222> LOCATION: (8)..(11)
<223> OTHER INFORMATION: Xaa represents any amino acid

<400> SEQUENCE: 118

Val Arg Arg Thr Thr Gly Arg Xaa Xaa Xaa Xaa
1               5                   10

<210> SEQ ID NO 119
<211> LENGTH: 11
<212> TYPE: PRT
<213> ORGANISM: hepatitis C virus

<400> SEQUENCE: 119

Val Arg Arg Thr Thr Gly Arg Thr Trp Ala Gln
1               5                   10

<210> SEQ ID NO 120
<211> LENGTH: 12
<212> TYPE: PRT
<213> ORGANISM: hepatitis C virus

<400> SEQUENCE: 120

His Glu Val Arg Asn Ala Ser Gly Val Tyr His Val
1               5                   10

<210> SEQ ID NO 121
<211> LENGTH: 12
<212> TYPE: PRT
<213> ORGANISM: hepatitis C virus
```

```
<400> SEQUENCE: 121

His Glu Val Arg Asn Ala Ser Gly Val Tyr His Leu
1               5                   10

<210> SEQ ID NO 122
<211> LENGTH: 12
<212> TYPE: PRT
<213> ORGANISM: hepatitis C virus

<400> SEQUENCE: 122

Tyr Glu Val His Ser Thr Thr Asp Gly Tyr His Val
1               5                   10

<210> SEQ ID NO 123
<211> LENGTH: 12
<212> TYPE: PRT
<213> ORGANISM: hepatitis C virus

<400> SEQUENCE: 123

Val Glu Val Lys Asn Thr Ser Gln Ala Tyr Met Ala
1               5                   10

<210> SEQ ID NO 124
<211> LENGTH: 12
<212> TYPE: PRT
<213> ORGANISM: hepatitis C virus

<400> SEQUENCE: 124

Ile Gln Val Lys Asn Asn Ser His Phe Tyr Met Ala
1               5                   10

<210> SEQ ID NO 125
<211> LENGTH: 12
<212> TYPE: PRT
<213> ORGANISM: hepatitis C virus

<400> SEQUENCE: 125

Val Gln Val Lys Asn Thr Ser Thr Met Tyr Met Ala
1               5                   10

<210> SEQ ID NO 126
<211> LENGTH: 12
<212> TYPE: PRT
<213> ORGANISM: hepatitis C virus

<400> SEQUENCE: 126

Val Gln Val Lys Asn Thr Ser His Ser Tyr Met Val
1               5                   10

<210> SEQ ID NO 127
<211> LENGTH: 12
<212> TYPE: PRT
<213> ORGANISM: hepatitis C virus

<400> SEQUENCE: 127

Val Gln Val Ala Asn Arg Ser Gly Ser Tyr Met Val
1               5                   10

<210> SEQ ID NO 128
<211> LENGTH: 12
<212> TYPE: PRT
<213> ORGANISM: hepatitis C virus
<220> FEATURE:
<221> NAME/KEY: MISC_FEATURE
```

```
<222> LOCATION: (7)..(7)
<223> OTHER INFORMATION: Xaa represents any amino acid

<400> SEQUENCE: 128

Val Glu Ile Lys Asn Thr Xaa Asn Thr Tyr Val Leu
1               5                   10

<210> SEQ ID NO 129
<211> LENGTH: 12
<212> TYPE: PRT
<213> ORGANISM: hepatitis C virus

<400> SEQUENCE: 129

Val Glu Ile Lys Asn Thr Ser Asn Thr Tyr Val Leu
1               5                   10

<210> SEQ ID NO 130
<211> LENGTH: 12
<212> TYPE: PRT
<213> ORGANISM: hepatitis C virus

<400> SEQUENCE: 130

Ile Asn Tyr Arg Asn Val Ser Gly Ile Tyr Tyr Val
1               5                   10

<210> SEQ ID NO 131
<211> LENGTH: 12
<212> TYPE: PRT
<213> ORGANISM: hepatitis C virus

<400> SEQUENCE: 131

Ile Asn Tyr Arg Asn Thr Ser Gly Ile Tyr His Val
1               5                   10

<210> SEQ ID NO 132
<211> LENGTH: 12
<212> TYPE: PRT
<213> ORGANISM: hepatitis C virus

<400> SEQUENCE: 132

Ile Asn Tyr His Asn Thr Ser Gly Ile Tyr His Ile
1               5                   10

<210> SEQ ID NO 133
<211> LENGTH: 12
<212> TYPE: PRT
<213> ORGANISM: hepatitis C virus

<400> SEQUENCE: 133

Thr Asn Tyr Arg Asn Val Ser Gly Ile Tyr His Val
1               5                   10

<210> SEQ ID NO 134
<211> LENGTH: 12
<212> TYPE: PRT
<213> ORGANISM: hepatitis C virus

<400> SEQUENCE: 134

Gln His Tyr Arg Asn Val Ser Gly Ile Tyr His Val
1               5                   10

<210> SEQ ID NO 135
<211> LENGTH: 12
<212> TYPE: PRT
<213> ORGANISM: hepatitis C virus
```

```
<400> SEQUENCE: 135

Ile Gln Val Lys Asn Ala Ser Gly Ile Tyr His Leu
1               5                   10

<210> SEQ ID NO 136
<211> LENGTH: 12
<212> TYPE: PRT
<213> ORGANISM: hepatitis C virus

<400> SEQUENCE: 136

Ala His Tyr Thr Asn Lys Ser Gly Leu Tyr His Leu
1               5                   10

<210> SEQ ID NO 137
<211> LENGTH: 12
<212> TYPE: PRT
<213> ORGANISM: hepatitis C virus

<400> SEQUENCE: 137

Leu Asn Tyr Ala Asn Lys Ser Gly Leu Tyr His Leu
1               5                   10

<210> SEQ ID NO 138
<211> LENGTH: 12
<212> TYPE: PRT
<213> ORGANISM: hepatitis C virus

<400> SEQUENCE: 138

Leu Glu Tyr Arg Asn Ala Ser Gly Leu Tyr Met Val
1               5                   10

<210> SEQ ID NO 139
<211> LENGTH: 11
<212> TYPE: PRT
<213> ORGANISM: hepatitis C virus

<400> SEQUENCE: 139

Ile Tyr Glu Met Asp Gly Met Ile Met His Tyr
1               5                   10

<210> SEQ ID NO 140
<211> LENGTH: 11
<212> TYPE: PRT
<213> ORGANISM: hepatitis C virus

<400> SEQUENCE: 140

Ile Tyr Glu Met Ser Gly Met Ile Leu His Ala
1               5                   10

<210> SEQ ID NO 141
<211> LENGTH: 11
<212> TYPE: PRT
<213> ORGANISM: hepatitis C virus

<400> SEQUENCE: 141

Val Tyr Glu Ala Lys Asp Ile Ile Leu His Thr
1               5                   10

<210> SEQ ID NO 142
<211> LENGTH: 11
<212> TYPE: PRT
<213> ORGANISM: hepatitis C virus
<220> FEATURE:
<221> NAME/KEY: MISC_FEATURE
```

```
<222> LOCATION: (5)..(5)
<223> OTHER INFORMATION: Xaa represents any amino acid

<400> SEQUENCE: 142

Val Trp Gln Leu Xaa Asp Ala Val Leu His Val
1               5                   10

<210> SEQ ID NO 143
<211> LENGTH: 11
<212> TYPE: PRT
<213> ORGANISM: hepatitis C virus

<400> SEQUENCE: 143

Val Trp Gln Leu Arg Asp Ala Val Leu His Val
1               5                   10

<210> SEQ ID NO 144
<211> LENGTH: 11
<212> TYPE: PRT
<213> ORGANISM: hepatitis C virus

<400> SEQUENCE: 144

Ile Trp Gln Met Gln Gly Ala Val Leu His Val
1               5                   10

<210> SEQ ID NO 145
<211> LENGTH: 11
<212> TYPE: PRT
<213> ORGANISM: hepatitis C virus

<400> SEQUENCE: 145

Val Trp Gln Leu Lys Asp Ala Val Leu His Val
1               5                   10

<210> SEQ ID NO 146
<211> LENGTH: 11
<212> TYPE: PRT
<213> ORGANISM: hepatitis C virus

<400> SEQUENCE: 146

Val Trp Gln Leu Glu Glu Ala Val Leu His Val
1               5                   10

<210> SEQ ID NO 147
<211> LENGTH: 11
<212> TYPE: PRT
<213> ORGANISM: hepatitis C virus
<220> FEATURE:
<221> NAME/KEY: MISC_FEATURE
<222> LOCATION: (5)..(6)
<223> OTHER INFORMATION: Xaa represents any amino acid

<400> SEQUENCE: 147

Thr Trp Gln Leu Xaa Xaa Ala Val Leu His Val
1               5                   10

<210> SEQ ID NO 148
<211> LENGTH: 11
<212> TYPE: PRT
<213> ORGANISM: hepatitis C virus

<400> SEQUENCE: 148

Val Tyr Glu Ala Asp His His Ile Leu His Leu
1               5                   10
```

<210> SEQ ID NO 149
<211> LENGTH: 11
<212> TYPE: PRT
<213> ORGANISM: hepatitis C virus

<400> SEQUENCE: 149

Val Tyr Glu Ala Asp His His Ile Leu Ala Leu
1               5                   10

<210> SEQ ID NO 150
<211> LENGTH: 11
<212> TYPE: PRT
<213> ORGANISM: hepatitis C virus

<400> SEQUENCE: 150

Val Phe Glu Ala Asp His His Ile Leu His Leu
1               5                   10

<210> SEQ ID NO 151
<211> LENGTH: 11
<212> TYPE: PRT
<213> ORGANISM: hepatitis C virus

<400> SEQUENCE: 151

Val Tyr Glu Ser Asp His His Ile Leu His Leu
1               5                   10

<210> SEQ ID NO 152
<211> LENGTH: 10
<212> TYPE: PRT
<213> ORGANISM: hepatitis C virus

<400> SEQUENCE: 152

Val Phe Glu Glu Thr Met Ile Leu His Leu
1               5                   10

<210> SEQ ID NO 153
<211> LENGTH: 11
<212> TYPE: PRT
<213> ORGANISM: hepatitis C virus

<400> SEQUENCE: 153

Val Tyr Glu Ala Glu Thr Leu Ile Leu His Leu
1               5                   10

<210> SEQ ID NO 154
<211> LENGTH: 11
<212> TYPE: PRT
<213> ORGANISM: hepatitis C virus

<400> SEQUENCE: 154

Val Tyr Glu Ala Asn Gly Met Ile Leu His Leu
1               5                   10

<210> SEQ ID NO 155
<211> LENGTH: 11
<212> TYPE: PRT
<213> ORGANISM: hepatitis C virus

<400> SEQUENCE: 155

Val Tyr Glu Ala Gly Asp Ile Ile Leu His Leu
1               5                   10

<210> SEQ ID NO 156
<211> LENGTH: 13

-continued

<212> TYPE: PRT
<213> ORGANISM: hepatitis C virus

<400> SEQUENCE: 156

Val Arg Glu Asp Asn His Leu Arg Cys Trp Met Ala Leu
1 5 10

<210> SEQ ID NO 157
<211> LENGTH: 13
<212> TYPE: PRT
<213> ORGANISM: hepatitis C virus

<400> SEQUENCE: 157

Val Arg Glu Asn Asn Ser Ser Arg Cys Trp Met Ala Leu
1 5 10

<210> SEQ ID NO 158
<211> LENGTH: 13
<212> TYPE: PRT
<213> ORGANISM: hepatitis C virus

<400> SEQUENCE: 158

Ile Arg Glu Gly Asn Ile Ser Arg Cys Trp Val Leu Pro
1 5 10

<210> SEQ ID NO 159
<211> LENGTH: 13
<212> TYPE: PRT
<213> ORGANISM: hepatitis C virus

<400> SEQUENCE: 159

Glu Asn Ser Ser Gly Arg Phe His Cys Trp Ile Pro Ile
1 5 10

<210> SEQ ID NO 160
<211> LENGTH: 13
<212> TYPE: PRT
<213> ORGANISM: hepatitis C virus

<400> SEQUENCE: 160

Glu Arg Ser Gly Asn Arg Thr Phe Cys Trp Thr Ala Val
1 5 10

<210> SEQ ID NO 161
<211> LENGTH: 13
<212> TYPE: PRT
<213> ORGANISM: hepatitis C virus

<400> SEQUENCE: 161

Glu Leu Gln Gly Asn Lys Ser Arg Cys Trp Ile Pro Val
1 5 10

<210> SEQ ID NO 162
<211> LENGTH: 13
<212> TYPE: PRT
<213> ORGANISM: hepatitis C virus

<400> SEQUENCE: 162

Glu Arg His Gln Asn Gln Ser Arg Cys Trp Ile Pro Val
1 5 10

<210> SEQ ID NO 163
<211> LENGTH: 13
<212> TYPE: PRT
<213> ORGANISM: hepatitis C virus

```
<400> SEQUENCE: 163

Glu Trp Lys Asp Asn Thr Ser Arg Cys Trp Ile Pro Val
1               5                   10

<210> SEQ ID NO 164
<211> LENGTH: 13
<212> TYPE: PRT
<213> ORGANISM: hepatitis C virus

<400> SEQUENCE: 164

Glu Arg Glu Gly Asn Ser Ser Arg Cys Trp Ile Pro Val
1               5                   10

<210> SEQ ID NO 165
<211> LENGTH: 13
<212> TYPE: PRT
<213> ORGANISM: hepatitis C virus

<400> SEQUENCE: 165

Val Arg Glu Gly Asn Gln Ser Arg Cys Trp Val Ala Leu
1               5                   10

<210> SEQ ID NO 166
<211> LENGTH: 13
<212> TYPE: PRT
<213> ORGANISM: hepatitis C virus

<400> SEQUENCE: 166

Val Arg Thr Gly Asn Gln Ser Arg Cys Trp Val Ala Leu
1               5                   10

<210> SEQ ID NO 167
<211> LENGTH: 13
<212> TYPE: PRT
<213> ORGANISM: hepatitis C virus

<400> SEQUENCE: 167

Val Arg Val Gly Asn Gln Ser Ser Cys Trp Val Ala Leu
1               5                   10

<210> SEQ ID NO 168
<211> LENGTH: 13
<212> TYPE: PRT
<213> ORGANISM: hepatitis C virus

<400> SEQUENCE: 168

Val Arg Val Gly Asn Gln Ser Arg Cys Trp Val Ala Leu
1               5                   10

<210> SEQ ID NO 169
<211> LENGTH: 13
<212> TYPE: PRT
<213> ORGANISM: hepatitis C virus

<400> SEQUENCE: 169

Val Lys Glu Gly Asn His Ser Arg Cys Trp Val Ala Leu
1               5                   10

<210> SEQ ID NO 170
<211> LENGTH: 13
<212> TYPE: PRT
<213> ORGANISM: hepatitis C virus

<400> SEQUENCE: 170
```

Val Lys Thr Gly Asn Thr Ser Arg Cys Trp Val Ala Leu
1               5                   10

<210> SEQ ID NO 171
<211> LENGTH: 13
<212> TYPE: PRT
<213> ORGANISM: hepatitis C virus

<400> SEQUENCE: 171

Ile Lys Ala Gly Asn Glu Ser Arg Cys Trp Leu Pro Val
1               5                   10

<210> SEQ ID NO 172
<211> LENGTH: 13
<212> TYPE: PRT
<213> ORGANISM: hepatitis C virus
<220> FEATURE:
<221> NAME/KEY: MISC_FEATURE
<222> LOCATION: (3)..(4)
<223> OTHER INFORMATION: Xaa represents any amino acid

<400> SEQUENCE: 172

Val Lys Xaa Xaa Asn Gln Ser Arg Cys Trp Val Gln Ala
1               5                   10

<210> SEQ ID NO 173
<211> LENGTH: 13
<212> TYPE: PRT
<213> ORGANISM: hepatitis C virus

<400> SEQUENCE: 173

Val Lys Thr Gly Asn Leu Thr Lys Cys Trp Leu Ser Ala
1               5                   10

<210> SEQ ID NO 174
<211> LENGTH: 13
<212> TYPE: PRT
<213> ORGANISM: hepatitis C virus

<400> SEQUENCE: 174

Val Arg Ser Gly Asn Thr Ser Arg Cys Trp Ile Pro Val
1               5                   10

<210> SEQ ID NO 175
<211> LENGTH: 10
<212> TYPE: PRT
<213> ORGANISM: hepatitis C virus

<400> SEQUENCE: 175

Val Lys Asn Ala Ser Val Pro Thr Ala Ala
1               5                   10

<210> SEQ ID NO 176
<211> LENGTH: 10
<212> TYPE: PRT
<213> ORGANISM: hepatitis C virus

<400> SEQUENCE: 176

Val Lys Asp Ala Asn Val Pro Thr Ala Ala
1               5                   10

<210> SEQ ID NO 177
<211> LENGTH: 10
<212> TYPE: PRT
<213> ORGANISM: hepatitis C virus -continued

```
<400> SEQUENCE: 177

Ala Arg Ile Ala Asn Ala Pro Ile Asp Glu
1               5                   10

<210> SEQ ID NO 178
<211> LENGTH: 10
<212> TYPE: PRT
<213> ORGANISM: hepatitis C virus

<400> SEQUENCE: 178

Val Ser Lys Pro Gly Ala Leu Thr Lys Gly
1               5                   10

<210> SEQ ID NO 179
<211> LENGTH: 10
<212> TYPE: PRT
<213> ORGANISM: hepatitis C virus

<400> SEQUENCE: 179

Val Ser Arg Pro Gly Ala Leu Thr Arg Gly
1               5                   10

<210> SEQ ID NO 180
<211> LENGTH: 10
<212> TYPE: PRT
<213> ORGANISM: hepatitis C virus

<400> SEQUENCE: 180

Val Asn Gln Pro Gly Ala Leu Thr Arg Gly
1               5                   10

<210> SEQ ID NO 181
<211> LENGTH: 10
<212> TYPE: PRT
<213> ORGANISM: hepatitis C virus

<400> SEQUENCE: 181

Val Ser Gln Pro Gly Ala Leu Thr Arg Gly
1               5                   10

<210> SEQ ID NO 182
<211> LENGTH: 10
<212> TYPE: PRT
<213> ORGANISM: hepatitis C virus

<400> SEQUENCE: 182

Val Ser Gln Pro Gly Ala Leu Thr Lys Gly
1               5                   10

<210> SEQ ID NO 183
<211> LENGTH: 10
<212> TYPE: PRT
<213> ORGANISM: hepatitis C virus

<400> SEQUENCE: 183

Val Ser Arg Pro Gly Ala Leu Thr Glu Gly
1               5                   10

<210> SEQ ID NO 184
<211> LENGTH: 10
<212> TYPE: PRT
<213> ORGANISM: hepatitis C virus

<400> SEQUENCE: 184
```

```
Ala Pro Tyr Ile Gly Ala Pro Leu Glu Ser
1               5                   10
```

<210> SEQ ID NO 185
<211> LENGTH: 10
<212> TYPE: PRT
<213> ORGANISM: hepatitis C virus

<400> SEQUENCE: 185

```
Ala Pro Tyr Thr Ala Ala Pro Leu Glu Ser
1               5                   10
```

<210> SEQ ID NO 186
<211> LENGTH: 10
<212> TYPE: PRT
<213> ORGANISM: hepatitis C virus

<400> SEQUENCE: 186

```
Ala Pro Ile Leu Ser Ala Pro Leu Met Ser
1               5                   10
```

<210> SEQ ID NO 187
<211> LENGTH: 10
<212> TYPE: PRT
<213> ORGANISM: hepatitis C virus

<400> SEQUENCE: 187

```
Val Pro Asn Ser Ser Val Pro Ile His Gly
1               5                   10
```

<210> SEQ ID NO 188
<211> LENGTH: 10
<212> TYPE: PRT
<213> ORGANISM: hepatitis C virus

<400> SEQUENCE: 188

```
Val Pro Asn Ala Ser Thr Pro Val Thr Gly
1               5                   10
```

<210> SEQ ID NO 189
<211> LENGTH: 10
<212> TYPE: PRT
<213> ORGANISM: hepatitis C virus

<400> SEQUENCE: 189

```
Val Gln Asn Ala Ser Val Ser Ile Arg Gly
1               5                   10
```

<210> SEQ ID NO 190
<211> LENGTH: 10
<212> TYPE: PRT
<213> ORGANISM: hepatitis C virus

<400> SEQUENCE: 190

```
Val Lys Ser Pro Cys Ala Ala Thr Ala Ser
1               5                   10
```

<210> SEQ ID NO 191
<211> LENGTH: 10
<212> TYPE: PRT
<213> ORGANISM: hepatitis C virus

<400> SEQUENCE: 191

```
Ser Pro Arg Met His His Thr Thr Gln Glu
```

```
<210> SEQ ID NO 192
<211> LENGTH: 10
<212> TYPE: PRT
<213> ORGANISM: hepatitis C virus

<400> SEQUENCE: 192

Ser Pro Arg Leu Tyr His Thr Thr Gln Glu
1               5                   10

<210> SEQ ID NO 193
<211> LENGTH: 10
<212> TYPE: PRT
<213> ORGANISM: hepatitis C virus

<400> SEQUENCE: 193

Thr Ser Arg Arg His Trp Thr Val Gln Asp
1               5                   10

<210> SEQ ID NO 194
<211> LENGTH: 10
<212> TYPE: PRT
<213> ORGANISM: hepatitis C virus

<400> SEQUENCE: 194

Ala Pro Lys Arg His Tyr Phe Val Gln Glu
1               5                   10

<210> SEQ ID NO 195
<211> LENGTH: 10
<212> TYPE: PRT
<213> ORGANISM: hepatitis C virus

<400> SEQUENCE: 195

Ser Pro Gln Tyr His Thr Phe Val Gln Glu
1               5                   10

<210> SEQ ID NO 196
<211> LENGTH: 10
<212> TYPE: PRT
<213> ORGANISM: hepatitis C virus

<400> SEQUENCE: 196

Ser Pro Gln His His Asn Phe Ser Gln Asp
1               5                   10

<210> SEQ ID NO 197
<211> LENGTH: 10
<212> TYPE: PRT
<213> ORGANISM: hepatitis C virus

<400> SEQUENCE: 197

Ser Pro Gln His His Ile Phe Val Gln Asp
1               5                   10

<210> SEQ ID NO 198
<211> LENGTH: 10
<212> TYPE: PRT
<213> ORGANISM: hepatitis C virus

<400> SEQUENCE: 198

Ser Pro Glu His His His Phe Val Gln Asp
1               5                   10
```

```
<210> SEQ ID NO 199
<211> LENGTH: 10
<212> TYPE: PRT
<213> ORGANISM: hepatitis C virus

<400> SEQUENCE: 199

Arg Pro Arg Arg His Trp Thr Thr Gln Asp
1               5                   10

<210> SEQ ID NO 200
<211> LENGTH: 10
<212> TYPE: PRT
<213> ORGANISM: hepatitis C virus

<400> SEQUENCE: 200

Arg Pro Arg Arg His Trp Thr Ala Gln Asp
1               5                   10

<210> SEQ ID NO 201
<211> LENGTH: 10
<212> TYPE: PRT
<213> ORGANISM: hepatitis C virus

<400> SEQUENCE: 201

Gln Pro Arg Arg His Trp Thr Thr Gln Asp
1               5                   10

<210> SEQ ID NO 202
<211> LENGTH: 10
<212> TYPE: PRT
<213> ORGANISM: hepatitis C virus

<400> SEQUENCE: 202

Arg Pro Arg Arg His Trp Thr Thr Gln Glu
1               5                   10

<210> SEQ ID NO 203
<211> LENGTH: 10
<212> TYPE: PRT
<213> ORGANISM: hepatitis C virus

<400> SEQUENCE: 203

Gln Pro Arg Arg His Trp Thr Val Gln Asp
1               5                   10

<210> SEQ ID NO 204
<211> LENGTH: 10
<212> TYPE: PRT
<213> ORGANISM: hepatitis C virus

<400> SEQUENCE: 204

Arg Pro Lys Tyr His Gln Val Thr Gln Asp
1               5                   10

<210> SEQ ID NO 205
<211> LENGTH: 10
<212> TYPE: PRT
<213> ORGANISM: hepatitis C virus

<400> SEQUENCE: 205

Arg Pro Arg Met His Gln Val Val Gln Glu
1               5                   10

<210> SEQ ID NO 206
```

-continued

```
<211> LENGTH: 10
<212> TYPE: PRT
<213> ORGANISM: hepatitis C virus

<400> SEQUENCE: 206

Arg Pro Arg Met Tyr Glu Ile Ala Gln Asp
1               5                   10

<210> SEQ ID NO 207
<211> LENGTH: 10
<212> TYPE: PRT
<213> ORGANISM: hepatitis C virus

<400> SEQUENCE: 207

Arg His Arg Gln His Trp Thr Val Gln Asp
1               5                   10

<210> SEQ ID NO 208
<211> LENGTH: 957
<212> TYPE: DNA
<213> ORGANISM: hepatitis C virus

<400> SEQUENCE: 208
atgagcacga atcctaaacc tcaaaaaaaa acaaacgta acaccaaccg tcgcccacag      60
gacgtcaagt tcccgggtgg cggtcagatc gttggtggag tttacttgtt gccgcgcagg    120
ggccctagat tgggtgtgcg cgcgacgaga aagacttccg agcggtcgca acctcgaggt    180
agacgtcagc ctatcccaa ggctcgtcgg cccgagggca ggacctgggc tcagcccggg     240 taccttggc ccctctatgg caatgagggc tgcgggtggg cgggatggct cctgtctccc     300
cgtggctctc ggcctagctg ggccccaca gaccccggc gtaggtcgcg caatttgggt      360
aaggtcatcg ataccttac gtgcggcttc gccgacctca tgggtacat accgctcgtc      420 ggcgcccctc ttggaggcgc tgccaggggc ctggcgcatg gcgtccgggt tctggaagac    480
ggcgtgaact atgcaacagg gaaccttcct ggttgctctt tctctatctt ccttctggcc    540
ctgctctctt gcttgactgt gcccgcttcg gcctaccaag tgcgcaactc cacgggcgtt    600
taccacgtca ccaatgattg ccctaactcg agtattgtgt acgaggcggc cgatgccatc    660
ctgcacactc cgggtgcgt ccctttgcgtt cgtgagggca acgcctcgag gtgttgggtg    720
gcgatgaccc ctacggtggc caccaggat ggcaaactcc ccgcgacgca gcttcgacgt     780
cacatcgatc tgcttgtcgg gagcgccacc ctctgttcgg ccctctacgt ggggacctta    840
tgcgggtctg tcttcttgt cggccaactg ttcaccttct ctcccaggcg ccactggacg     900
acgcaaggtt gcaattgctc tatctatccc ggccataaa cgggtcaccg catggca       957

<210> SEQ ID NO 209
<211> LENGTH: 957
<212> TYPE: DNA
<213> ORGANISM: hepatitis C virus

<400> SEQUENCE: 209
atgagcacaa atcctaaacc tcaaagaaaa accaaacgta acaccaaccg ccgcccacag     60
gacgttaagt tcccgggcgg tggtcagatc gttggtggag tttacctgtt gccgcgcagg    120 ggcccaggt tgggtgtgcg cgcgactagg aagacttccg agcggtcgca acctcgtgga    180
aggcgacaac ctatccccaa ggctcgccgg cccgagggta ggacctgggc tcagcccggg    240 taccttggc ccctctatgg caacgagggt atgggtggg caggatggct cctgtcaccc     300
cgtggctctc ggcctagttg ggccccaca gaccccggc gtaggtcgcg taatttgggt     360
```

```
aaggtcatcg ataccctta  catgcggcttc gccgacctca tggggtacat tccgcttgtc      420 ggcgccccc  taggggcgc  tgccagggcc ctggcacatg gtgtccgggt tctggaggac      480
ggcgtgaact atgcaacagg gaatctgccc ggttgctctt tctctatctt cctcttagct      540
ttgctgtctt gtttgaccat cccagcttcc gcttacgagg tgcgcaacgt gtccgggata      600
taccatgtca cgaacgactg ctccaactca agtattgtgt atgaggcagc ggacatgatc      660
atgcacaccc ccgggtgcgt gccctgcgtc cggagagta  atttctcccg ttgctgggta      720
gcgctcactc ccacgctcgc ggccaggaac agcagcatcc ccaccacgac aatacgacgc      780
cacgtcgatt tgctcgttgg ggcggctgct ctctgttccg ctatgtacgt tggggatctc      840
tgcggatccg tttttctcgt ctcccagctg ttcaccttct cacctcgccg gtatgagacg      900
gtacaagatt gcaattgctc aatctatccc ggccacgtat caggtcaccg catggct         957

<210> SEQ ID NO 210
<211> LENGTH: 957
<212> TYPE: DNA
<213> ORGANISM: hepatitis C virus

<400> SEQUENCE: 210
atgagcacga atcctaaacc tcaaagaaaa accaaacgta acaccaaccg ccgcccacag       60
gacgttaagt tcccgggtgg cggccagatc gttggcggag tttacttgtt gccgcgcagg      120
ggccccagag tgggtgtgcg cgcgacgagg aagacttccg agcggtcgca acctcgcggg      180
aggcgtcagc ctattcccaa ggcccgccga cccgagggaa ggtcctgggc gcagcccggg      240 taccccttggc ccctctatgg caacgagggc tgtgggtggg cgggatggct cctgtccccc      300
cgcggctctc ggcctagttg gggccttcct gaccccggc  ggaggtcacg caatttgggt      360
aaggtcatcg ataccctcac gtgtggcttc gccgacctca tggggtacat cccgctcgtc      420
ggcgctcctc taggggcgc  tgccagagct ctggcacatg gtgttagagt cctggaagac      480
ggcgtgaatt acgcaacagg gaacctcccc ggttgctctt tttctatctt cttgctcgct      540
cttctatcct gcctgacagt ccctgcttcg gcgtcggag  tgcgcaactc ttcggggtg       600 taccatgtca ccaatgattg ccccaatgcg tccgttgtgt acgagacgga gaacctgatc      660
atgcatctgc ccgggtgtgt gccctacgta cgcgagggca acgcctcgag gtgttgggtc      720
tcccttagtc ccaccgtagc cgccagggat tcgcgcgtcc ccgtcagtga ggttcggcgt      780
cgtgtcgact cgattgtcgg ggcgctgcg  ttctgttcgg ctatgtatgt aggggaccta      840
tgcggctcca tcttccttgt tggccagatc ttccacttct ctcccaggca ccattggacg      900
acgcaagact gcaattgctc catctaccca ggccatgtga caggtcatcg aatggct          957

<210> SEQ ID NO 211
<211> LENGTH: 957
<212> TYPE: DNA
<213> ORGANISM: hepatitis C virus

<400> SEQUENCE: 211
atgagcacaa atcctaaacc tcaaagaaaa accaaaagaa acaccaaccg tcgcccacaa       60
gacgttaagt ttccgggcgg cggccagatc gttggcggag tatacttgtt gccgcgcagg      120
ggccccaggt tgggtgtgcg cgcgacaagg aagacttcgg agcggtccca gccacgtgga      180
aggcgccagc ccatccctaa ggatcggcgc tccactggca atcctgggg  aaaaccagga      240 tacccctggc ccctatacgg gaatgaggga ctcggctggg caggatggct cctgtccccc      300
```

```
cgaggttccc gtccctcttg gggccccaat gaccccggc ataggtccg caacgtgggt     360 aaggtcatcg ataccctaac gtgcggcttt gccgacctca tggggtacat ccctgtcgta    420
ggcgccccgc tcggcggcgt cgccagagct ctcgcgcatg gcgtgagagt cctggaggac    480
ggggttaatt ttgcaacagg gaacttaccc ggttgctcct tttctatctt cttgctggcc    540
ctgctgtcct gcatcaccac cccggtctcc gctgccgaag tgaagaacat cagtaccggc    600
tacatggtga ccaacgactg caccaatgat agcattacct ggcaactcca ggctgctgtc    660
ctccacgtcc ccgggtgcgt cccgtgcgag aaagtgggga atacatctcg gtgctggata    720
ccggtctcac cgaatgtggc cgtgcagcag cccggcgccc tcacgcaggg cttacggacg    780
cacattgaca tggttgtgat gtccgccacg ctctgctccg ctctttacgt ggggggacctc    840 tgcggtgggg tgatgcttgc agcccagatg ttcattgtct cgccacagca ccactggttt    900
gtgcaagact gcaattgctc catctaccct ggtaccatca ctggacaccg catggcg       957

<210> SEQ ID NO 212
<211> LENGTH: 957
<212> TYPE: DNA
<213> ORGANISM: hepatitis C virus

<400> SEQUENCE: 212
atgagcacaa atcctaaacc tcaaagaaaa accaaaagaa acacaaaccg ccgcccacag     60
gacgttaagt tcccgggtgg cggtcagatc gttggcggag tttacttgct gccgcgcagg    120
ggccccaggt tgggtgtgcg cgcgacaagg aagacttctg agcgatccca gccgcgtgga    180
cgacgccagc ccatcccgaa agatcggcgc tccaccggca agtcctgggg aaagccagga    240
tatccttggc ccctgtacgg aaacgagggt gcggctggg cgggttggct cctgtccccc    300
cgcgggtctc gtcctacttg ggccccacc gaccccggc atagatcacg caatttgggc     360
agagtcatcg ataccattac gtgtggtttt gccgacctca tggggtacat ccctgtcgtt    420
ggcgccccgg ttggaggcgt cgccagagct ctggcacacg gtgttagggt cctggaggac    480
gggataaatt acgcaacagg gaatttaccc ggttgctctt tttctatctt tttgcttgct    540
cttctgtcat gcgtcacagt gccagtgtct gcagtggaag tcaggaacat tagttctagc    600
tactacgcca ctaatgattg ctcaaacaac agcatcacct ggcagctcac tgacgcagtt    660
ctccatcttc ctggatgcgt cccatgtgag aatgataatg gcaccttgca ttgctggata    720
caagtaacac ccaacgtggc tgtgaaacac cgcggtgcgc tcactcgtag cctgcgaaca    780
cacgtcgaca tgatcgtaat ggcagctacg gcctgctcgg ccttgtatgt gggagatgtg    840 tgcgggccg tgatgattct atcgcaggct ttcatggtat caccacaacg ccacaacttc    900
acccaagagt gcaactgttc catctaccaa ggtcacatca ccggccatcg catggca       957

<210> SEQ ID NO 213
<211> LENGTH: 957
<212> TYPE: DNA
<213> ORGANISM: hepatitis C virus

<400> SEQUENCE: 213
atgagcacaa atcctaaacc tcaaagaaaa accaaaagaa acactaaccg ccgcccacag     60
gacgtcaagt tcccgggcgg tggccagatc gttggcggag tatacttgct gccgcgcagg    120
ggcccgagat tgggtgtgcg cgcgacgagg aaaacttccg aacggtccca gccacgtggg    180
aggcgccagc ccatccctaa agatcggcgc accactggca agtcctgggg aaggccagga    240 taccccttggc ccctgtatgg gaatgagggc ctcggctggg cagggtggct cctgtccccc    300
```

-continued

| | |
|---|---|
| cgcggttctc gcccttcatg gggccccacc gaccccggc ataaatcgcg caacttgggt | 360 |
| aaggtcatcg atacctaac gtgcggtttt gccgacctca tggggtacat acccgtcgtt | 420 |
| ggcgctcccg ttggcggcgt tgccagagcc ctcgcccatg gggtgagggt tctggaggac | 480 |
| gggataaatt atgcaacggg gaatttgccc ggttgctctt tctctatctt tctcttggcc | 540 |
| ctcttgtctt gcatctctgt gccagttttcc gccgtgagg tcaaggacac cggcgactcc | 600 |
| tacatgccga ccaacgattg ctccaactct agtatcgttt ggcagcttga aggagcagtg | 660 |
| cttcatactc ctggatgcgt cccttgtgag cgtaccgcca acgtctctcg atgttgggtg | 720 |
| ccggttgccc ccaatctcgc cataagtcaa cctggcgctc tcactaaggg cctgcgagca | 780 |
| cacatcgata tcatcgtgat gtctgctacg gtctgttctg ccctttatgt ggggacgtg | 840 |
| tgtggcgcgc tgatgctggc cgctcaggtc gtcgtcgtgt cgccacaaca ccatacgttt | 900 |
| gtccaggaat gcaactgttc catatacccg ggccgcatta cgggacaccg catggct | 957 |

<210> SEQ ID NO 214
<211> LENGTH: 957
<212> TYPE: DNA
<213> ORGANISM: hepatitis C virus

<400> SEQUENCE: 214

| | |
|---|---|
| atgagcacaa atcctaaacc tcaaagaaaa accaaaagaa acactaaccg ccgcccacag | 60 |
| gacgtcaagt tcccgggcgg tggccagatc gttggtggag tatacttgtt gccgcgcagg | 120 |
| ggcccccggt tgggtgtgcg cgcgacgagg aaaacttccg agcggtccca gccacgtggg | 180 |
| aggcgccagc ccatccccaa agatcggcgc cccactggca agtcctgggg aaaaccagga | 240 |
| tacccttggc ccctgtacgg gaatgagggc tcggctgggg cagggtggct cctgtccccc | 300 |
| cgagggtctc gcccgtcatg ggcccaact gaccccggc acaggtcacg caacttgggt | 360 |
| aaggtcatcg atacctttac gtgtggcttt gccgacctca tggggtacat ccctgtcgtc | 420 |
| ggcgccccag ttggtggtgt cgccagagct ctcgcgcatg gcgtgagagt tctggaagac | 480 |
| gggataaact atgcaacagg gaacttgccc ggttgctcct tttctatctt cttattggcc | 540 |
| ctgctatctt gtatcactgt gccggtctcc ggcttgcagg tcaagaacac cagcagctct | 600 |
| tacatggtaa ccaatgactg ccagaacagt agcatcgtct ggcagctcag ggatgctgtt | 660 |
| cttcacgtcc ccgggtgtgt cccttgtgag gagaagggca acatatcccg ctgttggata | 720 |
| ccggtttcgc ccaatatagc tgtgagccaa cctggtgcgc ttaccaaggg cctgcggacg | 780 |
| catattgata ccatcattgc atccgctacg ttttgctctg ccctgtacat aggagacctg | 840 |
| tgtggcgcgg tgatgttggc ttctcaagtc ttcatcatct cgccccagca tcataagttt | 900 |
| gtccaggact gcaactgttc catatacccca ggccacatca ctggacatcg gatggcg | 957 |

<210> SEQ ID NO 215
<211> LENGTH: 957
<212> TYPE: DNA
<213> ORGANISM: hepatitis C virus

<400> SEQUENCE: 215

| | |
|---|---|
| atgagcacac ttcctaaacc tcaaagaaaa accaaaagaa acaccatccg tcgcccacag | 60 |
| gacgtcaagt tcccgggtgg cggacagatc gttggtggag tatacgtgtt gccgcgcagg | 120 |
| ggccccacgat tgggtgtgcg cgcgacgcgt aaaacttctg aacggtcaca gcctcgcgga | 180 |
| cgacgacagc ctatccccaa ggcgcgtcgg agcgaaggcc ggtcctgggc tcagcccggg | 240 |

```
taccccttggc ccctctatgg taacgagggc tgcgggtggg cagggtggct cctgtcccca      300
cgcggctccc gtccatcctg gggcccaaat gaccccggc ggaggtcccg caatttgggt        360
aaagtcatcg atacctaac gtgcggattc gccgacctca tggggtacat cccgctcgtc        420
ggcgctcctg taggaggcgt cgcaagagcc ctcgcgcatg gcgtgagggc ccttgaagac       480
gggataaatt tcgcaacagg gaacttgccc ggttgctcct tttctatctt ccttcttgct       540
ctgttctctt gcttaattca tccagcagcc agtctagagt ggcggaatac gtctggcctc      600
tacgtcctta ccaacgactg ttccaatagc agtattgtgt atgaggccga tgatgtcatt     660
ctgcacacac ccggctgtgt accttgtgtc caggacggca atacatctac gtgctggacc     720
ccagtgacac ctacagtggc agtcaggtac gtcggagcaa ctactgcttc gatacgcagt     780
catgtggacc tattagtagg cgcggccacg atgtgctctg cgctctacgt gggtgatatg    840
tgtgggctg tctttctcgt gggacaagcc ttcacgttca gcctcgacg ccatcaaacg      900
gtccagacct gtaactgctc gctgtaccca ggccatcttt caggacatcg aatggct      957
```

<210> SEQ ID NO 216
<211> LENGTH: 957
<212> TYPE: DNA
<213> ORGANISM: hepatitis C virus

<400> SEQUENCE: 216

```
atgagcacac ttcctaaacc tcaaagacaa accaaaagaa acacactccg tcgcccacag    60
aacgttaagt tcccgggcgg cggacagatc gttggtggag tatatgtgct gccgcgtagg    120
ggcccacgat tgggtgtgcg cgcagtacgt aagacttccg agcggtcgca gcctcgcaaa   180
cagcgtcacc ttatcccaa ggctcgctcg cgcgagggcc ggtcctgggc tcagcccggg     240
taccccttggc ccctctacgg gaataagggc tgtgggttgg caggatggct cttgtccccc   300
cgtggttctc gccctagttg gggcccaaat gaccccggc gtagatcccg caactttggt    360
aaggtcatcg atacctaac gtgtggattc gccgacctca tggggtacat tccgctcgtc    420
ggcgcccctg tggggggcgt cgcaagagcc ctcgctcatg gtgtgagggc acttggggac    480
ggagtgaact atgcaacagg gaatcttcct ggttgctcct tttctatttt cctcctcgct    540
ctcttctcct gcttgacttg ccccgcgtct ggcttagagt acacgaacac gtctggccta    600
tatgtgctta ccaacgactg ctctaatggg agcattgtgt acgaggccga agatgtgatc    660
ttgcacttac ccggatgcgt gccctgcgtc acaaccggca accaatcatc atgctggaca    720
acggtctcaa cgacggtggc cgttaggacc cttggcgtga ccaccgcgtc gatccgaacc    780
catgtggata tgctggtagg cgcacgacaa ctgtgttcgg cgctgtacgt cggggacgct    840
ttcgggctg tgtttcttgt gggacaagcg ttcaccttca gcctcgccg ccacacgacc     900
gtgcagacgt gcaactgctc gatatacca ggccatgttt caggacatcg tatggcg        957
```

<210> SEQ ID NO 217
<211> LENGTH: 957
<212> TYPE: DNA
<213> ORGANISM: hepatitis C virus

<400> SEQUENCE: 217

```
atgagcacac ttccaaaacc ccaaagaaaa accaaaagaa acaccatccg tcgcccacag    60
gacgtcaagt tcccgggcgg cggtcagatc gttggtggag tatacgtgtt gccgcgcagg   120
ggccctctat tgggtgtgcg cgctacacgt aagacttccg agcggtcaca gcctcgcgcg   180
cggcggcagc ctatccccaa ggcgcgtcgt ggcgagggac ggtcctgggc tgagcccggg   240
```

-continued

```
tacccttggc ccctctacgg taatgagggc tgcgggtggg cgggatggct cctgtccccc    300
cgcggttctc ggccgagctg gggcccaaat gacccccggc gaagatcccg caatttgggt    360
aaggtcatcg atacccttac atgcgggttc gccgacctca tggggtacat tccgctcgtc    420
ggcgcccccg tgggggcgt tgcaagggcc ctcgcgcatg gcgtgagggc tcttgaggac    480
gggattaact tcgcaacagg gaatttacct ggttgctcct tttctatctt cttgcttgct    540
ctcttctcat gcttggtctg tcctgcagca gggctcgagt accggaatgt atccggcctc    600
tacatactca ccaatgactg ttcgaacagc agcatagtgt atgaggccga ccatgtcatc    660
ttgcacttgc ccggttgcgt accctgcgtc caaaacaata acaccacgac gtgctggata    720
ccggtgactc cgacagtggc ggtcagtcac gtcggtgcga ccaccgcatc gatccgcggg    780
cacgtggatc tgctggtggg tacggctaca ttgtgttcgg cactttacgt cggtgacctt    840
tgcggggcag ttttcctcgt aggacaagca ttcacattca gaccccgacg ccaccagaca    900
gttcagcatt gcaactgctc actgtaccca ggtcatgttt caggtcatcg gatggct       957
```

<210> SEQ ID NO 218
<211> LENGTH: 957
<212> TYPE: DNA
<213> ORGANISM: hepatitis C virus

<400> SEQUENCE: 218

```
atgagcacac ttccaaaacc ccaaagaaaa accaaaagaa acaccatccg tcgcccacag     60
gacgttaagt tcccgggcgg cggccagatc gttggtggag tctacttact gccgcgcagg    120
ggcccaagat tgggtgtgcg cgcagttcgt aaaacttccg agcggtcaga accccgcaac    180
cggcggcagc ctatccccaa ggcacgtcgg agcgagggcc ggtcctgggc tcagcctggg    240
tacccttggc ctctttatgg caatgagggc tgtgggtggg caggatggct cttgtccccc    300
cgcggctctc ggccatcttg gggccccaat gacccccggc gaaggtctcg caacctgggt    360
aaagtcatcg ataccctaac gtgcggattc gccgatctca tggggtacat tccgctcgtc    420
ggcgctcctg tagggggcgt cgcaagagct ctcgcacatg gtgtgagagc ccttgaggac    480
ggaataaatt tcgcaacagg gaatttaccc ggttgctctt tctctatctt cttgcttgct    540
ttgctctctt gcttggtctg tcctgctgca gggattgaat accggaatgt gtctggcctc    600
tacgtgctca ccaacgactg ctctaacggc agtatcgtgt atgaggcccc tgaagtcatc    660
ttgcacttgc caggttgtgt gccctgcgtt caatcaggca actcctcgca atgctggatt    720
ccggtggcac caacagtggc ggttaagtac gctggcgcga ccactgcatc gatccgcagt    780
catgtggatc tgctggtggg agctgctacg ttgtgctccg cgctgtatgt tggcgatatg    840
tgtggagccg tcttcttggt gggacaggct ttcaccttca gacctcgtca gcacaacacg    900
gtgcagacct gcaattgctc actgtaccct ggtcacatat caggacacag gatggct       957
```

<210> SEQ ID NO 219
<211> LENGTH: 957
<212> TYPE: DNA
<213> ORGANISM: hepatitis C virus

<400> SEQUENCE: 219

```
atgagcacac ttccaaaacc ccaaagaaaa accaaaagaa acaccgtccg tcgcccgcaa     60
gacgttaagt tcccgggcgg cggccagatc gttggtggag tatacttgtt gccgcgcagg    120
ggcccacgat tgggtgtgcg cgcaactcgt aagacttcag agcggtcaca accccgcgga    180
```

-continued

```
cggcgacagc ctattcccaa ggcacgcccg agcggaggac ggtcctgggc gcagcctggg      240 taccccctggc ccctctatgg taacgagggc tgcgggtggg caggtggct tctgtctcct       300 cgcggctccc gaccgagttg gggccccaac gaccccggc gaaggtcccg caatttgggt        360
aaggtcatcg acactctcac atgcgggttc gccgatctca tggggtatat tccgctcgtc      420
ggcgctccgg taggaggcgt cgcgagggcc ctcgcacacg gggtaagggc tctcgaggac      480
ggaataaatt ttgcaacagg gaaccttccc ggttgctctt tttctatctt cttgcttgct      540
ctgctgtcat gcttgctttg ccctgcagtc gggttggagg ttcgcaacgc atccggtctc      600
tacatgctca ccaatgactg ctcaaacagc agcatagtat atgaggcgga agatgtgatc      660
ctgcacatgc ctggttgcgt tccctgcgtg cagaacggca acacatcgga gtgctggacc      720
ccggcgacac caacggtggc agtcagatac gctggtgcaa cgacggcttc cgtacgcgga      780
cacgtggatt tgctagtcgg cagtgccact ctgtgctccg cgctctatgt cggtgacctt      840 tgcgggggccg tcttccttgt ggggcaggcc tttacattca ggcctcgtcg tcatacgact      900
gtccagacct gcaactgctc gttgtaccca ggccatatca caggacatcg catggca        957
```

<210> SEQ ID NO 220
<211> LENGTH: 957
<212> TYPE: DNA
<213> ORGANISM: hepatitis C virus

<400> SEQUENCE: 220

```
atgagcacat ttcctaaacc tcaaagacaa cccaaaagaa acacacccg ccgcccacag       60 gacgtcaagt tcccgggcgg tggcagatc gttggtggag tatacgtatt gccgcgcagg      120
ggcccacgat tgggtgtgcg cgcagtgcgt aaatcttccg agcggtcgca acctcgcgga    180
cggcggcagc ctatccccaa ggcacgccga agcgagggcc ggtcctgggc ccagcctggg    240 taccccttggc ccctctatgg gaatgagggc tgtgggtggg caggatggct cctgtctccc    300
cgtggctccc gccctagttg gggcccaaat gaccccggc gtagatcacg caacttgggt      360
aaggtcatcg ataccctcac gtgtggattc gccgatctca tggggtacat tccgctcgtt    420 ggtgccccg tagggggcgt cgcaagggcc ctagcacatg gtgtgagggc tcttgaggac    480
ggaataaact ttgcaacagg gaatttgccc ggttgctcct tttctatctt ccttcttgct      540
ctcttctcat gcttggttc ccccgcagcg ggctagagt acaggaacac gtccggccta      600
tacatactta ccaacgactg ctctaacagc agcatcgtgt atgaggctga taatgtcatc    660
ctgcacatgc ccgctgtgt gccctgcact cgcgagggta accagtcaag gtgctggacg      720
ccagtaacac cgacagtggc tgtcaaacat cctggcgcag tcaccgcatc aatccgcagg    780
catgtggatt tgatggtggg tgcagccacg ctgtgttcag cactctatgt ggagatttg      840 tgcggggctg ttttccttgt gggccaagcg ttcactttca gagctcggca acattatacc    900
gtccagttgt gcaattgctc actataccca ggacacatta caggacatca tatggct        957
```

<210> SEQ ID NO 221
<211> LENGTH: 957
<212> TYPE: DNA
<213> ORGANISM: hepatitis C virus

<400> SEQUENCE: 221

```
atgagcacga atcctaaacc tcaaagaaaa accaaacgta acaccaaccg ccgcccatg        60 gacgtaaagt tcccgggtgg tggccagatc gttggcggag tttacttgtt gccgcgcagg     120 ggcccccaggt tgggtgtgcg cgcgactcga aagacttcgg agcggtcgca acctcgtggc    180
```

-continued

```
aggcgtcaac ctatccccaa ggcgcgccag ccagagggca gatcctgggc gcagcccggg    240 taccccttggc ccctctatgg caatgagggc tgcgggtggg cagggtggct cctgtctcct    300
cgcggctctc ggccatcttg gggcccaaat gatccccggc ggagatcgcg caatctgggt    360
aaggtcatcg ataccctgac gtgcggcttc gccgacctca tgggatacat cccgatcgtg    420 ggcgccccg tgggggcgt cgccagggct ctggcgcatg gcgtcagggc tgtggaggac    480
gggattaact atgcaacagg gaatcttccc ggttgctctt tctctatctt ccttttggca    540
cttctttcgt gcctcactgt tccagcgtcg gctgagcact accggaatgc ttcgggcatc    600
tatcacatca ccaatgattg tccgaattcc agtatagtct atgaagctga ccatcacatc    660
ctacacttgc cggggtgcgt accctgtgtg atgactggga acacatcgcg ttgctggacg    720
ccggtgacgc ctacagtggc tgtcgcacac ccgggcgctc cgcttgagtc gttccggcga    780
catgtggact taatggtagg cgcggccact ttgtgttctg ccctctatgt tggggacctc    840
tgcggaggtg ccttcctgat ggggcagatg atcactttc ggccgcgtcg ccactggacc    900
acgcaggagt gcaattgttc catctacact ggccatatca ccggccacag gatggcg       957
```

<210> SEQ ID NO 222  
<211> LENGTH: 957  
<212> TYPE: DNA  
<213> ORGANISM: hepatitis C virus

<400> SEQUENCE: 222

```
atgagcacaa atcctaaacc tcaaagaaaa accaaacgta acaccaaccg tcgccccatg    60
gatgtgaaat tcccgggcgg cggccagatc gttggcggag tttacttgct gccgcgcagg    120
ggcccccggt tgggtgtgcg cgcagctcgg aagacttcgg agcggtcaca acctcgtggc    180
aggcgtcagc ctatccccaa ggcgcgccgg tccgagggca ggtcctgggc tcagcccggg    240 taccccttggc ccctttacgg caatgagggc tgtgggtggg cagggtggct cctgtccccc    300
cgcggttcca ggccgtcttg gggcccaat gatccccggc gtaggtcccg taatctgggt    360
aaagtcatcg ataccctgac gtgtggcttc gccgacctca tgggatacat cccgctcgta    420
ggcgcccctg tgggtggcgt cgccagggcc ctggcgcatg gcgtcagggc cgtggaggac    480
ggaattaact acgcaacagg gaaccttcct ggttgctctt tctctatctt tcttcttgca    540
cttctctcgt gcctgacaac accagcatct gccgtgcact accggaatgc ttcgggcgtc    600
tatcatgtca ccaatgattg ccctaacacc agcatagtgt acgagacgga gcaccacatc    660
atgcacttgc agggtgtgt ccctgtgtg cggacggaga atacttctcg ctgctgggtg    720
cccttgaccc ccactgtggc cgcgccctat cccaacgcac cgttagagtc catgcgcagg    780
catgtagacc tgatggtggg tgcggctact atgtgttccg ccttctacat ggagatctg    840 tgtggaggcg tcttcctagt gggccagctg ttcgacttcc gaccgcgccg gcactggacc    900
acccaggatt gcaactgctc catctatcct ggtcacgtct cgggccacag gatggcc       957
```

<210> SEQ ID NO 223  
<211> LENGTH: 957  
<212> TYPE: DNA  
<213> ORGANISM: hepatitis C virus

<400> SEQUENCE: 223

```
atgagcacga atcctaaacc tcaaagaaaa accaaacgta acaccaaccg ccgccccatg    60
gacgttaagt tcccgggcgg tggccagatc gttggcggag tttacttgtt gccgcgcagg    120
```

-continued

```
ggccccaggt tgggtgtgcg cgcgactagg aagacttcgg agcggtcgca acctcgtggg      180
agacgtcagc ctatcccaa ggcacgtcga tctgagggaa ggtcctgggc tcagcccggg       240
tacccatggc ctctttacgg taatgagggt tgcgggtggg cgggatggct cctgtcacct      300
cgtggctctc gaccgtcttg gggcccaaat gatccccggc gaaggtcccg caacttgggt      360
aaggtcatcg ataccctaac ctgcggcttt gccgacctca tgggatacat cccgctcgta     420
ggcgcccccg tgggtggcgt cgccaggcc ctggcacacg gtgttagggc tgtggaggac       480
gggatcaatt atgcgacagg gaatcttccc ggttgctctt tctctatctt cttcttggca     540
cttctttcgt gcctgactgt tcccacctcg gccgtcaact atcgcaatgc ctcgggcatc     600
tatcacatca ccaatgactg cccgaactcg agcatagtgt acgagaccga gcaccacatc     660
ctacacctcc cagggtgttt accctgcgtg agggttggga atcagtcacg ctgctgggtg     720
gccctcactc ccaccgtggc ggcgccttac atcggcgctc cgcttgaatc cctccggagt     780
catgtggatc tgatggtagg tgccgctact gcgtgctccg ctctttacat cggagacctg     840
tgcggtggcg tattttggt tggtcagatg ttctctttcc agccgcggcg ccactggact      900
acgcaggact gcaattgttc catctacgcg gggcacgtta cgggccacag gatggca        957
```

<210> SEQ ID NO 224
<211> LENGTH: 957
<212> TYPE: DNA
<213> ORGANISM: hepatitis C virus

<400> SEQUENCE: 224

```
atgagcacga atcctaaacc tcaaagaaaa accaaacgta acaccaaccg ccgcccaatg      60
gacgttaagt tcccgggtgg cggccagatc gttggcggag tttacttgtt gccgcgcagg     120
ggccctagat tgggtgtgcg cgcgactagg aagacttcgg agcggtcgca acctcgtggg     180
aggcgccagc ctatcccaa ggcgcgccaa ctcgagggta ggtcctgggc tcagcctggg     240
tatccttggc cccttacgg caatgagggc tgcgggtggg cgggatggct cctgtcaccc      300
cgtggctctc ggccgtcttg gggcccgaat gatccccggc ggaggtcccg caacttgggt     360
aaggtcatcg ataccctaac ttgcggcttc gccgacctca tgggatacat cccggtcgta    420
ggcgcccccg tgggtggcgt cgccagagcc ctggcgcatg cgtcaggct tctggaggac       480 ggggtcaatt atgcaacagg gaatcttccc ggttgctctt tctctatctt cctcttggca     540
ctgctctcgt gcctgactgt tcccgcttcg gcctacaact atcgcaacag ctcgggtgtc     600
taccatgtca ccaacgattg cccgaactcg agcatagtct atgaaaccga ttaccacatc     660
ttacacctcc cgggatgcgt tccttgcgtg agggaaggga acaagtctac atgctgggtg     720
tctctcaccc ccaccgtggc tgcgcaacat ctgaatgctc cgcttgagtc tttgagacgt     780
cacgtggatc tgatggtggg cggcgccact ctctgctccg ccctctacat cggagacgtg     840
tgtgggggtg tgttcttggt cggtcaactg ttcaccttcc aacctcgccg ccactggacc     900
acccaagact gcaattgttc catctacaca ggacatatca caggacacag aatggct         957
```

<210> SEQ ID NO 225
<211> LENGTH: 957
<212> TYPE: DNA
<213> ORGANISM: hepatitis C virus

<400> SEQUENCE: 225

```
atgagcacga atcctaaact tcaaagaaaa accaaacgta acaccaaccg ccgcccatg       60 gacgttaagt tcccgggtgg tggccagatc gttggcggag tttacttgtt gccgcgcagg     120
```

-continued

```
ggccctaggt tgggtgtgcg cgcgactcgg aagacttcgg agcggtcgca acctcgtggg      180
aggcgccaac ctatccccaa ggcgcgccga tccgagggca gatcctgggc gcagcccggg      240
tatccttggc cccttacgg caatgagggc tgtgggtggg caggtggct cctgtcccct       300 cgcgggtctc ggccgtcttg gggccctaat gatccccggc ggaggtcccg caacctgggt      360
aaggtcatcg ataccctaac atgcggcttc gccgacctca tgggatacat cccgcttgta      420 ggcgccccg tgggtggcgt cgccagagcc ctggcacacg gtgttagggc tgtggaagac       480
gggatcaact acgcaacagg gaatctcccc ggttgctcct tttctatctt cctcttggca      540
cttctctcgt gcctcactgt tcccgcgtcg ggcgttaact atcgcaatgc ttcgggcgtt      600
tatcacatca ccaacgactg cccgaatgcg agcatagtgt acgagaccga caatcacatc      660
ttacacctcc cagggtgcgt accctgtgtg aagaccggga accagtcgcg gtgttgggtg      720
gccctcactc ccacagtggc gtcgccttac gtcggtgctc cgctcgagcc cttgcggcgc      780
catgtggacc tgatggtagg tgctgccacc gtgtgctccg ccctctacgt cggcgacctg      840
tgcggtggct tattcttggt aggccaaatg ttccacttcc aaccgcgacg ccactggacg      900
acccaggact gtaattgttc catctacgca gggcatatta cgggccatcg gatggct         957

<210> SEQ ID NO 226
<211> LENGTH: 957
<212> TYPE: DNA
<213> ORGANISM: hepatitis C virus

<400> SEQUENCE: 226
atgagcacga atcctaaacc tcaaagaaaa accaaaagaa acaccaaccg tcgcccacag      60
gacgtcaagt tcccgggcgg tggtcagatc gttggcggag tttacttgtt gccgcgcagg      120
ggccctagga tgggtgtgcg cgcgactcgg aagacttcgg aacggtcgca accccgtgga      180
cggcgtcagc ctattcccaa ggcgcgccag cccacgggcc ggtcctgggg tcaacccggg      240 taccctggc cccttacgc caatgagggc ctcgggtggg caggtggct gctctcccct        300 cgaggctctc ggcctaattg gggccccaat gaccccggc gaaaatcgcg taatttgggt      360
aaggtcatcg ataccctaac gtgcggattc gccgatctca tggggtatat cccgctcgta      420
ggcgccccca ttgggggcgt cgcaagggct ctcgcacacg gtgtgagggt ccttgaggac      480 gggggtaaact atgcaacagg gaatttaccc ggttgctctt tctctatctt tattcttgct      540
cttctctcgt gtctgaccgt tccggcctct gcagttccct accgaaatgc ctctgggatt      600
tatcatgtta ccaatgattg cccaaactct tccatagtct atgaggcaga taacctgatc      660
ctacacgcac ctggttgcgt gccttgtgtc atgacaggta atgtgagtag atgctgggtc      720
caaattaccc ctacactgtc agccccgagc ctcggagcag tcacggctcc tcttcggaga      780
gccgttgact acctagcggg aggggctgcc ctctgctccg cgttatacgt aggagacgcg      840 tgtgggcac tattcttggt aggccaaatg ttcacctata ggcctcgcca gcacgctacg      900
gtgcagaact gcaactgttc catttacagt ggccatgtta ccggccaccg gatggca         957

<210> SEQ ID NO 227
<211> LENGTH: 957
<212> TYPE: DNA
<213> ORGANISM: hepatitis C virus

<400> SEQUENCE: 227
atgagcacac ttccaaaacc ccaaagaaaa accaaaagaa acaccaaccg tcgcccaacg      60
```

```
gacgtcaagt tcccgggtgg cggtcagatc gttggcggag tttacttgtt gccgcgcagg      120
ggcccccggt tgggtgtgcg cgcgacgaga aagacttccg agcgatccca gcccagaggc      180
aggcgccaac ctataccaaa ggcgcgccag ccccagggca ggcactgggc tcagcccgga      240
tacccttggc ctctttatgg aaacgagggc tgtgggtggg caggttggct cctgtccccc      300
cgcggctccc ggccacattg gggcccaat gaccccggc gtcgatcccg aatttgggt        360 aaggtcatcg atacccTaac gtgtgggttc gccgatctca tggggtacat tcccgtcgtg     420
ggcgcgcctt tgggcggcgt cgcggctgcg ctcgcacatg gcgtgagggc aatcgaggac     480
gggatcaatt atgcaacagg gaatctcccc ggttgctctt tctctatctt ccttttggca     540
ctactctcgt gcctcacaac gccagcttcg gctcttacct acggcaactc cagtgggcta     600
taccatctca caaatgattg ccccaactcc agcatcgtgc tggaggcgga tgctatgatc     660
ttgcatttgc ctggatgctt gccttgtgtg agggtcgatg atcggtccac ctgttggcat     720
gctgtgaccc ccaccctggc cataccaaat gcttccacgc ccgcaacggg attccgcagg     780
catgtggatc ttcttgcggg cgccgcagtg gtttgctcat ccctgtacat cggggacctg     840
tgtggctctc tcttttttggc gggacaacta ttcaccttt c agccccgccg tcattggact     900
gtgcaagact gcaactgctc catctataca ggccacgtca ccggccacag gatggct        957
```

```
<210> SEQ ID NO 228
<211> LENGTH: 957
<212> TYPE: DNA
<213> ORGANISM: hepatitis C virus
<220> FEATURE:
<221> NAME/KEY: misc_feature
<222> LOCATION: (383)..(383)
<223> OTHER INFORMATION: n represents any nucleotide
<220> FEATURE:
<221> NAME/KEY: misc_feature
<222> LOCATION: (387)..(387)
<223> OTHER INFORMATION: n represents any nucleotide
<220> FEATURE:
<221> NAME/KEY: misc_feature
<222> LOCATION: (924)..(924)
<223> OTHER INFORMATION: n represents any nucleotide
<220> FEATURE:
<221> NAME/KEY: misc_feature
<222> LOCATION: (928)..(928)
<223> OTHER INFORMATION: n represents any nucleotide

<400> SEQUENCE: 228
```

```
atgagcacac ttccaaaacc ccaaagaaaa accaaaagaa atactaaccg tcgccctatg      60
gacgtcaagt tcccgggcgg cggccagatc gttggtggag tttacttgtt gccgcgcagg     120
ggccctcgtt tgggtgtgcg cgcgacgaga aagacctccg aacggtccca gcctagaggc     180
aggcgccagc ccataccaaa ggtacgccag ccgacaggcc gtagctgggg tcaacccggc     240
tacccttggc ccctttatgg caacgagggc tgcggatggg cgggatggct cctgtccccc     300
cgcgggtctc gtcctaattg gggccccaac gaccccggc gaaggtcccg caacttgggt      360
aaggtcatcg atacccttac atncggncta gccgacctca tggggtacat ccctgtccta     420
ggagggccgc ttggcggcgt tgcggctgcc ctggcgcatg gcgttagggc aatcgaggac     480
ggggtcaatt acgcaacagg gaatcttcct ggttgctcct tttctatctt cctcttagca     540
ctgttatcgt gcctcactac accagcctca gcaattcaag tcaagaacgc ctctgggatc     600
taccatctta ccaatgactg ctcgaacaac agcatcgttt tgaggcgga gaccatgata     660 ctgcatcttc caggttgtgt cccatgtatc aaggcgggga atgagtcacg atgttggctc     720
cctgtctccc ccaccttagc cgtccccaac tcatcagtgc caatccacgg gtttcgccga     780
```

```
cacgtagacc tcctcgttgg ggcagcggca ttttgttcgg ccatgtacat cggagacctc      840
tgtggtagca taatcttggt agggcagctt tttactttca ggcctaagta ccatcaggtt      900
acccaggatt gtaactgctc tatnaacnct ggccacgtca cgggacacag gatggca         957
```

<210> SEQ ID NO 229
<211> LENGTH: 319
<212> TYPE: PRT
<213> ORGANISM: hepatitis C virus

<400> SEQUENCE: 229

```
Met Ser Thr Asn Pro Lys Pro Gln Lys Lys Asn Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Thr Gly Leu Tyr His Val Thr Asn Asp Cys Pro
        195                 200                 205

Asn Ser Ser Ile Val Tyr Glu Ala Ala Asp Ala Ile Leu His Thr Pro
    210                 215                 220

Gly Cys Val Pro Cys Val Arg Glu Gly Asn Ala Ser Arg Cys Trp Val
225                 230                 235                 240

Ala Met Thr Pro Thr Val Ala Thr Arg Asp Gly Lys Leu Pro Ala Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
        275                 280                 285

Gln Leu Phe Thr Phe Ser Pro Arg Arg His Trp Thr Thr Gln Gly Cys
    290                 295                 300

Asn Cys Ser Ile Tyr Pro Gly His Ile Thr Gly His Arg Met Ala
305                 310                 315
```

<210> SEQ ID NO 230
<211> LENGTH: 319
<212> TYPE: PRT

<213> ORGANISM: hepatitis C virus

<400> SEQUENCE: 230

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gln Ile Val Gly
            20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
50                      55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Met Gly Trp Ala Gly Trp
                85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
            180                 185                 190

Glu Val Arg Asn Val Ser Gly Ile Tyr His Val Thr Asn Asp Cys Ser
        195                 200                 205

Asn Ser Ser Ile Val Tyr Glu Ala Ala Asp Met Ile Met His Thr Pro
    210                 215                 220

Gly Cys Val Pro Cys Val Arg Glu Ser Asn Phe Ser Arg Cys Trp Val
225                 230                 235                 240

Ala Leu Thr Pro Thr Leu Ala Ala Arg Asn Ser Ser Ile Pro Thr Thr
                245                 250                 255

Thr Ile Arg Arg His Val Asp Leu Leu Val Gly Ala Ala Ala Leu Cys
            260                 265                 270

Ser Ala Met Tyr Val Gly Asp Leu Cys Gly Ser Val Phe Leu Val Ser
        275                 280                 285

Gln Leu Phe Thr Phe Ser Pro Arg Arg Tyr Glu Thr Val Gln Asp Cys
    290                 295                 300

Asn Cys Ser Ile Tyr Pro Gly His Val Ser Gly His Arg Met Ala
305                 310                 315

<210> SEQ ID NO 231
<211> LENGTH: 319
<212> TYPE: PRT
<213> ORGANISM: hepatitis C virus

<400> SEQUENCE: 231

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gln Ile Val Gly
            20                  25                  30

Gly Val Tyr Leu Leu Pro Arg Arg Gly Pro Arg Leu Gly Val Arg Ala

-continued

```
                35                  40                  45
Thr Arg Lys Thr Ser Glu Arg Ser Gln Pro Arg Gly Arg Gln Pro
             50                  55                  60
Ile Pro Lys Asp Arg Arg Ser Thr Gly Lys Ser Trp Lys Pro Gly
 65                  70                  75                  80
Tyr Pro Trp Pro Leu Tyr Gly Asn Glu Gly Leu Gly Trp Ala Gly Trp
                 85                  90                  95
Leu Leu Ser Pro Arg Gly Ser Arg Pro Ser Trp Gly Pro Asn Asp Pro
                100                 105                 110
Arg His Arg Ser Arg Asn Val Gly Lys Val Ile Asp Thr Leu Thr Cys
                115                 120                 125
Gly Phe Ala Asp Leu Met Gly Tyr Ile Pro Val Val Gly Ala Pro Leu
                130                 135                 140
Gly Gly Val Ala Arg Ala Leu Ala His Gly Val Arg Val Leu Glu Asp
145                 150                 155                 160
Gly Val Asn Phe Ala Thr Gly Asn Leu Pro Gly Cys Ser Phe Ser Ile
                165                 170                 175
Phe Leu Leu Ala Leu Leu Ser Cys Ile Thr Thr Pro Val Ser Ala Ala
                180                 185                 190
Glu Val Lys Asn Ile Ser Thr Gly Tyr Met Val Thr Asn Asp Cys Thr
                195                 200                 205
Asn Asp Ser Ile Thr Trp Gln Leu Gln Ala Ala Val Leu His Val Pro
                210                 215                 220
Gly Cys Val Pro Cys Glu Lys Val Gly Asn Thr Ser Arg Cys Trp Ile
225                 230                 235                 240
Pro Val Ser Pro Asn Val Ala Val Gln Gln Pro Gly Ala Leu Thr Gln
                245                 250                 255
Gly Leu Arg Thr His Ile Asp Met Val Val Met Ser Ala Thr Leu Cys
                260                 265                 270
Ser Ala Leu Tyr Val Gly Asp Leu Cys Gly Val Met Leu Ala Ala
                275                 280                 285
Gln Met Phe Ile Val Ser Pro Gln His His Trp Phe Val Gln Asp Cys
                290                 295                 300
Asn Cys Ser Ile Tyr Pro Gly Thr Ile Thr Gly His Arg Met Ala
305                 310                 315

<210> SEQ ID NO 232
<211> LENGTH: 319
<212> TYPE: PRT
<213> ORGANISM: hepatitis C virus

<400> SEQUENCE: 232

Met Ser Thr Asn Pro Lys Pro Gln Arg Lys Thr Lys Arg Asn Thr Asn
 1               5                  10                  15
Arg Arg Pro Gln Asp Val Lys Phe Pro Gly Gly Gly Gln Ile Val Gly
                20                  25                  30
Gly Val Tyr Leu Leu Pro Arg Arg Gly Pro Arg Leu Gly Val Arg Ala
                35                  40                  45
Thr Arg Lys Thr Ser Glu Arg Ser Gln Pro Arg Gly Arg Arg Gln Pro
             50                  55                  60
Ile Pro Lys Asp Arg Arg Ser Thr Gly Lys Ser Trp Gly Lys Pro Gly
 65                  70                  75                  80
Tyr Pro Trp Pro Leu Tyr Gly Asn Glu Gly Cys Gly Trp Ala Gly Trp
                 85                  90                  95
```

```
Leu Leu Ser Pro Arg Gly Ser Arg Pro Thr Trp Gly Pro Thr Asp Pro
            100                 105                 110

Arg His Arg Ser Arg Asn Leu Gly Arg Val Ile Asp Thr Ile Thr Cys
            115                 120                 125

Gly Phe Ala Asp Leu Met Gly Tyr Ile Pro Val Val Gly Ala Pro Val
        130                 135                 140

Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Val Thr Val Pro Val Ser Ala Val
            180                 185                 190

Glu Val Arg Asn Ile Ser Ser Ser Tyr Tyr Ala Thr Asn Asp Cys Ser
            195                 200                 205

Asn Asn Ser Ile Thr Trp Gln Leu Thr Asp Ala Val Leu His Leu Pro
        210                 215                 220

Gly Cys Val Pro Cys Glu Asn Asp Asn Gly Thr Leu His Cys Trp Ile
225                 230                 235                 240

Gln Val Thr Pro Asn Val Ala Val Lys His Arg Gly Ala Leu Thr Arg
                245                 250                 255

Ser Leu Arg Thr His Val Asp Met Ile Val Met Ala Ala Thr Ala Cys
            260                 265                 270

Ser Ala Leu Tyr Val Gly Asp Val Cys Gly Ala Val Met Ile Leu Ser
            275                 280                 285

Gln Ala Phe Met Val Ser Pro Gln Arg His Asn Phe Thr Gln Glu Cys
        290                 295                 300

Asn Cys Ser Ile Tyr Gln Gly His Ile Thr Gly His Arg Met Ala
305                 310                 315

<210> SEQ ID NO 233
<211> LENGTH: 319
<212> TYPE: PRT
<213> ORGANISM: hepatitis C virus
<220> FEATURE:
<221> NAME/KEY: MISC_FEATURE
<222> LOCATION: (319)..(319)
<223> OTHER INFORMATION: Xaa represents any amino acid

<400> SEQUENCE: 233

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Asp Arg Arg Thr Thr Gly Lys Ser Trp Gly Arg Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg His Arg Ser Arg Asn Leu Gly Lys Val Ile Asp Thr Leu Thr Cys
            115                 120                 125

Gly Phe Ala Asp Leu Met Gly Tyr Ile Pro Val Val Gly Ala Pro Val
```

-continued

```
            130                 135                 140
Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
                165                 170                 175

Phe Leu Ser Ala Leu Leu Ser Cys Ile Ser Val Pro Val Ser Ala Val
                180                 185                 190

Glu Val Lys Asn Thr Ser Thr Ser Tyr Met Val Thr Asn Asp Cys Ser
                195                 200                 205

Asn Ser Ser Ile Val Trp Gln Leu Glu Gly Ala Val Leu His Thr Pro
210                 215                 220

Gly Cys Val Pro Cys Glu Gln Ile Gly Asn Ala Ser Arg Cys Trp Val
225                 230                 235                 240

Pro Val Ser Pro Asn Val Ala Ile Arg Gln Pro Gly Thr Leu Thr Lys
                245                 250                 255

Gly Leu Arg Ala His Val Asp Val Ile Val Met Ser Ala Thr Leu Cys
                260                 265                 270

Ser Ala Leu Tyr Val Gly Asp Val Cys Gly Ala Leu Met Ile Ala Ala
                275                 280                 285

Gln Ala Val Ile Ala Ser Pro Gln Arg His Thr Phe Val Gln Glu Cys
                290                 295                 300

Asn Cys Ser Ile Tyr Pro Gly His Ile Thr Gly His Arg Met Xaa
305                 310                 315

<210> SEQ ID NO 234
<211> LENGTH: 319
<212> TYPE: PRT
<213> ORGANISM: hepatitis C virus

<400> SEQUENCE: 234

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
                35                  40                  45

Thr Arg Lys Thr Ser Glu Arg Ser Gln Pro Arg Gly Arg Arg Gln Pro
                50                  55                  60

Ile Pro Lys Asp Arg Arg Pro Thr Gly Lys Ser Trp Gly Lys Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
                100                 105                 110

Arg His Arg Ser Arg Asn Leu Gly Lys Val Ile Asp Thr Leu Thr Cys
                115                 120                 125

Gly Phe Ala Asp Leu Met Gly Tyr Ile Pro Val Val Gly Ala Pro Val
130                 135                 140

Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Ile Thr Val Pro Val Ser Gly Leu
                180                 185                 190
```

```
Gln Val Lys Asn Thr Ser Ser Tyr Met Val Thr Asn Asp Cys Gln
            195                 200                 205

Asn Ser Ser Ile Val Trp Gln Leu Arg Asp Ala Val Leu His Val Pro
210                 215                 220

Gly Cys Val Pro Cys Glu Glu Lys Gly Asn Ile Ser Arg Cys Trp Ile
225                 230                 235                 240

Pro Val Ser Pro Asn Ile Ala Val Ser Gln Pro Gly Ala Leu Thr Lys
                245                 250                 255

Gly Leu Arg Thr His Ile Asp Thr Ile Ile Ala Ser Ala Thr Phe Cys
            260                 265                 270

Ser Ala Leu Tyr Ile Gly Asp Leu Cys Gly Ala Val Met Leu Ala Ser
            275                 280                 285

Gln Val Phe Ile Ile Ser Pro Gln His His Lys Phe Val Gln Asp Cys
            290                 295                 300

Asn Cys Ser Ile Tyr Pro Gly His Ile Thr Gly His Arg Met Ala
305                 310                 315

<210> SEQ ID NO 235
<211> LENGTH: 419
<212> TYPE: PRT
<213> ORGANISM: hepatitis C virus

<400> SEQUENCE: 235

Met Ser Thr Leu Pro Lys Pro Gln Arg Gln Thr Lys Arg Asn Thr Leu
1               5                   10                  15

Arg Arg Pro Gln Asn Val Lys Phe Pro Gly Gly Gln Ile Val Gly
            20                  25                  30

Gly Val Tyr Val Leu Pro Arg Arg Gly Pro Arg Leu Gly Val Arg Ala
            35                  40                  45

Val Arg Lys Thr Ser Glu Arg Ser Gln Pro Arg Lys Gln Arg His Leu
50                  55                  60

Ile Pro Lys Ala Arg Ser Arg Glu Gly Arg Ser Trp Ala Gln Pro Gly
65                  70                  75                  80

Tyr Pro Trp Pro Leu Tyr Gly Asn Lys Gly Cys Gly Leu Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Phe Gly Lys Val Ile Asp Thr Leu Thr Cys
            115                 120                 125

Gly Phe Ala Asp Leu Met Gly Tyr Ile Pro Leu Val Gly Ala Pro Val
130                 135                 140

Gly Gly Val Ala Arg Ala Leu Ala His Gly Val Arg Ala Leu Gly Asp
145                 150                 155                 160

Gly Val Asn Tyr Ala Thr Gly Asn Leu Pro Gly Cys Ser Phe Ser Ile
                165                 170                 175

Phe Leu Leu Ala Leu Phe Ser Cys Leu Thr Cys Pro Ala Ser Gly Leu
            180                 185                 190

Glu Tyr Thr Asn Thr Ser Gly Leu Tyr Val Leu Thr Asn Asp Cys Ser
            195                 200                 205

Asn Gly Ser Ile Val Tyr Glu Ala Glu Asp Val Ile Leu His Leu Pro
210                 215                 220

Gly Cys Val Pro Cys Val Thr Thr Gly Asn Gln Ser Ser Cys Trp Thr
225                 230                 235                 240

Thr Val Ser Thr Thr Val Ala Val Arg Thr Leu Gly Val Thr Thr Ala
                245                 250                 255
```

```
Ser Ile Arg Thr His Val Asp Met Leu Val Gly Ala Arg Gln Leu Cys
            260                 265                 270

Ser Ala Leu Tyr Val Gly Asp Ala Phe Gly Ala Val Phe Leu Val Gly
            275                 280                 285

Gln Ala Phe Thr Phe Arg Pro Arg His Thr Thr Val Gln Thr Cys
            290                 295                 300

Asn Cys Ser Ile Tyr Pro Gly His Val Ser Gly His Arg Met Ala Trp
305                 310                 315                 320

Asp Met Met Met Asn Trp Ser Pro Thr Ile Gly Leu Val Ile Ser His
                325                 330                 335

Leu Met Arg Leu Pro Gln Thr Leu Phe Asp Leu Val Ser Gly Thr His
                340                 345                 350

Trp Gly Val Met Ala Gly Leu Ala Tyr Phe Ser Met Gln Gly Asn Trp
                355                 360                 365

Ala Lys Val Val Ile Val Leu Ile Met Phe Ser Gly Val Asp Ala Asn
            370                 375                 380

Thr Tyr Thr Thr Ala Gly Ser Met Ala Gln Ser Ile Tyr Arg Leu Thr
385                 390                 395                 400

Asp Ile Phe Ser Thr Gly Pro Ser Gln Lys Leu Gln Leu Val Asn Ser
                405                 410                 415

Asn Gly Ser

<210> SEQ ID NO 236
<211> LENGTH: 383
<212> TYPE: PRT
<213> ORGANISM: hepatitis C virus

<400> SEQUENCE: 236

Met Ser Thr Asn Pro Lys Pro Gln Arg Lys Thr Lys Arg Asn Thr Asn
1               5                   10                  15

Arg Arg Pro Met Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Gln Leu Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Val Val Gly Ala Pro Val
    130                 135                 140

Gly Gly Val Ala Arg Ala Leu Ala His Gly Val Arg Leu Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Asn Tyr Arg Asn Ser Ser Gly Val Tyr His Val Thr Asn Asp Cys Pro
        195                 200                 205
```

```
Asn Ser Ser Ile Val Tyr Glu Thr Asp Tyr His Ile Leu His Leu Pro
    210                 215                 220

Gly Cys Val Pro Cys Val Arg Glu Gly Asn Lys Ser Thr Cys Trp Val
225                 230                 235                 240

Ser Leu Thr Pro Thr Val Ala Ala Gln His Leu Asn Ala Pro Leu Glu
            245                 250                 255

Ser Leu Arg Arg His Val Asp Leu Met Val Gly Gly Ala Thr Leu Cys
        260                 265                 270

Ser Ala Leu Tyr Ile Gly Asp Val Cys Gly Gly Val Phe Leu Val Gly
    275                 280                 285

Gln Leu Phe Thr Phe Gln Pro Arg Arg His Trp Thr Thr Gln Asp Cys
290                 295                 300

Asn Cys Ser Ile Tyr Thr Gly His Ile Thr Gly His Arg Met Ala Trp
305                 310                 315                 320

Asp Met Met Met Asn Trp Ser Pro Thr Ala Thr Leu Val Leu Ala Gln
            325                 330                 335

Leu Met Arg Ile Pro Gly Ala Met Val Asp Leu Leu Ala Gly Gly His
        340                 345                 350

Trp Gly Ile Leu Val Gly Ile Ala Tyr Phe Ser Met Gln Ala Asn Trp
    355                 360                 365

Ala Lys Val Ile Leu Val Leu Phe Leu Phe Ala Gly Val Asp Ala
370                 375                 380

<210> SEQ ID NO 237
<211> LENGTH: 319
<212> TYPE: PRT
<213> ORGANISM: hepatitis C virus
<220> FEATURE:
<221> NAME/KEY: MISC_FEATURE
<222> LOCATION: (102)..(102)
<223> OTHER INFORMATION: Xaa represents any amino acid
<220> FEATURE:
<221> NAME/KEY: MISC_FEATURE
<222> LOCATION: (105)..(105)
<223> OTHER INFORMATION: Xaa represents any amino acid
<220> FEATURE:
<221> NAME/KEY: MISC_FEATURE
<222> LOCATION: (114)..(114)
<223> OTHER INFORMATION: Xaa represents any amino acid

<400> SEQUENCE: 237

Met Ser Thr Asn Pro Lys Pro Gln Arg Lys Thr Lys Arg Asn Thr Asn
1               5                   10                  15

Arg Arg Pro Met Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Thr Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Xaa Ser Arg Xaa Ser Trp Gly Pro Asn Asp Pro
            100                 105                 110

Arg Xaa Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
```

-continued

```
            130                 135                 140
Gly Gly Val Ala Arg Ala Leu Ala His Gly Val Arg Ala Val Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Val Pro Thr Ser Ala Val
                180                 185                 190

Asn Tyr Arg Asn Ala Ser Gly Ile Tyr His Ile Thr Asn Asp Cys Pro
            195                 200                 205

Asn Ala Ser Ile Val Tyr Glu Thr Glu Asn His Ile Leu His Leu Pro
210                 215                 220

Gly Cys Val Pro Cys Val Arg Thr Gly Asn Gln Ser Arg Cys Trp Val
225                 230                 235                 240

Ala Leu Thr Pro Thr Val Ala Ser Pro Tyr Ala Gly Ala Pro Leu Glu
                245                 250                 255

Pro Leu Arg Arg His Val Asp Leu Met Val Gly Ala Ala Thr Met Cys
            260                 265                 270

Ser Ala Leu Tyr Ile Gly Asp Leu Cys Gly Gly Leu Phe Leu Val Gly
            275                 280                 285

Gln Met Phe Thr Phe Gln Pro Arg Arg His Trp Thr Thr Gln Asp Cys
290                 295                 300

Asn Cys Ser Ile Tyr Thr Gly His Ile Thr Gly His Arg Met Ala
305                 310                 315

<210> SEQ ID NO 238
<211> LENGTH: 319
<212> TYPE: PRT
<213> ORGANISM: hepatitis C virus

<400> SEQUENCE: 238

Met Ser Thr Asn Pro Lys Leu Gln Arg Lys Thr Lys Arg Asn Thr Asn
1               5                   10                  15

Arg Arg Pro Met Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
130                 135                 140

Gly Gly Val Ala Arg Ala Leu Ala His Gly Val Arg Ala Val Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Gly Val
                180                 185                 190
```

```
Asn Tyr Arg Asn Ala Ser Gly Val Tyr His Ile Thr Asn Asp Cys Pro
        195                 200                 205

Asn Ala Ser Ile Val Tyr Glu Thr Asp Asn His Ile Leu His Leu Pro
        210                 215                 220

Gly Cys Val Pro Cys Val Lys Thr Gly Asn Gln Ser Arg Cys Trp Val
225                 230                 235                 240

Ala Leu Thr Pro Thr Val Ala Ser Pro Tyr Val Gly Ala Pro Leu Glu
        245                 250                 255

Pro Leu Arg Arg His Val Asp Leu Met Val Gly Ala Ala Thr Val Cys
        260                 265                 270

Ser Ala Leu Tyr Val Gly Asp Leu Cys Gly Gly Leu Phe Leu Val Gly
        275                 280                 285

Gln Met Phe Thr Phe Gln Pro Arg Arg His Trp Thr Thr Gln Asp Cys
        290                 295                 300

Asn Cys Ser Ile Tyr Ala Gly His Ile Thr Gly His Arg Met Ala
305                 310                 315

<210> SEQ ID NO 239
<211> LENGTH: 319
<212> TYPE: PRT
<213> ORGANISM: hepatitis C virus

<400> SEQUENCE: 239

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
        20                  25                  30

Gly Val Tyr Leu Leu Pro Arg Arg Gly Pro Arg Met Gly Val Arg Ala
        35                  40                  45

Thr Arg Lys Thr Ser Glu Arg Ser Gln Pro Arg Gly Arg Arg Gln Pro
        50                  55                  60

Ile Pro Lys Ala Arg Gln Pro Thr Gly Arg Ser Trp Gly Gln Pro Gly
65                  70                  75                  80

Tyr Pro Trp Pro Leu Tyr Ala Asn Glu Gly Leu Gly Trp Ala Gly Trp
                85                  90                  95

Leu Leu Ser Pro Arg Gly Ser Arg Pro Asn Trp Gly Pro Asn Asp Pro
            100                 105                 110

Arg Arg Lys Ser Arg Asn Leu Gly Lys Val Ile Asp Thr Leu Thr Cys
        115                 120                 125

Gly Phe Ala Asp Leu Met Gly Tyr Ile Pro Leu Val Gly Gly Pro Ile
        130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Ile Leu Ala Leu Leu Ser Cys Leu Thr Val Pro Ala Ser Ala Val
            180                 185                 190

Pro Tyr Arg Asn Ala Ser Gly Ile Tyr His Val Thr Asn Asp Cys Pro
        195                 200                 205

Asn Ser Ser Ile Val Tyr Glu Ala Asp Asn Leu Ile Leu His Ala Pro
        210                 215                 220

Gly Cys Val Pro Cys Val Met Thr Gly Asn Val Ser Arg Cys Trp Val
225                 230                 235                 240

Gln Ile Thr Pro Thr Leu Ser Ala Pro Ser Leu Gly Ala Val Thr Ala
        245                 250                 255
```

-continued

```
Pro Leu Arg Arg Ala Val Asp Tyr Leu Ala Gly Gly Ala Ala Leu Cys
            260                 265                 270

Ser Ala Leu Tyr Val Gly Asp Ala Cys Gly Ala Leu Phe Leu Val Gly
        275                 280                 285

Gln Met Phe Thr Tyr Arg Pro Arg Gln His Ala Thr Val Gln Asn Cys
    290                 295                 300

Asn Cys Ser Ile Tyr Ser Gly His Val Thr Gly His Arg Met Ala
305                 310                 315

<210> SEQ ID NO 240
<211> LENGTH: 383
<212> TYPE: PRT
<213> ORGANISM: hepatitis C virus

<400> SEQUENCE: 240

Met Ser Thr Leu Pro Lys Pro Gln Arg Lys Thr Lys Arg Asn Thr Asn
1               5                   10                  15

Arg Arg Pro Thr Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Gln Pro Gln Gly Arg His Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro His Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Val Val Gly Ala Pro Leu
    130                 135                 140

Gly Gly Val Ala Ala Ala Leu Ala His Gly Val Arg Ala Ile Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Thr Pro Ala Ser Ala Leu
            180                 185                 190

Thr Tyr Gly Asn Ser Ser Gly Leu Tyr His Leu Thr Asn Asp Cys Pro
        195                 200                 205

Asn Ser Ser Ile Val Leu Glu Ala Asp Ala Met Ile Leu His Leu Pro
    210                 215                 220

Gly Cys Leu Pro Cys Val Arg Val Asp Asp Arg Ser Thr Cys Trp His
225                 230                 235                 240

Ala Val Thr Pro Thr Leu Ala Ile Pro Asn Ala Ser Thr Pro Ala Thr
                245                 250                 255

Gly Phe Arg Arg His Val Asp Leu Leu Ala Gly Ala Ala Val Val Cys
            260                 265                 270

Ser Ser Leu Tyr Ile Gly Asp Leu Cys Gly Ser Leu Phe Leu Ala Gly
        275                 280                 285

Gln Leu Phe Thr Phe Gln Pro Arg Arg His Trp Thr Val Gln Asp Cys
    290                 295                 300

Asn Cys Ser Ile Tyr Thr Gly His Val Thr Gly His Arg Met Ala Trp
```

```
                            305                 310                 315                 320
Asp Met Met Met Asn Trp Ser Pro Thr Thr Thr Leu Val Leu Ser Ser
                325                 330                 335
Ile Leu Arg Val Pro Glu Ile Cys Ala Ser Val Ile Phe Gly Gly His
            340                 345                 350
Trp Gly Ile Leu Leu Ala Val Ala Tyr Phe Gly Met Ala Gly Asn Trp
        355                 360                 365
Leu Lys Val Leu Ala Val Leu Phe Leu Phe Ala Gly Val Glu Ala
    370                 375                 380

<210> SEQ ID NO 241
<211> LENGTH: 193
<212> TYPE: PRT
<213> ORGANISM: hepatitis C virus

<400> SEQUENCE: 241

Thr Cys Gly Phe Ala Asp Leu Met Gly Tyr Ile Pro Leu Val Gly Ala
1               5                   10                  15
Pro Val Gly Gly Val Ala Arg Ala Leu Glu His Gly Val Arg Ala Val
            20                  25                  30
Glu Asp Gly Ile Asn Tyr Ala Thr Gly Asn Leu Pro Gly Cys Ser Phe
        35                  40                  45
Ser Ile Ser Leu Leu Ala Leu Leu Ser Cys Leu Thr Val Pro Thr Ser
    50                  55                  60
Ala Val Asn Tyr Arg Asn Ala Ser Gly Val Tyr His Ile Thr Asn Asp
65                  70                  75                  80
Cys Pro Asn Ser Ser Ile Val Tyr Glu Ala Asp Tyr His Ile Leu His
                85                  90                  95
Leu Pro Gly Cys Leu Pro Cys Val Arg Val Gly Asn Gln Ser Arg Cys
            100                 105                 110
Trp Val Ala Leu Thr Pro Thr Val Ala Ala Pro Tyr Val Gly Ala Pro
        115                 120                 125
Leu Glu Ser Leu Arg Ser His Val Asp Leu Met Val Gly Ala Ala Thr
    130                 135                 140
Val Cys Ser Ala Leu Tyr Ile Gly Asp Leu Cys Gly Gly Val Phe Leu
145                 150                 155                 160
Val Gly Gln Met Phe Ser Phe Gln Pro Arg Arg His Trp Thr Thr Gln
                165                 170                 175
Asp Cys Asn Cys Ser Ile Tyr Ala Gly His Val Thr Gly His Arg Met
            180                 185                 190
Ala

<210> SEQ ID NO 242
<211> LENGTH: 193
<212> TYPE: PRT
<213> ORGANISM: hepatitis C virus

<400> SEQUENCE: 242

Thr Cys Gly Phe Ala Asp Leu Met Gly Tyr Ile Pro Leu Val Gly Ala
1               5                   10                  15
Pro Val Gly Gly Val Ala Arg Ala Leu Ala His Gly Val Arg Ala Val
            20                  25                  30
Glu Asp Gly Ile Asn Tyr Ala Thr Gly Asn Leu Pro Gly Cys Ser Phe
        35                  40                  45
Ser Ile Phe Leu Leu Ala Leu Leu Ser Cys Leu Thr Val Pro Ala Ser
    50                  55                  60
```

```
Ala Val His Tyr His Asn Thr Ser Gly Ile Tyr His Leu Thr Asn Asp
 65                  70                  75                  80

Cys Pro Asn Ser Ser Ile Val Phe Glu Ala Val His Ile Leu His
                 85                  90                  95

Leu Pro Gly Cys Val Pro Cys Val Arg Thr Gly Asn Gln Ser Arg Cys
                100                 105                 110

Trp Val Ala Leu Thr Pro Thr Leu Ala Ala Pro Tyr Leu Gly Ala Pro
                115                 120                 125

Leu Glu Ser Met Arg Arg His Val Asp Leu Met Val Gly Thr Ala Thr
                130                 135                 140

Leu Cys Ser Ala Leu Tyr Val Gly Asp Leu Cys Gly Gly Ile Phe Leu
145                 150                 155                 160

Ala Gly Gln Met Phe Thr Phe Arg Pro Arg Leu His Trp Thr Thr Gln
                165                 170                 175

Glu Cys Asn Cys Ser Thr Tyr Pro Gly His Ile Thr Gly His Arg Met
                180                 185                 190

Ala

<210> SEQ ID NO 243
<211> LENGTH: 193
<212> TYPE: PRT
<213> ORGANISM: hepatitis C virus

<400> SEQUENCE: 243

Thr Cys Gly Phe Ala Asp Leu Met Gly Tyr Ile Pro Leu Val Gly Ala
 1               5                  10                  15

Pro Val Gly Gly Val Ala Arg Ala Leu Ala His Gly Val Arg Ala Val
                20                  25                  30

Glu Asp Gly Ile Asn Tyr Ala Thr Gly Asn Leu Pro Gly Cys Ser Phe
                35                  40                  45

Ser Ile Phe Leu Leu Ala Leu Leu Ser Cys Leu Thr Val Pro Ala Ser
        50                  55                  60

Ala Gln His Tyr Arg Asn Ile Ser Gly Ile Tyr His Val Thr Asn Asp
 65                  70                  75                  80

Cys Pro Asn Ser Ser Ile Val Tyr Glu Ala Asp His His Ile Met His
                 85                  90                  95

Leu Pro Gly Cys Val Pro Cys Val Arg Thr Gly Asn Thr Ser Arg Cys
                100                 105                 110

Trp Val Pro Leu Thr Pro Thr Val Ala Ala Pro Tyr Val Gly Ala Pro
                115                 120                 125

Leu Glu Ser Met Arg Arg His Val Asp Leu Met Val Gly Ala Ala Thr
                130                 135                 140

Val Cys Ser Ala Leu Tyr Ile Gly Asp Leu Cys Gly Gly Val Phe Leu
145                 150                 155                 160

Val Gly Gln Met Phe Thr Phe Arg Pro Arg Arg His Trp Thr Thr Gln
                165                 170                 175

Asp Cys Asn Cys Ser Ile Tyr Asp Gly His Ile Thr Gly His Arg Met
                180                 185                 190

Ala

<210> SEQ ID NO 244
<211> LENGTH: 193
<212> TYPE: PRT
<213> ORGANISM: hepatitis C virus
```

-continued

```
<400> SEQUENCE: 244

Thr Cys Gly Phe Ala Asp Leu Met Gly Tyr Ile Pro Leu Val Gly Ala
1               5                   10                  15

Pro Val Gly Gly Val Ala Arg Ala Leu Ala His Gly Val Arg Ala Val
            20                  25                  30

Glu Asp Gly Ile Asn Tyr Ala Thr Gly Asn Leu Pro Gly Cys Ser Phe
        35                  40                  45

Ser Ile Phe Leu Leu Val Leu Leu Ser Arg Leu Thr Val Pro Ala Ser
    50                  55                  60

Ala Gln His Tyr Arg Asn Ala Ser Gly Ile Tyr His Val Thr Asn Asp
65                  70                  75                  80

Cys Pro Asn Ser Ser Ile Val Tyr Glu Ala Asp His His Ile Met His
                85                  90                  95

Leu Pro Gly Cys Val Pro Cys Val Arg Thr Gly Asn Val Ser Arg Cys
            100                 105                 110

Trp Ile Pro Leu Thr Pro Thr Val Ala Val Pro Tyr Leu Gly Ala Pro
        115                 120                 125

Leu Thr Ser Val Arg Gln His Val Asp Leu Met Val Gly Ala Ala Thr
    130                 135                 140

Leu Cys Ser Ala Leu Tyr Ile Gly Asp His Cys Gly Gly Val Phe Leu
145                 150                 155                 160

Ala Gly Gln Met Val Ser Phe Gln Pro Arg Arg His Trp Thr Thr Gln
                165                 170                 175

Asp Cys Asn Cys Ser Ile Tyr Val Gly His Ile Thr Gly His Arg Met
            180                 185                 190

Ala

<210> SEQ ID NO 245
<211> LENGTH: 149
<212> TYPE: PRT
<213> ORGANISM: hepatitis C virus
<220> FEATURE:
<221> NAME/KEY: MISC_FEATURE
<222> LOCATION: (14)..(14)
<223> OTHER INFORMATION: Xaa represents any amino acid
<220> FEATURE:
<221> NAME/KEY: MISC_FEATURE
<222> LOCATION: (20)..(20)
<223> OTHER INFORMATION: Xaa represents any amino acid
<220> FEATURE:
<221> NAME/KEY: MISC_FEATURE
<222> LOCATION: (120)..(120)
<223> OTHER INFORMATION: Xaa represents any amino acid
<220> FEATURE:
<221> NAME/KEY: MISC_FEATURE
<222> LOCATION: (134)..(134)
<223> OTHER INFORMATION: Xaa represents any amino acid

<400> SEQUENCE: 245

Asp Gly Ile Asn Tyr Ala Thr Gly Asn Ile Pro Gly Cys Xaa Phe Ser
1               5                   10                  15

Ile Phe Leu Xaa Ala Leu Leu Ser Cys Leu Thr Val Pro Ala Ser Ala
            20                  25                  30

Thr Asn Tyr Arg Asn Val Ser Gly Ile Tyr His Val Thr Asn Asp Cys
        35                  40                  45

Pro Asn Ser Ser Ile Val Tyr Glu Ala Asp His His Ile Leu Ala Leu
    50                  55                  60

Pro Gly Cys Val Pro Cys Val Arg Val Gly Asn Gln Ser Arg Cys Trp
65                  70                  75                  80
```

```
Val Ala Leu Thr Pro Thr Val Ala Ala Pro Tyr Thr Ala Ala Pro Leu
                85                  90                  95

Glu Ser Leu Arg Ser His Val Asp Leu Met Val Gly Ala Ala Thr Val
            100                 105                 110

Cys Ser Ala Leu Tyr Ile Gly Xaa Leu Cys Gly Gly Leu Phe Leu Val
        115                 120                 125

Gly Gln Met Phe Ser Xaa Gln Pro Arg Arg His Trp Thr Thr Gln Asp
    130                 135                 140

Cys Asn Cys Ser Ile
145

<210> SEQ ID NO 246
<211> LENGTH: 119
<212> TYPE: PRT
<213> ORGANISM: hepatitis C virus

<400> SEQUENCE: 246

Tyr His Ile Thr Asn Asp Cys Pro Asn Ser Ser Val Val Tyr Glu Thr
1               5                   10                  15

Asp His His Ile Leu His Leu Pro Gly Cys Val Pro Cys Val Arg Thr
            20                  25                  30

Gly Asn Val Ser Arg Cys Trp Thr Pro Val Thr Pro Thr Val Ala Ala
        35                  40                  45

Val Ser Val Asp Ala Pro Leu Glu Ser Phe Arg Arg His Val Asp Leu
    50                  55                  60

Met Val Gly Ala Ala Thr Leu Cys Ser Val Leu Tyr Val Gly Asp Leu
65                  70                  75                  80

Cys Gly Gly Ala Phe Leu Val Gly Gln Met Phe Thr Phe Gln Pro Arg
                85                  90                  95

Arg His Trp Thr Thr Gln Asp Cys Asn Cys Ser Ile Tyr Thr Gly His
            100                 105                 110

Ile Thr Gly His Arg Met Ala
        115

<210> SEQ ID NO 247
<211> LENGTH: 94
<212> TYPE: PRT
<213> ORGANISM: hepatitis C virus

<400> SEQUENCE: 247

Pro Gln Arg Lys Thr Lys Arg Asn Thr Ile Arg Arg Pro Gln Asp Val
1               5                   10                  15

Lys Phe Pro Gly Gly Gly Gln Ile Val Gly Gly Val Tyr Val Leu Pro
            20                  25                  30

Arg Arg Gly Pro Arg Leu Gly Val Cys Ala Thr Arg Lys Thr Ser Glu
        35                  40                  45

Arg Ser Gln Pro Arg Gly Arg Arg Gln Pro Ile Pro Lys Ala Arg Arg
    50                  55                  60

Ser Glu Gly Arg Ser Trp Ala Gln Pro Gly Tyr Pro Trp Pro Leu Tyr
65                  70                  75                  80

Gly Asn Glu Gly Cys Gly Trp Ala Gly Trp Leu Leu Ser Pro
                85                  90

<210> SEQ ID NO 248
<211> LENGTH: 100
<212> TYPE: PRT
<213> ORGANISM: hepatitis C virus
```

-continued

```
<400> SEQUENCE: 248

Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Gln Ile Val Gly
            20                  25                  30

Gly Val Tyr Val Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro
            100

<210> SEQ ID NO 249
<211> LENGTH: 100
<212> TYPE: PRT
<213> ORGANISM: hepatitis C virus

<400> SEQUENCE: 249

Met Ser Thr Asn Pro Lys Pro Gln Arg Lys Thr Lys Arg Asn Thr Asn
1               5                   10                  15

Arg Arg Pro Met Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro
            100

<210> SEQ ID NO 250
<211> LENGTH: 68
<212> TYPE: PRT
<213> ORGANISM: hepatitis C virus

<400> SEQUENCE: 250

Thr Asn Arg Arg Pro Thr Asp Val Lys Phe Pro Gly Gly Gly Gln Ile
1               5                   10                  15

Val Gly Gly Val Tyr Leu Leu Pro Arg Arg Gly Pro Arg Leu Gly Val
            20                  25                  30

Arg Ala Thr Gly Lys Thr Ser Glu Arg Ser Gln Pro Arg Gly Arg Arg
        35                  40                  45

Gln Pro Ile Pro Lys Ala Arg Arg Ser Glu Gly Arg Ser Trp Ala Gln
    50                  55                  60

Pro Gly Phe Pro
65

<210> SEQ ID NO 251
<211> LENGTH: 80
<212> TYPE: PRT
```

```
<213> ORGANISM: hepatitis C virus

<400> SEQUENCE: 251

Lys Thr Lys Arg Asn Thr Asn Arg Arg Pro Met Asp Val Lys Phe Pro
1               5                   10                  15

Gly Gly Gly Gln Ile Val Gly Val Tyr Leu Leu Pro Arg Arg Gly
            20                  25                  30

Pro Arg Leu Gly Val Arg Ala Thr Arg Lys Thr Ser Glu Arg Ser Gln
            35                  40                  45

Pro Arg Gly Arg Gln Pro Ile Pro Lys Ala Arg Arg Ser Glu Gly
            50                  55                  60

Arg Ser Trp Ala Gln Pro Gly Tyr Pro Trp Pro Leu Tyr Gly Asn Glu
65                  70                  75                  80

<210> SEQ ID NO 252
<211> LENGTH: 74
<212> TYPE: PRT
<213> ORGANISM: hepatitis C virus

<400> SEQUENCE: 252

Thr Asn Arg Arg Pro Met Asp Val Lys Phe Pro Gly Gly Gly Gln Ile
1               5                   10                  15

Val Gly Gly Val Tyr Leu Leu Pro Arg Arg Gly Pro Arg Leu Gly Val
            20                  25                  30

Arg Ala Thr Arg Lys Thr Ser Glu Arg Ser Gln Pro Arg Gly Arg Arg
            35                  40                  45

Gln Pro Ile Pro Lys Ala Arg Arg Ser Glu Gly Arg Ser Trp Ala Gln
            50                  55                  60

Pro Gly Tyr Pro Trp Pro Leu Tyr Gly Lys
65                  70

<210> SEQ ID NO 253
<211> LENGTH: 100
<212> TYPE: PRT
<213> ORGANISM: hepatitis C virus

<400> SEQUENCE: 253

Met Ser Thr Asn Pro Lys Pro Gln Arg Lys Thr Lys Arg Asn Thr Asn
1               5                   10                  15

Arg Arg Pro Met Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
            50                  55                  60

Ile Pro Lys Ala Arg Arg Ser Glu Gly Arg Ser Trp Ala Gln Ala Gly
65                  70                  75                  80

Tyr Pro Trp Pro Leu Tyr Gly Asn Glu Gly Cys Gly Trp Ala Gly Trp
            85                  90                  95

Leu Leu Ser Pro
            100

<210> SEQ ID NO 254
<211> LENGTH: 128
<212> TYPE: PRT
<213> ORGANISM: hepatitis C virus

<400> SEQUENCE: 254
```

-continued

```
Val Glu Val Lys Asp Thr Gly Asp Ser Tyr Met Pro Thr Asn Asp Cys
1               5                   10                  15

Ser Asn Ser Ser Ile Val Trp Gln Leu Glu Gly Ala Val Leu His Thr
            20                  25                  30

Pro Gly Cys Val Pro Cys Glu Arg Thr Ala Asn Val Ser Arg Cys Trp
        35                  40                  45

Val Pro Val Ala Pro Asn Leu Ala Ile Ser Gln Pro Gly Ala Leu Thr
    50                  55                  60

Lys Gly Leu Arg Ala His Ile Asp Ile Ile Val Met Ser Ala Thr Val
65                  70                  75                  80

Cys Ser Ala Leu Tyr Val Gly Asp Val Cys Gly Ala Leu Met Leu Ala
                85                  90                  95

Ala Gln Val Val Val Val Ser Pro Gln His His Thr Phe Val Gln Glu
            100                 105                 110

Cys Asn Cys Ser Ile Tyr Pro Gly Arg Ile Thr Gly His Arg Met Ala
        115                 120                 125

<210> SEQ ID NO 255
<211> LENGTH: 128
<212> TYPE: PRT
<213> ORGANISM: hepatitis C virus

<400> SEQUENCE: 255

Leu Glu Trp Arg Asn Thr Ser Gly Leu Tyr Val Leu Thr Asn Asp Cys
1               5                   10                  15

Ser Asn Ser Ser Ile Val Tyr Glu Ala Asp Asp Val Ile Leu His Thr
            20                  25                  30

Pro Gly Cys Ile Pro Cys Val Gln Asp Gly Asn Thr Ser Thr Cys Trp
        35                  40                  45

Thr Pro Val Thr Pro Thr Val Ala Val Lys Tyr Val Gly Ala Thr Thr
    50                  55                  60

Ala Ser Ile Arg Ser His Val Asp Leu Leu Val Gly Ala Ala Thr Met
65                  70                  75                  80

Cys Ser Ala Leu Tyr Val Gly Asp Met Cys Gly Ala Val Phe Leu Val
                85                  90                  95

Gly Gln Ala Phe Thr Phe Arg Pro Arg Arg His Gln Thr Val Gln Thr
            100                 105                 110

Cys Asn Cys Ser Leu Tyr Pro Gly His Leu Ser Gly His Arg Met Ala
        115                 120                 125

<210> SEQ ID NO 256
<211> LENGTH: 128
<212> TYPE: PRT
<213> ORGANISM: hepatitis C virus

<400> SEQUENCE: 256

Glu His Tyr Arg Asn Ala Ser Gly Ile Tyr His Ile Thr Asn Asp Cys
1               5                   10                  15

Pro Asn Ser Ser Ile Val Tyr Glu Ala Asp His His Ile Leu His Leu
            20                  25                  30

Pro Gly Cys Val Pro Cys Val Met Thr Gly Asn Thr Ser Arg Cys Trp
        35                  40                  45

Thr Pro Val Thr Pro Thr Val Ala Val Ala His Pro Gly Ala Pro Leu
    50                  55                  60

Glu Ser Phe Arg Arg His Val Asp Leu Met Val Gly Ala Ala Thr Leu
65                  70                  75                  80
```

```
Cys Ser Ala Leu Tyr Val Gly Asp Leu Cys Gly Gly Ala Phe Leu Met
                85                  90                  95

Gly Gln Met Ile Thr Phe Arg Pro Arg Arg His Trp Thr Thr Gln Glu
            100                 105                 110

Cys Asn Cys Ser Ile Tyr Thr Gly His Ile Thr Gly His Arg Met Ala
        115                 120                 125
```

<210> SEQ ID NO 257
<211> LENGTH: 128
<212> TYPE: PRT
<213> ORGANISM: hepatitis C virus

<400> SEQUENCE: 257

```
Glu His Tyr Arg Asn Ala Ser Gly Ile Tyr His Ile Thr Asn Asp Cys
1               5                   10                  15

Pro Asn Ser Ser Val Val Tyr Glu Thr Asp His His Ile Leu His Leu
            20                  25                  30

Pro Gly Cys Val Pro Cys Val Arg Ala Gly Asn Val Ser Arg Cys Trp
        35                  40                  45

Thr Pro Val Thr Pro Thr Val Ala Ala Val Ser Met Asp Ala Pro Leu
    50                  55                  60

Glu Ser Phe Arg Arg His Val Asp Leu Met Val Gly Ala Ala Thr Val
65                  70                  75                  80

Cys Ser Val Leu Tyr Val Gly Asp Leu Cys Gly Gly Ala Phe Leu Val
                85                  90                  95

Gly Gln Met Phe Thr Phe Gln Pro Arg Arg His Trp Thr Thr Gln Asp
            100                 105                 110

Cys Asn Cys Ser Ile Tyr Thr Gly His Ile Thr Gly His Arg Met Ala
        115                 120                 125
```

<210> SEQ ID NO 258
<211> LENGTH: 128
<212> TYPE: PRT
<213> ORGANISM: hepatitis C virus

<400> SEQUENCE: 258

```
Val His Tyr Arg Asn Ala Ser Gly Val Tyr His Val Thr Asn Asp Cys
1               5                   10                  15

Pro Asn Thr Ser Ile Val Tyr Glu Thr Glu His His Ile Met His Leu
            20                  25                  30

Pro Gly Cys Val Pro Cys Val Arg Thr Glu Asn Thr Ser Arg Cys Trp
        35                  40                  45

Val Pro Leu Thr Pro Thr Val Ala Ala Pro Tyr Pro Asn Ala Pro Leu
    50                  55                  60

Glu Ser Met Arg Arg His Val Asp Leu Met Val Gly Ala Ala Thr Met
65                  70                  75                  80

Cys Ser Ala Phe Tyr Ile Gly Asp Leu Cys Gly Gly Val Phe Leu Val
                85                  90                  95

Gly Gln Leu Phe Asp Phe Arg Pro Arg Arg His Trp Thr Thr Gln Asp
            100                 105                 110

Cys Asn Cys Ser Ile Tyr Pro Gly His Val Ser Gly His Arg Met Ala
        115                 120                 125
```

<210> SEQ ID NO 259
<211> LENGTH: 128
<212> TYPE: PRT
<213> ORGANISM: hepatitis C virus -continued

```
<400> SEQUENCE: 259

Ile His Tyr Arg Asn Ala Ser Gly Val Tyr His Val Thr Asn Asp Cys
  1               5                  10                  15

Pro Asn Ser Ser Ile Val Tyr Glu Ala Asp His His Ile Leu His Leu
                 20                  25                  30

Pro Gly Cys Leu Pro Cys Val Arg Val Gly Asn Gln Ser Arg Cys Trp
             35                  40                  45

Val Ala Leu Ser Pro Thr Val Ala Pro Tyr Ile Gly Ala Pro Val
         50                  55                  60

Glu Ser Phe Arg Arg His Val Asp Met Met Val Gly Ala Ala Thr Val
 65                  70                  75                  80

Cys Ser Ala Leu Tyr Ile Gly Asp Leu Cys Gly Gly Val Phe Leu Val
                 85                  90                  95

Gly Gln Met Phe Ser Phe Arg Pro Arg His Trp Thr Thr Gln Asp
                100                 105                 110

Cys Asn Cys Ser Ile Tyr Ala Gly His Ile Thr Gly His Gly Met Ala
                115                 120                 125

<210> SEQ ID NO 260
<211> LENGTH: 128
<212> TYPE: PRT
<213> ORGANISM: hepatitis C virus

<400> SEQUENCE: 260

Val Asn Tyr Arg Asn Ala Ser Gly Ile Tyr His Ile Thr Asn Asp Cys
  1               5                  10                  15

Pro Asn Ser Ser Ile Val Tyr Glu Thr Glu His His Ile Leu His Leu
                 20                  25                  30

Pro Gly Cys Leu Pro Cys Val Arg Val Gly Asn Gln Ser Arg Cys Trp
             35                  40                  45

Val Ala Leu Thr Pro Thr Val Ala Ala Pro Tyr Ile Gly Ala Pro Leu
         50                  55                  60

Glu Ser Leu Arg Ser His Val Asp Leu Met Val Gly Ala Ala Thr Ala
 65                  70                  75                  80

Cys Ser Ala Leu Tyr Ile Gly Asp Leu Cys Gly Gly Val Phe Leu Val
                 85                  90                  95

Gly Gln Met Phe Ser Phe Gln Pro Arg Arg His Trp Thr Thr Gln Asp
                100                 105                 110

Cys Asn Cys Ser Ile Tyr Ala Gly His Val Thr Gly His Arg Met Ala
                115                 120                 125

<210> SEQ ID NO 261
<211> LENGTH: 169
<212> TYPE: PRT
<213> ORGANISM: hepatitis C virus

<400> SEQUENCE: 261

Leu Ala His Gly Val Arg Ala Val Glu Asp Gly Ile Asn Tyr Ala Thr
  1               5                  10                  15

Gly Asn Leu Pro Gly Cys Ser Phe Ser Ile Phe Leu Leu Ala Leu Leu
                 20                  25                  30

Ser Cys Leu Thr Val Pro Ala Ser Ala Val His Tyr His Asn Thr Ser
             35                  40                  45

Gly Ile Tyr His Leu Thr Asn Asp Cys Pro Asn Ser Ser Ile Val Phe
         50                  55                  60

Glu Ala Val His His Ile Leu His Leu Pro Gly Cys Val Pro Cys Val
```

```
                 65                  70                  75                  80
Arg Thr Gly Asn Gln Ser Arg Cys Trp Val Ala Leu Thr Pro Thr Leu
                85                  90                  95
Ala Ala Pro Tyr Leu Gly Ala Pro Leu Glu Ser Met Arg Arg His Val
               100                 105                 110
Asp Leu Met Val Gly Thr Ala Thr Leu Cys Ser Ala Leu Tyr Val Gly
               115                 120                 125
Asp Leu Cys Gly Gly Ile Phe Leu Ala Gly Gln Met Phe Thr Phe Arg
               130                 135                 140
Pro Arg Leu His Trp Thr Thr Gln Glu Cys Asn Cys Ser Thr Tyr Pro
145                 150                 155                 160
Gly His Ile Thr Gly His Arg Met Ala
                165

<210> SEQ ID NO 262
<211> LENGTH: 128
<212> TYPE: PRT
<213> ORGANISM: hepatitis C virus

<400> SEQUENCE: 262

Val His Tyr His Asn Thr Ser Gly Ile Tyr His Ile Thr Asn Asp Cys
1               5                  10                  15
Pro Asn Ser Ser Ile Val Phe Glu Ala Glu His His Ile Leu His Leu
                20                  25                  30
Pro Gly Cys Val Pro Cys Val Arg Thr Gly Asn Gln Ser Arg Cys Trp
            35                  40                  45
Ile Ala Leu Thr Pro Thr Leu Ala Ala Pro His Ile Gly Ala Pro Leu
        50                  55                  60
Glu Ser Met Arg Arg His Val Asp Leu Met Val Gly Thr Ala Thr Leu
65                  70                  75                  80
Cys Ser Ala Leu Tyr Ile Gly Asp Leu Cys Gly Gly Ile Phe Leu Val
                85                  90                  95
Gly Gln Met Phe Asn Phe Arg Pro Arg Leu His Trp Thr Thr Gln Glu
               100                 105                 110
Cys Asn Cys Ser Ile Tyr Pro Gly His Ile Thr Gly His Arg Met Ala
               115                 120                 125

<210> SEQ ID NO 263
<211> LENGTH: 128
<212> TYPE: PRT
<213> ORGANISM: hepatitis C virus

<400> SEQUENCE: 263

Val Pro Tyr Arg Asn Ala Ser Gly Ile Tyr His Val Thr Asn Asp Cys
1               5                  10                  15
Pro Asn Ser Ser Ile Val Tyr Glu Ala Asp Asp Leu Ile Leu His Ala
                20                  25                  30
Pro Gly Cys Val Pro Cys Val Arg Lys Asp Asn Val Ser Arg Cys Trp
            35                  40                  45
Val Gln Ile Thr Pro Thr Leu Ser Ala Pro Ser Phe Gly Ala Val Thr
        50                  55                  60
Ala Pro Leu Arg Arg Ala Val Asp Tyr Leu Val Gly Ala Ala Leu
65                  70                  75                  80
Cys Ser Ala Leu Tyr Val Gly Asp Ala Cys Gly Ala Leu Phe Leu Val
                85                  90                  95
Gly Gln Met Phe Thr Tyr Arg Pro Arg Gln His Ala Thr Val Gln Asp
```

```
              100                 105                 110
Cys Asn Cys Ser Ile Tyr Ser Gly His Val Thr Gly His Gln Met Ala
         115                 120                 125
```

<210> SEQ ID NO 264
<211> LENGTH: 340
<212> TYPE: DNA
<213> ORGANISM: hepatitis C virus

<400> SEQUENCE: 264

| | | | | | |
|---|---|---|---|---|---|
| ctccacagtc | actgagagcg | acatccgtac | ggaggaggca | atctaccaat | gttgtgacct | 60 |
| cgaccccaa | gcccgcgtgg | ccatcaagtc | cctcaccgag | aggctttatg | ttgggggccc | 120 |
| tcttaccaat | tcaagggggg | agaactgcgg | ctatcgcagg | tgccgcgcga | gcggcgtact | 180 |
| gacaactagc | tgtggtaaca | ccctcacttg | ctacatcaag | gcccgggcag | cctgtcgagc | 240 |
| cgcagggctc | caggactgca | ccatgctcgt | gtgtggcgac | gacttagtcg | ttatctgtga | 300 |
| aagcgcgggg | gtccaggagg | acgcggcgag | cctgagagcc | | | 340 |

<210> SEQ ID NO 265
<211> LENGTH: 340
<212> TYPE: DNA
<213> ORGANISM: hepatitis C virus

<400> SEQUENCE: 265

| | | | | | |
|---|---|---|---|---|---|
| ctcaacggtc | actgagaatg | acatccgtac | tgaggaatca | atttaccaat | gttgtgactt | 60 |
| ggcccccgaa | gccaggcagg | ccataaggtc | gctcacagag | cggctttatg | tcggggggtcc | 120 |
| cctgactaat | tcgaaggggc | agaactgcgg | ttatcgccgg | tgccgcgcaa | gtggcgtgct | 180 |
| gacgactagc | tgcggcaaca | ccctcacatg | ttacttgaag | gccactgcgg | cctgtcgagc | 240 |
| tgcaaagctc | caggactgca | cgatgctcgt | gaacggagac | gaccttgtcg | ttatctgtga | 300 |
| gagtgcggga | acccaggagg | atgcggcggc | cctacgagcc | | | 340 |

<210> SEQ ID NO 266
<211> LENGTH: 340
<212> TYPE: DNA
<213> ORGANISM: hepatitis C virus
<220> FEATURE:
<221> NAME/KEY: misc_feature
<222> LOCATION: (1)..(1)
<223> OTHER INFORMATION: n represents any nucleotide

<400> SEQUENCE: 266

| | | | | | |
|---|---|---|---|---|---|
| ntcaacagtc | accgagaacg | acatccgtgt | tgaggagtca | atttaccaat | gttgtgactt | 60 |
| ggcccccgag | gccagacagg | ccataaagtc | gctcacagag | cggctttata | tcggggggtcc | 120 |
| cctgactaat | tcaagggggc | agaactgtgg | ctatcgccga | tgccgcgcaa | gcggcgtgct | 180 |
| gacgaccagc | tgcggtaata | cccttacatg | ttacctaaag | gcctctgcag | cctgtcgagc | 240 |
| tgcgaagctc | caggactgca | cgatgctcgt | gtgcggggac | gaccttgtcg | ttatctgtga | 300 |
| aagcgcggga | acccaagagg | acgcggcgag | cctacgagtc | | | 340 |

<210> SEQ ID NO 267
<211> LENGTH: 340
<212> TYPE: DNA
<213> ORGANISM: hepatitis C virus

<400> SEQUENCE: 267

| | | | | | |
|---|---|---|---|---|---|
| ctcaaccgtc | actgagagag | acatcaggac | tgaggagtcc | atatatcggg | cttgttcctt | 60 |

```
gcccgaggag gcccacactg ccatacactc actgactgag agactttacg tgggagggcc      120
catgttcaac agcaagggcc agacctgcgg gtacaggcgt tgccgcgcca gcgggtgtgct     180 taccactagc atgggaaca ccatcacatg ctatgtgaaa gccttagcgg cctgtaaggc       240
tgcagggata attgcgccca caatgctggt atgcggcgat gacttggttg tcatctcaga     300
gagccagggg accgaggagg acgagcggaa cctgagagcc                            340
```

<210> SEQ ID NO 268
<211> LENGTH: 340
<212> TYPE: DNA
<213> ORGANISM: hepatitis C virus

<400> SEQUENCE: 268

```
ctcaaccgtc acggagaggg acataagaac agaagaatcc atatatcagg cttgttctct      60
gcctcaagaa gccagaactg tcatacactc gctcactgag agactttacg taggagggcc     120
catgacaaac agcaagggc aatcctgcgg ctacaggcgt tgccgcgcaa gcggtgtttt      180
caccaccagc atgggaata ccatgacatg ttacatcaaa gcccttgcag cgtgtaaggc       240
tgcagggatc gtggaccctg ttatgttggt gtgtggagac gacctggtcg tcatctcaga     300
gagccaaggt aacgaggagg acgagcgaaa cctgagagct                            340
```

<210> SEQ ID NO 269
<211> LENGTH: 340
<212> TYPE: DNA
<213> ORGANISM: hepatitis C virus

<400> SEQUENCE: 269

```
ctcaactgtc actgaacagg acatcagggt ggaagaggag atataccaat gctgtaacct      60
tgaaccggag gccaggagag tgatctcctc cctcacggag cggctttact gcgggggccc     120
tatgttcaac agcaaggggg cccaatgtgg ttatcgccgg tgccgtgcca gtggagtcct     180
gcctaccagc ttcggcaaca caatcacttg ttacatcaag gccacagcgg ctgcgaaggc      240
cgcaggcctc cggaacccgg actttcttgt ctgcggagat gatctggtcg tagtggctga     300
gagcgatggc gtcgatgagg atagagcagc cctgagagcc                            340
```

<210> SEQ ID NO 270
<211> LENGTH: 340
<212> TYPE: DNA
<213> ORGANISM: hepatitis C virus

<400> SEQUENCE: 270

```
ctctactgtc actgaacatg acatcaggac ggaggaggag atataccaat gctgtgacct      60
tgagccagag gctcggaagg cgatcagcgc tctcacagag cggctgtaca tcggaggtcc     120
catgtacaac agtaagggc tccagtgcgg ctatcgccgc tgccgcgcca gcggcgtctt      180
gcctaccagc ttcggcaata caataacctg ttacatcaag gccactgcag ccagcagggc      240
tgcgggtctc aaagacccat ctttccttgt ctgcggagac gatttggtgg ttgtatctga     300
aagctgcggc gtcgaggagg acagagcagc tctgcgagcc                            340
```

<210> SEQ ID NO 271
<211> LENGTH: 340
<212> TYPE: DNA
<213> ORGANISM: hepatitis C virus

<400> SEQUENCE: 271

```
ctccactgta accgaaaagg acatcagggt cgaggaggag gtctatcagt gttgtgacct      60
```

```
ggagcccgaa gcccgcaagg caattaccgc cctaacagag agactctacg tgggcggtcc      120
catgcataac agcaagggag acctgtgcgg gtatcgcaga tgtcgcgcaa gcggcgtcta      180
caccaccagc ttcgggaaca cactgacgtg ctacctcaaa gcctcagccg ctatcaaagc      240
ggcggggctg agagactgca ccatgttggt ctgtggtgat gacctggttg tcatcgctga      300
gagcgatggc gtagaggagg acaaacgacc cctcggagcc                            340
```

<210> SEQ ID NO 272
<211> LENGTH: 340
<212> TYPE: DNA
<213> ORGANISM: hepatitis C virus

<400> SEQUENCE: 272

```
ctccactgta accgaaaagg acatcagggt cgaggaggag gtatatcagt gttgtgacct      60
ggagcccgag gcccgcagag caattaccgc cctaacagag agactctacg tgggcggtcc      120
catgcataac agcaggggag acctgtgcgg gtatcgcaga tgccgtgcga gcggcgtcta      180
caccaccagc ttcgggaaca cactgacgtg ctatctcaaa gcctcagccg ctatcagagc      240
ggcggggctg agagactgca ccatgttggt ctgtggtgat gacctggtcg tcattgctga      300
aagcgatggc gtagaggagg acaaacgagc cctcggagcc                            340
```

<210> SEQ ID NO 273
<211> LENGTH: 340
<212> TYPE: DNA
<213> ORGANISM: hepatitis C virus

<400> SEQUENCE: 273

```
ctccactgta accgaaaaag acatcagggt cgaggaggag gtatatcagt gttgtgacct      60
ggagcccgaa gcccgcaagg taattaccgc cctaacagag agactctatg tgggcggtcc      120
catgcataat agcaaaggag acctgtgcgg gtatcgcaga tgccgcgcaa gcggcgtcta      180
caccaccagc ttcgggaaca cactgacgtg ctatctcaaa gcctcagccg ccatcagggc      240
gtcagggctg agagactgca ctatgctggt ctatggtgac gacctggtcg tcattgccga      300
gagcgatggc gtagaggagg acaaacgagc cctcggagtc                            340
```

<210> SEQ ID NO 274
<211> LENGTH: 340
<212> TYPE: DNA
<213> ORGANISM: hepatitis C virus

<400> SEQUENCE: 274

```
ctccactgta accgaaaagg acatcagggt cgaggaggag gtgtatcagt gttgtgacct      60
ggagcccgag gcccgcaagg caattactgc cctaacagag agactctatg tgggcggtcc      120
catgcataac agcaagggag acctgtgtgg gtatcgcaga tgccgcgcaa gcggcgtcta      180
caccaccagc ttcgggaaca cactgacgtg ctacctcaaa gcctcagccg ctatcagagc      240
ggcggggctg agagactgca ccatgttggt ctgtggtgat gacctggtcg tcatcgctga      300
gagcgatggc gttgaggagg acaaacgagc cctcggagcc                            340
```

<210> SEQ ID NO 275
<211> LENGTH: 340
<212> TYPE: DNA
<213> ORGANISM: hepatitis C virus
<220> FEATURE:
<221> NAME/KEY: misc_feature
<222> LOCATION: (329)..(329)

<223> OTHER INFORMATION: n represents any nucleotide

<400> SEQUENCE: 275

```
ctccactgtg actgagagag acatcaaggt cgaagaagaa gtctatcagt gttgtgatct      60
ggagcccgag gcccgcaagg taatagccgc cctcacggag agactctacg tgggcggccc     120
catgcataac agcaagggag accctttgcgg gtatcgtaga tgccgcgcga gcggcgtata   180
caccaccagc ttcgggaaca caatgacgtg ctaccttaag gcctcagcag ccatcagggc    240
tgcggggcta aaggattgca ccatgctggt ttgcggtgac gacctagtcg tgatcgccga    300
gagcggtggc gttgaggagg acaaacganc cctcggagct                          340
```

<210> SEQ ID NO 276
<211> LENGTH: 340
<212> TYPE: DNA
<213> ORGANISM: hepatitis C virus

<400> SEQUENCE: 276

```
ctccacggtg accgaaaggg atatcaggac cgaggaagag atctaccagt gctgcgacct    60
ggagcccgaa gcccgcaagg tgatatccgc cctaacggaa agactctacg tgggcggtcc   120
catgtacaac tccaagggg acctatgcgg gcaacggagg tgccgcgcaa gcggggtcta  180
caccaccagc ttcgggaaca ctgtaacgtg ttatctcaag gccgttgcgg ctactagggc   240
cgcaggtctg aaaggttgca gcatgctggt ttgtggagac gacttagtcg tcatctgcga  300
gagcggcggc gtagaggagg atgcaagagc cctccgagcc                          340
```

<210> SEQ ID NO 277
<211> LENGTH: 340
<212> TYPE: DNA
<213> ORGANISM: hepatitis C virus

<400> SEQUENCE: 277

```
ctcgaccgtt accgaacatg acataatgac tgaagagtct atttaccaat cattgtactt    60
gcagcctgag gcgcgtgtgg caatacggtc actcacccaa cgcctgtact gtggaggccc   120
catgtataac agcaaggggc aacaatgtgg ttatcgtaga tgccgcgcca gcggcgtctt  180
caccactagt atgggcaaca ccatgacgtg ctacattaag gctttagcct cctgtagagc   240
cgcaaagctc caggactgca cgctcctggt gtgtggtgat gatcttgtgg ccatttgcga  300
gagccagggg acgcacgagg ataaagcgag cctgagagcc                          340
```

<210> SEQ ID NO 278
<211> LENGTH: 113
<212> TYPE: PRT
<213> ORGANISM: hepatitis C virus

<400> SEQUENCE: 278

```
Ser Thr Val Thr Glu Ser Asp Ile Arg Thr Glu Glu Ala Ile Tyr Gln
1               5                   10                  15

Cys Cys Asp Leu Asp Pro Gln Ala Arg Val Ala Ile Lys Ser Leu Thr
            20                  25                  30

Glu Arg Leu Tyr Val Gly Gly Pro Leu Thr Asn Ser Arg Gly Glu Asn
        35                  40                  45

Cys Gly Tyr Arg Arg Cys Arg Ala Ser Gly Val Leu Thr Thr Ser Cys
    50                  55                  60

Gly Asn Thr Leu Thr Cys Tyr Ile Lys Ala Arg Ala Ala Cys Arg Ala
65                  70                  75                  80
```

```
Ala Gly Leu Gln Asp Cys Thr Met Leu Val Cys Gly Asp Asp Leu Val
                85                  90                  95

Val Ile Cys Glu Ser Ala Gly Val Gln Glu Asp Ala Ala Ser Leu Arg
            100                 105                 110

Ala

<210> SEQ ID NO 279
<211> LENGTH: 113
<212> TYPE: PRT
<213> ORGANISM: hepatitis C virus

<400> SEQUENCE: 279

Ser Thr Val Thr Glu Asn Asp Ile Arg Thr Glu Ser Ile Tyr Gln
1               5                   10                  15

Cys Cys Asp Leu Ala Pro Glu Ala Arg Gln Ala Ile Arg Ser Leu Thr
                20                  25                  30

Glu Arg Leu Tyr Val Gly Gly Pro Leu Thr Asn Ser Lys Gly Gln Asn
            35                  40                  45

Cys Gly Tyr Arg Arg Cys Arg Ala Ser Gly Val Leu Thr Thr Ser Cys
    50                  55                  60

Gly Asn Thr Leu Thr Cys Tyr Leu Lys Ala Thr Ala Ala Cys Arg Ala
65                  70                  75                  80

Ala Lys Leu Gln Asp Cys Thr Met Leu Val Asn Gly Asp Asp Leu Val
                85                  90                  95

Val Ile Cys Glu Ser Ala Gly Thr Gln Glu Asp Ala Ala Ala Leu Arg
            100                 105                 110

Ala

<210> SEQ ID NO 280
<211> LENGTH: 74
<212> TYPE: PRT
<213> ORGANISM: hepatitis C virus

<400> SEQUENCE: 280

Ile Tyr Gln Cys Cys Asp Leu His Pro Asp Ala Arg Ala Ala Ile Lys
1               5                   10                  15

Asn Leu Thr Glu Arg Leu Tyr Val Gly Gly Pro Leu Thr Asn Ser Lys
                20                  25                  30

Gly Glu Asn Cys Gly Tyr Arg Arg Cys Arg Ala Ser Gly Val Leu Thr
            35                  40                  45

Thr Ser Cys Gly Asn Thr Leu Thr Cys Tyr Ile Lys Ala Leu Ala Ala
    50                  55                  60

Cys Arg Ala Ala Gly Leu Arg Asp Cys Thr
65                  70

<210> SEQ ID NO 281
<211> LENGTH: 113
<212> TYPE: PRT
<213> ORGANISM: hepatitis C virus

<400> SEQUENCE: 281

Ser Thr Val Thr Glu Arg Asp Ile Arg Thr Glu Glu Ser Ile Tyr Arg
1               5                   10                  15

Ala Cys Ser Leu Pro Glu Glu Ala His Thr Ala Ile His Ser Leu Thr
                20                  25                  30

Glu Arg Leu Tyr Val Gly Gly Pro Met Phe Asn Ser Lys Gly Gln Thr
            35                  40                  45
```

```
Cys Gly Tyr Arg Arg Cys Arg Ala Ser Gly Val Leu Thr Thr Ser Met
         50                  55                  60

Gly Asn Thr Ile Thr Cys Tyr Val Lys Ala Leu Ala Ala Cys Lys Ala
 65              70                  75                  80

Ala Gly Ile Ile Ala Pro Thr Met Leu Val Cys Gly Asp Asp Leu Val
                 85                  90                  95

Val Ile Ser Glu Ser Gln Gly Thr Glu Glu Asp Glu Arg Asn Leu Arg
            100                 105                 110

Ala
```

<210> SEQ ID NO 282
<211> LENGTH: 113
<212> TYPE: PRT
<213> ORGANISM: hepatitis C virus

<400> SEQUENCE: 282

```
Ser Thr Val Thr Glu Arg Asp Ile Arg Thr Glu Glu Ser Ile Tyr Gln
 1               5                  10                  15

Ala Cys Ser Leu Pro Gln Glu Ala Arg Thr Val Ile His Ser Leu Thr
             20                  25                  30

Glu Arg Leu Tyr Val Gly Gly Pro Met Thr Asn Ser Lys Gly Gln Ser
         35                  40                  45

Cys Gly Tyr Arg Arg Cys Arg Ala Ser Gly Val Phe Thr Thr Ser Met
         50                  55                  60

Gly Asn Thr Met Thr Cys Tyr Ile Lys Ala Leu Ala Ala Cys Lys Ala
 65              70                  75                  80

Ala Gly Ile Val Asp Pro Val Met Leu Val Cys Gly Asp Asp Leu Val
                 85                  90                  95

Val Ile Ser Glu Ser Gln Gly Asn Glu Glu Asp Glu Arg Asn Leu Arg
            100                 105                 110

Ala
```

<210> SEQ ID NO 283
<211> LENGTH: 74
<212> TYPE: PRT
<213> ORGANISM: hepatitis C virus

<400> SEQUENCE: 283

```
Ile Tyr Gln Ser Cys Ser Leu Pro Glu Glu Ala Arg Thr Ala Ile His
 1               5                  10                  15

Ser Leu Thr Glu Arg Leu Tyr Val Gly Gly Pro Met Thr Asn Ser Lys
             20                  25                  30

Gly Gln Ser Cys Gly Tyr Arg Arg Cys Arg Ala Ser Ala Val Leu Thr
         35                  40                  45

Thr Ser Met Gly Asn Thr Leu Thr Cys Tyr Val Lys Ala Arg Ala Ala
         50                  55                  60

Cys Asn Ala Ala Gly Ile Val Ala Pro Thr
 65                  70
```

<210> SEQ ID NO 284
<211> LENGTH: 113
<212> TYPE: PRT
<213> ORGANISM: hepatitis C virus

<400> SEQUENCE: 284

```
Ser Thr Val Thr Glu Arg Asp Ile Arg Thr Glu Glu Ser Ile Tyr Leu
 1               5                  10                  15
```

```
Ala Cys Ser Leu Pro Glu Gln Ala Arg Thr Ala Ile His Ser Leu Thr
            20                  25                  30

Glu Arg Leu Tyr Val Gly Gly Pro Met Leu Asn Ser Lys Gly Gln Thr
        35                  40                  45

Cys Gly Tyr Arg Arg Cys Arg Ala Ser Gly Val Phe Thr Thr Ser Met
50                  55                  60

Gly Asn Thr Ile Thr Cys Tyr Val Lys Ala Gln Ala Ala Cys Lys Ala
65                  70                  75                  80

Ala Gly Ile Ile Ala Pro Thr Met Leu Val Cys Gly Asp Asp Leu Val
                85                  90                  95

Val Ile Ser Glu Ser Gln Gly Thr Glu Glu Asp Glu Arg Asn Leu Arg
                100                 105                 110

Ala

<210> SEQ ID NO 285
<211> LENGTH: 71
<212> TYPE: PRT
<213> ORGANISM: hepatitis C virus

<400> SEQUENCE: 285

Leu Thr Glu Arg Leu Tyr Cys Gly Gly Pro Met Phe Asn Ser Lys Gly
1               5                   10                  15

Ala Gln Cys Gly Tyr Arg Arg Cys Arg Ala Ser Gly Val Leu Pro Thr
            20                  25                  30

Ser Phe Gly Asn Thr Ile Thr Cys Tyr Ile Lys Ala Thr Ala Ala Ala
        35                  40                  45

Arg Ala Ala Gly Leu Arg Asn Pro Asp Phe Leu Val Cys Gly Asp Asp
    50                  55                  60

Leu Val Val Ala Glu Ser
65              70

<210> SEQ ID NO 286
<211> LENGTH: 71
<212> TYPE: PRT
<213> ORGANISM: hepatitis C virus

<400> SEQUENCE: 286

Leu Thr Glu Arg Leu Tyr Cys Gly Gly Pro Met Phe Asn Ser Lys Gly
1               5                   10                  15

Ala Gln Cys Gly Tyr Arg Arg Cys Arg Ala Ser Gly Val Leu Pro Thr
            20                  25                  30

Ser Phe Gly Asn Thr Ile Thr Cys Tyr Ile Lys Ala Thr Ala Ala Ala
        35                  40                  45

Lys Ala Ala Gly Leu Arg Ser Pro Asp Phe Leu Val Cys Gly Asp Asp
    50                  55                  60

Leu Val Val Ala Glu Ser
65              70

<210> SEQ ID NO 287
<211> LENGTH: 71
<212> TYPE: PRT
<213> ORGANISM: hepatitis C virus

<400> SEQUENCE: 287

Leu Thr Glu Arg Leu Tyr Cys Gly Gly Pro Met Phe Asn Ser Lys Gly
1               5                   10                  15

Ala Gln Cys Gly Tyr Arg Arg Cys Arg Ala Ser Gly Val Leu Pro Thr
            20                  25                  30
```

-continued

Ser Phe Gly Asn Thr Ile Thr Cys Tyr Ile Lys Ala Thr Ala Ala Ala
             35                  40                  45

Lys Ala Ala Gly Leu Arg Asn Pro Asp Phe Leu Val Cys Gly Asp Asp
     50                  55                  60

Leu Val Val Val Ala Glu Ser
65                  70

<210> SEQ ID NO 288
<211> LENGTH: 113
<212> TYPE: PRT
<213> ORGANISM: hepatitis C virus

<400> SEQUENCE: 288

Ser Thr Val Thr Glu His Asp Ile Arg Thr Glu Glu Ile Tyr Gln
1               5                  10                  15

Cys Cys Asp Leu Glu Pro Glu Ala Arg Lys Ala Ile Ser Ala Leu Thr
             20                  25                  30

Glu Arg Leu Tyr Ile Gly Gly Pro Met Tyr Asn Ser Lys Gly Leu Gln
             35                  40                  45

Cys Gly Tyr Arg Arg Cys Arg Ala Ser Gly Val Leu Pro Thr Ser Phe
     50                  55                  60

Gly Asn Thr Ile Thr Cys Tyr Ile Lys Ala Lys Ala Ala Ser Arg Ala
65                  70                  75                  80

Ala Gly Leu Lys Asp Pro Ser Phe Leu Val Cys Gly Asp Asp Leu Val
             85                  90                  95

Val Val Ser Glu Ser Cys Gly Val Glu Asp Arg Ala Ala Leu Arg
             100                 105                 110

Ala

<210> SEQ ID NO 289
<211> LENGTH: 113
<212> TYPE: PRT
<213> ORGANISM: hepatitis C virus

<400> SEQUENCE: 289

Ser Thr Val Thr Glu Lys Asp Ile Arg Val Glu Glu Val Tyr Gln
1               5                  10                  15

Cys Cys Asp Leu Glu Pro Glu Ala Arg Lys Ala Ile Thr Ala Leu Thr
             20                  25                  30

Glu Arg Leu Tyr Val Gly Gly Pro Met His Asn Ser Lys Gly Asp Leu
             35                  40                  45

Cys Gly Tyr Arg Arg Cys Arg Ala Ser Gly Val Tyr Thr Thr Ser Phe
     50                  55                  60

Gly Asn Thr Leu Thr Cys Tyr Leu Lys Ala Ser Ala Ile Lys Ala
65                  70                  75                  80

Ala Gly Leu Arg Asp Cys Thr Met Leu Val Cys Gly Asp Asp Leu Val
             85                  90                  95

Val Ile Ala Glu Ser Asp Gly Val Glu Glu Asp Lys Arg Pro Leu Gly
             100                 105                 110

Ala

<210> SEQ ID NO 290
<211> LENGTH: 113
<212> TYPE: PRT
<213> ORGANISM: hepatitis C virus

<400> SEQUENCE: 290

-continued

```
Ser Thr Val Thr Glu Lys Asp Ile Arg Val Glu Glu Val Tyr Gln
1               5                   10                  15

Cys Cys Asp Leu Glu Pro Glu Ala Arg Arg Ala Ile Thr Ala Leu Thr
                20                  25                  30

Glu Arg Leu Tyr Val Gly Gly Pro Met His Asn Ser Arg Gly Asp Leu
            35                  40                  45

Cys Gly Tyr Arg Arg Cys Arg Ala Ser Gly Val Tyr Thr Thr Ser Phe
        50                  55                  60

Gly Asn Thr Leu Thr Cys Tyr Leu Lys Ala Ser Ala Ala Ile Arg Ala
65                  70                  75                  80

Ala Gly Leu Arg Asp Cys Thr Met Leu Val Cys Gly Asp Asp Leu Val
                85                  90                  95

Val Ile Ala Glu Ser Asp Gly Val Glu Glu Asp Lys Arg Ala Leu Gly
            100                 105                 110

Ala
```

```
<210> SEQ ID NO 291
<211> LENGTH: 113
<212> TYPE: PRT
<213> ORGANISM: hepatitis C virus

<400> SEQUENCE: 291

Ser Thr Val Thr Glu Lys Asp Ile Arg Val Glu Glu Val Tyr Gln
1               5                   10                  15

Cys Cys Asp Leu Glu Pro Glu Ala Arg Lys Val Ile Thr Ala Leu Thr
                20                  25                  30

Glu Arg Leu Tyr Val Gly Gly Pro Met His Asn Ser Lys Gly Asp Leu
            35                  40                  45

Cys Gly Tyr Arg Arg Cys Arg Ala Ser Gly Val Tyr Thr Thr Ser Phe
        50                  55                  60

Gly Asn Thr Leu Thr Cys Tyr Leu Lys Ala Ser Ala Ala Ile Arg Ala
65                  70                  75                  80

Ser Gly Leu Arg Asp Cys Thr Met Leu Val Tyr Gly Asp Asp Leu Val
                85                  90                  95

Val Ile Ala Glu Ser Asp Gly Val Glu Glu Asp Lys Arg Ala Leu Gly
            100                 105                 110

Val
```

```
<210> SEQ ID NO 292
<211> LENGTH: 113
<212> TYPE: PRT
<213> ORGANISM: hepatitis C virus

<400> SEQUENCE: 292

Ser Thr Val Thr Glu Lys Asp Ile Arg Val Glu Glu Val Tyr Gln
1               5                   10                  15

Cys Cys Asp Leu Glu Pro Glu Ala Arg Lys Ala Ile Thr Ala Leu Thr
                20                  25                  30

Glu Arg Leu Tyr Val Gly Gly Pro Met His Asn Ser Lys Gly Asp Leu
            35                  40                  45

Cys Gly Tyr Arg Arg Cys Arg Ala Ser Gly Val Tyr Thr Thr Ser Phe
        50                  55                  60

Gly Asn Thr Leu Thr Cys Tyr Leu Lys Ala Ser Ala Ala Ile Arg Ala
65                  70                  75                  80

Ala Gly Leu Arg Asp Cys Thr Met Leu Val Cys Gly Asp Asp Leu Val
```

-continued

```
                85                  90                  95
Val Ile Ala Glu Ser Asp Gly Val Glu Glu Asp Lys Arg Ala Leu Gly
            100                 105                 110

Ala

<210> SEQ ID NO 293
<211> LENGTH: 113
<212> TYPE: PRT
<213> ORGANISM: hepatitis C virus
<220> FEATURE:
<221> NAME/KEY: MISC_FEATURE
<222> LOCATION: (110)..(110)
<223> OTHER INFORMATION: Xaa represents any amino acid

<400> SEQUENCE: 293

Ser Thr Val Thr Glu Arg Asp Ile Lys Val Glu Glu Val Tyr Gln
1               5                   10                  15

Cys Cys Asp Leu Glu Pro Glu Ala Arg Lys Val Ile Ala Ala Leu Thr
            20                  25                  30

Glu Arg Leu Tyr Val Gly Gly Pro Met His Asn Ser Lys Gly Asp Leu
        35                  40                  45

Cys Gly Tyr Arg Arg Cys Arg Ala Ser Gly Val Tyr Thr Thr Ser Phe
    50                  55                  60

Gly Asn Thr Met Thr Cys Tyr Leu Lys Ala Ser Ala Ala Ile Arg Ala
65                  70                  75                  80

Ala Gly Leu Lys Asp Cys Thr Met Leu Val Cys Gly Asp Asp Leu Val
                85                  90                  95

Val Ile Ala Glu Ser Gly Gly Val Glu Glu Asp Lys Arg Xaa Leu Gly
            100                 105                 110

Ala

<210> SEQ ID NO 294
<211> LENGTH: 113
<212> TYPE: PRT
<213> ORGANISM: hepatitis C virus

<400> SEQUENCE: 294

Ser Thr Val Thr Glu Arg Asp Ile Arg Val Glu Glu Val Tyr Gln
1               5                   10                  15

Cys Cys Asp Leu Glu Pro Glu Thr Arg Lys Val Ile Ser Ala Leu Thr
            20                  25                  30

Glu Arg Leu Tyr Val Gly Gly Pro Met His Asn Ser Arg Gly Asp Leu
        35                  40                  45

Cys Gly Tyr Arg Arg Cys Arg Ala Ser Gly Val Tyr Thr Thr Ser Phe
    50                  55                  60

Gly Asn Thr Leu Thr Cys Phe Leu Lys Ala Thr Ala Ala Thr Lys Ala
65                  70                  75                  80

Ala Gly Leu Lys Asp Cys Thr Met Leu Val Cys Gly Asp Asp Leu Val
                85                  90                  95

Val Ile Ala Glu Ser Asp Gly Val Glu Glu Asp Arg Arg Ala Leu Gly
            100                 105                 110

Ala

<210> SEQ ID NO 295
<211> LENGTH: 113
<212> TYPE: PRT
<213> ORGANISM: hepatitis C virus
```

```
<400> SEQUENCE: 295

Ser Thr Val Thr Glu Arg Asp Ile Arg Thr Glu Glu Ile Tyr Gln
1               5                   10                  15

Cys Cys Asp Leu Glu Pro Glu Ala Arg Lys Val Ile Ser Ala Leu Thr
                20                  25                  30

Glu Arg Leu Tyr Val Gly Gly Pro Met Tyr Asn Ser Lys Gly Asp Leu
            35                  40                  45

Cys Gly Gln Arg Arg Cys Arg Ala Ser Gly Val Tyr Thr Thr Ser Phe
        50                  55                  60

Gly Asn Thr Val Thr Cys Tyr Leu Lys Ala Val Ala Thr Arg Ala
65                  70                  75                  80

Ala Gly Leu Lys Gly Cys Ser Met Leu Val Cys Gly Asp Asp Leu Val
                85                  90                  95

Val Ile Cys Glu Ser Gly Gly Val Glu Glu Asp Ala Arg Ala Leu Arg
                100                 105                 110

Ala

<210> SEQ ID NO 296
<211> LENGTH: 113
<212> TYPE: PRT
<213> ORGANISM: hepatitis C virus

<400> SEQUENCE: 296

Ser Thr Val Thr Glu Arg Asp Ile Arg Val Glu Glu Ile Tyr Gln
1               5                   10                  15

Cys Cys Asp Leu Glu Pro Glu Ala Arg Lys Val Ile Ser Ala Leu Thr
                20                  25                  30

Glu Arg Leu Tyr Lys Gly Gly Pro Met Tyr Asn Ser Lys Gly Asp Leu
            35                  40                  45

Cys Gly Leu Arg Arg Cys Arg Ala Ser Gly Val Tyr Thr Thr Ser Phe
        50                  55                  60

Gly Asn Thr Val Thr Cys Tyr Leu Lys Ala Thr Ala Ala Thr Arg Ala
65                  70                  75                  80

Ala Gly Leu Lys Asp Cys Thr Met Leu Val Cys Gly Asp Asp Leu Val
                85                  90                  95

Val Ile Ala Glu Ser Gly Gly Val Glu Glu Asp Ala Arg Ala Leu Arg
                100                 105                 110

Ala

<210> SEQ ID NO 297
<211> LENGTH: 113
<212> TYPE: PRT
<213> ORGANISM: hepatitis C virus
<220> FEATURE:
<221> NAME/KEY: MISC_FEATURE
<222> LOCATION: (22)..(22)
<223> OTHER INFORMATION: Xaa represents any amino acid
<220> FEATURE:
<221> NAME/KEY: MISC_FEATURE
<222> LOCATION: (8)..(8)
<223> OTHER INFORMATION: Xaa represents any amino acid
<220> FEATURE:
<221> NAME/KEY: MISC_FEATURE
<222> LOCATION: (24)..(24)
<223> OTHER INFORMATION: Xaa represents any amino acid

<400> SEQUENCE: 297

Pro Thr Val Thr Glu Arg Asp Xaa Arg Val Glu Glu Glu Val Tyr Gln
1               5                   10                  15
```

-continued

```
Cys Cys Asn Leu Glu Xaa Asp Xaa Arg Lys Val Ile Asn Ala Leu Thr
             20                  25                  30

Glu Arg Leu Tyr Val Gly Gly Pro Met His Asn Ser Lys Gly Asp Leu
         35                  40                  45

Cys Gly Ile Arg Arg Cys Arg Ala Ser Gly Val Tyr Thr Thr Ser Phe
     50                  55                  60

Gly Asn Thr Leu Thr Cys Tyr Leu Lys Ala Thr Ala Ala Thr Arg Ala
 65                  70                  75                  80

Ala Gly Leu Lys Asp Cys Thr Met Leu Val Cys Gly Asp Asp Leu Val
             85                  90                  95

Val Ile Ala Glu Ser Ile Gly Ile Asp Glu Asp Lys Gln Ala Leu Arg
            100                 105                 110

Thr
```

<210> SEQ ID NO 298
<211> LENGTH: 113
<212> TYPE: PRT
<213> ORGANISM: hepatitis C virus
<220> FEATURE:
<221> NAME/KEY: MISC_FEATURE
<222> LOCATION: (4)..(4)
<223> OTHER INFORMATION: Xaa represents any amino acid
<220> FEATURE:
<221> NAME/KEY: MISC_FEATURE
<222> LOCATION: (109)..(109)
<223> OTHER INFORMATION: Xaa represents any amino acid
<220> FEATURE:
<221> NAME/KEY: MISC_FEATURE
<222> LOCATION: (111)..(111)
<223> OTHER INFORMATION: Xaa represents any amino acid

<400> SEQUENCE: 298

```
Ser Thr Val Xaa Glu Arg Asp Ile Arg Thr Glu Gly Glu Val Tyr Gln
 1               5                  10                  15

Cys Cys Asp Leu Glu Pro Glu Ala Arg Lys Val Ile Thr Ala Leu Thr
             20                  25                  30

Glu Arg Leu Tyr Val Gly Gly Pro Met Phe Asn Ser Lys Gly Asp Leu
         35                  40                  45

Cys Gly Gln Arg Arg Cys Arg Ala Ser Gly Val Phe Thr Thr Ser Phe
     50                  55                  60

Gly Asn Thr Leu Thr Cys Tyr Leu Lys Ala Thr Ala Ala Thr Arg Ala
 65                  70                  75                  80

Ala Gly Leu Lys Asp Cys Thr Met Leu Val Cys Gly Asp Asp Leu Val
             85                  90                  95

Val Ile Ser Glu Ser Ala Gly Val Glu Glu Asp Pro Xaa Thr Xaa Arg
            100                 105                 110

Pro
```

<210> SEQ ID NO 299
<211> LENGTH: 74
<212> TYPE: PRT
<213> ORGANISM: hepatitis C virus

<400> SEQUENCE: 299

```
Val Tyr Gln Cys Cys Asn Leu Glu Pro Glu Ala Arg Lys Ala Ile Thr
 1               5                  10                  15

Ala Leu Thr Glu Arg Leu Tyr Val Gly Gly Pro Met His Asn Ser Lys
             20                  25                  30

Gly Asp Leu Cys Gly Tyr Arg Arg Cys Arg Ala Ser Gly Val Phe Thr
         35                  40                  45
```

-continued

Thr Ser Phe Gly Asn Thr Leu Thr Cys Tyr Leu Lys Ala Thr Ala Ala
    50                  55                  60

Ile Arg Ala Ala Gly Leu Arg Asp Cys Thr
65                  70

<210> SEQ ID NO 300
<211> LENGTH: 113
<212> TYPE: PRT
<213> ORGANISM: hepatitis C virus

<400> SEQUENCE: 300

Ser Thr Val Thr Glu His Asp Ile Met Thr Glu Glu Ser Ile Tyr Gln
1               5                   10                  15

Ser Cys Asp Leu Gln Pro Glu Ala Arg Ala Ile Arg Ser Leu Thr
            20                  25                  30

Gln Arg Leu Tyr Cys Gly Gly Pro Met Tyr Asn Ser Lys Gly Gln Gln
            35                  40                  45

Cys Gly Tyr Arg Arg Cys Arg Ala Ser Gly Val Phe Thr Thr Ser Met
    50                  55                  60

Gly Asn Thr Met Thr Cys Tyr Ile Lys Ala Leu Ala Ser Cys Arg Ala
65                  70                  75                  80

Ala Arg Leu Arg Asp Cys Thr Leu Leu Val Cys Gly Asp Asp Leu Val
                85                  90                  95

Ala Ile Cys Glu Ser Gln Gly Thr His Glu Asp Glu Ala Ser Leu Arg
                100                 105                 110

Ala

<210> SEQ ID NO 301
<211> LENGTH: 113
<212> TYPE: PRT
<213> ORGANISM: hepatitis C virus

<400> SEQUENCE: 301

Ser Thr Val Thr Glu His Asp Ile Met Thr Glu Glu Ser Ile Tyr Gln
1               5                   10                  15

Ser Leu Tyr Leu Gln Pro Glu Ala Arg Val Ala Ile Arg Ser Leu Thr
            20                  25                  30

Gln Arg Leu Tyr Cys Gly Gly Pro Met Tyr Asn Ser Lys Gly Gln Gln
            35                  40                  45

Cys Gly Tyr Arg Arg Cys Arg Ala Ser Gly Val Phe Thr Thr Ser Met
    50                  55                  60

Gly Asn Thr Met Thr Cys Tyr Ile Lys Ala Leu Ala Ser Cys Arg Ala
65                  70                  75                  80

Ala Lys Leu Gln Asp Cys Thr Leu Leu Val Cys Gly Asp Asp Leu Val
                85                  90                  95

Ala Ile Cys Glu Ser Gln Gly Thr His Glu Asp Lys Ala Ser Leu Arg
                100                 105                 110

Ala

<210> SEQ ID NO 302
<211> LENGTH: 13
<212> TYPE: PRT
<213> ORGANISM: hepatitis C virus -continued

```
<400> SEQUENCE: 302

Ser Ala Gly Thr Gln Glu Asp Ala Ala Ser Leu Arg Val
1               5                   10
```

What is claimed is:

1. An isolated HCV polynucleic acid consisting of a sequence which codes an HCV protein, said polynucleic acid which codes an HCV protein being selected from the group consisting of:
   (i) the nucleotide sequence consisting of SEQ ID NO: 51; and
   (ii) a nucleotide sequence consisting of at least 60 up to 447 contiguous nucleotides of SEQ ID NO:51; and
   the complement of the polynucleic acid of (i) or (ii).

2. An isolated HCV polynucleic acid which is selected from:
   (i) a polynucleic acid sequence consisting of a sequence encoding an HCV polyprotein consisting of an amino acid sequence selected from the group consisting of SEQ ID NOs: 62, 138, 155, 174, and 190,
   (iii) or the complement of the polynucleic acid of (i).

3. A recombinant polypeptide encoded by a polynucleic acid according to claim 1 or claim 2.

4. A method for production of a recombinant polypeptide, comprising:
   transformation of an appropriate isolated cellular host with a recombinant vector, in which a polynucleic acid according to claim 1 or 2 has been inserted under the control of the appropriate regulatory elements, the polynucleic acid thus being an insert,
   culturing the resultant host cell under conditions enabling the expression of said insert, and
   harvesting said polypeptide.

5. A recombinant expression vector comprising a polynucleic acid according to claim 1 or claim 2 operably linked to prokaryotic, eukaryotic or viral transcription and translation control elements.

6. An isolated host cell transformed with a recombinant vector according to claim 5.

7. An isolated peptide encoded by a polynucleic acid according to claim 2.

* * * * *